United States Patent
Uchida et al.

(10) Patent No.: US 9,701,689 B2
(45) Date of Patent: Jul. 11, 2017

(54) SUBSTITUTED PYRIDINES AND PYRIDAZINES AS CCR10 RECEPTOR INHIBITORS

(71) Applicant: KYOWA HAKKO KIRIN CO., LTD., Tokyo (JP)

(72) Inventors: Kenji Uchida, Tokyo (JP); Toshimi Kanai, Tokyo (JP); Masakazu Homma, Tokyo (JP); Seiji Aratake, Tokyo (JP); Tatsuya Ishimori, Tokyo (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 92 days.

(21) Appl. No.: 14/648,180

(22) PCT Filed: Nov. 29, 2013

(86) PCT No.: PCT/JP2013/082127
§ 371 (c)(1),
(2) Date: May 28, 2015

(87) PCT Pub. No.: WO2014/084330
PCT Pub. Date: Jun. 5, 2014

(65) Prior Publication Data
US 2015/0299214 A1    Oct. 22, 2015

(30) Foreign Application Priority Data

Nov. 30, 2012 (JP) .................. 2012-263100

(51) Int. Cl.
| | | |
|---|---|---|
| *A61K 31/44* | (2006.01) |
| *A61K 31/50* | (2006.01) |
| *C07D 213/46* | (2006.01) |
| *C07D 237/10* | (2006.01) |
| *C07D 491/107* | (2006.01) |
| *C07D 401/14* | (2006.01) |
| *C07D 405/14* | (2006.01) |
| *C07D 413/14* | (2006.01) |
| *C07D 213/82* | (2006.01) |
| *C07D 401/06* | (2006.01) |
| *C07D 417/14* | (2006.01) |
| *C07D 409/14* | (2006.01) |
| *C07D 471/04* | (2006.01) |
| *C07D 487/04* | (2006.01) |

(52) U.S. Cl.
CPC ....... *C07D 491/107* (2013.01); *C07D 213/82* (2013.01); *C07D 401/06* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01)

(58) Field of Classification Search
CPC ...... A61K 31/44; A61K 31/50; C07D 213/46; C07D 237/10

USPC ................. 514/247, 355; 544/224; 546/315
See application file for complete search history.

(56) References Cited

U.S. PATENT DOCUMENTS

| 6,977,263 | B2 | 12/2005 | Astles et al. |
| 8,354,401 | B2 | 1/2013 | Ishibuchi et al. |
| 8,673,908 | B2 | 3/2014 | Amishiro et al. |
| 2003/0187020 | A1 | 10/2003 | Astles et al. |
| 2005/0228018 | A1 | 10/2005 | Astles et al. |
| 2010/0022589 | A1 | 1/2010 | McCoull et al. |
| 2011/0237584 | A1 | 9/2011 | Amishiro et al. |
| 2011/0263571 | A1 | 10/2011 | Ishibuchi et al. |
| 2014/0221340 | A1 | 8/2014 | Yamamoto et al. |

FOREIGN PATENT DOCUMENTS

| CA | 2893115 | * | 6/2014 |
| CN | 1439003 A | | 8/2003 |
| WO | WO 02/18335 A | | 3/2002 |
| WO | WO 2007/017264 A2 | | 2/2007 |
| WO | WO 2008/012532 A2 | | 1/2008 |
| WO | WO 2009/052078 A1 | | 4/2009 |
| WO | WO 2010/050461 A1 | | 5/2010 |
| WO | WO 2010/053182 A1 | | 5/2010 |
| WO | WO 2013/031931 A1 | | 5/2013 |

OTHER PUBLICATIONS

Jordan, V. C. Nature Reviews: Drug Discovery, 2, 2003, 205.*
Hackam, et al. JAMA, 296(14), 2006, 1731-1732.*
Chinese Patent Office, Notification of First Office Action in Chinese Patent Application No. 201380069470.7 (Jun. 29, 2016).
Chen et al., *International Immunology*, 18(8): 1233-1242 (2006).
Duhen et al., *Nature Immunology*, 10(8): 857-863 (2009).
Hijnen et al., *Journal of Allergy Clinical Immunology*, 113(2): 334-340 (2004).

(Continued)

*Primary Examiner* — Douglas M Willis
(74) *Attorney, Agent, or Firm* — Leydig, Voit & Mayer, Ltd.

(57) ABSTRACT

The present invention provides a heterocyclic compound represented by the following formula (I)

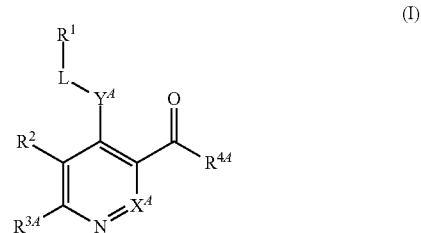

or a pharmaceutically acceptable salt thereof, in which $X^A$, $R^1$, $Y^A$, $R^2$, $R^{3A}$, and $R^{4A}$ are as defined herein. The compound of formula (I) inhibits a C-C chemokine receptor type 10 (CCR10) receptor and is useful as a prophylactic and/or therapeutic agent for skin diseases.

18 Claims, No Drawings

(56) References Cited

OTHER PUBLICATIONS

Hijnen et al., *The Journal of Investigative Dermatology*, 125: 1149-1155 (2005).
Homey et al., *Clinics in Dermatology*, 26: 539-545 (2008).
Homey et al., *Journal of Allergy Clinical Immunology*, 118(1): 178-189 (2006).
Homey et al., *Nature Medicine*, 8(2): 157-165 (2002).
Kagami et al., *European Journal of Immunology*, 38: 647-657 (2008).
Mirshahpanah et al., *Experimental Dermatology*, 17: 30-34 (2008).
Trifari et al., *Nature Immunology*, 10(8): 864-871 (2009).
Japanese Patent Office, International Search Report in International Patent Application No. PCT/JP2013/082127 (Dec. 24, 2013).

\* cited by examiner

SUBSTITUTED PYRIDINES AND PYRIDAZINES AS CCR10 RECEPTOR INHIBITORS

CROSS-REFERENCE TO RELATED APPLICATIONS

This patent application is the U.S. national phase of International Patent Application No. PCT/JP2013/082127, filed Nov. 29, 2013, which claims the benefit of Japanese Patent Application No. 2012-263100, filed on Nov. 30, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 950 bytes ASCII (Text) file named "7720962SequenceListing.txt," created May 28, 2015.

FIELD OF THE INVENTION

The present invention relates to a nitrogen-containing heterocyclic compound or a pharmaceutically acceptable salt thereof useful as an agent for the prophylaxis and/or treatment of skin diseases, and the like.

BACKGROUND OF THE INVENTION

Chemokine is a series of families of small inflammatory cytokines having a strong chemotactic activity and being composed of about 70-120 amino acids, and is a chemotactic cytokine released from a wide variety of cells in order to lead various cells such as monocyte, macrophage, T cell, eosinophil, basophil, neutrophil and the like to the inflammatory site. The chemokine family was originally defined by 4 conserved cysteine residues in an amino acid sequence, namely, classified into two subfamilies of CXC-chemokine family and CC-chemokine family based on the configuration of the first cysteine pair (two residues) on the N terminal side. In the CXC-chemokine family including CXCL1, Mig, CX3CL1, IL-8, Gro-α, NAP-2, IP-10 and the like, these two cysteine residues are separated by one of the amino acid residues other than cysteine; on the other hand, in the CC-chemokine family including RANTES(CCL5), MCP-1 (CCL2), MCP-2(CCL8), MCP-3(CCL7), MCP-4(CCL13), MIP-1α(CCL3), MIP-1β(CCL4), Eotaxin(CCL11), Eotaxin-2(CCL24), Eotaxin-3(CCL26), PARC(CCL18), TARC(CCL17), MDC(CCL22), LARC(CCL20), ELC (CCL19), SLC(CCL21), I-309(CCL1), TECK(CCL25), CTACK(CCL27), MEC(CCL28) and the like, these two cysteine residues are contiguous. Thereafter, the C chemokine family having, of the four cysteine residues originally present, only two cysteine residues corresponding to the second and the fourth residues from the N terminal side, and the CX3C chemokine family having a sequence having three amino acid residues different from cysteine between the first two cysteine residues on the N terminal side were found.

Ten kinds of receptors have been reported as the chemokine receptor that CC-chemokine family binds to. That is, CCR1 (alias, CKR1 or CC-CKR-1) bindable with MIP-1α, MIP-1β, MCP-3, RANTES and the like, CCR2A (alias, CKR2A or CC-CKR-2A) and CCR2B (alias, CKR2B or CC-CKR-2B) bindable with MCP-1, MCP-2, MCP-3, MCP-4 and the like, CCR3 (alias, CKR-3 or CC-CKR-3) bindable with Eotaxin, Eotaxin-2, RANTES, MCP-2, MCP-3 and the like, CCR4 (alias, CKR4 or CC-CKR-4) bindable with TARC, MDC and the like, CCR5 (alias, CKR-5 or CC-CKR-5) bindable with MIP-1α, RANTES, MIP-1β and the like, CCR6 (alias, GPRCY4) bindable with LARC and the like, CCR7 (alias, EBI-1) bindable with ELC, SLC and the like, CCR8 bindable with 1-309 and the like, CCR9 (alias, GPR9-6) bindable with TECK and the like, and CCR10 bindable with CTACK, MEC and the like are known [Nature Reviews Immunology, 2002, vol. 2, page 106].

Chemokine receptors have different expression cells depending on the kind of the receptor. For example, CCR1 is expressed in various cells such as monocyte, T cell, mast cell, eosinophil, basophil and the like, and CCR2 is expressed in various cells such as dendritic cell, B cell, basophil, eosinophil, vascular endothelial cell, fibroblast, platelet, T cell and the like. On the other hand, some receptors are expressed only in some cells such as CCR3 expressed in eosinophils and basophil, and CCR9 expressed in T cells.

Since involvement of chemokine receptor in various diseases has been reported, a medicament modulating a chemokine receptor activity is expected to be a therapeutic drug for various diseases [Expert Opinion on Investigational Drugs, 2010, vol. 19, page 345]. Heretofore, plural chemokine receptor activity modulators have been used as therapeutic drugs. For example, it has been clarified that, when CD4+T cells are infected with HIV, HIV invades into the cells via CCR5, and therefore, CCR5 antagonist is used as a therapeutic drug for HIV infection. Also, as a medicament for mobilization of stem cells in autologous stem cell transplantation in patients with non-Hodgkin lymphoma and multiple myeloma, a combined use of an antagonist of CXCR4 which is a receptor of CXC-chemokine family with G-CSF has been approved. Besides these, CCR3 antagonist, CCR9 antagonist, antibody to CCR4 and the like are under clinical tests [Expert Opinion on Investigational Drugs, 2010, vol. 19, page 345].

As diseases involving a chemokine receptor, inflammatory diseases such as asthma, rhinitis, dermatitis, allergic disease and the like, immunoregulatory disorders and diseases, autoimmune diseases such as rheumatoid arthritis, lupus erythematosus, generalized scleroderma, Sjogren's syndrome, Celiac disease and the like, and the like are known [Current Opinion in Immunology, 2001, vol. 13, page 670]. Involvement of chemokine receptors such as CCR1; CCR2A; CCR2B; CCR3; CCR4; CCR5; CCR6; CCR7; CCR8; CCR9; CCR10; CXCR3 and CXCR4 which are receptors of CXC-chemokine family; and the like in the onset of these diseases has been reported. Among these, as a disease involving CCR4, CCR8, CCR9, CCR10 and the like, skin diseases and the like are known [Journal of Investigative Dermatology, 2009, vol. 129, page 2552].

As skin diseases involving a chemokine receptor, acne vulgaris, drug eruption, contact dermatitis, pollen dermatitis, urticaria, psoriasis, atopic dermatitis, Candida dermatitis, seborrheic dermatitis, eczema, Stevens-Johnson syndrome, toxic epidermal necrosis, erythema multiforme, pityriasis rosea, lichen planus, lichen pilaris (keratosis pilaris), herpes simplex, lupus erythematosus, keloid, scabies, generalized scleroderma and dermatitis as a side effect of anti-cancer agents and the like are known. In these skin diseases, various chemokines are highly expressed in the skin. For example, it is known that, in psoriasis, expression of chemokines such as MCP-1, RANTES, TARC, MDC, CTACK, CXCL1, Gro-α, IL-8, Mig, IP-10, CX3CL1 and the like increases in the dermatitis site and T cells and neutrophils infiltrate into the skin via CCR4; CCR6; CCR10; and CXCR1, CXCR2 and CXCR3, which are receptors of CXC chemokine family; and the like (non-patent document 1), in To atopic dermatitis, expression of chemokine such as 1-309, MCP-1, MIP-1α, MIP-1β, RANTES, Eotaxin, MCP-4, PARC, LARC, MDC, Eotaxin-3, CTACK and the like increases in the dermatitis site and T cells, monocyte, eosinophils infiltrate into the skin via CCR1; CCR2A; CCR2B; CCR3; CCR4; CCR5; CCR6; CCR8; CCR10; CX3CR1 which is the receptor of CX3C chemokine family; and the like (non-patent document 2) and the like. Also, it has been reported that anti-CTACK antibody suppresses dermatitis in various dermatitis models and the like (for example, non-patent documents 3, 4, 5, 6 and the like). As a medicament that modulates chemokine receptor activity in skin diseases and the like in which these chemokine receptors are involved, pyrazolopyrimidine derivatives are known (patent document 3).

CCR10 is a chemokine receptor belonging to the C-C chemokine family [Genomics, 1994, vol. 23, page 609], and mainly expressed in the cells localized in the skin such as Cutaneous lymphocyte-associated antigen (CLA) positive skin-homing T cells, skin vascular endothelial cell, skin fibroblast, skin keratinocyte and the like. As a chemokine whose receptor is CCR10, two kinds of Cutaneous T-cell attracting chemokine (CTACK: alias CCL27) and Mucosae-associated epithelial chemokine (MEC: alias CCL28) are known. CCR10 and ligand thereof are said to be involved in the immunity of epithelial cells [Protein & Cell, 2012, vol. 3, page 571].

In recent years, involvement of CCR10 in atopic dermatitis has been reported. CTACK is selectively expressed in skin keratinocytes, and skin-homing CCR10 positive cells selectively migrate into CTACK. In patients with atopic dermatitis, expression of CTACK in the lesion skin is promoted, and in atopic dermatitis patients, the blood level of CTACK shows a positive correlation with the severity of dermatitis (non-patent document 7). Also, in the lesion skin of atopic dermatitis patients, localization of CCR10 positive T cells is found, and the CCR10 mRNA expression level of peripheral blood CD4 positive T cells of atopic dermatitis patients is higher than that of healthy adult (non-patent document 8). Furthermore, IL-22 is highly expressed in the skin lesion of atopic dermatitis patients, suppresses filaggrin production of the skin and is involved in the destruction of skin barrier. CCR10 is selectively expressed in Th22 cells that highly produce IL-22 (non-patent documents 9 and 10).

The role of CTACK and CCR10 in dermatitis has been studied by using mouse dermatitis model. When chronic contact dermatitis involving type 2 helper T cell is developed in keratinocyte selective CTACK highly expressing mouse, infiltration of CCR10 positive T cells in the skin tissue and skin tumentia significantly increase as compared to wild-type mouse (non-patent document 11).

On the other hand, among the nitrogen-containing heterocyclic compounds, as a pyridine compound, for example, the compounds represented by the following formulas (A) and (B) (patent document 1, 2) and the like are known as a compound having aliphatic heterocyclic carbonyl at the 3-position.

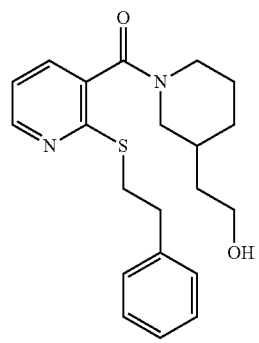

(A)

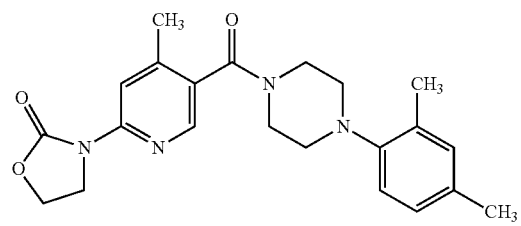

(B)

PRIOR ARTS DOCUMENTS

Patent Documents patent document 1: WO08/012532
patent document 2: WO10/050461
patent document 3: WO13/031931

Non-Patent Documents non-patent document 1: "Clinical Dermatology", 2008, vol. 26, page 539
non-patent document 2: "Journal of Allergy and Clinical Immunology", 2006, vol. 118, page 178
non-patent document 3: "Nature Medicine", 2002, vol. 8, page 157-165
non-patent document 4: "International Immunology", 2006, vol. 18, page 1233-1242
non-patent document 5: "European Journal of Immunology", 2008, vol. 38, page 647-657
non-patent document 6: "Experimental Dermatology", 2007, vol. 17, page 30-34
non-patent document 7: "Journal of Allergy and Clinical Immunology", 2004, vol. 113, page 334
non-patent document 8: "Journal of Investigative Dermatology", 2005, vol. 125, page 1149
non-patent document 9: "Nature Immunology", 2009, vol. 10, page 857
non-patent document 10: "Nature Immunology, 2009, vol. 10, page 864
non-patent document 11: "European Journal of Immunology", 2008, vol. 38, page 647

BRIEF SUMMARY OF THE INVENTION

Problems to be Solved by the Invention

An object of the present invention is to provide a nitrogen-containing heterocyclic compound or a pharmaceutically acceptable salt thereof, which is useful as an agent for the prophylaxis and/or treatment of skin diseases, and the like.

Means of Solving the Problems

The present invention relates to the following (1)-(36).
(1) A nitrogen-containing heterocyclic compound represented by the formula (I)

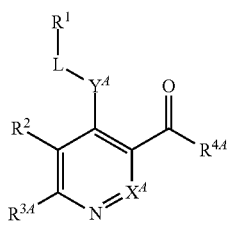

(wherein, $X^A$ represents CH or a nitrogen atom,
$R^1$ represents cycloalkyl optionally having substituent(s), aryl optionally having substituent(s), an aromatic heterocyclic group optionally having substituent(s), or an aliphatic heterocyclic group optionally having substituent(s),
L represents a bond or alkylene,
$Y^A$ represents —NH—, —O—, —NH—C(=O)—, —S—, —NH—NR$^{1a}$— (wherein,
$R^{1a}$ represents lower alkyl), or a bond (provided $Y^A$ and L do not represent a bond at the same time),
$R^2$ represents a hydrogen atom, cyano, halogen, lower alkyl optionally having substituent(s), or lower alkoxy optionally having substituent(s),
$R^{3A}$ represents the following formula ($R^{3A}$-1) or ($R^{3A}$-2)

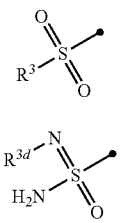

(wherein, $R^3$ represents hydroxy, lower alkyl optionally having substituent(s), aryl optionally having substituent(s), or —NR$^{3a}$R$^{3b}$ [wherein, R$^{3a}$ and R$^{3b}$ are the same or different and each represents a hydrogen atom, lower alkyl optionally having substituent(s), lower alkoxy optionally having substituent(s), cycloalkyl optionally having substituent(s), aryl optionally having substituent(s), an aromatic heterocyclic group optionally having substituent(s), an aliphatic heterocyclic group optionally having substituent(s) or —C(=O)R$^{3c}$ (wherein R$^{3c}$ represents lower alkyl optionally having substituent(s), lower alkoxy optionally having substituent(s), lower alkylamino optionally having substituent(s), cycloalkylamino optionally having substituent(s), or cycloalkyl optionally having substituent(s)), or R$^{3a}$ and R$^{3b}$ form, together with the adjacent nitrogen atom, a nitrogen-containing heterocyclic group optionally having substituent(s)], and
$R^{3d}$ represents a hydrogen atom, lower alkanoyl, aroyl, or lower alkylcarbamoyl}, and
$R^{4A}$ represents the following formula ($R^{4A}$-1), ($R^{4A}$-2) ($R^{4A}$-4) ($R^{4A}$-5) ($R^{4A}$-6)

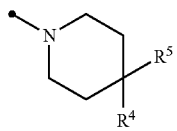

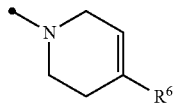

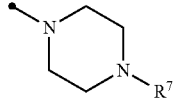

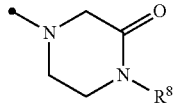

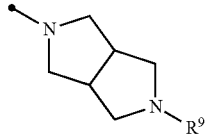

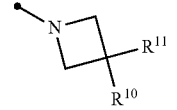

[wherein, $R^4$ and $R^5$ are the same or different and each represents a hydrogen atom, hydroxy, cyano, lower alkyl optionally having substituent(s), aryl optionally having substituent(s), lower alkoxy optionally having substituent(s), or —C(=O)R$^{4c}$ (wherein, R$^{4c}$ represents amino, alkyl optionally having substituent(s) or lower alkoxy optionally having substituent(s)), or R$^4$ and R$^5$ form, together with the adjacent carbon atom, an aliphatic heterocyclic group optionally having substituent(s), $R^6$, $R^7$, $R^8$ and $R^9$ represent aryl optionally having substituent(s), $R^{10}$ and $R^{11}$ are the same or different and each represents a hydrogen atom, hydroxy, cyano, lower alkyl optionally having substituent(s), aryl optionally having substituent(s), lower alkoxy optionally having substituent(s), or —C(=O)R$^{4c}$ (wherein, R$^{4c}$ represents amino, alkyl optionally having substituent(s) or lower alkoxy optionally having substituent(s)), or $R^{10}$ and $R^{11}$ form, together with the adjacent carbon atom, an aliphatic heterocyclic group optionally having substituent(s)]), or a pharmaceutically acceptable salt thereof.
(2) The nitrogen-containing heterocyclic compound or the pharmaceutically acceptable salt thereof according to (1), wherein $X^A$ is CH.
(3) The nitrogen-containing heterocyclic compound or the pharmaceutically acceptable salt thereof according to (1) or (2), wherein L is a bond.
(4) The nitrogen-containing heterocyclic compound or the pharmaceutically acceptable salt thereof according to any of (1)-(3), wherein $Y^A$ is —NH— or —O—.
(5) The nitrogen-containing heterocyclic compound or the pharmaceutically acceptable salt thereof according to any of (1)-(4), wherein $R^1$ is aryl optionally having substituent(s).

(6) The nitrogen-containing heterocyclic compound or the pharmaceutically acceptable salt thereof according to any of (1)-(4), wherein $R^1$ is phenyl optionally having substituent(s).
(7) The nitrogen-containing heterocyclic compound or the pharmaceutically acceptable salt thereof according to any of (1)-(6), wherein $R^2$ is a hydrogen atom, halogen or lower alkyl optionally having substituent(s).
(8) The nitrogen-containing heterocyclic compound or the pharmaceutically acceptable salt thereof according to any of (1)-(6), wherein $R^2$ is a hydrogen atom.
(9) The nitrogen-containing heterocyclic compound or the pharmaceutically acceptable salt thereof according to any of (1)-(6), wherein $R^2$ is halogen.
(10) The nitrogen-containing heterocyclic compound or the pharmaceutically acceptable salt thereof according to any of (1)-(6), wherein $R^2$ is lower alkyl optionally having substituent(s).
(11) The nitrogen-containing heterocyclic compound or the pharmaceutically acceptable salt thereof according to any of (1)-(10), wherein $R^{3A}$ is the following formula ($R^{3A}$-1)

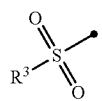

(wherein $R^3$ is as defined above).
(12) The nitrogen-containing heterocyclic compound or the pharmaceutically acceptable salt thereof according to (11), wherein $R^3$ is —$NR^{3a}R^{3b}$ (wherein $R^{3a}$ and $R^{3b}$ are each as defined above).
(13) The nitrogen-containing heterocyclic compound or the pharmaceutically acceptable salt thereof according to (12), wherein $R^{3a}$ and $R^{3b}$ are the same or different and each is a hydrogen atom, or an aromatic heterocyclic group optionally having substituent(s).
(14) The nitrogen-containing heterocyclic compound or the pharmaceutically acceptable salt thereof according to (12), wherein $R^{3a}$ and $R^{3b}$ are hydrogen atoms.
(15) The nitrogen-containing heterocyclic compound or the pharmaceutically acceptable salt thereof according to (12), wherein $R^{3a}$ is a hydrogen atom, and $R^{3b}$ is an aromatic heterocyclic group optionally having substituent(s).
(16) The nitrogen-containing heterocyclic compound or the pharmaceutically acceptable salt thereof according to any of (1)-(15), wherein $R^{4A}$ is the following formula ($R^{4A}$-1)

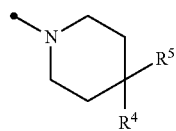

(wherein $R^4$ and $R^5$ are each as defined above).
(17) The nitrogen-containing heterocyclic compound or the pharmaceutically acceptable salt thereof according to (16), wherein $R^4$ and $R^5$ are the same or different and each is a hydrogen atom, or aryl optionally having substituent(s).
(18) The nitrogen-containing heterocyclic compound or the pharmaceutically acceptable salt thereof according to (16), wherein $R^4$ and $R^5$ are the same or different and each is a hydrogen atom, or phenyl optionally having substituent(s).
(19) The nitrogen-containing heterocyclic compound or the pharmaceutically acceptable salt thereof according to (16), wherein $R^4$ is a hydrogen atom and $R^5$ is phenyl optionally having substituent(s).
(20) A medicament comprising, as an active ingredient, the nitrogen-containing heterocyclic compound or the pharmaceutically acceptable salt thereof described in any of (1)-(19).
(21) A CCR10 receptor antagonist comprising, as an active ingredient, the nitrogen-containing heterocyclic compound or the pharmaceutically acceptable salt thereof described in any of (1)-(19).
(22) An agent for the prophylaxis and/or treatment of a skin disease, comprising, as an active ingredient, the nitrogen-containing heterocyclic compound or the pharmaceutically acceptable salt thereof described in any of (1)-(19).
(23) The agent for the prophylaxis and/or treatment of a skin disease according to (22), wherein the skin disease is a skin disease selected from acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.
(24) The agent for the prophylaxis and/or treatment of a skin disease according to (22), wherein the skin disease is a skin disease selected from contact dermatitis and atopic dermatitis.
(25) A method of inhibiting a CCR10 receptor, comprising a step of administering an effective amount of the nitrogen-containing heterocyclic compound or the pharmaceutically acceptable salt thereof described in any of (1)-(19).
(26) A method for the prophylaxis and/or treatment of a skin disease, comprising a step of administering an effective amount of the nitrogen-containing heterocyclic compound or the pharmaceutically acceptable salt thereof described in any of (1)-(19).
(27) The method according to (26), wherein the skin disease is a skin disease selected from acne vulgaris, drug eruption, contact dermatitis, dermatitis due to venomous moth, pollen dermatitis, urticaria, psoriasis, atopic dermatitis, *Candida* dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.
(28) The method according to (26), wherein the skin disease is a skin disease selected from contact dermatitis and atopic dermatitis.
(29) The nitrogen-containing heterocyclic compound or the pharmaceutically acceptable salt thereof described in any of (1)-(19) for use in inhibition of a CCR10 receptor.
(30) The nitrogen-containing heterocyclic compound or the pharmaceutically acceptable salt thereof described in any of (1)-(19) for use in the prophylaxis and/or treatment of a skin disease.

(31) The nitrogen-containing heterocyclic compound or the pharmaceutically acceptable salt thereof according to (30), wherein the skin disease is a skin disease selected from acne vulgaris, drug eruption, contact dermatitis, dermatitis due to venomous moth, pollen dermatitis, urticaria, psoriasis, atopic dermatitis, Candidal dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(32) The nitrogen-containing heterocyclic compound or the pharmaceutically acceptable salt thereof according to (30), wherein the skin disease is a skin disease selected from contact dermatitis and atopic dermatitis.

(33) Use of the nitrogen-containing heterocyclic compound or the pharmaceutically acceptable salt thereof described in any of (1)-(19) for the manufacture of a CCR10 receptor antagonist.

(34) Use of the nitrogen-containing heterocyclic compound or the pharmaceutically acceptable salt thereof described in any of (1)-(19) for the manufacture of an agent for the prophylaxis and/or treatment of a skin disease.

(35) The use according to (34), wherein the skin disease is a skin disease selected from acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies and linear dermatitis.

(36) The use according to (34), wherein the skin disease is a skin disease selected from contact dermatitis and atopic dermatitis.

The nitrogen-containing heterocyclic compound or the pharmaceutically acceptable salt thereof of the present invention is useful as, for example, a prophylactic and/or therapeutic agent for skin diseases and the like.

According to the present invention, a nitrogen-containing heterocyclic compound or a pharmaceutically acceptable salt thereof useful as a prophylactic and/or therapeutic agent for skin diseases, and the like are provided.

DETAILED DESCRIPTION OF THE INVENTION

Hereinafter a compound represented by the general formula (I) is referred to as compound (I). Compounds having the other formula numbers are referred to in the same manner.

In a definition of each group in the general formula (I),
examples of the lower alkyl, and the lower alkyl moiety m of the lower alkoxy, the lower alkylamino, the lower alkanoyl and the lower alkylcarbamoyl include linear or branched alkyl having 1-10 carbon atoms, and more specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl and the like.

Examples of the alkylene include groups recited as examples of the aforementioned lower alkyl from which one hydrogen atom has been removed, and the like.

Examples of the cycloalkyl and the cycloalkyl moiety of the cycloalkylamino include cycloalkyl having 3-12 carbon atoms, and more specific examples thereof include cyclopropyl, cyclobutyl, cyclopentyl, cyclohexyl, cycloheptyl, cyclooctyl and the like. Also, the cycloalkyl may include bicyclic or tricyclic cycloalkyl fused with phenyl or 4- to 6-membered cycloalkyl. Examples of the bicyclic or tricyclic cycloalkyl fused with phenyl include 2,3-dihydro-1H-indenyl, 1,2,3,4-tetrahydronaphthalenyl and the like. Examples of the bicyclic or tricyclic cycloalkyl fused with 4- to 6-membered cycloalkyl include octahydro-1H-indenyl, decahydronaphthalenyl, bicyclo[2.2.1]heptanyl, bicyclo[3.2.1]octanyl and the like.

Examples of the aryl and the aryl moiety of the aroyl include aryl having 6-14 carbon atoms, and more specific examples thereof include phenyl, naphthyl, azulenyl, anthryl and the like. Also, the aryl may include phenyl fused with 5- to 8-membered cycloalkyl. Examples of the phenyl fused with 5- to 8-membered cycloalkyl include cycloalkyl-fused phenyl having 9-12 carbon atoms, and more specific examples thereof include 2,3-dihydro-1H-indenyl, 1,2,3,4-tetrahydronaphthalenyl and the like.

Examples of the aliphatic heterocyclic group, and the aliphatic heterocyclic group formed together with the adjacent carbon atom include a 3- to 7-membered monocyclic aliphatic heterocyclic group containing at least one atom selected from a nitrogen atom, an oxygen atom and a sulfur atom, a bicyclic or tricyclic fused aliphatic heterocyclic group, in which 3- to 8-membered rings are fused, and which contains at least one atom selected from a nitrogen atom, an oxygen atom and a sulfur atom, and the like, and more specific examples thereof include aziridinyl, azetidinyl, pyrrolidinyl, piperidino, piperidinyl, azepanyl, 1,2,5,6-tetrahydropyridyl, imidazolidinyl, pyrazolidinyl, piperazinyl, homopiperazinyl, pyrazolinyl, oxiranyl, tetrahydrofuranyl, tetrahydro-2H-pyranyl, 5,6-dihydro-2H-pyranyl, oxazolidinyl, morpholino, morpholinyl, thioxazolidinyl, thiomorpholinyl, 2H-oxazolyl, 2H-thioxazolyl, dihydroindolyl, dihydroisoindolyl, dihydrobenzofuranyl, benzimidazolidinyl, dihydrobenzooxazolyl, dihydrobenzothioxazolyl, benzodioxolinyl, tetrahydroquinolyl, tetrahydroisoquinolyl, dihydro-2H-chromanyl, dihydro-1H-chromanyl, dihydro-2H-thiochromanyl, dihydro-1H-thiochromanyl, tetrahydroquinoxalinyl, tetrahydroquinazolinyl, dihydrobenzodioxanyl, dihydroisobenzofuranyl, 7-oxabicyclo[2.2.1]heptanyl and the like.

Examples of the aromatic heterocyclic group include a 5- or 6-membered monocyclic aromatic heterocyclic group containing at least one atom selected from a nitrogen atom, an oxygen atom and a sulfur atom, a bicyclic or tricyclic fused aromatic heterocyclic group, in which 3- to 8-membered rings are fused, and which contains at least one atom selected from a nitrogen atom, an oxygen atom and a sulfur atom, and the like, and more specific examples thereof include furyl, thienyl, pyrrolyl, imidazolyl, pyrazolyl, oxazolyl, isoxazolyl, oxadiazolyl, thiazolyl, isothiazolyl, thiadiazolyl, triazolyl, tetrazolyl, pyridyl, pyridazinyl, pyrimidinyl, pyrazinyl, triazinyl, benzofuranyl, benzothiophenyl, benzoxazolyl, benzothiazolyl, isoindolyl, indolyl, indazolyl, benzimidazolyl, benzotriazolyl, oxazolopyrimidinyl, thiazolopyrimidinyl, pyrrolopyridinyl, pyrrolopyrimidinyl, imidazopyridinyl, purinyl, quinolinyl, isoquinolinyl, cinnolinyl, phthalazinyl, quinazolinyl, quinoxalinyl, naphthyridinyl and the like.

Examples of the nitrogen-containing heterocyclic group, which is formed together with the adjacent nitrogen atom include a 5- or 6-membered monocyclic heterocyclic group (said the monocyclic heterocyclic group may contain other nitrogen atom(s), oxygen atom(s) or sulfur atom(s)), a bicyclic or tricyclic fused heterocyclic group, in which 3- to 8-membered rings are fused, and which contains at least one nitrogen atom (said the fused heterocyclic group may contain other nitrogen atom(s), oxygen atom(s) or sulfur atom(s)), and the like, and more specific examples thereof include aziridinyl, azetidinyl, pyrrolidinyl, piperidino, azepanyl, pyrrolyl, imidazolidinyl, imidazolyl, pyrazolidinyl, pyrazolinyl, pyrazolyl, piperazinyl, homopiperazinyl, oxazolidinyl, 2H-oxazolyl, thioxazolidinyl, 2H-thioxazolyl, morpholino, thiomorpholinyl, dihydroindolyl, dihydroisoindolyl, indolyl, isoindolyl, tetrahydroquinolyl, tetrahydroisoquinolyl, dihydrobenzooxazolyl, dihydrobenzothioxazolyl, benzimidazolidinyl, benzimidazolyl, dihydroindazolyl, indazolyl, benzotriazolyl, pyrrolopyridinyl, pyrrolopyrimidinyl, imidazopyridinyl, purinyl, dihydroisobenzofuranyl and the like.

Halogen means each atom of fluorine, chlorine, bromine or iodine.

Examples of the substituent in the lower alkyl optionally having substituent(s), the lower alkoxy optionally having substituent(s), and the lower alkylamino optionally having substituent(s), which may be the same or different and in number of 1 to 3, include substituents selected from the group comprising halogen, hydroxy, mercapto, nitro, cyano, carboxy, carbamoyl optionally having substituent(s) (examples of the substituent in the substituted carbamoyl include 1 to 2 substituents selected from hydroxy, $C_{1-10}$ alkyl, $C_{1-10}$ alkoxy, $C_{3-8}$ cycloalkyl and the like), $C_{3-8}$ cycloalkyl, $C_{6-14}$ aryl, an aliphatic heterocyclic group, an aromatic heterocyclic group optionally having substituent(s) (examples of the substituent in the substituted aromatic heterocyclic group include 1 to 3 substituents selected from $C_{1-10}$ alkyl and the like), $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^XR^Y$ (wherein $R^X$ and $R^Y$ are the same or different and each represents a hydrogen atom, $C_{1-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl or the like), $C_{2-11}$ alkanoyl, $C_{7-15}$ aroyl, $C_{1-10}$ alkoxycarbonyl, $C_{8-14}$ aryloxycarbonyl, aliphatic heterocyclic carbonyl and the like.

Examples of the substituent in the aryl optionally having substituent(s), the phenyl optionally having substituent(s), and the aromatic heterocyclic group optionally having substituent(s), which may be the same or different and in number of 1 to 3, include substituents selected from the group comprising halogen, hydroxy, mercapto, nitro, cyano, carboxy, carbamoyl, $C_{1-10}$ alkyl optionally having substituent(s) (examples of the substituent in the substituted $C_{1-10}$ alkyl include 1 to 3 substituents selected from halogen, hydroxy, $C_{1-10}$ alkoxy and the like), $C_{3-8}$ cycloalkyl, $C_{8-14}$ aryl, aliphatic heterocyclic group, aromatic heterocyclic group, $C_{1-10}$ alkoxy optionally having substituent(s) (examples of the substituent in the substituted $C_{1-10}$ alkoxy include 1 to 3 substituents selected from halogen, hydroxy, $C_{1-10}$ alkoxy and the like), $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{Xa}R^{Ya}$ (wherein $R^{Xa}$ and $R^{Ya}$ are the same or different and each represents a hydrogen atom, $C_{2-10}$ alkyl, $C_{3-8}$ cycloalkyl, $C_{6-14}$ aryl, an aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl or the like), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl, $C_{1-10}$ alkylsulfonyl and the like. When the aryl optionally having substituent(s) is phenyl fused with cycloalkyl optionally having substituent(s), the substituent thereof includes oxo in addition to those mentioned above.

Examples of the substituent in the cycloalkyl optionally having substituent(s), the cycloalkylamino optionally having substituent(s), the aliphatic heterocyclic group optionally having substituent(s), the nitrogen-containing heterocyclic group optionally having substituent(s), which is formed together with the adjacent nitrogen atom, and the aliphatic heterocyclic group optionally having substituent(s), which is formed together with the adjacent nitrogen atom, which may be the same or different and in number of 1 to 3, include substituents selected from the group comprising oxo, halogen, hydroxy, mercapto, nitro, cyano, carboxy, carbamoyl, $C_{1-10}$ alkyl, trifluoromethyl, $C_{3-8}$ cycloalkyl, $C_{6-14}$ aryl, aliphatic heterocyclic group, aromatic heterocyclic group, $C_{1-10}$ alkoxy, $C_{3-8}$ cycloalkoxy, $C_{6-14}$ aryloxy, $C_{7-16}$ aralkyloxy, $C_{2-11}$ alkanoyloxy, $C_{7-15}$ aroyloxy, $C_{1-10}$ alkylthio, —$NR^{Xb}R^{Yb}$ (wherein $R^{Xb}$ and $R^{Yb}$ are the same or different and each represents a hydrogen atom, $C_{1-10}$ alkyl, $C_{3-8}$ cycloalkyl, $C_{6-14}$ aryl, aromatic heterocyclic group, $C_{7-16}$ aralkyl, $C_{2-11}$ alkanoyl, $C_{7-15}$ aroyl, $C_{1-10}$ alkoxycarbonyl, $C_{7-16}$ aralkyloxycarbonyl or the like), $C_{2-11}$ alkanoyl, $C_{7-15}$ aroyl, $C_{1-10}$ alkoxycarbonyl, $C_{6-14}$ aryloxycarbonyl, $C_{1-10}$ alkylcarbamoyl, di-$C_{1-10}$ alkylcarbamoyl and the like.

Examples of the $C_{1-10}$ alkyl shown herein and the $C_{1-10}$ alkyl moiety in the $C_{1-10}$ alkoxy, the $C_{2-11}$ alkanoyloxy, the $C_{1-10}$ alkylthio, the $C_{2-11}$ alkanoyl, the $C_{1-10}$ alkoxycarbonyl, the $C_{1-10}$ alkylcarbamoyl, the di-$C_{1-10}$ alkylcarbamoyl and the $C_{1-10}$ alkylsulfonyl shown herein include the groups recited as examples of the aforementioned lower alkyl. The two $C_{1-10}$ alkyl moieties in the di-$C_{1-10}$ alkylcarbamoyl may be the same or different.

Examples of the $C_{3-8}$ cycloalkyl and the cycloalkyl moiety of the $C_{3-8}$ cycloalkoxy include the groups recited as examples of the aforementioned cycloalkyl.

Examples of the $C_{6-14}$ aryl and the aryl moiety of the $C_{6-14}$ aryloxy, the $C_{7-15}$ aroyl, the $C_{7-15}$ aroyloxy and the $C_{6-14}$ aryloxycarbonyl include the groups recited as examples of the aforementioned aryl.

Examples of the $C_{7-16}$ aralkyl and the aralkyl moiety of the $C_{7-16}$ aralkyloxy and the $C_{7-16}$ aralkyloxycarbonyl include benzyl, phenethyl, phenylpropyl, phenylbutyl, phenylpentyl, phenylhexyl, phenylheptyl, phenyloctyl, phenylnonyl, phenyldecyl, naphthylmethyl, naphthylethyl, naphthylpropyl, naphthylbutyl, naphthylpentyl, naphthylhexyl, anthrylmethyl, anthrylethyl and the like.

Examples of the aliphatic heterocyclic group and the aliphatic heterocyclic group moiety of the aliphatic heterocyclic carbonyl include the groups recited as examples of the aforementioned aliphatic heterocyclic group.

Examples of the aromatic heterocyclic group and the halogen include the groups recited as examples of the aforementioned aromatic heterocyclic group and the aforementioned halogen, respectively.

In each group of compound (I), as $R^1$, for example, phenyl optionally having substituent(s) is preferable. As the substituent of the phenyl optionally having substituent(s), for example, $C_{1-10}$ alkyl or halogen is preferable, and the number thereof is preferably 1 or 2.

As $Y^A$, for example, —NH— is preferable.

As $R^2$, for example, a hydrogen atom, halogen, or $C_{1-13}$ alkyl optionally having substituent(s) is preferable. More preferably, halogen or $C_{1-10}$ alkyl is selected.

When $R^3$ is the following formula ($R^{3A}$-3)

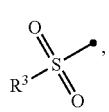

as $R^3$, for example, —$NR^{3a}R^{3b}$ (wherein $R^{3a}$ and $R^{3b}$ are each as defined above) is preferable, and more preferably, the formula wherein $R^{3a}$ is a hydrogen atom, and $R^{3b}$ is an aromatic heterocyclic group is selected. Also, the formula wherein $R^{3a}$ and $R^{3b}$ are hydrogen atoms is further preferable.

When $R^{44}$ is the following formula ($R^{44\text{-}1}$)

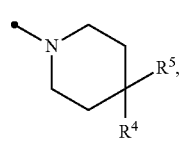

as $R^4$, for example, a hydrogen atom or $C_{1\text{-}10}$ alkoxy is preferable, and more preferably, the formula wherein $R^4$ is a hydrogen atom is selected, and as $R^5$, for example, a phenyl optionally having substituent(s) is preferable, and as the substituent of the phenyl optionally having substituent(s), for example, halogen is preferable, and the number thereof is preferably 0 or 1. Also, the formula wherein $R^4$ and $R^5$ form a dihydrobenzofuran ring together with the adjacent carbon atom is also preferable.

As compound (I), a compound wherein one or more of the above-mentioned preferable substituents are respectively combined is preferable. Furthermore, compounds obtained by limiting compounds (I) described in (2)-(19) in "Means of Solving the Problems" with preferable substituents shown above are preferable. Compounds obtained by limiting compounds (I) described in (2)-(19) in "Means of Solving the Problems" with a combination of two or more preferable substituents shown above are more preferable.

The pharmaceutically acceptable salt of compound (I) comprises, for example, pharmaceutically acceptable acid addition salts, metal salts, ammonium salts, organic amine addition salts, amino acid addition salts and the like. Examples of the pharmaceutically acceptable acid addition salt of compound (I) include, but are not limited to, inorganic acid salts such as hydrochloride, hydrobromide, nitrate, sulfate, phosphate and the like, organic acid salts such as acetate, oxalate, maleate, fumarate, citrate, benzoate, methanesulfonate and the like, and the like. Examples of the pharmaceutically acceptable metal salt include, but are not limited to, sodium salt, potassium salt, magnesium salt, calcium salt, aluminum salt, zinc salt and the like. Examples of the pharmaceutically acceptable ammonium salt include, but are not limited to, salts such as ammonium salt, tetramethylammonium salt and the like. Examples of the pharmaceutically acceptable organic amine addition salt include, but are not limited to, addition salts of morpholine, piperidine and the like. Examples of the pharmaceutically acceptable amino acid addition salt include, but are not limited to, addition salts of lysine, glycine, phenylalanine, aspartic acid, glutamic acid and the like.

Also, the pharmaceutically acceptable salt of compound (I) comprises quaternary ammonium salt. The quaternary ammonium salt is a compound wherein a nitrogen atom is quaternized by Rx (Rx is, for example, lower alkyl or lower alkyl substituted with phenyl and the like, wherein each lower alkyl is as defined above).

Further, the pharmaceutically acceptable salt of compound (I) includes N-oxide form. The N-oxide form is a compound wherein a nitrogen atom is oxidized. An N-oxide form of compound (I) can be obtained from compound (I) wherein it is not N-oxide by any oxidation method and using an oxidation reagent such as m-chloroperbenzoic acid, air oxidation, liver extract and the like.

The skin disease in the present invention refers to a disease with a lesion appearing on the skin. Specific examples include acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies, linear dermatitis and the like. However, the skin diseases in the present invention are not limited to these.

The treatment in the present invention refers to conversion, mitigation or inhibition of the progression of the disease or condition to be applied, or one or more symptoms of such disease or condition. It further includes application for inhibition of the progression of symptoms before remission of the disease, or when they are mild. In skin diseases, aggravation and remission may repeat periodically and chronically. The therapeutic agent and/or prophylactic agent of the present invention are/is also used for prolongation of the remission period or prevention of aggravation. The prophylactic agent is also used for the prevention of the onset of the disease.

The aggravation used in the present specification refers to exacerbation of the symptoms of a disease.

The remission used in the present specification refers to temporary or permanent mitigation or disappearance of the symptoms of a disease. Time of remission refers to a remission state, and remission length means a period when the state of remission continues.

The present invention also comprises prodrugs of compound (I). The prodrug of compound (I) is a compound converted to compound (I) as a result of a reaction with an enzyme, gastric acid and the like in the body. As prodrugs, many kinds of prodrugs are known, and a suitable prodrug can be selected from a known document (for example, Development of Pharmaceutical Product, Hirokawa Publishing INC., 1990, vol. 7, page 163) and synthesized by a known method. Examples of the prodrug of compound (I) when compound (I) has amino include a compound wherein the amino is acylated, alkylated or phosphorylated; examples thereof when compound (I) has hydroxy include a compound wherein the hydroxy is acylated, alkylated, phosphorylated or borated; and examples thereof when compound (I) has carboxy include a compound wherein the carboxy is esterified or amidated and the like. Also, the prodrug of compound (I) may be any of hydrate, non-hydrate and solvate and, like compound (I), may form a salt with a pharmaceutically acceptable acid or base.

A preferable compound used in the present specification is a compound having not only pharmacological activity but also desirable properties in one or more items from various evaluation items requested for pharmaceutical products such as a prophylactic and/or therapeutic agent for skin diseases and the like, such as physical stability, stability under physiological conditions, safety for living organisms and the like.

Compound (I) or a pharmaceutically acceptable salt thereof of the present invention sometimes shows an unpreferable action on living organisms. Even in such case, it can exhibit usefulness as a prophylactic and/or therapeutic agent for skin diseases or as a pharmaceutical product, by employing an appropriate dose and administration method, while reducing the unpreferable action.

Among compound (I) of the present invention, stereoisomers such as geometric isomer, optical isomer and the like, tautomer and the like may exist. The present invention comprises all possible isomers and mixtures thereof including them, and the mixing ratio thereof may be any value.

Compound (I) or a pharmaceutically acceptable salt thereof of the present invention is sometimes present as an adduct with water or various solvents, and such adduct is also comprised in the present invention.

A part or all of the respective atoms in compound (I) may be replaced by corresponding isotope atom(s), respectively, and the present invention also comprises such compounds replaced by such isotope atom(s). For example, a part or all of hydrogen atoms in compound (I) may be a hydrogen atom having an atomic weight of 2 (deuterium atom). A compound incorporating a radioisotope such as $^3$H (tritium) or $^{14}$C from among the isotopes is useful for examining the tissue distribution of a compound and screening for an agent for the prophylaxis and/or treatment of skin diseases.

For example, a compound wherein a part or all of the respective atoms in compound (I) is/are replaced by corresponding isotope atom(s), respectively, can be produced by using a commercially available building block and in the same manner as in each of the production methods described in the following. Also, a compound wherein a part or all of the hydrogen atoms in compound (I) is/are replaced by deuterium atom(s) can be synthesized by, for example, 1) a method using deuterium peroxide, to deuterate carboxylic acid and the like under basic conditions (U.S. Pat. No. 3,849,458), 2) a method using an iridium complex as a catalyst, to deuterate alcohol, carboxylic acid and the like by using deuterium oxide as a deuterium source [J. Am. Chem. Soc., Vol. 124, No. 10, 2092 (2002)], 3) a method using palladium carbon as a catalyst, to deuterate fatty acid by using only a deuterium gas as a deuterium source [LIPIDS, Vol. 9, No. 11, 913(1974)], 4) a method using a metal such as platinum, palladium, rhodium, ruthenium, iridium and the like as catalysts, to deuterate acrylic acid, methyl acrylate, methacrylic acid, methyl methacrylate and the like by using deuterium oxide, or deuterium oxide and deuterium gas, as a deuterium source (JP-B-5-19536, JP-A-61-277648 and JP-A-61-275241), 5) a method using a catalyst such as palladium, nickel, copper or chromite copper and the like, to deuterate acrylic acid, methyl methacrylate and the like by using deuterium oxide as deuterium source (JP-A-63-19863B) and the like.

The isotope atom used in the present specification refers to an atom having an atom value or mass number different from the atom value or mass number generally found in nature. Examples of the isotope atom in the compound of the present invention include $^2$H, $^3$H, $^{13}$C, $^{14}$C, $^{15}$N, $^{17}$O, $^{18}$O, $^{31}$P, $^{32}$P, $^{35}$S, $^{18}$F, $^{36}$Cl and the like.

Next, production methods of compound (I) are explained.

Incidentaly, in the production methods shown below, when a defined group changes under the conditions of the production methods or is inappropriate for performing the production methods, the desired compound can be produced by using the methods for introducing and removing a protecting group conventionally used in the synthetic organic chemistry (for example, methods described in Protective Groups in Organic Synthesis, third edition, T. W. Greene, John Wiley & Sons Inc., 1999 and the like) and the like. Also, if necessary, the order of the reaction steps such as substituent introduction and the like, can be changed.

Production Method 1

Among compounds (I), compound (Ia) wherein $Y^A$ is —NH—, —O—, —S— or —NH—NR$^{1a}$— (wherein R$^{1a}$ is as defined above), R$^{3A}$ is the aforementioned formula (R$^{3A}$-1), and R$^3$ is hydroxy, and compound (Ib) wherein R$^3$ is —NR$^{3a}$R$^{3b}$ (wherein R$^{3a}$ and R$^{3b}$ are the same or different and each is as defined above) can be produced according to, for example, the following steps.

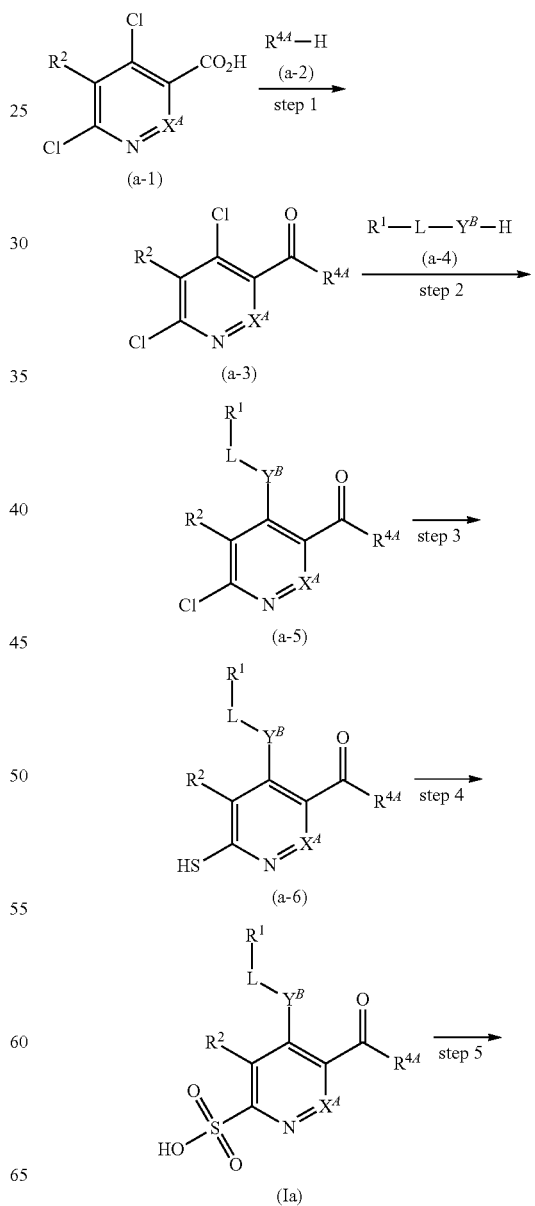

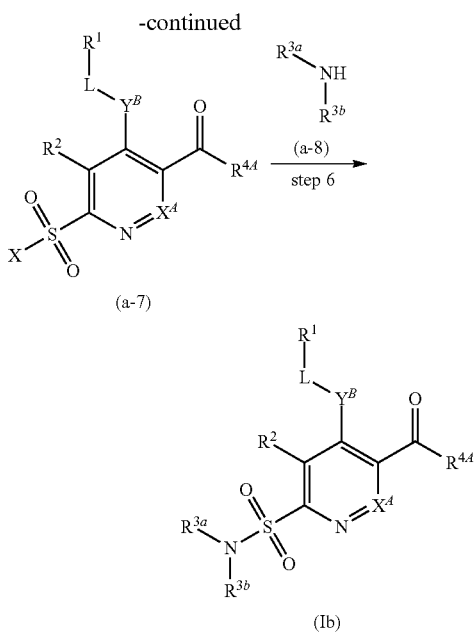

[wherein $R^1$, L, $R^2$, $R^{3a}$, $R^{3b}$, $R^{4A}$, and $X^A$ are each as defined above, $Y^B$ represents —NH—, —O—, —S— or —NH—$NR^{1a}$— (wherein $R^{1a}$ is as defined above), and X represents a fluorine atom, a chlorine atom or a bromine atom]

Step 1

Compound (a-3) can be produced by reacting compound (a-1) and 0.5-5 equivalents of compound (a-2) in a solvent in the presence of 1-5 equivalents of a condensing agent, and, if necessary, in the presence of 1-5 equivalents of an additive, for 5 min to 72 hr at a temperature between −20° C. and the boiling point of the solvent to be used.

Examples of the condensing agent include 1,3-dicyclohexanecarbodiimide (DCC), 1-ethyl-3-(3-dimethylaminopropyl)carbodiimide.hydrochloride (EDC), carbonyldiimidazole (CDI), 2-chloro-1-methylpyridinium iodide, O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU) and the like.

Examples of the additive include 1-hydroxybenzotriazole.monohydrate (HOBt), triethylamine, N,N-diisopropylethylamine and the like.

Examples of the solvent include methanol, ethanol, dichloromethane, chloroform, 1,2-dichloroethane, toluene, ethyl acetate, acetonitrile, diethyl ether, tetrahydrofuran (THF), 1,2-dimethoxyethane (DME), dioxane, N,N-dimethylformamide (DMF), N,N-dimethylacetamide (DMA), N-methylpyrrolidone (NMP), pyridine, water and the like, and these are used singly or in a mixture.

Compound (a-1) can be obtained as a commercially available product, or can be obtained by a known method [for example, Jikken Kagaku Kouza, 5th ed., vol. 16, p. 1, Maruzen Company, Limited (2005) and the like] or a method analogous thereto.

Compound (a-2) can be obtained as a commercially available product, or can be obtained by a known method [for example, Jikken Kagaku Kouza, 5th ed., vol. 14, p. 351, Maruzen Company, Limited (2005) and the like] or a method analogous thereto.

Step 2

Compound (a-5) can be produced by reacting compound (a-3) and 1 equivalent to a large excess amount of compound (a-4) in a solvent in the presence of 1 equivalent to a large excess amount of a base at a temperature between −78° C. and 150° C. for 5 min-72 hr.

Examples of the base include n-butyllithium, sec-butyllithium, tert-butyllithium, phenyllithium, sodium hydride, lithiumdiisopropylamide, hexamethyldisilasanelithium, potassium tert-butoxide, potassium carbonate, potassium hydroxide, sodium hydroxide, sodium methoxide, triethylamine, diisopropylethylamine, N-methylmorpholine, pyridine, 1,8-diazabicyclo[5.4.0]-7-undecene (DBU) and the like.

Examples of the solvent include dichloromethane, chloroform, 1,2-dichloroethane, toluene, diethyl ether, THF, DME, dioxane, hexane and the like, and these are used singly or in a mixture.

Also, compound (a-5) can be produced by reacting compound (a-3) and 1-5 equivalents of compound (a-4) in a solvent in the presence of 0.001-1 equivalent of a palladium catalyst, if necessary, 0.002-2 equivalents of an additive, and, if necessary, 0.1-10 equivalents of a base, for 5 min to 72 hr at a temperature between −20° C. and the boiling point of the solvent to be used.

Examples of the palladium catalyst include palladium acetate, tris(dibenzylideneacetone)dipalladium, tetrakis(triphenylphosphine)palladium, 1,1'-bis(diphenylphosphino)ferrocenedichloropalladium.dichloromethane 1:1 adduct, [1,3-bis(2,6-diisopropylphenyl)imidazol-2-ylidene](3-chloropyridyl)palladium(II) dichloride (PEPPSI™) and the like.

Examples of the additive include triphenylphosphine, 2,2'-bis(diphenylphosphino)-1,1'-binaphthyl, 4,5-bis(diphenylphosphino)-9,9-dimethylxanthene, 2-di-tert-butylphosphino-2',4',6'-triisopropylbiphenyl and the like.

Examples of the base include potassium carbonate, potassium phosphate, potassium hydroxide, sodium hydroxide, potassium tert-butoxide, sodium tert-butoxide, cesium carbonate, triethylamine, diisopropylethylamine, N-methylmorpholine, pyridine, DBU and the like.

Examples of the solvent include dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Compound (a-4) can be obtained as a commercially available product, or can be obtained by a known method [for example, Jikken Kagaku Kouza, 5th ed., 14 vol., p. 351, Maruzen Company, Limited (2005), Jikken Kagaku Kouza, 5th ed., 14 vol., p. 1, Maruzen Company, Limited (2005), Organic Syntheses, Coll. Vol. 4, p. 401 (1963) and the like] or a method analogous thereto.

Step 3

Compound (a-6) can be produced by treating compound (a-5) with 1 equivalent to a large excess amount of sodium sulfide or 1 equivalent to a large excess amount of hydrogen sulfide sodium in a solvent at a temperature between −20° C. and 150° C. for 5 min to 72 hr.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water and the like, and these are used singly or in a mixture.

Also, compound (a-6) can be produced by (i) treating compound (a-5) in the presence of 1-10 equivalents of methyl 3-mercaptopropionate in a solvent, and in the presence of 0.001-1 equivalent of a palladium catalyst, if necessary, 0.002-2 equivalents of an additive, and, if necessary, 0.1-10 equivalents of a base, for 5 min to 72 hr at a temperature between −20° C. and the boiling point of the used solvent, and (ii) treating the obtained compound in a solvent in the presence of 0.1-10 equivalents of a base for 5 min to 72 hr at a temperature between −78° C. and the boiling point of the solvent to be used.

Examples of the palladium catalyst to be used in (i) include palladium acetate, tris(dibenzylideneacetone)dipalladium, tetrakis(triphenylphosphine)palladium, 1,1'-bis(diphenylphosphino)ferrocenedichloropalladium dichloromethane 1:1 adduct, PEPPSI™ and the like.

Examples of the additive to be used in (i) include triphenylphosphine, 2,2'-bis(diphenylphosphino)-1,1'-binaphthyl, 4,5-bis(diphenylphosphino)-9,9-dimethylxanthene, 2-di-tert-butylphosphino-2',4',6'-triisopropyibiphenyl and the like.

Examples of the base to be used in (i) include potassium carbonate, potassium phosphate, potassium hydroxide, sodium hydroxide, potassium tert-butoxide, sodium tert-butoxide, cesium carbonate, triethylamine, diisopropylethylamine, N-methylmorpholine, pyridine, DBU and the like.

Examples of the solvent to be used in (i) include dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Examples of the base to be used in (ii) include potassium carbonate, potassium phosphate, potassium hydroxide, sodium hydroxide, potassium tert-butoxide, sodium tert-butoxide, cesium carbonate, triethylamine, diisopropylethylamine, N-methylmorpholine, pyridine, DBU and the like.

Examples of the solvent to be used in (ii) include dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Step 4

Compound (Ia) can be produced by treating compound (a-6) with 2 equivalents to a large excess amount of an oxidant, and, if necessary, 0.1-10 equivalents of an additive in a solvent, for 5 min to 72 hr at a temperature between 0° C. and the boiling point of the solvent to be used.

Examples of the oxidant include metachloroperbenzoic acid (m-CPBA), benzoyl peroxide, peracetic acid, hydrogen peroxide water, sodium periodate, potassium nitrate, potassium permanganate, sulfuryl chloride, benzyltrimethylammonium chloride/N-chlorosuccinimide, sodium hypochlorite/hydrochloric acid and the like.

Examples of the additive include hydrochloric acid, sulfuric acid, formic acid, acetic acid, trifluoroacetic acid, p-toluenesulfonic acid, methanesulfonic acid and the like, and these are used singly or in a mixture.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, water and the like, and these are used singly or in a mixture.

Step 5

Compound (a-7) can be produced by treating compound (Ia) with 1 equivalent to a large excess amount of a halogenating agent, and 0.1-10 equivalents of an additive where necessary, in a solvent or without solvent at a temperature between −20° C. and 150° C. for 5 min-72 hr.

Examples of the halogenating agent include fluorinating agents such as (diethylamino)sulfur trifluoride, morpholinosulfur trifluoride, 1,1,2,2-tetrafluoroethyl-N,N-dimethylamine and the like, chlorinating agents such as thionyl chloride, oxalyl chloride, phosphorus oxychloride, sulfuryl chloride and the like, brominating agents such as thionyl bromide, phosphorus oxybromide and the like, and the like.

Examples of the additive include DMF, pyridine, N,N-diisopropylethylamine and the like.

Examples of the solvent include dichloromethane, chloroform, 1,2-dichloroethane, toluene, ethyl acetate, acetonitrile, diethyl ether, THF, DME, dioxane, DMF, DMA, NMP, pyridine and the like, and these are used singly or in a mixture.

Step 6

Compound (Ib) can be produced by reacting compound (a-7) and 1 equivalent to a large excess amount of compound (a-8) in a solvent or without solvent, if necessary, in the presence of 1 equivalent to a large excess amount of a base at a temperature between −20° C. and 150° C. for 5 min-72 hr.

Examples of the base include potassium carbonate, potassium hydroxide, sodium hydroxide, potassium tert-butoxide, triethylamine, diisopropylethylamine, N-methylmorpholine, pyridine, DBU, 4-dimethylaminopyridine (DMAP) and the like.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, pyridine, water and the like, and these are used singly or in a mixture.

Compound (a-8) can be obtained as a commercially available product, or can be obtained by a known method [for example, Jikken Kagaku Kouza, 5th ed., vol. 14, p. 351, Maruzen Company, Limited (2005) and the like] or a method analogous thereto.

Production Method 2

Among compounds (Ib), wherein $R^{3a}$ is a hydrogen atom, and $R^{3b}$ is $-C(=O)R^{3c}$ (wherein $R^{3c}$ is as defined above), compound (Ic) wherein $R^{3c}$ is lower alkyl optionally having substituent(s) or cycloalkyl optionally having substituent(s), compound (Id) wherein $R^{3c}$ is lower alkylamino optionally having substituent(s) or cycloalkylamino optionally having substituent(s), and compound (Ie) wherein $R^{3c}$ is lower alkoxy optionally having substituent(s) can be produced according to, for example, the following steps.

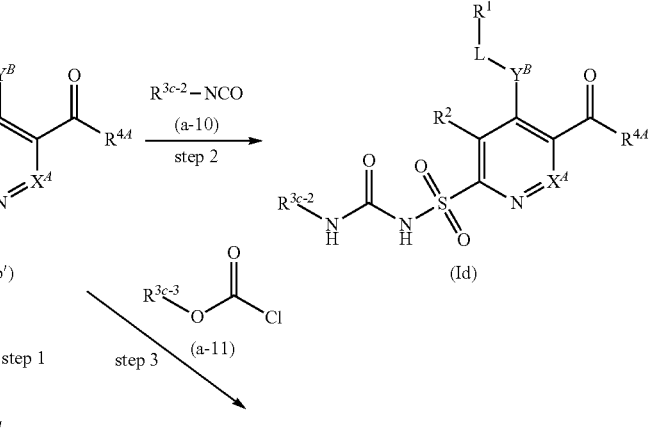

-continued

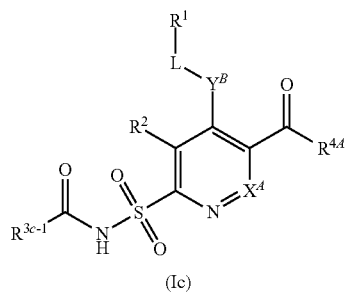

(Ic)

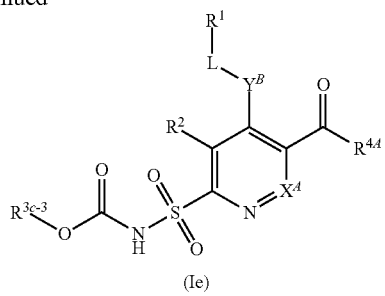

(Ie)

(wherein $R^1$, L, $R^2$, $R^{4A}$, $X^A$ and $Y^B$ are each as defined above, $R^{3c-1}$ represents lower alkyl optionally having substituent(s) or cycloalkyl optionally having substituent(s) in the definitions of $R^{3c}$, $R^{3c-2}$ represents lower alkyl moiety optionally having substituent(s) in lower alkylamino optionally having substituent(s) in the definition of $R^{3c}$, or cycloalkyl moiety optionally having substituent(s) in cycloalkylamino optionally having substituent(s) in the definition of $R^{3c}$, and $R^{3c-3}$ represents lower alkyl moiety optionally having substituent(s) in lower alkoxy optionally having substituent(s) in the definition of $R^{3c}$)

Step 1

Compound (Ic) can be produced by (i) treating compound (a-9) in a solvent or without solvent in the presence of 0.1-10 equivalents of a condensing agent, and, if necessary, in the presence of 1-5 equivalents of an additive, at a temperature between −20° C. and 150° C. for 5 min to 72 hr, and then (ii) reacting 1-10 equivalents of compound (Ib') in a solvent or without solvent, if necessary, in the presence of 1-10 equivalents of a base at a temperature between −20° C. and 150° C. for 5 min-72 hr.

Examples of the condensing agent to be used in (i) include DCC, EDC, CDI, 2-chloro-1-methylpyridinium iodide, HBTU, HATU and the like.

Examples of the additive to be used in (i) include HOBt, triethylamine, N,N-diisopropylethylamine and the like.

Examples of the solvent to be used in (i) include dichloromethane, chloroform, 1,2-dichloroethane, toluene, ethyl acetate, acetonitrile, diethyl ether, THF, DME, dioxane, DMF, DMA, NMP, pyridine and the like, and these are used singly or in a mixture.

Examples of the base to be used in (ii) include potassium carbonate, potassium hydroxide, sodium hydroxide, potassium tert-butoxide, triethylamine, diisopropylethylamine, N-methylmorpholine, pyridine, DBU, DMAP and the like.

Examples of the solvent to be used in (ii) include dichloromethane, chloroform, 1,2-dichloroethane, toluene, ethyl acetate, acetonitrile, diethyl ether, THF, DME, dioxane, DMF, DMA, NMP, pyridine, water and the like, and these are used singly or in a mixture.

Compound (Ib') is obtained in the same manner as in Production method 1, step 6.

Compound (a-9) can be obtained as a commercially available product, or can be obtained by a known method [for example, Jikken Kagaku Kouza, 5th ed., vol. 16, p. 1, Maruzen Company, Limited (2005) and the like] or a method analogous thereto.

Step 2

Compound (Id) can be produced by reacting compound (Ib') and 1-10 equivalents of compound (a-10) in a solvent or without solvent in the presence of 1-10 equivalents of a base for 5 min to 72 hr at a temperature between −20° C. and the boiling point of the solvent to be used.

Examples of the base include potassium carbonate, potassium hydroxide, sodium hydroxide, potassium tert-butoxide, triethylamine, diisopropylethylamine, N-methylmorpholine, pyridine, DBU, DMAP and the like.

Examples of the solvent include dichloromethane, chloroform, 1,2-dichloroethane, toluene, ethyl acetate, acetonitrile, diethyl ether, THF, DME, dioxane, DMF, DMA, NMP, pyridine and the like, and these are used singly or in a mixture.

Compound (a-10) can be obtained as a commercially available product, or can be obtained by a known method [for example, Jikken Kagaku Kouza, 5th ed., vol. 14, p. 484, Maruzen Company, Limited (2005)] or a method analogous thereto.

Step 3

Compound (Ie) can be produced by reacting compound (Ib') and 1-10 equivalents of compound (a-11) in a solvent or without solvent in the presence of 1-10 equivalents of a base for 5 min to 72 hr at a temperature between −20° C. and the boiling point of the solvent to be used.

Examples of the base include potassium acetate, sodium hydrogen carbonate, potassium carbonate, potassium hydroxide, sodium hydroxide, potassium tert-butoxide, triethylamine, diisopropylethylamine, N-methylmorpholine, pyridine, DBU, DMAP and the like.

Examples of the solvent include dichloromethane, chloroform, 1,2-dichloroethane, toluene, ethyl acetate, acetonitrile, diethyl ether, THF, DME, dioxane, DMF, DMA, NMP, pyridine and the like, and these are used singly or in a mixture.

Compound (a-11) can be obtained as a commercially available product, or can be obtained by a known method [for example, Organic Syntheses, Vol. 23, p. 13 (1943); Coll. Vol. 3, p. 167 (1955)] or a method analogous thereto.

Production Method 3

Among compounds (T), compound (If) wherein $Y^A$ is —NH—, —O—, —S— or —NH—NR$^{1a}$— (wherein $R^{1a}$ is as defined above), $R^{3A}$ is the aforementioned formula ($R^{3A}$-1), and $R^3$ is lower alkyl optionally having substituent(s) or aryl optionally having substituent(s) can be produced according to, for example, the following steps.

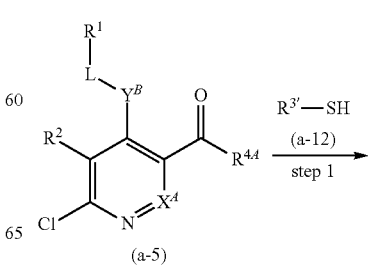

-continued

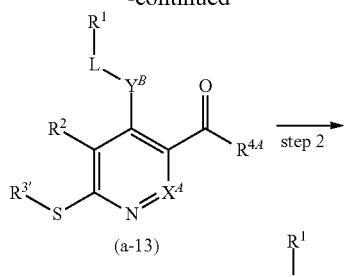

(a-13)

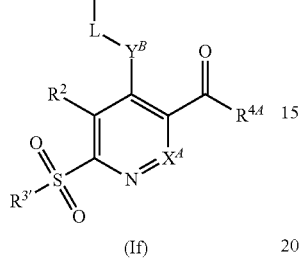

(If)

(wherein $R^1$, L, $R^2$, $R^{4A}$, $X^A$ and $Y^B$ are each as defined above, and $R^{3'}$ represents lower alkyl optionally having substituent(s) or aryl optionally having substituent(s) in the definition of $R^3$)

Step 1

Compound (a-13) can be produced by reacting compound (a-5) and 1-10 equivalents of compound (a-12) in a solvent at a temperature between −20° C. and 150° C. for 5 min to 72 hr.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, pyridine, water and the like, and these are used singly or in a mixture.

Compound (a-12) can be obtained as a commercially available product, or can be obtained by a known method [for example, Organic Syntheses, Coll. Vol. 4, p. 401 (1963) and the like] or a method analogous thereto.

Step 2

Compound (If) can be produced by treating compound (a-13) with 2-10 equivalents of an oxidant in a solvent at a temperature between −20° C. and 150° C. for 5 min-72 hr.

Examples of the oxidant include metachloroperbenzoic acid, benzoyl peroxide, peracetic acid, hydrogen peroxide water, sodium periodate, potassium permanganate and the like.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP, pyridine, water and the like, and these are used singly or in a mixture.

Production Method 4

Among compounds (I), compound (Ig) wherein $Y^A$ is —NH—, —O—, —S— or —NH—NR$^{1a}$— (wherein $R^{1a}$ is as defined above), $R^{3A}$ is the aforementioned formula ($R^{3A}$-2), and $R^{3d}$ is lower alkanoyl or aroyl can be produced according to, for example, the following steps.

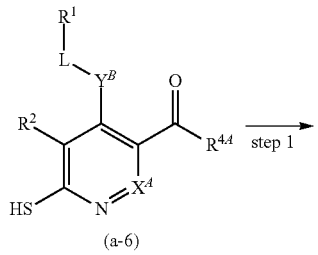

(a-6)

-continued

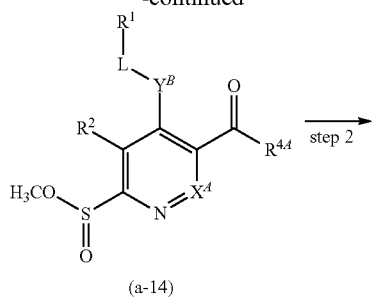

(a-14)

(a-15)

(a-17)

(Ig)

(wherein $R^1$, L, $R^2R^{4A}$, $X^A$ and $Y^B$ are each as defined above, $R^{3d-1}$ represents lower alkyl moiety or aryl moiety of lower alkanoyl or aroyl in the definition of $R^{3d}$)

Step 1

Compound (a-14) can be produced by treating compound (a-6) in the presence of 2-10 equivalents of N-bromosuccinimide and 1 equivalent to a large excess amount of methanol in a solvent or without solvent at a temperature between −20° C. and 150° C. for 5 min to 72 hr.

Examples of the solvent include methanol, dichloromethane, chloroform, 1,2-dichloroethane, toluene, ethyl acetate, acetonitrile, diethyl ether, THF, DME, dioxane, DMF, DMA, NMP, pyridine and the like, and these are used singly or in a mixture.

Step 2

Compound (a-15) can be produced by treating compound (a-14) with 1-10 equivalents of an amine reagent in a solvent at a temperature between −78° C. and 150° C. for 5 min to 72 hr.

Examples of the amine reagent include lithium bis(trimethylsilyl)amide, sodium bis(trimethylsilyl)amide, ammonia, lithium amide, potassium amide and the like.

Examples of the solvent include dichloromethane, chloroform, 1,2-dichloroethane, toluene, diethyl ether, THY, DME, dioxane, hexane and the like, and these are used singly or in a mixture.

Step 3

Compound (a-17) can be produced by reacting compound (a-15) and 1 equivalent to a large excess amount of compound (a-16) in a solvent in the presence of 1-10 equivalents of a base at a temperature between −78° C. and 150° C. for 5 min to 72 hr.

Examples of the base include n-butyllithium, sec-butyllithium, tert-butyllithium, phenyllithium, lithium diisopropylamide, potassium tert-butoxide and the like.

Examples of the solvent include dichloromethane, chloroform, 1,2-dichloroethane, toluene, diethyl ether, THF, DME, dioxane, hexane and the like, and these are used singly or in a mixture.

Compound (a-16) can be obtained as a commercially available product, or can be obtained by a known method [for example, Jikken Kagaku Kouza, 5th ed., vol. 16, p. 107, Maruzen Company, Limited (2005) and the like] or a method analogous thereto.

Step 4

Compound (Ig) can be produced by treating compound (a-17) in the presence of 1-10 equivalents of a chlorinating agent and 1-10 equivalents of an amine reagent in a solvent at a temperature between −78° C. and 150° C. for 5 min to 72 hr.

Examples of the chlorinating agent include N-chlorosuccinimide, tert-butyl hypochlorite, 1-chloro-1H-benzotriazole, chlorine and the like.

Examples of the amine reagent include hexamethyldisilasane and ammonia.

Examples of the solvent include dichloromethane, chloroform, 1,2-dichloroethane, toluene, ethyl acetate, acetonitrile, diethyl ether, THF, DME, dioxane, DMF, DMA, NMP, pyridine and the like, and these are used singly or in a mixture.

Production Method 5

Among compounds (I), compound (Ih) wherein $Y^A$ is —NH—, —O—, —S— or —NH—NR$^{1a}$— (wherein $R^{1a}$ is as defined above), $R^{3A}$ is to the aforementioned formula ($R^{3A}$-2), and $R^{3d}$ is a hydrogen atom can be produced according to, for example, the following steps.

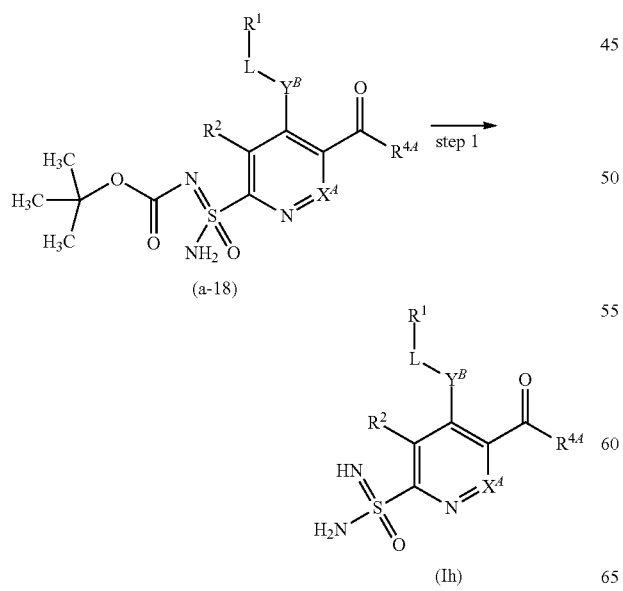

(wherein $R^1$, L, $R^2$, $R^{4A}$, $X^A$ and $Y^B$ are each as defined above)

Step 1

Compound (Ih) can be produced by treating compound (a-18) with 1 equivalent to a large excess amount of an acid in a solvent or without solvent at a temperature between −78° C. and 150° C. for 5 min to 72 hr.

Examples of the acid include hydrochloric acid, sulfuric acid, formic acid, acetic acid, trifluoroacetic acid, p-toluenesulfonic acid, methanesulfonic acid, titanium tetrachloride, boron trifluoride and the like.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Compound (a-18) can be obtained using di-tert-butyl dicarbonate instead of compound (a-16) by a method similar to that of production method 4, step 3.

Production Method 6

Among compounds (I), compound (Ii) wherein $Y^A$ is —NH—, —O—, —S— or —NH—NR$^{1a}$— (wherein $R^{1a}$ is as defined above), $R^{3A}$ is the aforementioned formula ($R^{3A}$-2), and $R^{3d}$ is lower alkylcarbamoyl can be produced according to, for example, the following steps.

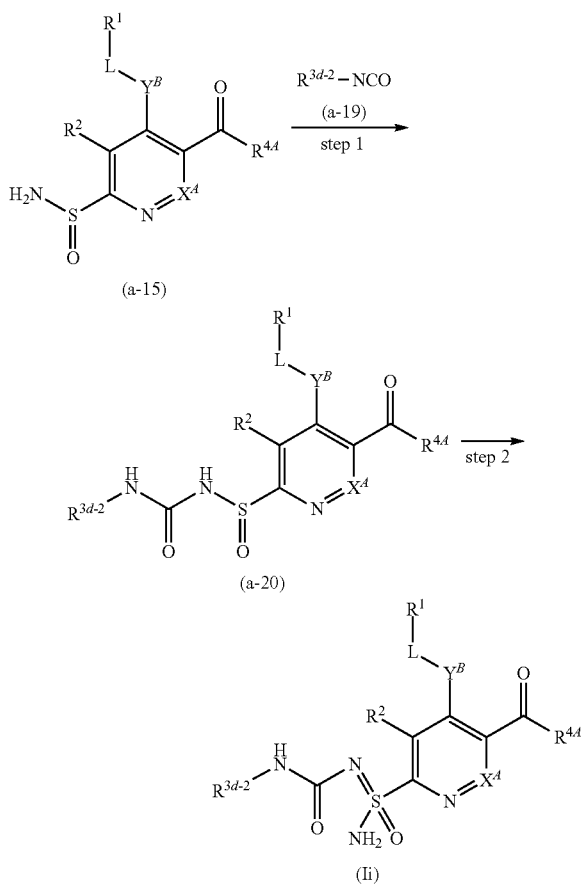

(wherein $R^1$, L, $R^2$, $R^{4A}$, $X^A$ and $Y^B$ are each as defined above, and $R^{3d-2}$ represents lower alkyl moiety of lower alkylcarbamoyl in the definition of $R^{3d}$)

Step 1

Compound (a-20) can be produced by reacting compound (a-15) and 1 equivalent to a large excess amount of compound (a-19) in a solvent in the presence of 1-10 equivalents of a base at a temperature between −78° C. and 150° C. for 5 min to 72 hr.

Examples of the base include n-butyllithium, sec-butyllithium, tert-butyllithium, phenyllithium, lithium diisopropylamide, potassium tert-butoxide and the like.

Examples of the solvent include dichloromethane, chloroform, 1,2-dichloroethane, toluene, diethyl ether, THF, DME, dioxane, hexane and the like, and these are used singly or in a mixture.

Compound (a-19) can be obtained as a commercially available product, or can be obtained by a known method [for example, Jikken Kagaku Kouza, 5th ed., vol. 14, p. 484, Maruzen Company, Limited (2005) and the like] or a method analogous thereto.

Step 2

Compound (Ii) can be produced using compound (a-20) by a method similar to that of production method 4, step 4.

Production Method 7

Among compounds (I), compound (7j) wherein $Y^A$ is —NH—C(=O)— can be produced according to, for example, the following steps.

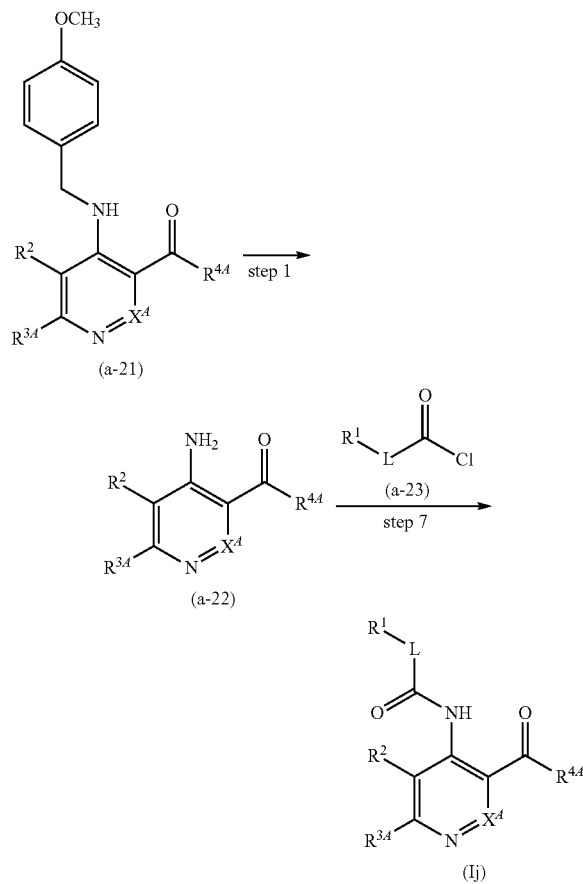

(wherein $R^1$, L, $R^2$, $R^{3A}$, $R^{4A}$ and $X^A$ are each as defined above)

Step 1

Compound (a-22) can be produced by treating compound (a-21) with 1 equivalent to a large excess amount of an acid in a solvent or without solvent at a temperature between −78° C. and 150° C. for 5 min to 72 hr.

Examples of the acid include hydrochloric acid, sulfuric acid, formic acid, acetic acid, trifluoroacetic acid, p-toluenesulfonic acid, methanesulfonic acid, titanium tetrachloride, boron trifluoride and the like.

Examples of the solvent include methanol, ethanol, dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Compound (a-21) can be obtained according to the methods described in Production methods 1-6.

Step 2

Compound (Ij) can be produced using compound (a-22) and compound (a-23) by a method similar to that of production method 2, step 3.

Compound (a-23) can be obtained as a commercially available product, or can be obtained by a known method [for example, Jikken Kagaku Kouza, 5th ed., vol. 16, p. 98, Maruzen Company, Limited (2005) and the like] or a method analogous thereto.

Production Method 8

Among compounds (I), compound (Ik) wherein $Y^A$ is a bond, L is alkylene, $R^{3A}$ is the aforementioned formula ($R^{3A}$-1), and $R^3$ is hydroxy, and compound (Ik') wherein $R^3$ is —$NR^{3a}R^{3b}$ (wherein $R^{3a}$ and $R^{3b}$ are the same or different and each is as defined above) can be produced according to, for example, the following steps.

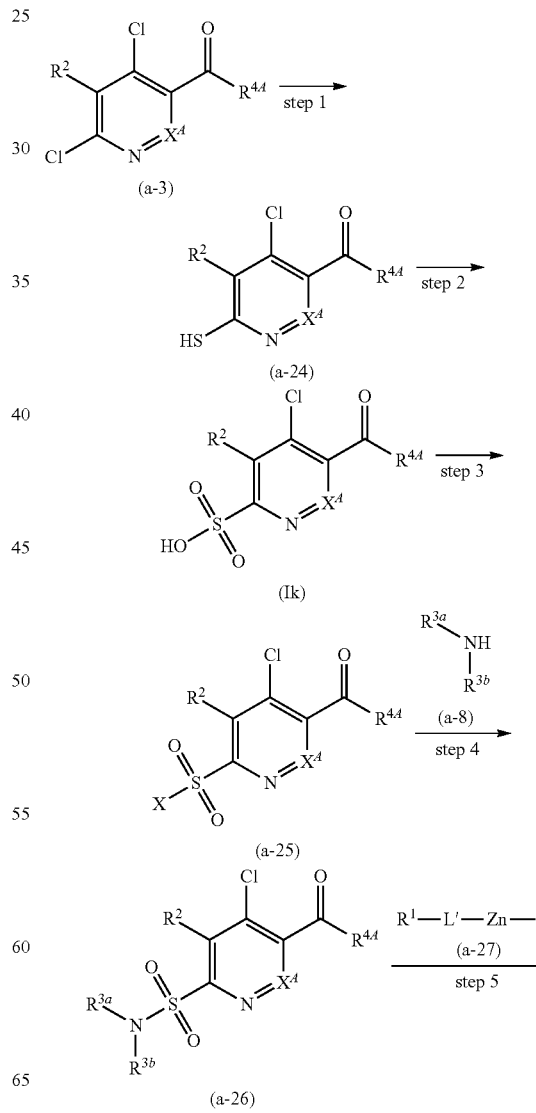

-continued

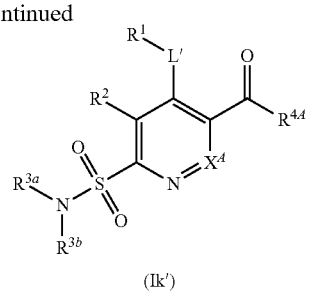

(Ik')

(wherein $R^1$, $R^2$, $R^{3a}$, $R^{3b}$, $R^{4A}$, $X^A$ and X are each as defined above, L' represents alkylene, and $X^B$ represents a chlorine atom or a bromine atom)

Step 1

Compound (a-24) can be produced by (i) treating compound (a-3) in the presence of 1-10 equivalents of methyl 3-mercaptopropionate in a solvent in the presence of 0.001-1 equivalent of a palladium catalyst, if necessary, 0.002-2 equivalents of an additive, if necessary, and 0.1-10 equivalents of a base, for 5 min to 72 hr at a temperature between −20° C. and the boiling point of the solvent to be used, and (ii) treating the obtained compound in a solvent in the presence of 0.1-10 equivalents of a base, for 5 min to 72 hr at a temperature between −78° C. and the boiling point of the solvent to be used.

Examples of the palladium catalyst to be used in (i) include palladium acetate, tris(dibenzylideneacetone)dipalladium, tetrakis(triphenylphosphine)palladium, 1,1'-bis(diphenylphosphino)ferrocenedichloropalladium.dichloromethane 1:1 adduct, PEPPSI™ and the like.

Examples of the additive to be used in (i) include triphenylphosphine, 2,2'-bis(diphenylphosphino)-1,1'-binaphthyl, 4,5-bis(diphenylphosphino)-9,9-dimethylxanthene, 2-di-tert-butylphosphino-2',4',6'-triisopropylbiphenyl and the like.

Examples of the base to be used in (i) include potassium carbonate, potassium phosphate, potassium hydroxide, sodium hydroxide, potassium tert-butoxide, sodium tert-butoxide, cesium carbonate, triethylamine, diisopropylethylamine, N-methylmorpholine, pyridine, DBU and the like.

Examples of the solvent to be used in (i) include dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Examples of the base to be used in (ii) include potassium carbonate, potassium phosphate, potassium hydroxide, sodium hydroxide, potassium tert-butoxide, sodium tert-butoxide, cesium carbonate, triethylamine, diisopropylethylamine, N-methylmorpholine, pyridine, DBU and the like.

Examples of the solvent to be used in (ii) include dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Step 2

Compound (Ik) can be produced using compound (a-24) by a method similar to that of Production method 1, step 4.

Step 3

Compound (a-25) can be produced using compound (Ik) by a method similar to that of Production method 1, step 5.

Step 4

Compound (a-26) can be produced using compound (a-25) compound (a-8) and by a method similar to that of Production method 1, step 6.

Step 5

Compound (Ik') can be produced by reacting compound (a-26) and 1-5 equivalents of compound (a-27) in a solvent in the presence of 0.001-1 equivalents of a palladium catalyst, and, if necessary, in the presence of 0.002-2 equivalents of an additive, for 5 min to 72 hr at a temperature between −20° C. and the boiling point of the solvent to be used.

Examples of the palladium catalyst include palladium acetate, tris(dibenzylideneacetone)dipalladium, tetrakis(triphenylphosphine)palladium, 1,1'-bis(diphenylphosphino)ferrocenedichloropalladium dichloromethane 1:1 adduct, PEPPSI™ and the like.

Examples of the additive include triphenylphosphine, 2,2'-bis(diphenylphosphino)-1,1'-binaphthyl, 4,5-bis(diphenylphosphino)-9,9-dimethylxanthene, 2-di-tert-butylphosphino-2',4',6'-triisopropylbiphenyl and the like.

Examples of the solvent include dichloromethane, chloroform, 1,2-dichloroethane, toluene, ethyl acetate, acetonitrile, diethyl ether, THF, DME, dioxane, DMF, DMA, NMP and the like, and these are used singly or in a mixture.

Compound (a-27) can be obtained as a commercially available product or by a known method [for example, Jikken Kagaku Kouza, 5th ed., vol. 18, p. 78, Maruzen Company, Limited (2005) and the like] or a method analogous thereto.

Also, among compounds (I), a compound wherein $Y^A$ is a bond, L is alkylene, $R^{3A}$ is the aforementioned formula ($R^{3A}$-1), $R^3$ is lower alkyl optionally having substituent(s) or aryl optionally having substituent(s) can be produced by using compound (a-3) according to the methods of Production method 3, step 1, Production method 3, step 2, and Production method 8, step 5. Among compounds (I), a compound wherein $Y^A$ is a bond, L is alkylene, $R^{3A}$ is the aforementioned formula ($R^{3A}$-2), and $R^{3d}$ is lower alkanoyl or aroyl can be produced according to the methods of Production method 8, step 1, Production method 4, and Production method 8, step 5. Among compounds (I), a compound wherein $Y^A$ is a bond, L is alkylene, $R^{3A}$ is the aforementioned formula ($R^{3A}$-2), and $R^{3d}$ is a hydrogen atom can be produced according to the methods of Production method 8, step 1, Production method 4, step 1, Production method 4, step 2, Production method 5, step 1, and Production method 8, step 5. Among compounds (I), a compound wherein $Y^A$ is a bond, L is alkylene, $R^{3A}$ is the aforementioned formula ($R^{3A}$-2), and $R^{3d}$ is lower alkylcarbamoyl can be produced according to the methods of Production method 8, step 1, Production method 4, step 1, Production method 4, step 2, Production method 6, step 1, Production method 6, step 2, and Production method 8, step 5.

Conversion of a functional group contained in R', $R^2$, $R^{3A}$, $R^{4A}$ and the like in compound (I) and each intermediates in the above-mentioned Production methods can also be performed by a known method (for example, the method described in Comprehensive Organic Transformations 2nd edition, R. C. Larock, Vch Verlagsgesellschaft Mbh, 1999 and the like) or a method analogous thereto.

The intermediates and the desired compounds in the above-mentioned production methods can be isolated and purified by applying separation and purification methods usually used in the synthetic organic chemistry such as filtration, extraction, washing, drying, concentration, recrystallization, various chromatographies and the like. Also, intermediates can also be subjected to a next reaction without particular purification.

To obtain a salt of compound (I), when compound (I) is obtained in a form of a salt, it can be directly purified. Or, when compound (I) is obtained in a free foil, it may be dissolved or suspended in a suitable solvent, and an acid or a base is added thereto to form a salt, and then the salt may be isolated and purified.

Specific examples of compound (I) of the present invention are shown in Table 1 to Table 27. However, the compounds of the present invention are not limited to them.

TABLE 1

| compound No. | —L—R$^1$ | —R$^2$ | —R$^3$ |
|---|---|---|---|
| 1 | F-tolyl | H | OH |
| 2 | F-tolyl | H | NH$_2$ |
| 3 | isobenzofuran | H | NH$_2$ |
| 4 | quinoline | H | NH$_2$ |
| 5 | F-tolyl | H | cyclopropyl-NH |
| 6 | F-tolyl | H | NH-CH$_2$-C(O)-NH-CH$_3$ |
| 7 | F-tolyl | H | pyrrolidinyl-NH-C(O)-CH$_3$ |
| 8 | F-pyridyl | H | N-methyl-pyrrolidinone-NH |
| 9 | F-tolyl | H | piperazinyl |

TABLE 2

| Compound No. | —L—R$^1$ | —R$^2$ | —R$^3$ |
|---|---|---|---|
| 10 | F-tolyl | H | piperidinyl-NH$_2$ |
| 11 | F-tolyl | H | isoxazol-NH |
| 12 | F-tolyl | H | methyl-isoxazol-NH |
| 13 | F-tolyl | H | NH-C(O)-CH$_3$ |
| 14 | F-tolyl | H | NH-C(O)-difluorocyclopropyl |
| 15 | benzyl | H | NH$_2$ |
| 16 | benzyl | H | NH-C(O)-NH-CH$_2$CH$_2$CH$_3$ |
| 17 | Cl, CH$_3$, H$_3$C-phenyl | H | NH$_2$ |
| 18 | Cl, CH$_3$, H$_3$C-phenyl | H | NH-C(O)-NH-CH(CH$_3$)$_2$ |
| 19 | Cl, CH$_3$, H$_3$C-phenyl | H | NH-C(O)-O-CH$_2$CH$_3$ |
| 20 | Cl-tolyl | H | NH$_2$ |

TABLE 3

| Compound No. | —L—R$^1$ | —R$^2$ | —R$^3$ |
|---|---|---|---|
| 21 | Cl-tolyl | H | NH-C(O)-NH-cyclopropyl |

TABLE 3-continued

| Compound No. | —L—R¹ | —R² | —R³ |
|---|---|---|---|
| 22 | 4-F, 2-CH₃-phenyl | H | —NH—C(O)—NH—CH₂CH₃ |
| 23 | 4-F, 2-CH₃-phenyl | H | —N(CH₃)—C(O)—NH—CH₂CH₃ |
| 24 | 4-F, 2-CH₃-phenyl | Cl | OH |
| 25 | 4-F, 2-CH₃-phenyl | Cl | NH₂ |
| 26 | 3-CH₃-phenyl | Cl | NH₂ |
| 27 | 2,4-diF-phenyl | Cl | NH₂ |
| 28 | 4-Cl, 2-F-phenyl | Cl | NH₂ |
| 29 | 4-H₃CO-phenyl | Cl | NH₂ |
| 30 | 4-H₃CO, 2-F-phenyl | Cl | NH₂ |
| 31 | 4-F, 3-CH₃-phenyl | Cl | NH₂ |

TABLE 4

| Compound No. | —L—R¹ | —R² | —R³ |
|---|---|---|---|
| 32 | 4-H₃CO, 3-F-phenyl | Cl | NH₂ |
| 33 | 2-CH₃-phenyl | Cl | NH₂ |
| 34 | 2,4,5-triF-phenyl | Cl | NH₂ |
| 35 | 4-F, 2-CH₃-phenyl | Cl | 4-methyl-morpholine-3-carboxamide-N-methyl |
| 36 | 4-F, 2-CH₃-phenyl | Cl | 1-amino-cyclopropane-N-methylcarboxamide |
| 37 | 4-F, 2-CH₃-phenyl | Cl | (2S,3R)-3-hydroxy-2-(methylamino)-N-methylbutanamide |
| 38 | 4-F, 2-CH₃-phenyl | Cl | —NH-(4-methoxyphenyl) |
| 39 | 4-F, 2-CH₃-phenyl | Cl | —NH-(1-methyl-1H-pyrazol-3-yl) |
| 40 | 4-F, 2-CH₃-phenyl | Cl | —NH-(5-methylisoxazol-3-yl) |
| 41 | 4-F, 2-CH₃-phenyl | Cl | —NH-(3-methylisoxazol-5-yl) |

TABLE 5
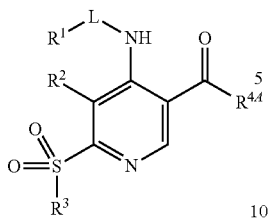

TABLE 6
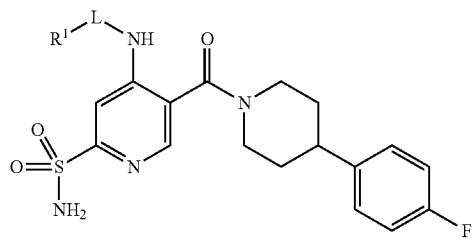
| Compound No. | —L—R¹ |
|---|---|
| 50 | 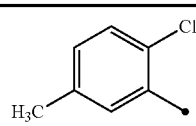 |
| 51 | 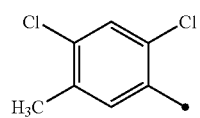 |
| 52 | 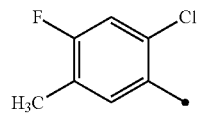 |
| 53 | 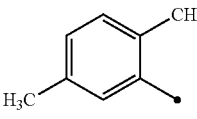 |
| 54 | 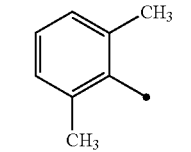 |
| 55 | 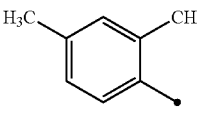 |
| 56 | 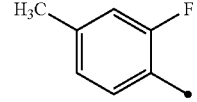 |
| 57 | 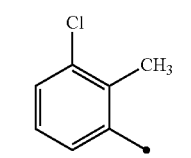 |
| 58 | 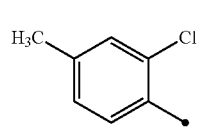 |
| 59 | 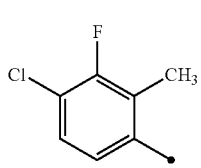 |
TABLE 6-continued
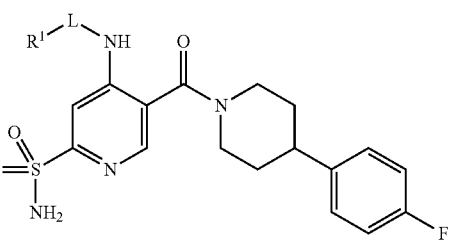
| Compound No. | —L—R¹ |
|---|---|
| 60 | 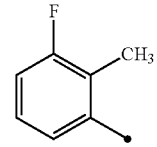 |
| 61 |  |
| 62 | 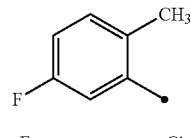 |
| 63 | 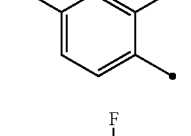 |
| 64 | 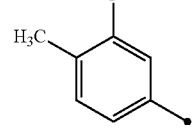 |
| 65 | 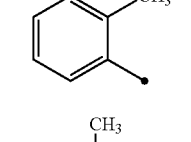 |
| 66 | 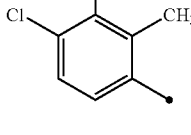 |
| 67 | 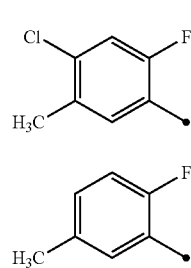 |
| 68 | |

TABLE 6-continued
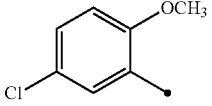
| Compound No. | —L—R¹ |
|---|---|
| 69 | 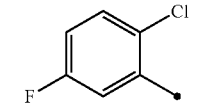 |
| 70 | 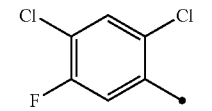 |
| 71 | 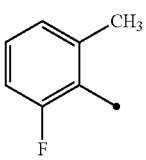 |
| 72 | 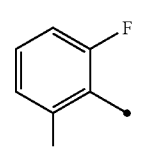 |
| 73 | 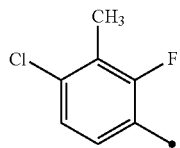 |
TABLE 7
| Compound No. | —L—R¹ |
|---|---|
| 74 | 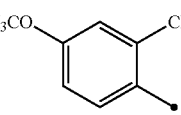 |
| 75 | 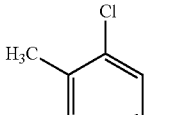 |
| 76 | 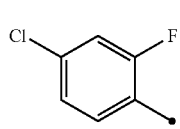 |
TABLE 7-continued
| Compound No. | —L—R¹ |
|---|---|
| 77 | 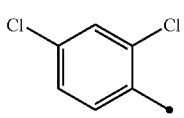 |
| 78 | 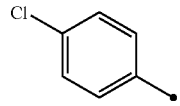 |
| 79 | 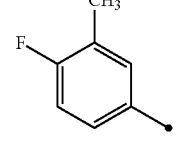 |
| 80 | 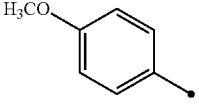 |
| 81 | 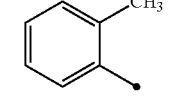 |
| 82 | 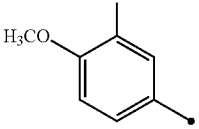 |
| 83 | 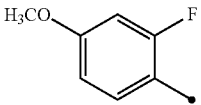 |
| 84 | 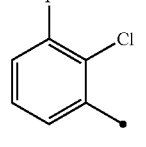 |
| 85 | 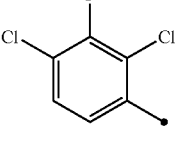 |
| 86 | 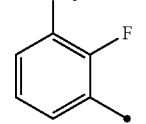 |
| 87 |  |

TABLE 7-continued
| Compound No. | —L—R¹ |
|---|---|
| 88 | 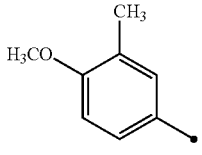 |
| 89 | 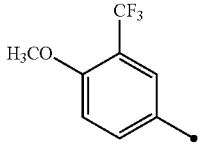 |
| 90 | 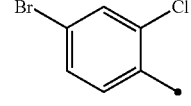 |
| 91 | 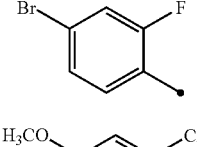 |
| 92 | 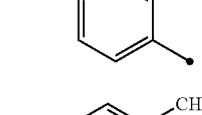 |
| 93 | 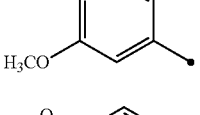 |
| 94 | 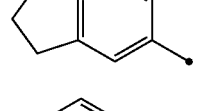 |
| 95 | 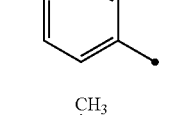 |
| 96 | 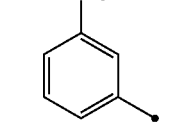 |
| 97 | 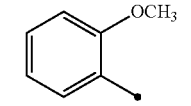 |
| 98 | 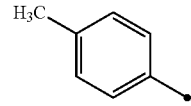 |
| 99 | 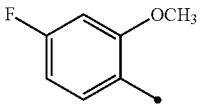 |
| 100 | 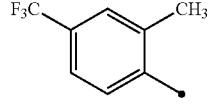 |
TABLE 8
| Compound No. | —L—R¹ | —R³ |
|---|---|---|
| 101 | 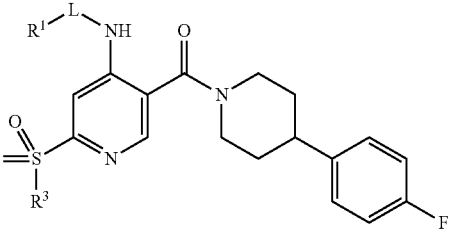 | NH₂ |
| 102 | 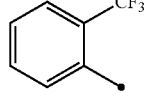 | NH₂ |
| 103 | 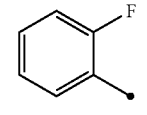 | NH₂ |
| 104 | 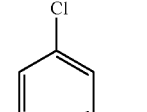 | NH₂ |
| 105 | 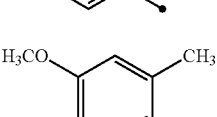 | NH₂ |
| 106 | 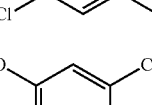 | NH₂ |
| 107 | 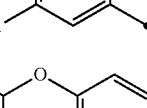 | NH₂ |

TABLE 8-continued

| Compound No. | —L—R¹ | —R³ |
|---|---|---|
| 108 | 4-isopropylphenyl | NH₂ |
| 109 | 5-chloro-2-methylphenyl | NH₂ |
| 110 | 3,5-dimethylphenyl | NH₂ |
| 111 | 4-fluoro-2-methylphenyl | —NH—CH₃ |
| 112 | 4-fluoro-2-methylphenyl | —NH—CH₂CH₂—OCH₃ |
| 113 | 4-fluoro-2-methylphenyl | —NH—CH₂—C(O)—OCH₃ |
| 114 | 5-fluoro-2-methylpyridyl | —N(CH₂C(O)OCH₂CH₃)₂ |
| 115 | 4-fluoro-2-methylphenyl | —NH—CH₂—C(O)NH₂ |
| 116 | 4-fluoro-2-methylphenyl | pyrrolidin-2-yl-C(O)OCH₃ |

TABLE 9

| Compound No. | —R³ |
|---|---|
| 117 | pyrrolidin-2-yl-C(O)NH-CH₃ |
| 118 | —NH—CH₂—C(O)OH |
| 119 | pyrrolidin-1-yl |
| 120 | pyrrolidin-2-yl-C(O)OH |
| 121 | piperidin-1-yl |
| 122 | morpholin-4-yl |
| 123 | pyrrolidin-2-yl-C(O)NH₂ |
| 124 | 4-acetylpiperazin-1-yl |
| 125 | —N(CH₃)₂ |

TABLE 9-continued
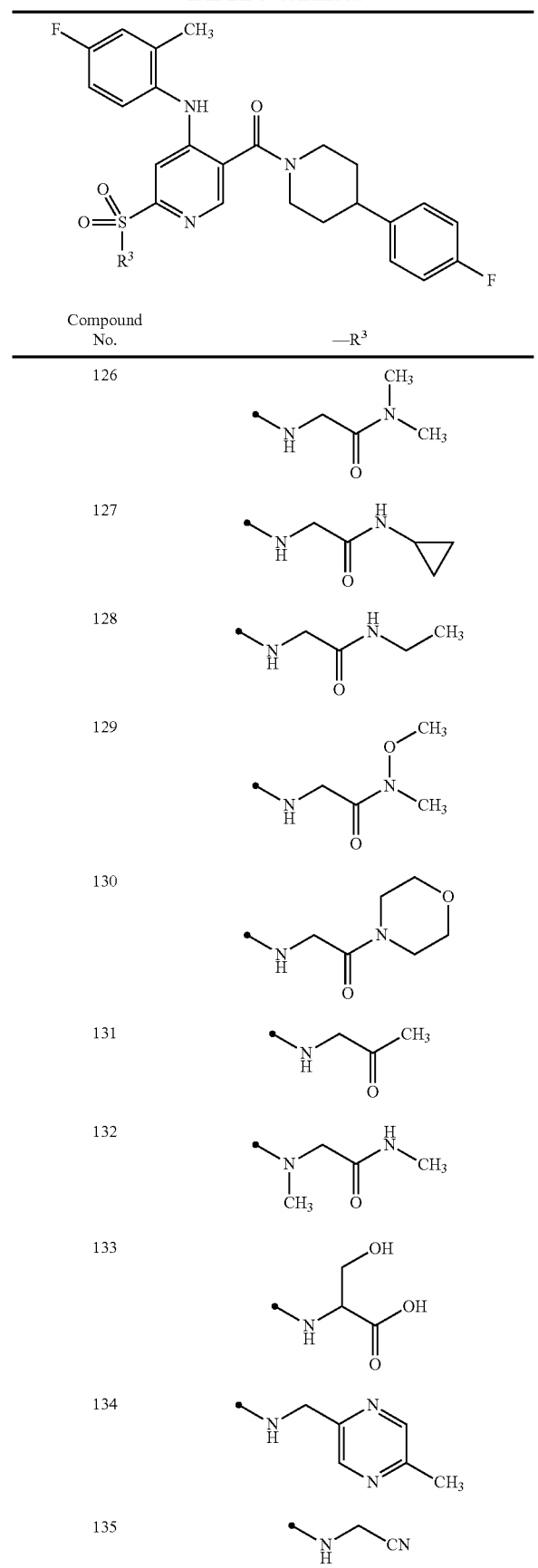
TABLE 9-continued
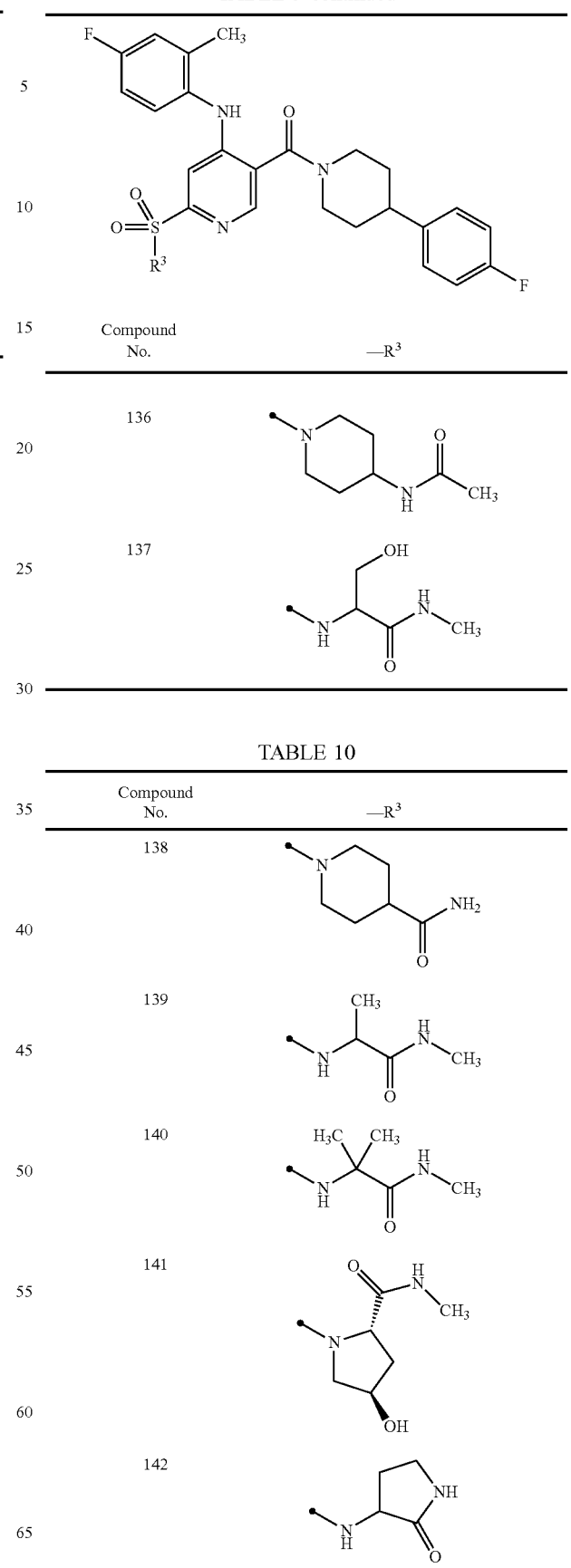

TABLE 10-continued
| Compound No. | —R³ |
|---|---|
| 143 | 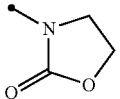 |
| 144 | 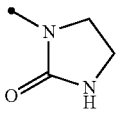 |
| 145 | 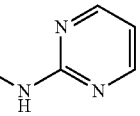 |
| 146 | 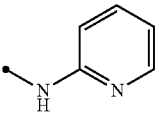 |
| 147 | 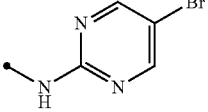 |
| 148 | 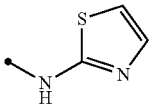 |
| 149 | 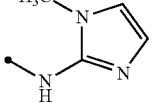 |
| 150 | 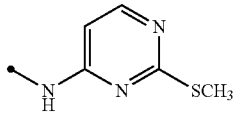 |
| 151 | 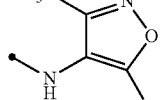 |
| 152 | 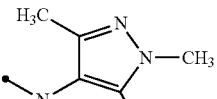 |
| 153 |  |
| 154 |  |
| 155 |  |
| 156 |  |
| 157 |  |
| 158 |  |
| 159 |  |
| 160 |  |

TABLE 11
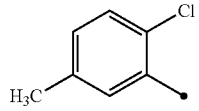
| Compound No. | —L—R¹ | —R² | —R³ |
|---|---|---|---|
| 161 | 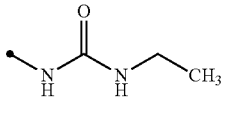 | H | 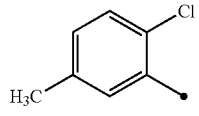 |
| 162 | 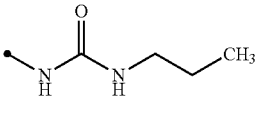 | H | 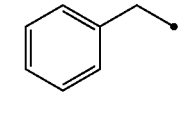 |
| 163 | 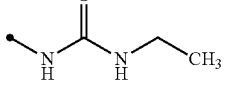 | H | 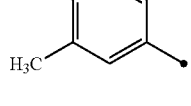 |
| 164 | 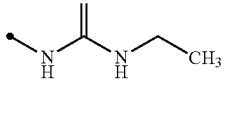 | H | 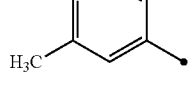 |
| 165 | 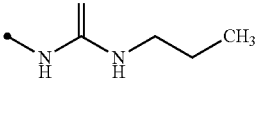 | H | 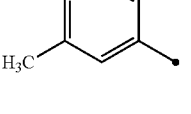 |
| 166 | 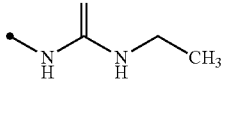 | H | 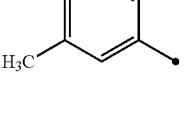 |
| 167 | 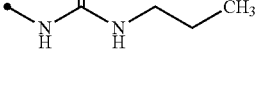 | H | 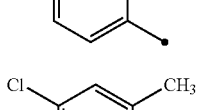 |
| 168 | 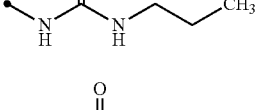 | H |  |
| 169 |  | H | |

TABLE 12
| Compound No. | —L—R¹ | —R² | —R³ |
|---|---|---|---|
| 170 | 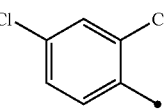 4-Cl, 2-CH₃ phenyl | H | 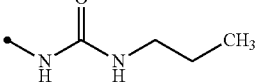 —NH-C(O)-NH-propyl |
| 171 | 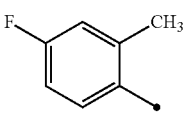 4-F, 2-CH₃ phenyl | H | 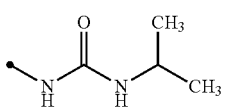 —NH-C(O)-NH-iPr |
| 172 | 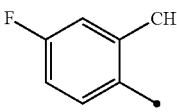 4-F, 2-CH₃ phenyl | H | 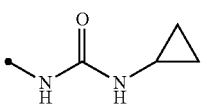 —NH-C(O)-NH-cyclopropyl |
| 173 | 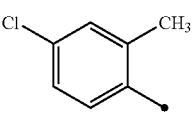 4-Cl, 2-CH₃ phenyl | H | 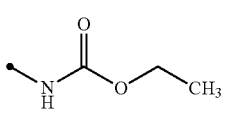 —NH-C(O)-O-ethyl |
| 174 | 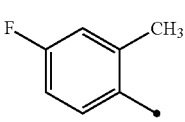 4-F, 2-CH₃ phenyl | H | 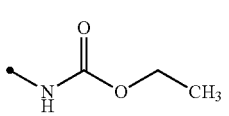 —NH-C(O)-O-ethyl |
| 175 | 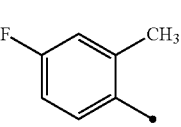 4-F, 2-CH₃ phenyl | H | 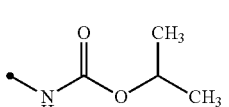 —NH-C(O)-O-iPr |
| 176 | 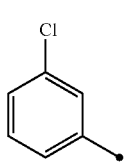 3-Cl phenyl | Cl | NH₂ |
| 177 | 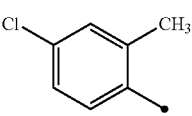 4-Cl, 2-CH₃ phenyl | Cl | NH₂ |
| 178 | 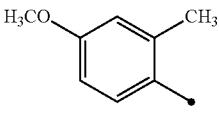 4-OCH₃, 2-CH₃ phenyl | Cl | NH₂ |
| 179 | 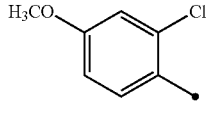 4-OCH₃, 2-Cl phenyl | Cl | NH₂ |
| 180 | 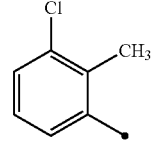 3-Cl, 2-CH₃ phenyl | Cl | NH₂ |

TABLE 13

| Compound No. | —L—R¹ | —R² | —R³ |
|---|---|---|---|
| 181 | 3-Cl-4-methylphenyl | Cl | NH₂ |
| 182 | 2,6-difluorophenyl | Cl | NH₂ |
| 183 | cyclopropylmethyl | Cl | NH₂ |
| 184 | 4-F-2-methylphenyl | Cl | 1-(4-aminopiperidinyl) |
| 185 | 4-F-2-methylphenyl | Cl | —NH—CH(CH₂OH)—C(=O)—NHCH₃ |
| 186 | 4-F-2-methylphenyl | Cl | —NH—CH(CH₂OH)—C(=O)—N(CH₃)₂ |
| 187 | 4-F-2-methylphenyl | Cl | 4,4-dimethyl-2-oxo-oxazolidin-3-yl |
| 188 | 4-F-2-methylphenyl | Cl | —NH-(thiazol-2-yl) |
| 189 | 4-F-2-methylphenyl | Cl | —NH-(3,5-dimethylisoxazol-4-yl) |
| 190 | 4-F-2-methylphenyl | Cl | —NH-(isoxazol-3-yl) |
| 191 | 4-F-2-methylphenyl | Cl | —NH-phenyl |

TABLE 14

Structure: R¹—L—Y^A attached to pyridazine-type ring with R², R^3A, X^A, and C(=O)—R^4A substituents.

| Compoud No. | —Y^A—L—R¹ | —R² | —R^3A | —R^4A | X^A |
|---|---|---|---|---|---|
| 192 | —NH-(4-F-2-methylphenyl) | Cl | 1-(pyrrolo[3,2-b]pyridin-1-ylsulfonyl) | 4-(4-fluorophenyl)piperidin-1-yl | CH |
| 193 | —NH-(4-F-2-methylphenyl) | Cl | —S(=O)₂—NH—O—CH₃ | 4-(4-fluorophenyl)piperidin-1-yl | CH |

TABLE 14-continued

| Compoud No. | —Y^A—L—R^1 | —R^2 | —R^{3A} | —R^{4A} | X^A |
|---|---|---|---|---|---|
| 194 | 4-F, 2-CH₃ anilino (NH) | Cl | benzoyl-N=S(=O)(NH₂)— | 4-(4-fluorophenyl)piperidin-1-yl | CH |
| 195 | 4-F, 2-CH₃ anilino (NH) | Cl | H₂N-S(=O)₂— | 4-cyano-4-phenylpiperidin-1-yl | CH |
| 196 | 4-Cl, 2-CH₃ anilino (NH) | CH₃ | H₂N-S(=O)₂— | 4-(4-fluorophenyl)piperidin-1-yl | CH |
| 197 | 3-Cl anilino (NH) | CH₃ | H₂N-S(=O)₂— | 4-(4-fluorophenyl)piperidin-1-yl | CH |
| 198 | 4-F, 2-CH₃ anilino (NH) | Cl | ethyl-NH-C(=O)-N=S(=O)(NH₂)— | 4-(4-fluorophenyl)piperidin-1-yl | CH |
| 199 | 3-CH₃ anilino (NH) | Cl | H₂N-S(=O)₂— | 4-hydroxy-4-(4-fluorophenyl)piperidin-1-yl | CH |
| 200 | 4-F, 2-CH₃ anilino (NH) | Cl | HN=S(=O)(NH₂)— | 4-(4-fluorophenyl)piperidin-1-yl | CH |

TABLE 15

| Compound No. | —Y⁴—L—R¹ | —R² | —R³,⁴ | —R⁴,⁴ | X⁴ |
|---|---|---|---|---|---|
| 201 | 3-methylphenyl-NH- | Cl | H₂N-SO₂- | 4-phenyl-4-(CO₂CH₃)-piperidin-1-yl | CH |
| 202 | 3-methylphenyl-NH- | Cl | H₂N-SO₂- | 4-(4-fluorophenyl)-3,6-dihydro-2H-pyridin-1-yl | CH |
| 203 | 3-methylphenyl-NH- | Cl | H₂N-SO₂- | 4-phenyl-4-(CONH₂)-piperidin-1-yl | CH |
| 204 | 2-methylphenyl-NH- | Cl | H₃C-CH₂-SO₂- | 4-(4-fluorophenyl)-piperidin-1-yl | CH |
| 205 | 2-methylphenyl-NH- | Cl | phenyl-SO₂- | 4-(4-fluorophenyl)-piperidin-1-yl | CH |
| 206 | 3-methylphenyl-NH- | Cl | H₂N-SO₂- | 4-(2-chlorophenyl)-piperazin-1-yl | CH |
| 207 | cyclohexyl-NH- | CH₃ | H₂N-SO₂- | 4-(4-fluorophenyl)-piperidin-1-yl | CH |
| 208 | 3-methylphenyl-NH- | Cl | H₂N-SO₂- | 4-(4-fluorophenyl)-4-(OCH₃)-piperidin-1-yl | CH |
| 209 | 3-methylphenyl-NH- | Cl | H₂N-SO₂- | 4-(4-fluorophenyl)-3-oxopiperazin-1-yl | CH |
| 210 | 3-methylphenyl-S- | Cl | H₂N-SO₂- | 4-(4-fluorophenyl)-piperidin-1-yl | CH |

TABLE 16

| Compound No. | —Y^A—L—R^1 | —R^2 | —R^{3A} | —R^{4A} | X^A |
|---|---|---|---|---|---|
| 211 | benzamide-NH- | Cl | H2N-SO2- | -N(piperidine)-C6H4-F | CH |
| 212 | benzyl-CH2- | Cl | H2N-SO2- | -N(piperidine)-C6H4-F | CH |
| 213 | 3-methylphenyl-NH- | Cl | H2N-SO2- | -N(octahydropyrrolo[3,4-b]pyrrole)-N-C6H4-F | CH |
| 214 | tetrahydropyran-4-yl-CH2-NH- | CH3 | H2N-SO2- | -N(piperidine)-C6H4-F | CH |
| 215 | cyclohexyl-NH- | CH3 | isoxazol-3-yl-NH-SO2- | -N(piperidine)-C6H4-F | CH |
| 216 | 3-methylphenyl-NH- | Cl | H2N-SO2- | -N(piperidine)(COCH3)-C6H4-F | CH |
| 217 | 7-oxabicyclo[2.2.1]heptyl-NH- | Cl | H2N-SO2- | -N(piperidine)-C6H4-F | CH |
| 218 | 3-methylphenyl-NH- | Cl | H2N-SO2- | -N(piperidine)-tetrahydroquinoline | CH |
| 219 | 2,4-dimethylpyrimidin-5-yl-NH- | Cl | H2N-SO2- | -N(piperidine)-C6H4-F | CH |
| 220 | 1-phenylethyl-NH- | CH3 | H2N-SO2- | -N(piperidine)-C6H4-F | CH |

TABLE 17
| Compound No. | —Y$^A$—L— R$^1$ | —R$^2$ | —R$^{3A}$ | —R$^{4A}$ | X$^A$ |
|---|---|---|---|---|---|
| 221 | 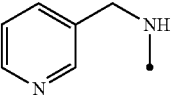 | CH$_3$ | 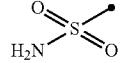 | 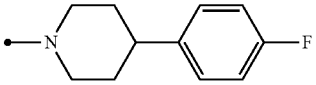 | CH |
| 222 | 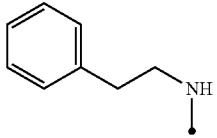 | CH$_3$ | 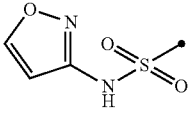 | 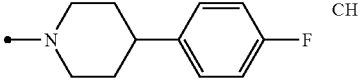 | CH |
| 223 | 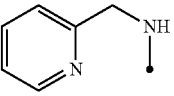 | CH$_3$ | 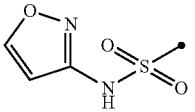 | 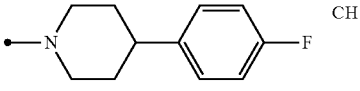 | CH |
| 224 | 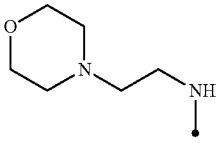 | CH$_3$ | 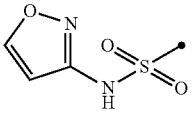 | 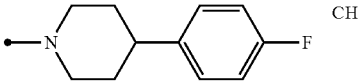 | CH |
| 225 | 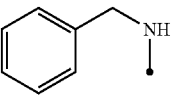 | F | 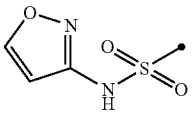 | 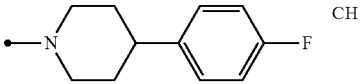 | CH |
| 226 | 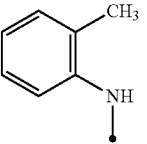 | CH$_3$ | 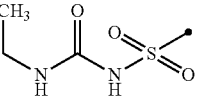 | 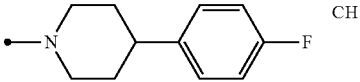 | CH |
| 227 | 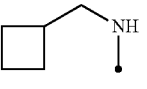 | CH$_3$ | 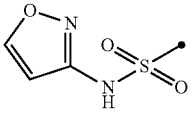 | 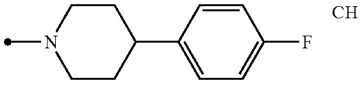 | CH |
| 228 | 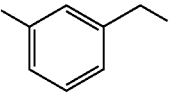 | CH$_3$ | 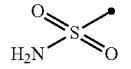 | 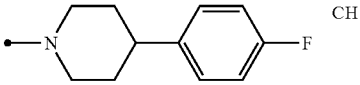 | CH |
| 229 | 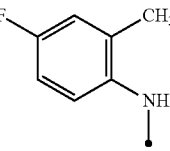 | H | 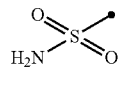 | 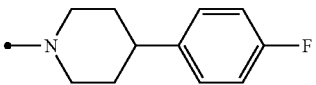 | N |
| 230 | 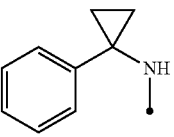 | Cl | 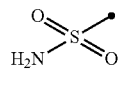 | 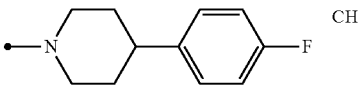 | CH |

TABLE 18

| Compound No. | —Y⁴—L—R¹ | —R² | —R^{3A} | —R^{4A} | X^A |
|---|---|---|---|---|---|
| 231 | thiophen-2-ylmethyl-NH- | Cl | H₂N-SO₂- | 4-(4-fluorophenyl)piperidin-1-yl | CH |
| 232 | 5-chloro-2-methylphenyl-NH- | CH₃ | isoxazol-3-yl-NH-SO₂- | 4-(4-fluorophenyl)piperidin-1-yl | CH |
| 233 | 3-fluorophenyl-NH- | CH₃ | isoxazol-3-yl-NH-SO₂- | 4-(4-fluorophenyl)piperidin-1-yl | CH |
| 234 | 4-methoxy-2-methylphenyl-NH- | CH₃ | isoxazol-3-yl-NH-SO₂- | 4-(4-fluorophenyl)piperidin-1-yl | CH |
| 235 | 2-fluoro-4-methylphenyl-NH- | CH₃ | isoxazol-3-yl-NH-SO₂- | 4-(4-fluorophenyl)piperidin-1-yl | CH |
| 236 | norbornan-2-yl-NH- | Cl | H₂N-SO₂- | 4-(4-fluorophenyl)piperidin-1-yl | CH |
| 237 | indan-1-yl-NH- | Cl | H₂N-SO₂- | 4-(4-fluorophenyl)piperidin-1-yl | CH |
| 238 | 3-fluorophenyl-O- | Cl | H₂N-SO₂- | 4-(4-fluorophenyl)piperidin-1-yl | CH |
| 239 | 2-ethylphenyl-NH- | CH₃ | isoxazol-3-yl-NH-SO₂- | 4-(4-fluorophenyl)piperidin-1-yl | CH |
| 240 | 4-fluoro-2-methylphenyl-NH- | Cl | H₂N-SO₂- | 4-(4-fluorophenyl)piperidin-1-yl | N |

TABLE 19
| Compound No. | —Y^A—L—R^1 | —R^2 | —R^{3A} | —R^{4A} | X^A |
|---|---|---|---|---|---|
| 241 | 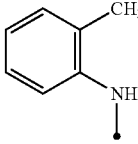 | CH_3 | 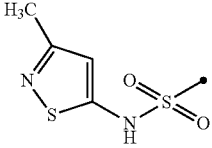 | 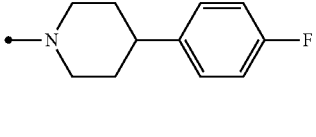 | CH |
| 242 | 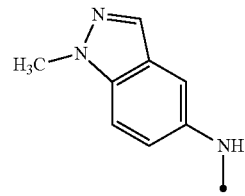 | Cl | 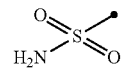 | 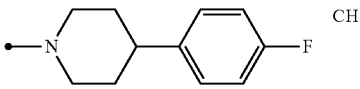 | CH |
| 243 | 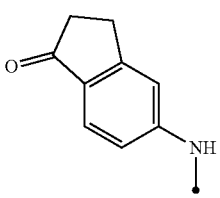 | Cl | 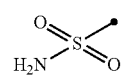 | 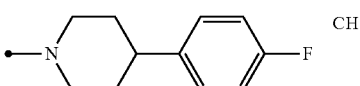 | CH |
| 244 | 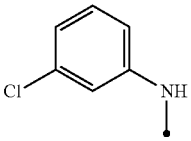 | CH_3 | 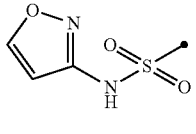 | 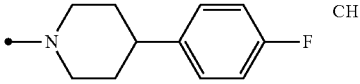 | CH |
| 245 | 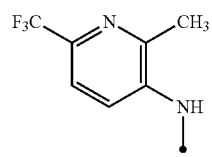 | CH_3 | 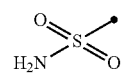 | 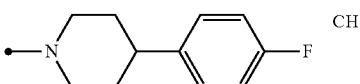 | CH |
| 246 | 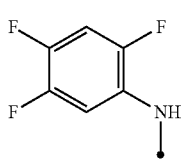 | CH_3 | 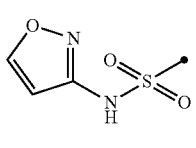 | 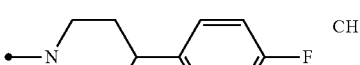 | CH |
| 247 | 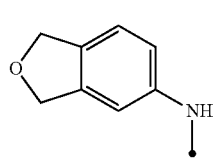 | CH_3 | 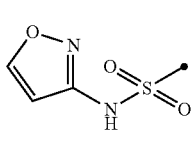 | 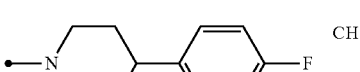 | CH |
| 248 | 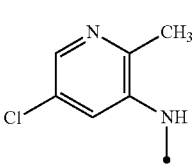 | CH_3 | 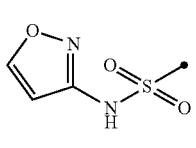 | 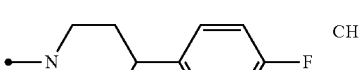 | CH |
| 249 | 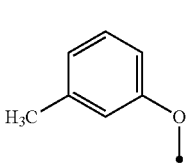 | CH_3 | 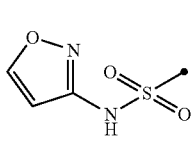 | 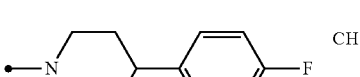 | CH |

TABLE 19-continued
| Compoud No. | —Y⁴—L—R¹ | —R² | —R³,⁴ | —R⁴,⁴ | X⁴ |
|---|---|---|---|---|---|
| 250 | 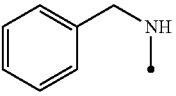 | CH₃ | 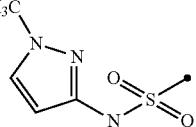 | 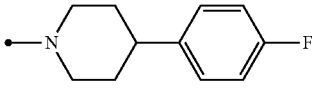 | CH |
TABLE 20
| Compoud No. | —Y⁴—L—R¹ | —R² | —R³,⁴ | —R⁴,⁴ | X⁴ |
|---|---|---|---|---|---|
| 251 | 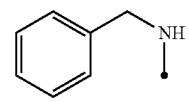 | CH₃ | 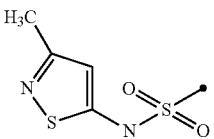 | 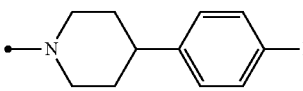 | CH |
| 252 | 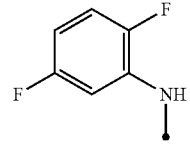 | CH₃ | 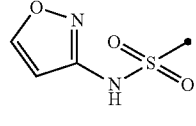 | 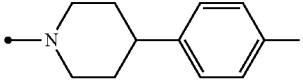 | CH |
| 253 | 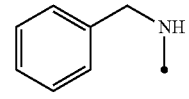 | CH₃ | 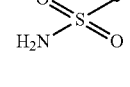 | 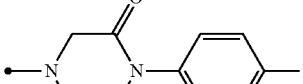 | CH |
| 254 | 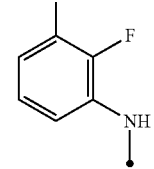 | CH₃ | 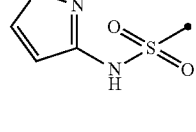 | 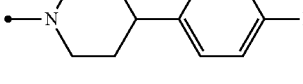 | CH |
| 255 | 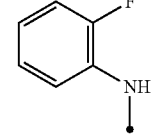 | CH₃ | 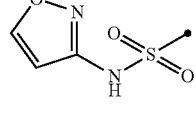 | 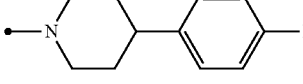 | CH |
| 256 | 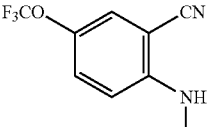 | Cl | 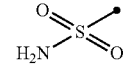 | 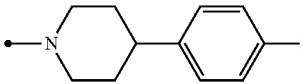 | CH |
| 257 | 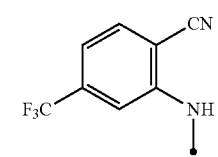 | Cl | 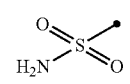 | 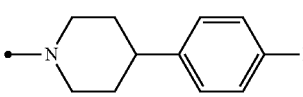 | CH |

TABLE 20-continued
| Compoud No. | —Y$^A$—L—R$^1$ | —R$^2$ | —R$^{3A}$ | —R$^{4A}$ | X$^A$ |
|---|---|---|---|---|---|
| 258 | 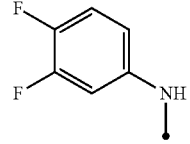 | CH$_3$ | 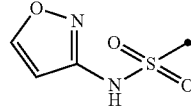 | 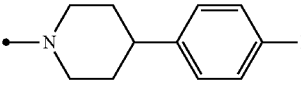 | CH |
| 259 | 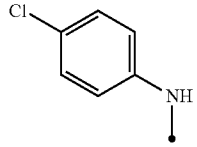 | CH$_3$ | 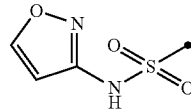 | 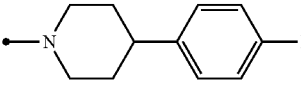 | CH |
| 260 | 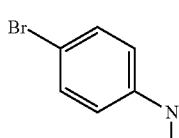 | CH$_3$ | 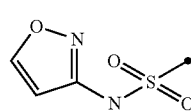 | 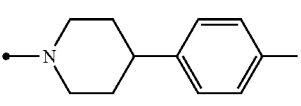 | CH |
TABLE 21
| Compoud No. | —Y$^A$—L—R$^1$ | —R$^2$ | —R$^{3A}$ | —R$^{4A}$ | X$^A$ |
|---|---|---|---|---|---|
| 261 | 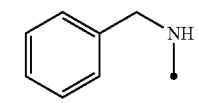 | CH$_3$ | 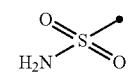 | 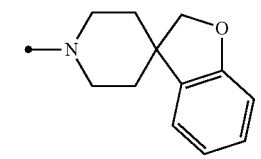 | CH |
| 262 | 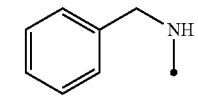 | CH$_3$ | 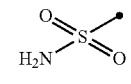 | 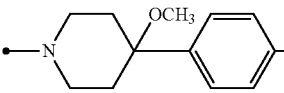 | CH |
| 263 | 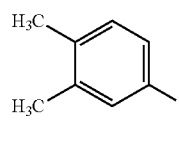 | CH$_3$ | 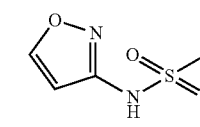 | 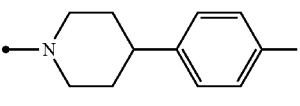 | CH |
| 264 | 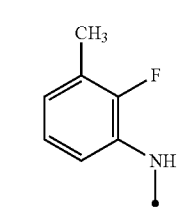 | CH$_3$ | 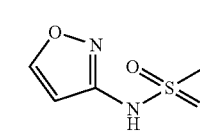 | 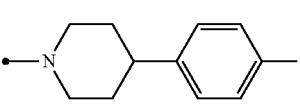 | CH |
| 265 | 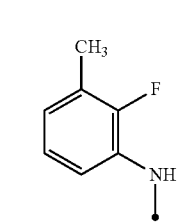 | CH$_3$ | 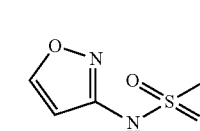 | 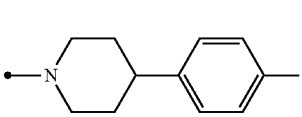 | CH |

TABLE 21-continued

| Compoud No. | —Y$^A$—L—R$^1$ | —R$^2$ | —R$^{3A}$ | —R$^{4A}$ | X$^A$ |
|---|---|---|---|---|---|
| 266 | 4-F, 2-CH₃-phenyl-NH- | CH₃ | 3-methyl-isothiazol-5-yl-NH-S(O)₂- | 4-(4-fluorophenyl)piperidin-1-yl | CH |
| 267 | 3-F-phenyl-NH- | CH₃ | 3-methyl-isothiazol-5-yl-NH-S(O)₂- | 4-(4-fluorophenyl)piperidin-1-yl | CH |
| 268 | 2-F, 5-OCH₃-phenyl-NH- | CH₃ | isoxazol-3-yl-NH-S(O)₂- | 4-(4-fluorophenyl)piperidin-1-yl | CH |
| 269 | 4-F, 3-OCH₃-phenyl-NH- | CH₃ | isoxazol-3-yl-NH-S(O)₂- | 4-(4-fluorophenyl)piperidin-1-yl | CH |
| 270 | 4-Cl, 2-F-phenyl-NH- | CH₃ | isoxazol-3-yl-NH-S(O)₂- | 4-(4-fluorophenyl)piperidin-1-yl | CH |

TABLE 22

| Compoud No. | —Y$^A$—L—R$^1$ | —R$^2$ | —R$^{3A}$ | —R$^{4A}$ | X$^A$ |
|---|---|---|---|---|---|
| 271 | 2-F, 5-Cl-phenyl-NH- | CH₃ | isoxazol-3-yl-NH-S(O)₂- | 4-(4-fluorophenyl)piperidin-1-yl | CH |
| 272 | 2-Cl, 3-F-phenyl-NH- | CH₃ | isoxazol-3-yl-NH-S(O)₂- | 4-(4-fluorophenyl)piperidin-1-yl | CH |
| 273 | 2-Cl, 4-F-phenyl-NH- | CH₃ | isoxazol-3-yl-NH-S(O)₂- | 4-(4-fluorophenyl)piperidin-1-yl | CH |

TABLE 22-continued

| Compound No. | —Y⁴—L—R¹ | —R² | —R³,⁴ | —R⁴,⁴ | X⁴ |
|---|---|---|---|---|---|
| 274 | 2-Cl, 5-F phenyl-NH- | CH₃ | isoxazol-3-yl-NH-S(O)₂- | 4-(4-fluorophenyl)piperidin-1-yl | CH |
| 275 | 2,3,5-trifluorophenyl-NH- | CH₃ | isoxazol-3-yl-NH-S(O)₂- | 4-(4-fluorophenyl)piperidin-1-yl | CH |
| 276 | 3-methylphenyl-NH- | CH₃ | 3-methylisothiazol-5-yl-NH-S(O)₂- | 4-(4-fluorophenyl)piperidin-1-yl | CH |
| 277 | phenyl-NH- | CH₃ | 3-methylisothiazol-5-yl-NH-S(O)₂- | 4-(4-fluorophenyl)piperidin-1-yl | CH |
| 278 | 1-phenylcyclopropyl-NH- | Cl | H₂N-S(O)₂- | 4-(4-fluorophenyl)-3-oxopiperazin-1-yl | CH |
| 279 | 3,4-dichlorophenyl-NH- | CH₃ | isoxazol-3-yl-NH-S(O)₂- | 4-(4-fluorophenyl)piperidin-1-yl | CH |
| 280 | 2,4-dichlorophenyl-NH- | CH₃ | isoxazol-3-yl-NH-S(O)₂- | 4-(4-fluorophenyl)piperidin-1-yl | CH |

TABLE 23

| Compound No. | —Y⁴—L—R¹ | —R² | —R³,⁴ | —R⁴,⁴ | X⁴ |
|---|---|---|---|---|---|
| 281 | 2,5-dichlorophenyl-NH- | CH₃ | isoxazol-3-yl-NH-S(O)₂- | 4-(4-fluorophenyl)piperidin-1-yl | CH |

TABLE 23-continued

| Compound No. | —Y$^A$—L—R$^1$ | —R$^2$ | —R$^{3,A}$ | —R$^{4,A}$ | X$^A$ |
|---|---|---|---|---|---|
| 282 | N(CH$_3$)-Ph-NH- | Cl | H$_2$N-SO$_2$- | piperidine-4-(4-fluorophenyl) | CH |
| 283 | 3-Cl-Ph-NH- | Cl | H$_2$N-SO$_2$- | azetidine-3-(4-fluorophenyl) | CH |
| 284 | Ph-CH$_2$-NH- | CH$_3$ | H$_2$N-SO$_2$- | azetidine-3-(4-fluorophenyl) | CH |
| 285 | 3-Cl-Ph-NH- | CH$_3$ | H$_2$N-SO$_2$- | azetidine-3-(4-fluorophenyl) | CH |
| 286 | 2-CH$_3$-Ph-NH- | CH$_3$ | H$_2$N-SO$_2$- | azetidine-3-(4-fluorophenyl) | CH |
| 287 | 2-CH$_3$-Ph-NH- | CH$_2$CH$_3$ | isoxazol-3-yl-NH-SO$_2$- | piperidine-4-(4-fluorophenyl) | CH |
| 288 | 2,4-(CN)$_2$-Ph-NH- | Cl | H$_2$N-SO$_2$- | piperidine-4-(4-fluorophenyl) | CH |
| 289 | 4-CH$_3$-Ph-O- | CH$_3$ | H$_2$N-SO$_2$- | piperidine-4-(4-fluorophenyl) | CH |
| 290 | 4-Cl-2-CN-Ph-NH- | Cl | H$_2$N-SO$_2$- | piperidine-4-(4-fluorophenyl) | CH |

TABLE 24

| Compound No. | —Y⁴—L—R¹ | —R² | —R³ᴬ | —R⁴ᴬ | X⁴ |
|---|---|---|---|---|---|
| 291 | 4-(F₃C)-C₆H₄-NH- | Cl | H₂N-SO₂- (sulfamoyl) | 4-(4-fluorophenyl)piperidin-1-yl | CH |
| 292 | 2-methylphenyl-NH- | CH₃ | isoxazol-3-yl-NH-SO₂- | 3-(4-fluorophenyl)azetidin-1-yl | CH |
| 293 | phenyl-NH- | CH₂CH₃ | isoxazol-3-yl-NH-SO₂- | 4-(4-fluorophenyl)piperidin-1-yl | CH |
| 294 | 3-fluoro-2-methylphenyl-NH- | CH₂CH₃ | isoxazol-3-yl-NH-SO₂- | 4-(4-fluorophenyl)piperidin-1-yl | CH |
| 295 | (1-phenylcyclopropyl)-NH- | Cl | H₂N-SO₂- | 4-(4-fluorophenyl)-4-methoxypiperidin-1-yl | CH |
| 296 | (1-phenylcyclopropyl)-NH- | Cl | H₂N-SO₂- | 4-phenylpiperidin-1-yl | CH |
| 297 | (1-phenylcyclopropyl)-NH- | Cl | H₂N-SO₂- | spiro[benzofuran-3,4'-piperidin]-1'-yl | CH |
| 298 | 4-cyanophenyl-NH- | CH₃ | isoxazol-3-yl-NH-SO₂- | 4-(4-fluorophenyl)piperidin-1-yl | CH |
| 299 | 4-fluorophenyl-NH- | CH₃ | 3-methylisothiazol-5-yl-NH-SO₂- | 4-(4-fluorophenyl)piperidin-1-yl | CH |

TABLE 24-continued

| Compoud No. | —Y⁴—L—R¹ | —R² | —R³ᴬ | —R⁴ᴬ | Xᴬ |
|---|---|---|---|---|---|
| 300 | 4-methylphenyl-NH- | CH₃ | 3-methyl-isothiazol-5-yl-NHSO₂- | 4-(4-fluorophenyl)piperidin-1-yl | CH |

TABLE 25

| Compoud No. | —Y⁴—L—R¹ | —R² | —R³ᴬ | —R⁴ᴬ | XA |
|---|---|---|---|---|---|
| 301 | 3,4-difluorophenyl-NH- | CH₃ | 3-methyl-isothiazol-5-yl-NHSO₂- | 4-(4-fluorophenyl)piperidin-1-yl | CH |
| 302 | 4-chlorophenyl-NH- | Cl | H₂NSO₂- | 4-(4-fluorophenyl)piperidin-1-yl | CH |
| 303 | 5-acetyl-2-methylphenyl-NH- | Cl | H₂NSO₂- | 4-(4-fluorophenyl)piperidin-1-yl | CH |
| 304 | 2-methylphenyl-NH- | CH₃ | H₂NSO₂- | 4-methoxy-4-(4-fluorophenyl)piperidin-1-yl | CH |
| 305 | 2-methylphenyl-NH- | CH₃ | H₂NSO₂- | spiro[benzofuran-3,4'-piperidin]-1'-yl | CH |
| 306 | 3-chlorophenyl-NH- | Cl | H₂NSO₂- | 4-methoxy-4-(4-fluorophenyl)piperidin-1-yl | CH |
| 307 | 3-chlorophenyl-NH- | Cl | H₂NSO₂- | spiro[benzofuran-3,4'-piperidin]-1'-yl | CH |

TABLE 25-continued
| Compound No. | —Y^A—L—R^1 | —R^2 | —R^{3A} | —R^{4A} | X^A |
|---|---|---|---|---|---|
| 308 | 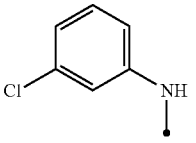 | Cl | 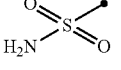 | 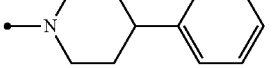 | CH |
| 309 | 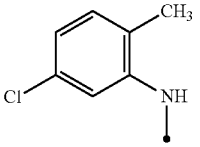 | Cl | 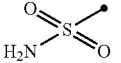 | 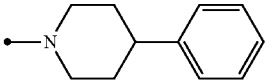 | CH |
| 310 | 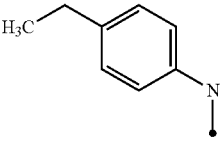 | Cl | 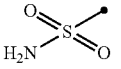 | 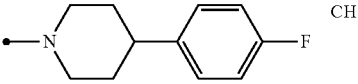 | CH |
TABLE 26
| Compound No. | —Y^A—L—R^1 | —R^2 | —R^{3A} | —R^{4A} | X^A |
|---|---|---|---|---|---|
| 311 | 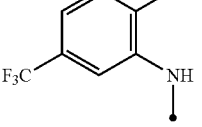 | Cl | 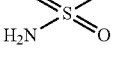 | 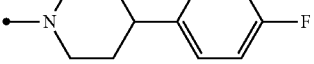 | CH |
| 312 | 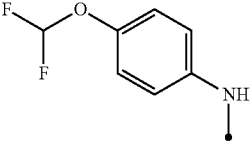 | Cl | 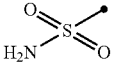 | 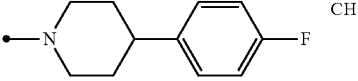 | CH |
| 313 | 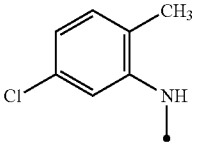 | Cl | 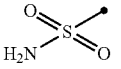 |  | CH |
| 314 | 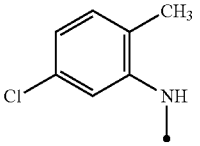 | Cl | 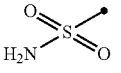 | 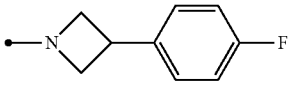 | CH |
| 315 | 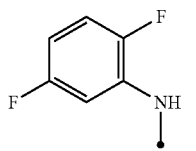 | CH_3 | 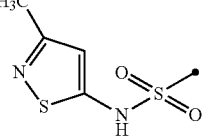 | 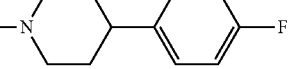 | CH |

TABLE 26-continued

| Compound No. | —Y⁴—L—R¹ | —R² | —R³,⁴ | —R⁴,⁴ | X⁴ |
|---|---|---|---|---|---|
| 316 | 2,4-difluorophenyl-NH- | CH₃ | 3-methylisothiazol-5-yl-NH-SO₂- | 4-(4-fluorophenyl)piperidin-1-yl | CH |
| 317 | 2-methylphenyl-NH- | Cl | 1-methyl-1H-pyrazol-3-yl-NH-SO₂- | 4-(4-fluorophenyl)piperidin-1-yl | CH |
| 318 | 2-methyl-4-nitrophenyl-NH- | Cl | H₂N-SO₂- | 4-(4-fluorophenyl)piperidin-1-yl | CH |
| 319 | 3-bromophenyl-NH- | Cl | H₂N-SO₂- | 4-(4-fluorophenyl)piperidin-1-yl | CH |
| 320 | 2-cyano-4,5-dimethylphenyl-NH- | Cl | H₂N-SO₂- | 4-(4-fluorophenyl)piperidin-1-yl | CH |

TABLE 27

| Compound No. | —Y⁴—L—R¹ | —R² | —R³,⁴ | —R⁴,⁴ | X⁴ |
|---|---|---|---|---|---|
| 321 | 2-cyano-5-methoxyphenyl-NH- | Cl | H₂N-SO₂- | 4-(4-fluorophenyl)piperidin-1-yl | CH |
| 322 | 2-cyano-4-nitrophenyl-NH- | Cl | H₂N-SO₂- | 4-(4-fluorophenyl)piperidin-1-yl | CH |
| 323 | 5-chloro-2-methylphenyl-NH- | Cl | H₂N-SO₂- | spiro[isobenzofuran-3,4'-piperidin]-1'-yl | CH |

TABLE 27-continued

| Compoud No. | —Y⁴—L—R¹ | —R² | —R³,⁴ | —R⁴,⁴ | X⁴ |
|---|---|---|---|---|---|
| 324 | 2-Cl, 5-OMe phenyl-NH- | Cl | H₂N-SO₂- | 4-(4-fluorophenyl)piperidin-1-yl | CH |
| 325 | 2-Cl, 5-F phenyl-NH- | Cl | H₂N-SO₂- | 4-(4-fluorophenyl)piperidin-1-yl | CH |
| 326 | 2,5-dimethylpyridin-3-yl-NH- | Cl | H₂N-SO₂- | 4-(4-fluorophenyl)piperidin-1-yl | CH |
| 327 | 2,6-dichloropyridin-3-yl-NH- | Cl | H₂N-SO₂- | 4-(4-fluorophenyl)piperidin-1-yl | CH |
| 328 | 2-F, 4-Me phenyl-NH- | Cl | H₂N-SO₂- | 4-(4-fluorophenyl)piperidin-1-yl | CH |
| 329 | 4-methanesulfonyl-2-methylphenyl-NH- | Cl | H₂N-SO₂- | 4-(4-fluorophenyl)piperidin-1-yl | CH |
| 330 | 1-phenylcyclopropyl-NH- | Cl | H₂N-SO₂- | 3-(4-fluorophenyl)azetidin-1-yl | CH |
| 331 | 2-methylphenyl-NH- | CH₃ | H₂N-SO₂- | 4-(4-fluorophenyl)piperidin-1-yl | CH |

Next, pharmacological effects of a representative compound are specifically explained by Experimental Examples.
[Experimental Example 1] CCR10 Antagonistic Effect
(1) Preparation of Human CCR10-Inducible Expression Plasmid
A CCR10-inducible expression plasmid was prepared according to a known method [Analytical Biochemistry, 2006, vol. 400, page 163]. A DNA encoding human CCR10 was obtained by PCR. Using human chromosome DNA (100 ng; manufactured by Clontech) as a template, synthetic DNA having the sequences depicted in SEQ ID NOs: 1 and 2 as a human CCR10 cDNA specific primer, and Pyrobest DNA Polymerase (manufactured by TAKARA SHUZO CO. LTD.) as an enzyme, a DNA encoding human CCR10 was obtained by PCR. As a buffer for PCR, the buffer attached to the enzyme to be used, which was diluted 10-fold with deionized water, was used. Using Thermal Cycler DNA Engine (manufactured by MJ Research), PCR was performed by 35 cycles of reactions composed of an incubation at 94° C. for 30 sec, at an anneal temperature of 58° C. for 30 sec, and at 72° C. for 1 min after treating at 90° C. for 2 min.

The amplified PCR fragment was cleaved with HindIII and NotI, then a human CCR10 DNA fragment was recovered by the agarose gel electrophoresis method. The fragment was incorporated between the corresponding restriction enzyme sites (HindIII-NotI) of an inducible expression vector to construct a human CCR10-inducible expression plasmid.

Using a primer specific to the sequence of plasmid (synthetic DNA having the sequences shown in SEQ ID NOs: 3 and 4), the sequence of human CCR10 DNA region was determined. For the determination of the base sequence, DNA Sequencer 377 (manufactured by Perkin Elmer. Co.) and a reaction kit (ABI Prism (registered trade mark) Big-Dye (registered trade mark) Terminator Cycle Sequencing Ready Reaction kit: manufactured by Applied Biosystems) were used. The sequence of human CCR10 DNA was identical with the sequence (NM 016602) registered in GenBank.

(2) Preparation of Human CCR10 Expressing Cell for Calcium Assay

Cells for detecting signals from human CCR10 in calcium assay were prepared. According to a known method [Analytical.Biochemistry (Analy Biochem), 2006, vol. 400, page 163], human CCR10-inducible expressing cells whose host cell is KJMGER8 cell (Namalwa cell-derived cell line) were prepared. Human CCR10-inducible expression plasmid produced above and Gα16 expression plasmid were co-transfected into the KJMGER8 cells by the electroporation method [Cytotechnology, 1990, vol. 3, page 133], whereby the signals from human CCR10 could be detected by calcium assay (hereinafter to be referred to as hCCR10G16 cell). A Ga16 expression plasmid was produced by incorporating human Ga16 DNA into expression vector pAMoh (WO 03/087366). Expression of human CCR10 was induced by cultivating hCCR10G16 cells in the presence of 10 nmol/L β-estradiol (manufactured by Sigma Ltd.) for 24 hr.

(3) Calcium Assay of Human CCR10

Cells expressing human CCR10 induced by the above-mentioned method were suspended in RPMI1640 medium (manufactured by Invitrogen), and adjusted to a cell density of $2\times10^6$ cells/mL. The cells were blended with an equivalent volume of a loading buffer prepared according to the attached protocol of Fluo-3 calcium assay kit (manufactured by Molecular Devices Corporation), and incubated at 37° C. for several dozen minutes. This mixture was dispensed to a 384 well clear-bottom plate (manufactured by Corning Incorporated) at 40 µL/well. To this plate was added a solution of the test compound in dimethyl sulfoxide (DMSO), which was diluted 37-fold with RPMI1640 medium, at 5 µL/well, and the mixture was incubated at 37° C. for 30 min. 300 nmol/L human recombinant CTACK (manufactured by R&D Systems, Inc.) diluted with RPMI1640 medium containing 1 w/v % bovine serum albumin (manufactured by Sigma Ltd.) was added at 5 µL/well and, variation of intracellular calcium ion concentration for about 5 min after the addition was measured by a screening apparatus (FDSS; manufactured by Hamamatsu Photonics K.K.). The difference between the maximum fluorescence intensity and the minimum fluorescence intensity measured in the 5 minutes was calculated and taken as the measured value (maximum fluorescence intensity−minimum fluorescence intensity).

The inhibition rate of the test compound against increase of calcium ion concentration was calculated by the following formula.

$$\text{inhibition rate against increase of calcium ion concentration (\%)} = \left(1 - \frac{\text{test compound addition group} - \text{blank}}{\text{control} - \text{blank}}\right) \times 100$$

test compound addition group: average measurement value of variation of intracellular calcium ion concentration of the test compound addition group control: average measurement value as measured by adding, instead of a solution of the test compound, DMSO 37-fold diluted with RPMI1640 medium, adding 300 nmol/L CTACK diluted with RPMI1640 medium containing 1 w/v % bovine serum albumin, and measuring variation of intracellular calcium ion concentration blank: average measurement value as measured by adding, instead of a solution of the test compound, DMSO 37-fold diluted with RPMI1640 medium, adding, instead of a medium containing CTACK, RPMI1640 medium containing 1 w/v % bovine serum albumin, and measuring variation of intracellular calcium ion concentration A concentration-reaction curve was drawn from the inhibition rate against increase of calcium ion concentration when treated with not less than 5 concentrations of the test compound at 3- to 10-fold common ratio, and $IC_{50}$ value was calculated.

Compounds 1-53, 55-96, 98-100, 102-107, 109-182, 184-331 inhibited an increase in the calcium ion concentration by not less than 50% at a concentration of not more than 1000 nmol/L. Compound (I) or a pharmaceutically acceptable salt thereof was considered to have a CCR10 antagonistic action, and to be useful as a prophylactic and/or therapeutic agent for the diseases involving CCR10.

Therefore, compound (I) or a pharmaceutically acceptable salt thereof was considered to be useful as a prophylactic and/or therapeutic agent for the diseases involving CCR10, for example, skin diseases [for example, acne vulgaris, drug eruption, contact dermatitis, dermatitis due to venomous moth, pollen dermatitis, urticaria, psoriasis, atopic dermatitis, Candida dermatitis, seborrheic dermatitis, eczema, Stevens-Johnson syndrome, toxic epidermal necrosis, erythema multiforme, erythema nodosum, granuloma annulare, pityriasis rosea, rosacea, lichen planus, lichen pilaris (keratosis pilaris), photosensitivity, solar dermatitis, miliaria, herpes simplex, Kaposi's varicelliform eruption, impetigo contagiosa, staphylococcal scalded skin syndrome, erysipelas, slap cheek, lupus erythematosus, keloid, Hailey-Hailey disease, scabies, linear dermatitis and the like] and the like.

[Experimental Example 2] Suppressive Action on Dinitrofluorobenzene-induced Auricle Edema Reaction in Mouse BALB/c mice (female, supplied by CHARLES RIVER LABORATORIES JAPAN, INC.) were purchased at the age of 5 weeks. After quarantine and acclimation, mice showing smooth body weight increase and free of abnormality in appearance were used and the test was started at the age of 7 weeks. The mice were housed in a breeding room at room temperature 19-25° C., humidity 30-70%, 12 hr lighting per day (7 a.m.-7 p.m.) with 3 mice in each plastic gauge, and bred on with free ingestion of a commercially available solid feed and water.

Two days before the test, the abdomen of the BALB/c mice was shaved, and the mice were immunized by applying 100 µL of a solution {concentration 0.5% [weight (w)/volume (v) %]} of dinitrofluorobenzene (manufactured by Nacalai Tesque) in acetone (manufactured by Wako Pure Chemical Industries, Ltd.) to the shaved part. The reaction was induced by applying dinitrofluorobenzene-acetone solution [concentration 0.2% (w/v %)] to the front and the back of auricle (10 μL to each, total 20 μL) on day 5 after the immunization. A test compound dissolved in acetone at concentration of 0.1% or 1% (w/v %) was administered by applying same to the front and the back of auricle (10 μL to each, total 20 μL) 1 hr before and 3 hr after induction of the reaction. After application, the applied part was air-dried with a dryer.

The group applying administered with the test compound was taken as a test compound administration group, and the group applying administered with acetone as a solvent instead of the test compound was taken as a solvent administration group. Also, the group free of immunization and reaction induction but applying administered with acetone instead of the test compound was taken as a normal group. The thickness of auricle was measured using a dial thickness gauge (G-1A manufactured by OZAKI MFG. CO., LTD.) immediately before and 24 hr after induction of the reaction, and the difference thereof was taken as auricle edema. The suppression rate (%) of auricle edema was calculated according to the following formula. The results are shown in Table 28.

$$\text{auricle edema suppression rate (\%)} = \frac{\text{value of solvent administration group} - \text{value of test compound administration group}}{\text{value of solvent administration group} - \text{value of normal group}} \times 100$$

TABLE 28

| compound No. | test compound concentration (%) | auricle edema suppression rate (%) |
|---|---|---|
| 11 | 1 | 32 |
| 21 | 0.1 | 26 |
| 22 | 1 | 47 |
| 25 | 1 | 47 |
| 176 | 1 | 42 |
| 232 | 1 | 39 |
| 233 | 1 | 24 |
| 241 | 1 | 27 |
| 259 | 1 | 38 |
| 291 | 1 | 35 |

Compounds 11, 21, 22, 25, 176, 232, 233, 241, 259 and 291 showed a suppressive action on auricle edema response, and compound (I) or a pharmaceutically acceptable salt thereof was considered to be useful as a prophylactic and/or therapeutic agent for contact dermatitis or atopic dermatitis.

While compound (I) or a pharmaceutically acceptable salt thereof used in the present invention can be directly administered singly, it is generally desirable to provide as various pharmaceutical preparations. Also, such pharmaceutical preparations are used for animals or human.

The pharmaceutical preparation of the present invention can contain, as an active ingredient, compound (I) or a pharmaceutically acceptable salt thereof singly or in a mixture with any other active ingredient for the treatment. Also, such pharmaceutical preparation is produced by any method known in the technical field of formulation study, by mixing the active ingredient with one or more kinds of pharmaceutically acceptable carriers (for example, diluent, solvent, excipient and the like).

As the administration route, it is desirable to use a route the most effective for the treatment and, for oral, or, parenteral routes such as intravenous, external or the like can be mentioned.

Examples of the administration form include tablet, injection, ointment or the like.

For example, tablet and the like suitable for oral administration can be produced using excipient such as lactose and the like, disintegrant such as starch and the like, lubricant such as magnesium stearate and the like, binder such as hydroxypropylcellulose and the like, and the like.

For example, injection and the like suitable for intravenous administration can be produced using diluent or solvent such as salt solution, glucose solution or a mixture of salt water and glucose solution and the like, and the like.

For example, ointment suitable for external preparation can be produced using a base material such as petrolatum and the like, and an additive such as stearyl alcohol and the like.

While the dose and administration frequency of compound (I) or a pharmaceutically acceptable salt thereof used in the present invention vary depending on the administration form, age and body weight of patients, nature or severity of the symptoms to be treated, and the like, it is generally 0.01-1000 mg, preferably 0.05-100 mg, by oral administration to an adult, which is administered in one to several portions per day. For intravenous administration, external use and the like, 0.001-1000 mg, preferably 0.01-100 mg, is administered to an adult in one to several portions per day. However, such dose and administration frequency vary depending on the aforementioned various conditions.

The present invention is explained in more detail in the following by referring to Examples and Reference Examples. The scope of the present invention is not limited by these Examples and Reference Examples.

The proton nuclear magnetic resonance spectrum ($^1$H NMR) used in the Examples were measured at 270 MHz, 300 MHz or 400 MHz, and exchanging proton may not be observed clearly depending on the compound and measurement conditions. The indication of the multiplicity of the signals is conventional, where br means an apparently broad signal. For nomenclature of each synthesized compound, ChemBioDraw Ultra version 11.0.1 was used where necessary.

Example 1

4-(4-fluoro-2-methylphenylamino)-5-[4-(4-fluorophenyl)piperidine-1-carbonyl]pyridine-2-sulfonic acid (compound 1)

(step 1) 4,6-Dichloronicotinic acid (19.4 g, 101 mmol) was dissolved in DMF (300 mL), HATU (50.0 g, 131 mmol), N,N-diisopropylethylamine (53 mL, 0.30 mol) and 4-(4-fluorophenyl)piperidine hydrochloride (26.2 g, 121 mmol) were added, and the mixture was stirred at room temperature for 5 hr. To the reaction mixture was added saturated aqueous sodium hydrogen carbonate solution, and the mixture was extracted with ethyl acetate. The organic layer was washed with 10% aqueous citric acid solution and water, and dried over anhydrous magnesium sulfate. The solvent was evaporated under reduced pressure. The residue was purified by silica gel column chromatography (hexane/ethyl acetate=1/1), and reslurried with a mixed solvent (1:1) of 2-propanol and ethyl acetate to give (4,6-dichloropyridin-3- yl][4-(4-fluorophenyl)piperidin-1-yl]methanone (25.5 g, 71%).

ESIMS m/z: 353 (M+H)$^+$ (step 2) 4-Fluoro-2-methylaniline (5.2 mL, 45 mmol) was dissolved in THF (40 mL), 1.0 mol/L lithium bis(trimethylsilyl)amide/THF solution (45 mL, 45 mmol) was added dropwise at −78° C., and the mixture was stirred at −78° C. for 1 hr. To the reaction mixture was added (4,6-dichloropyridin-3-yl) [4-(4-fluorophenyl)piperidin-1-yl]methanone (4.00 g, 11.3 mmol) obtained in step 1, and the mixture was stirred at −78° C. for 30 min and at 0° C. for 30 min. To the reaction mixture was added saturated aqueous ammonium chloride solution, and the mixture was extracted with ethyl acetate. The organic layer was dried over anhydrous magnesium sulfate, and the solvent was evaporated under reduced pressure. The residue was purified by silica gel column chromatography (hexane/ethyl acetate=1/1) to give [6-chloro-4-(4-fluoro-2-methylphenylamino)pyridin-3-yl][4-(4-fluorophenyl)piperidin-1-yl]methanone (6.00 g, quantitative).

ESIMS m/z: 442 (M+H)$^+$ (step 3) [6-Chloro-4-(4-fluoro-2-methylphenylamino)pyridin-3-yl][4-(4-fluorophenyl)piperidin-1-yl]methanone (1.00 g, 2.26 mmol) obtained in step 2 was dissolved in DMF (9 mL), sodium hydrogen sulfide n hydrate (906 mg, 11.3 mmol) was added, and the mixture was stirred at 120° C. for 2 hr. To the reaction mixture was added saturated aqueous sodium chloride solution, and the mixture was extracted with ethyl acetate. The organic layer was washed with water, and dried over anhydrous magnesium sulfate. The solvent was evaporated under reduced pressure. The residue was purified by silica gel column chromatography (chloroform/methanol=20/1), and reslurried with ethyl acetate to give [4-(4-fluoro-2-methylphenylamino)-6-mercaptopyridin-3-yl][4-(4-fluorophenyl)piperidin-1-yl]methanone (845 mg, 85%).

ESIMS m/z: 440 (M+H)$^+$ (step 4) [4-(4-Fluoro-2-methylphenylamino)-6-mercaptopyridin-3-yl][4-(4-fluorophenyl)piperidin-1-yl]methanone (50.0 mg, 0.114 mmol) obtained in step 3 was dissolved in acetonitrile (2 mL), 30% aqueous hydrogen peroxide solution (1.0 mL, 9.8 mmol) was added, and the mixture was stirred at room temperature for 17 hr. To the reaction mixture was added saturated aqueous sodium chloride solution, and the mixture was extracted with ethyl acetate. The organic layer was dried over anhydrous magnesium sulfate, and the solvent was evaporated under reduced pressure to give compound 1 (54.7 mg, 99%).

ESIMS m/z: 488 (M+H)$^+$; $^1$H NMR (300 MHz, DMSO-d$_6$, δ): 1.58-1.83 (m, 4H), 2.18 (s, 3H), 2.74-2.93 (m, 3H), 3.65-3.83 (m, 1H), 4.44-4.65 (m, 1H), 6.59 (s, 1H), 7.08-7.26 (m, 3H), 7.28-7.38 (m, 4H), 8.29 (s, 1H), 9.73 (s, 1H).

Example 2

4-(4-fluoro-2-methylphenylamino)-5-[4-(4-fluorophenyl)piperidine-1-carbonyl]pyridine-2-sulfonamide (compound 2)

Compound 1 (55.6 mg, 0.114 mmol) was dissolved in acetonitrile (1 mL), N,N-diisopropylethylamine (0.20 mL, 1.1 mmol) and phosphorus oxychloride (0.11 mL, 1.1 mmol) were added under ice-cooling, and the mixture was stirred at room temperature for 30 min. The reaction mixture was dissolved in acetonitrile (1 mL), and added dropwise to a solution of 25% aqueous ammonia solution (0.78 mL, 11 mmol) in acetonitrile (1 mL) under ice-cooling, and the mixture was stirred at room temperature for 1 hr. To the reaction mixture were added water and saturated aqueous sodium hydrogen carbonate solution, and the mixture was extracted with ethyl acetate. The organic layer was dried over anhydrous magnesium sulfate, the solvent was evaporated under reduced pressure, and the residue was purified by silica gel column chromatography (ethyl acetate) to give compound 2 (28.6 mg, 52%).

ESIMS m/z: 487 (M+H)$^+$; $^1$H NMR (400 MHz, CDCl$_3$, δ): 1.65-1.77 (m, 2H), 1.97-2.04 (m, 2H), 2.24 (s, 3H), 2.80-2.90 (m, 1H), 3.03-3.23 (m, 2H), 4.23-4.75 (m, 2H), 5.17 (s, 2H), 6.94-7.05 (m, 4H), 7.14-7.23 (m, 4H), 8.08 (s, 1H), 8.31 (s, 1H).

Example 3

4-(1,3-dihydroisobenzofuran-5-ylamino)-5-[4-(4-fluorophenyl)piperidine-1-carbonyl]pyridine-2-sulfonamide (compound 3)

(step 1) Using (4,6-dichloropyridin-3-yl)[4-(4-fluorophenyl)piperidin-1-yl]methanone (800 mg, 2.27 mmol) obtained in Example 1, step 1, and 1,3-dihydroisobenzofuran-5-amine (459 mg, 3.40 mmol), and in the same manner as in Example 1, step 2, [6-chloro-4-(1,3-dihydroisobenzofuran-5-ylamino)pyridin-3-yl][4-(4-fluorophenyl)piperidin-1-yl]methanone (1.00 g, 98%) was obtained.

ESIMS m/z: 452 (M+H)$^+$ (step 2) Using [6-chloro-4-(1,3-dihydroisobenzofuran-5-ylamino)pyridin-3-yl][4-(4-fluorophenyl)piperidin-1-yl]methanone (1.00 g, 2.22 mmol) obtained in step 1, and in the same manner as in Example 1, step 3, a crude product of [4-(1,3-dihydroisobenzofuran-5-ylamino)-6-mercaptopyridin-3-yl][4-(4-fluorophenyl)piperidin-1-yl]methanone was obtained and used for the next reaction without purification.

ESIMS m/z: 450 (M+H)$^+$ (step 3) Using a crude product of [4-(1,3-dihydroisobenzofuran-5-ylamino)-6-mercaptopyridin-3-yl][4-(4-fluorophenyl)piperidin-1-yl]methanone obtained in step 2, and in the same manner as in Example 1, step 4, 4-(1,3-dihydroisobenzofuran-5-ylamino)-5-[4-(4-fluorophenyl)piperidine-1-carbonyl]pyridine-2-sulfonic acid (1.00 g, yield of 2 steps 91%) was obtained.

ESIMS m/z: 498 (M+H)$^+$ (step 4) Using 4-(1,3-dihydroisobenzofuran-5-ylamino)-5-[4-(4-fluorophenyl)piperidine-1-carbonyl]pyridine-2-sulfonic acid (200 mg, 0.400 mmol) obtained in step 3, and in the same manner as in Example 2, compound 3 (28.9 mg, 14%) was obtained.

ESIMS m/z: 497 (M+H)$^+$; $^1$H NMR (300 MHz, CDCl$_3$, δ): 1.50-1.90 (m, 4H), 2.70-2.95 (m, 2H), 3.15-3.35 (m, 1H), 3.45-3.80 (m, 1H), 4.50-4.75 (m, 1H), 5.00 (s, 4H), 7.05-7.50 (m, 10H), 8.30 (s, 1H), 8.70 (s, 1H).

Example 4

5-[4-(4-fluorophenyl)piperidine-1-carbonyl]-4-(quinolin-6-ylamino)pyridine-2-sulfonamide (compound 4)

(step 1) Using (4,6-dichloropyridin-3-yl)[4-(4-fluorophenyl)piperidin-1-yl]methanone (800 mg, 2.26 mmol) obtained in Example 1, step 1, and quinolin-6-amine (490 mg, 3.40 mmol), and in the same manner as in Example 1, step 2, [6-chloro-4-(quinolin-6-ylamino)pyridin-3-yl][4-(4- fluorophenyl)piperidin-1-yl]methanone (800 mg, 80%) was obtained.

ESIMS m/z: 461 (M+H)$^+$ (step 2) Using [6-chloro-4-(quinolin-6-ylamino)pyridin-3-yl][4-(4-fluorophenyl)piperidin-1-yl]methanone (1.18 g, 2.56 mmol) obtained in step 1, and in the same manner as in Example 1, step 3, a crude product of [4-(4-fluorophenyl)piperidin-1-yl][6-mercapto-4-(quinolin-6-ylamino)pyridin-3-yl]methanone was obtained and used for the next reaction without purification.

ESIMS m/z: 459 (M+H)$^+$ (step 3) Using a crude product of [4-(4-fluorophenyl)piperidin-1-yl][6-mercapto-4-(quinolin-6-ylamino)pyridin-3-yl]methanone obtained in step 2, and in the same manner as in Example 1, step 4, 5-[4-(4-fluorophenyl)piperidine-1-carbonyl]-4-(quinolin-6-ylamino)pyridine-2-sulfonic acid (900 mg, yield of 2 steps 69%) was obtained.

ESIMS m/z: 507 (M+H)$^+$ (step 4) Using 5-[4-(4-fluorophenyl)piperidine-1-carbonyl]-4-(quinolin-6-ylamino)pyridine-2-sulfonic acid (450 mg, 0.890 mmol) obtained in step 3, and in the same manner as in Example 2, compound 4 (21.7 mg, 5%) was obtained.

ESIMS m/z: 506 (M+H)$^+$; $^1$H NMR (300 MHz, DMSO-d$_6$, δ): 1.50-1.85 (m, 4H), 2.65-2.95 (m, 2H), 3.15-3.35 (m, 1H), 3.55-3.85 (m, 1H), 4.45-4.80 (m, 1H), 7.05-7.85 (m, 10H), 8.04 (d, J=9.0 Hz, 1H), 8.29 (d, J=7.5 Hz, 1H), 8.38 (s, 1H), 8.81-8.86 (m, 1H), 9.10 (s, 1H).

Example 5

N-cyclopropyl-4-(4-fluoro-2-methylphenylamino)-5-[4-(4-fluorophenyl)piperidine-1-carbonyl]pyridine-2-sulfonamide (compound 5)

[4-(4-Fluoro-2-methylphenylamino)-6-mercaptopyridin-3-yl][4-(4-fluorophenyl)piperidin-1-yl]methanone (100 mg, 0.228 mmol) obtained in Example 1, step 3 was dissolved in acetonitrile (1.14 mL), potassium nitrate (46 mg, 0.455 mmol) and sulfuryl chloride (0.037 mL, 0.455 mmol) were added under ice-cooling, and the mixture was stirred for 1 hr. To the reaction mixture was added cyclopropylamine (0.08 mL, 1.138 mmol), and the mixture was stirred at 0° C. for 1 hr. Saturated brine was added to the reaction mixture, and the mixture was extracted with ethyl acetate. The organic layer was dried over anhydrous magnesium sulfate, and the solvent was evaporated under reduced pressure. The residue was purified by silica gel column chromatography (chloroform/methanol-100/0-92/8) to give compound 5 (40 mg, 33%).

ESIMS m/z: 527 (M+H)$^+$; $^1$H NMR (270 MHz, CDCl$_3$, δ): 0.56-0.72 (m, 4H), 1.67-1.76 (m, 2H), 1.98-2.03 (m, 2H), 2.25 (s, 3H), 2.30-2.37 (m, 1H), 2.81-2.89 (m, 1H), 3.12-3.18 (m, 2H), 4.50-4.54 (m, 2H), 5.21 (s, 1H), 6.95-7.05 (m, 4H), 7.15-7.26 (m, 4H), 8.04 (s, 1H), 8.35 (s, 1H).

Example 6

2-{4-(4-fluoro-2-methylphenylamino)-5-[4-(4-fluorophenyl)piperidine-1-carbonyl]pyridine-2-sulfonamide}-N-methylacetamide (compound 6)

(step 1) Using [4-(4-fluoro-2-methylphenylamino)-6-mercaptopyridin-3-yl][4-(4-fluorophenyl)piperidin-1-yl]methanone (200 mg, 0.455 mmol) obtained in Example 1, step 3, and methyl 2-aminoacetate hydrochloride (286 mg, 2.28 mmol), and in the same manner as in Example 5, methyl 2-{4-(4-fluoro-2-methylphenylamino)-5-[4-(4-fluorophenyl)piperidine-1-carbonyl]pyridine-2-sulfonamide}acetate (compound 113) (52 mg, 20%) was obtained.

ESIMS m/z: 559 (M+H)$^+$ (step 2) Compound 113 (150 mg, 0.269 mmol) was dissolved in methanol (3.0 mL), 4 mol/L aqueous sodium hydroxide solution (1.00 mL, 4.00 mmol) was added, and the mixture was stirred at room temperature for 30 min. To the reaction mixture was added saturated aqueous ammonium chloride solution, and the mixture was extracted with ethyl acetate. The organic layer was washed with saturated aqueous sodium chloride solution, and dried over anhydrous magnesium sulfate. The solvent was evaporated under reduced pressure. The residue was purified by silica gel column chromatography (chloroform/methanol=100/0-90/10) to give 2-{4-(4-fluoro-2-methylphenylamino)-5-[4-(4-fluorophenyl)piperidine-1-carbonyl]pyridine-2-sulfonamide}acetic acid (compound 118) (35 mg, 24%).

ESIMS m/z: 545 (M+H)$^+$ (step 3) Compound 118 (26 mg, 0.048 mmol) was dissolved in dichloromethane (2.0 mL), HOBt (43.9 mg, 0.286 mmol), 2.0 mol/L methylamine/THF solution (0.239 mL, 0.477 mmol) and EDC (54.9 mg, 0.286 mmol) were added, and the mixture was stirred at room temperature for 6 hr. To the reaction mixture was added 2 mol/L hydrochloric acid, and the mixture was extracted with ethyl acetate. The organic layer was washed with saturated aqueous sodium chloride solution, and dried over anhydrous magnesium sulfate. The solvent was evaporated under reduced pressure. The residue was purified by preparative thin layer chromatography (chloroform/methanol=90/10) to give compound 6 (24 mg, 90%).

ESIMS m/z: 558 (M+H)$^+$; $^1$H NMR (400 MHz, CDCl$_3$, δ): 1.60-1.75 (m, 4H), 1.95-2.03 (m, 2H), 2.25 (s, 3H), 2.80 (d, J=4.8 Hz, 3H), 2.82-2.90 (m, 1H), 3.01-3.25 (m, 1H), 3.75 (d, J=6.0 Hz, 2H), 4.20-4.75 (m, 1H), 6.12 (t, J=6.0 Hz, 1H), 6.71-6.77 (m, 1H), 6.94-7.06 (m, 4H), 7.15-7.22 (m, 4H), 8.10 (s, 1H), 8.30 (s, 1H).

Example 7

N-{1-{4-(4-fluoro-2-methylphenylamino)-5-[4-(4-fluorophenyl)piperidine-1-carbonyl]pyridin-2-ylsulfonyl}pyrrolidin-3-yl}acetamide (compound 7)

Using compound 1 (300 mg, 0.615 mmol) and N-(pyrrolidin-3-yl)acetamide (0.362 mL, 3.08 mmol), and in the same manner as in Example 2, compound 7 (32 mg, 8.7%) was obtained.

ESIMS m/z: 598 (M+H)$^+$ $^1$H NMR (400 MHz, CDCl$_3$, δ): 1.62-1.76 (m, 2H), 1.91-2.05 (m, 4H), 1.98 (s, 3H), 2.09-2.18 (m, 1H), 2.25 (s, 3H), 2.81-2.90 (m, 1H), 3.04-3.24 (m, 2H), 3.42 (dd, J=8.8, 16.4 Hz, 1H), 3.49-3.58 (m, 2H), 3.66 (dd, J=4.8, 10.6 Hz, 1H), 4.47-4.55 (m, 2H), 6.87 (d, J=6.8 Hz, 1H), 6.94-7.05 (m, 4H), 7.15-7.23 (m, 4H), 8.01 (s, 1H), 8.26 (s, 1H).

Example 8

4-(4-fluoro-2-methylphenylamino)-5-[4-(4-fluorophenyl)piperidine-1-carbonyl]-N-(1-methyl-2-oxopyrrolidin-3-yl)pyridine-2-sulfonamide (compound 8)

Using compound 1 (96.4 mg, 0.198 mmol) and 3-amino-1-(226 mg, 1.98 mmol), and in the same manner as in Example 2, compound 8 (65.8 mg, 57%) was obtained.

ESIMS m/z: 584 (M+H)$^+$; $^1$H NMR (400 MHz, CDCl$_3$, δ): 1.24-1.29 (m, 1H), 1.63-1.79 (m, 2H), 1.95-2.03 (m, 2H), 2.05-2.18 (m, 1H), 2.27 (s, 3H), 2.58-2.70 (m, 1H), 2.79-2.90 (m, 2H), 2.86 (s, 3H), 3.03-3.20 (m, 2H), 3.27-3.34 (m, 2H), 4.08-4.17 (m, 1H), 6.55 (s, 1H), 6.94-7.06 (m, 4H), 7.15-7.29 (m, 4H), 8.10 (s, 1H), 8.34 (s, 1H).

Example 9

[4-(4-fluoro-2-methylphenylamino)-6-(piperazin-1-ylsulfonyl)pyridin-3-yl][4-(4-fluorophenyl)piperidin-1-yl]methanone (compound 9)

(step 1) Using compound 1 (300 mg, 0.615 mmol) and tert-butyl piperazine-1-carboxylate (573 mg, 3.08 mmol), and in the same manner as in Example 2, tert-butyl 4-{4-(4-fluoro-2-methylphenylamino)-5-[4-(4-fluorophenyl)piperidine-1-carbonyl]pyridin-2-ylsulfonyl}piperazine-1-carboxylate (30 mg, 7.4%) was obtained.

ESIMS m/z: 656 (M+H)$^+$ (step 2) tert-Butyl 4-{4-(4-fluoro-2-methylphenylamino)-5-[4-(4-fluorophenyl)piperidine-1-carbonyl]pyridin-2-ylsulfonyl}piperazine-1-carboxylate (30 mg, 0.046 mmol) obtained in step 1 was dissolved in dichloromethane (2.0 mL), trifluoroacetic acid (0.035 mL, 0.457 mmol) was added, and the mixture was stirred at room temperature for 1 hr. The solvent of the reaction mixture was evaporated under reduced pressure. The residue was purified by preparative thin layer chromatography (chloroform/methanol=90/10) to give compound 9 (7.0 mg, 28%).

ESIMS m/z: 556 (M+H)$^+$; $^1$H NMR (400 MHz, CDCl$_3$, δ): 1.63-1.78 (m, 2H), 1.95-2.07 (m, 4H), 2.25 (s, 3H), 2.80-2.90 (m, 1H), 2.95 (dd, J=4.8, 4.8 Hz, 4H), 3.07-3.18 (m, 1H), 3.31 (dd, J=4.8, 4.8 Hz, 4H), 4.25-4.73 (m, 1H), 6.95-7.05 (m, 4H), 7.13 (s, 1H), 7.16-7.27 (m, 3H), 8.05 (s, 1H), 8.34 (s, 1H).

Example 10

[6-(4-aminopiperidin-1-ylsulfonyl)-4-(4-fluoro-2-methylphenylamino)pyridin-3-yl][4-(4-fluorophenyl)piperidin-1-yl]methanone (compound 10)

(step 1) Using compound 1 (135 mg, 0.277 mmol) and tert-butyl piperidin-4-ylcarbamate (554 mg, 2.77 mmol), and in the same manner as in Example 2, tert-butyl 1-{4-(4-fluoro-2-methylphenylamino)-5-[4-(4-fluorophenyl)piperidine-1-carbonyl]pyridin-2-ylsulfonyl}piperidin-4-ylcarbamate (178.6 mg, 96%) was obtained.

ESIMS m/z: 670 (M+H)$^+$ (step 2) Using tert-butyl 1-{4-(4-fluoro-2-methylphenylamino)-5-[4-(4-fluorophenyl)piperidine-1-carbonyl]pyridin-2-ylsulfonyl}piperidin-4-ylcarbamate (175 mg, 0.261 mmol) obtained in step 1, and in the same manner as in Example 9, step 2, compound 10 (112.6 mg, 76%) was obtained.

ESIMS m/z: 570 (M+H)$^+$; $^1$H NMR (400 MHz, DMSO-d$_6$, δ): 1.55-1.90 (m, 8H), 2.16 (s, 3H), 2.55-2.65 (m, 2H), 2.68-2.92 (m, 4H), 3.48-3.58 (m, 4H), 4.50-4.70 (m, 2H), 6.64 (s, 1H), 7.08-7.19 (m, 3H), 7.20-7.43 (m, 4H), 8.26 (s, 1H), 8.45 (s, 1H).

Example 11

4-(4-fluoro-2-methylphenylamino)-5-[4-(4-fluorophenyl)piperidine-1-carbonyl]-N-(isoxazol-3-yl)pyridine-2-sulfonamide (compound 11)

Compound 1 (300 mg, 0.615 mmol) was dissolved in acetonitrile (5 mL), N,N-diisopropylethylamine (0.32 mL, 1.8 mmol) and phosphorus oxychloride (0.17 mL, 1.8 mmol) were added under ice-cooling, and the mixture was stirred at room temperature for 1 hr. The reaction mixture was dissolved in acetonitrile (3 mL), to a solution of isoxazol-3-amine (0.45 mL, 6.2 mmol) and pyridine (0.99 mL, 12 mmol) in acetonitrile (3 mL) was added dropwise under ice-cooling, and the mixture was stirred at room temperature for 24 hr. To the reaction mixture was added 2 mol/L hydrochloric acid, and the mixture was extracted with ethyl acetate. The organic layer was dried over anhydrous magnesium sulfate, the solvent was evaporated under reduced pressure, and the residue was purified by silica gel column chromatography (ethyl acetate) to give compound 11 (57.6 mg, 17%).

ESIMS m/z: 554 (M+H)$^+$; $^1$H NMR (300 MHz, CDCl$_3$, δ): 1.46-1.74 (m, 4H), 1.92-2.03 (m, 2H), 2.19 (s, 3H), 2.76-2.89 (m, 1H), 3.00-3.21 (m, 1H), 4.25-4.70 (m, 1H), 6.53 (d, J=1.8 Hz, 1H), 6.90-7.19 (m, 8H), 8.16 (s, 1H), 8.20 (d, J=1.8 Hz, 1H), 8.36 (s, 1H).

Example 12

4-(4-fluoro-2-methylphenylamino)-5-[4-(4-fluorophenyl)piperidine-1-carbonyl]-N-(3-methylisoxazol-5-yl)pyridine-2-sulfonamide (compound 12)

Using compound 1 (100 mg, 0.205 mmol) and 3-methylisoxazol-5-amine (291 mg 2.96 mmol), and in the same manner as in Example 11, compound 12 (18.8 mg, 17%) was obtained.

ESIMS m/z: 568 (M+H)$^+$; $^1$H NMR (300 MHz, CDCl$_3$, δ): 1.20-1.36 (m, 1H), 1.56-1.76 (m, 2H), 1.92-2.03 (m, 3H), 2.17 (s, 3H), 2.20 (s, 3H), 2.76-2.89 (m, 1H), 3.00-3.21 (m, 1H), 4.25-4.70 (m, 1H), 5.63 (s, 1H), 6.90-7.06 (m, 4H), 7.11-7.21 (m, 4H), 8.19 (s, 1H), 8.32 (s, 1H).

Example 13

N-{4-(4-fluoro-2-methylphenylamino)-5-[4-(4-fluorophenyl)piperidine-1-carbonyl]pyridine-2-sulfonyl}acetamide (compound 13)

Acetic acid (0.071 mL, 1.23 mmol) was dissolved in DMF (2.5 mL), CDI (200 mg, 1.23 mmol) was added, and the mixture was stirred at room temperature for 2 hr. To the reaction mixture were added compound 2 (120 mg, 0.247 mmol) and DBU (0.22 mL, 1.48 mmol), and the mixture was stirred at 70° C. for 18 hr. To the reaction mixture was added 10% aqueous citric acid solution, and the mixture was extracted with ethyl acetate. The organic layer was dried over anhydrous magnesium sulfate, and the solvent was evaporated under reduced pressure. The residue was purified by silica gel column chromatography (chloroform/methanol=100/0-95/5) to give compound 13 (76 mg, 58%).

ESIMS m/z: 529 (M+H)$^+$; $^1$H NMR (400 MHz, CDCl$_3$, δ): 1.67-1.76 (m, 2H), 2.00-2.04 (m, 2H), 2.08 (s, 3H), 2.27 (s, 3H), 2.81-2.89 (m, 1H), 3.10-3.20 (m, 2H), 4.46-4.60 (m, 2H), 6.97-7.06 (m, 4H), 7.17-7.25 (m, 3H), 7.42 (s, 1H), 8.04 (s, 1H), 8.35 (s, 1H).

Example 14

2,2-difluoro-N-{4-(4-fluoro-2-methylphenylamino)-5-[4-(4-fluorophenyl)piperidine-1-carbonyl]pyridine-2-sulfonyl}cyclopropanecarboxamide (compound 14)

Using compound 2 (120 mg, 0.247 mmol) and 2,2-difluoropropanecarboxylic acid (151 mg, 1.233 mmol), and in the same manner as in Example 13, compound 14 (37 mg, 26%) was obtained.

ESIMS m/z: 591 (M+H)+; 1H NMR (400 MHz, CDCl3, δ): 1.62-1.77 (m, 3H), 1.99-2.10 (m, 3H), 2.27 (s, 3H), 2.65-2.72 (m, 1H), 2.81-2.89 (m, 1H), 3.10-3.20 (m, 2H), 4.45-4.53 (m, 2H), 6.97-7.06 (m, 4H), 7.17-7.25 (m, 3H), 7.52 (s, 1H), 8.29 (s, 1H), 8.35 (s, 1H).

Example 15

4-(benzylamino)-5-[4-(4-fluorophenyl)piperidine-1-carbonyl]pyridine-2-sulfonamide (compound 15)

(step 1) Using 4-(benzylamino)-6-chloronicotinic acid (3.55 g, 13.5 mmol) obtained by the method described in US2012/108566, and in the same manner as in Example 1, step 1, [4-(benzylamino)-6-chloropyridin-3-yl][4-(4-fluorophenyl)piperidin-1-yl]methanone (5.66 g, 99%) was obtained.

ESIMS m/z: 424 (M+H)+

(step 2) Using [4-(benzylamino)-6-chloropyridin-3-yl][4-(4-fluorophenyl)piperidin-1-yl]methanone (0.5 g, 1.18 mmol) obtained in step 1, and in the same manner as in Example 1, so step 3, [4-(benzylamino)-6-mercaptopyridin-3-yl][4-(4-fluorophenyl)piperidin-1-yl]methanone (0.3 g, 60%) was obtained.

ESIMS m/z: 422 (M+H)+

(step 3) Using [4-(benzylamino)-6-mercaptopyridin-3-yl][4-(4-fluorophenyl)piperidin-1-yl]methanone (0.3 g, 0.71 mmol), and 25% aqueous ammonia (0.436 g, 6.41 mmol) obtained in step 2, and in the same manner as in Example 5, compound 15 (0.17 g, 51%) was obtained.

ESIMS m/z: 469 (M+1H NMR (270 MHz, CDCl3, δ): 1.57-1.70 (m, 2H), 1.92-2.04 (m, 2H), 2.75-2.85 (m, 1H), 3.10-3.20 (m, 2H), 4.26-4.53 (m, 4H), 5.11 (br s, 2H), 6.70 (br t, J=5.9 Hz, 1H), 6.97-7.04 (m, 2H), 7.11-7.16 (m, 2H), 7.30-7.40 (m, 6H), 8.22 (s, 1H).

Example 16

4-(benzylamino)-5-[4-(4-fluorophenyl) piperidine-1-carbonyl]-N-(propylcarbamoyl)pyridine-2-sulfonamide (compound 16)

Compound 15 (55 mg, 0.12 mmol) was dissolved in acetone (1 mL), potassium carbonate (32 mg, 0.24 mmol) and n-propyl isocyanate (15 mg, 0.18 mmol) were added, and the mixture was stirred under reflux for 2 hr. To the reaction mixture was added 10% aqueous citric acid solution, and the mixture was extracted with chloroform. The organic layer was dried over anhydrous magnesium sulfate, and the solvent was evaporated under reduced pressure. The residue was purified by silica gel column chromatography (chloroform/methanol=100/0-95/5) to give compound 16 (22 mg, 34%).

ESIMS m/z: 554 (M+H)+; 1H NMR (270 MHz, CDCl3, δ): 0.88 (t, J 7.5 Hz, 1H), 1.49 (td, J=14.5, 7.5 Hz, 2H), 1.58-1.70 (m, 2H), 1.92-1.98 (m, 2H), 2.76-2.84 (m, 1H), 3.06-3.19 (m, 4H), 4.27-4.50 (m, 4H), 5.11 (br s, 2H), 6.73 (br t, J=5.5 Hz, 1H), 6.80 (br t, J=5.5 Hz, 1H), 6.98-7.05 (m, 2H), 7.12-7.17 (m, 2H), 7.31-7.40 (m, 6H), 8.24 (s, 1H).

Example 17

4-(4-chloro-2,5-dimethylphenylamino)-5-[4-(4-fluorophenyl)piperidine-1-carbonyl]pyridine-2-sulfonamide (compound 17)

(step 1) Methyl 4,6-dichloronicotinate (3.0 g, 14.6 mmol) was dissolved in ethanol (30 mL), 2,5-dimethylaniline (2.65 g, 21.8 mmol) and 12 mol/L hydrochloric acid (0.485 mL, 5.82 mmol) were added, and the mixture was stirred under reflux for 24 hr. The solvent of the reaction mixture was evaporated under reduced pressure, saturated aqueous sodium hydrogen carbonate solution was added, and the mixture was extracted with chloroform. The organic layer was dried over anhydrous magnesium sulfate, and the solvent was evaporated under reduced pressure. The residue was purified by silica gel column chromatography (chloroform/methanol=100/0-99/1) to give methyl 6-chloro-4-(2,5-dimethylphenylamino)nicotinate (4.23 g, quantitative).

ESIMS m/z: 291 (M+H)+

(step 2) Methyl 6-chloro-4-(2,5-dimethylphenylamino) nicotinate (4.23 g, 14.6 mmol) obtained in step 1 was dissolved in ethanol (22 mL), 4 mol/L aqueous sodium hydroxide solution (22 mL, 87 mmol) was added, and the mixture was stirred under reflux for 1 hr. The solvent of the reaction mixture was evaporated under reduced pressure, and 4 mol/L hydrochloric acid (45 mL) was added under ice-cooling. The precipitated solid was collected by filtration, and washed with water to give 6-chloro-4-(2,5-dimethylphenylamino)nicotinic acid (1.97 g, 49%).

ESIMS m/z: 277 (M+H)+

(step 3) Using 6-chloro-4-(2,5-dimethylphenylamino) nicotinic acid (1.97 g, 7.12 mmol) obtained in step 2, and in the same manner as in Example 1, step 1, [6-chloro-(2,5-dimethylphenylamino)pyridin-3-yl][4-(4-fluorophenyl)piperidin-1-yl]methanone (2.93 g, 94%) was obtained.

ESIMS m/z: 438 (M+H)+

(step 4) Using [6-chloro-(2,5-dimethylphenylamino)pyridin-3-yl][4-(4-fluorophenyl)piperidin-1-yl]methanone (2.9 g, 6.62 mmol) obtained in step 3, and in the same manner as in Example 1, step 3, [4-(2,5-dimethylphenylamino)-6-mercaptopyridin-3-yl][4-(4-fluorophenyl)piperidin-1-yl]methanone (2.77 g, 96%) was obtained.

ESIMS m/z: 436 (M+H)+

(step 5) Using [4-(2,5-dimethylphenylamino)-6-mercaptopyridin-3-yl][4-(4-fluorophenyl)piperidin-1-yl]methanone (2.7 g, 6.20 mmol) obtained in step 4, and 25% aqueous ammonia (3.80 g, 55.8 mmol), and in the same manner as in Example 5, compound 17 (1.25 g, 39%) was obtained.

ESIMS m/z: 517 (M+H)+; 1H NMR (300 MHz, CDCl3, δ): 1.63-1.77 (m, 2H), 1.95-2.00 (m, 2H), 2.17 (s, 3H), 2.33 (s, 3H), 2.79-2.87 (m, 1H), 2.97-3.20 (m, 2H), 4.26-4.53 (m, 2H), 5.58 (br s, 2H), 6.97-7.04 (m, 2H), 7.10 (s, 1H), 7.12-7.20 (m, 2H), 7.23 (s, 1H), 7.29 (s, 1H), 8.12 (s, 1H), 8.30 (s, 1H).

Example 18

4-(4-chloro-2,5-dimethylphenylamino)-5-[4-(4-fluorophenyl)piperidine-1-carbonyl]-N-(isopropylcarbamoyl)pyridine-2-sulfonamide (compound 18)

Using compound 17 (80 mg, 0.16 mmol) and isopropyl isocyanate (16 mg, 0.19 mmol), and in the same manner as in Example 16, compound 18 (33 mg, 35%) was obtained.

ESIMS m/z: 602 (M+H)+; 1H NMR (270 MHz, CDCl3, δ): 1.12 (d, J=6.6 Hz, 6H), 1.63-1.76 (m, 2H), 1.97-2.01 (m, 2H), 2.17 (s, 3H), 2.34 (s, 3H), 2.79-2.88 (m, 1H), 3.07-3.17 (m, 2H), 3.85-3.93 (m, 1H), 4.41-4.53 (m, 2H), 6.52 (br t, J=6.9 Hz, 1H), 6.98-7.04 (m, 3H), 7.10 (s, 1H), 7.11-7.21 (m, 3H), 7.29 (s, 1H), 8.19 (s, 1H), 8.32 (s, 1H).

Example 19 ethyl 4-(4-chloro-2,5-dimethylphenylamino)-5-[4-(4-fluorophenyl)piperidine-1-carbonyl]pyridin-2-ylsulfonylcarbamate (compound 19)

Compound 17 (120 mg, 0.23 mmol) was dissolved in a mixed solvent of acetonitrile (1 mL) and dichloromethane (1 mL), ethyl chloroformate (0.33 mL, 0.3 mmol) and N,N-diisopropylethylamine (0.1 mL, 0.56 mmol) were added, and the mixture was stirred at room temperature for 20 hr. To the reaction mixture was added 10% aqueous citric acid solution, and the mixture was extracted with chloroform. The organic layer was dried over anhydrous magnesium sulfate, and the solvent was evaporated under reduced pressure. The residue was purified by silica gel column chromatography (chloroform/methanol=100/0-95/5) to give compound 19 (40 mg, 29%).

ESIMS m/z: 589 (M+H)$^+$; $^1$H NMR (300 MHz, CDCl$_3$, δ): 1.17 (t, J=7.1 Hz, 3H), 1.64-1.74 (m, 2H), 1.97-2.04 (m, 2H), 2.20 (s, 3H), 2.35 (s, 3H), 2.80-2.86 (m, 1H), 3.05-3.16 (m, 2H), 4.12 (q, J=7.1 Hz, 2H), 4.40-4.60 (m, 2H), 6.98-7.04 (m, 2H), 7.14-7.19 (m, 3H), 7.29 (s, 1H), 7.46 (s, 1H), 8.19 (s, 1H), 8.35 (s, 1H), 8.86 (br s, 1H).

Example 20

4-(4-chloro-2-methylphenylamino)-5-[4-(4-fluorophenyl)piperidine-1-carbonyl]pyridine-2-sulfonamide (compound 20)

(step 1) Using methyl 4,6-dichloronicotinate (5.0 g, 24.3 mmol) and 4-chloro-2-methylaniline (5.15 g, 36.4 mmol), and in the same manner as in Example 17, step 1, methyl 6-chloro-4-(4-chloro-2-methylphenylamino)nicotinate (4.37 g, 58%) was obtained.

ESIMS m/z: 311 (M+H)$^+$ (step 2) Using methyl 6-chloro-4-(4-chloro-2-methylphenylamino)nicotinate (4.37 g, 14.0 mmol) obtained in step 1, and in the same manner as in Example 17, step 2, 6-chloro-4-(4-chloro-2-methylphenylamino)nicotinic acid (4.2 g, quantitative) was obtained.

ESIMS m/z: 297 (M+H)$^+$ (step 3) Using 6-chloro-4-(4-chloro-2-methylphenylamino)nicotinic acid (4.17 g, 14.0 mmol) obtained in step 2, and in the same manner as in Example 1, step 1, [6-chloro-4-(4-chloro-2-methylphenylamino)pyridin-3-yl][4-(4-fluorophenyl)piperidin-1-yl]methanone (4.70 g, 73%) was obtained.

ESIMS m/z: 458 (M+H)$^+$ (step 4) Using [6-chloro-4-(4-chloro-2-methylphenylamino)pyridin-3-yl][4-(4-fluorophenyl)piperidin-1-yl]methanone (4.70 g, 10.25 mmol) obtained in step 3, and in the same manner as in Example 1, step 3, [4-(4-chloro-2-methylphenylamino)-6-mercaptopyridin-3-yl][4-(4-fluorophenyl)piperidin-1-yl]methanone (3.63 g, 78%) was obtained.

ESIMS m/z: 456 (M+H)$^+$ (step 5) Using [4-(4-chloro-2-methylphenylamino)-6-mercaptopyridin-3-yl][4-(4-fluorophenyl)piperidin-1-yl]methanone (1.82 g, 3.99 mmol) obtained in step 4, and 25% aqueous ammonia (2.45 g, 35.9 mmol), and in the same manner as in Example 5, compound 20 (0.756 g, 38%) was obtained.

ESIMS m/z: 503 (M+H)$^+$; $^1$H NMR (400 MHz, CDCl$_3$, δ): 1.66-1.77 (m, 2H), 1.98-2.02 (m, 2H), 2.24 (s, 3H), 2.81-2.88 (m, 1H), 3.03-3.21 (m, 2H), 4.34-4.68 (m, 2H), 5.09 (br s, 2H), 6.99-7.03 (m, 2H), 7.16-7.23 (m, 4H), 7.31 (br s, 2H), 8.21 (s, 1H), 8.33 (s, 1H).

Example 21

4-(4-chloro-2-methylphenylamino)-N-(cyclopropylcarbamoyl)-5-[4-(4-fluorophenyl)piperidine-1-carbonyl]pyridine-2-sulfonamide (compound 21)

Using compound 20 (100 mg, 0.20 mmol) and cyclopropyl isocyanate (20 mg, 0.24 mmol), and in the same manner as in Example 16, compound 21 (48 mg, 41%) was obtained.

ESIMS m/z: 586 (M+H)$^+$; $^1$H NMR (300 MHz, CDCl$_3$, δ): 0.49-0.54 (m, 2H), 0.75-0.77 (m, 2H), 1.65-1.77 (m, 2H), 1.98-2.03 (m, 2H), 2.24 (s, 3H), 2.60-2.65 (m, 1H), 2.80-2.89 (m, 1H), 3.06-3.18 (m, 2H), 4.34-4.58 (m, 2H), 6.67-6.85 (m, 1H), 6.99-7.04 (m, 2H), 7.16-7.23 (m, 5H), 7.31-7.32 (m, 1H), 8.30 (s, 1H), 8.34 (s, 1H).

Example 22

N-(ethylcarbamoyl)-4-(4-fluoro-2-methylphenylamino)-5-[4-(4-fluorophenyl)piperidine-1-carbonyl]pyridine-2-sulfonamide (compound 22)

Using compound 2 (1.3 g, 2.67 mmol) and ethyl isocyanate (0.275 mL, 3.47 mmol), and in the same manner as in Example 16, compound 22 (0.86 g, 58%) was obtained.

ESIMS m/z: 558 (M+H)$^+$; $^1$H NMR (300 MHz, CDCl$_3$, δ): 1.11 (t, J=7.1 Hz, 3H), 1.65-1.76 (m, 2H), 1.97-2.07 (m, 2H), 2.23 (s, 3H), 2.80-2.88 (m, 1H), 3.13-3.29 (m, 4H), 4.38-4.63 (m, 2H), 6.62-6.69 (m, 1H), 6.92-7.04 (m, 4H), 7.16-7.24 (m, 4H), 8.17 (s, 1H), 8.34 (s, 1H).

Example 23

N-(ethylcarbamoyl)-4-(4-fluoro-2-methylphenylamino)-5-[4-(4-fluorophenyl)piperidine-1-carbonyl]-N-methylpyridine-2-sulfonamide (compound 23)

Compound 2 (56.0 mg, 0.115 mmol) was dissolved in acetone (0.92 mL), ethyl isocyanate (0.011 mL, 0.138 mmol) and potassium carbonate (20.7 mg, 0.150 mmol) were added, and the mixture was stirred at 120° C. for 4 hr. The reaction mixture was allowed to cool to room temperature, methyl p-toluenesulfonate (0.026 mL, 0.173 mmol) was added, and the mixture was stirred at 50° C. for 3 hr. To the reaction mixture were added water and saturated aqueous ammonium chloride solution, and the mixture was extracted with ethyl acetate. The solvent was evaporated under reduced pressure, and the residue was purified by silica gel column chromatography (heptane/ethyl acetate=1/1) to give compound 23 (18.5 mg, 28%).

ESIMS m/z: 572 (M+H)$^+$; $^1$H NMR (400 MHz, CDCl$_3$, δ): 1.10 (t, J=7.2 Hz, 3H), 1.23-1.31 (m, 2H), 1.65-1.78 (m, 2H), 1.97-2.05 (m, 2H), 2.25 (s, 3H), 2.80-2.91 (m, 1H), 3.04-3.32 (m, 5H), 3.19 (s, 3H), 6.95-7.08 (m, 3H), 7.12 (s, 1H), 7.15-7.23 (m, 4H), 8.14 (s, 1H), 8.31 (s, 1H).

Example 24

3-chloro-4-(4-fluoro-2-methylphenylamino)-5-[4-(4-fluorophenyl)piperidine-1-carbonyl]pyridine-2-sulfonic acid (compound 24)

(step 1) Using 4,5,6-trichloronicotinic acid (964 mg, 4.26 mmol) obtained by the method described in the document (Journal of Medicinal Chemistry, 2006, 49, p. 441), and in the same manner as in Example 1, step 2, 5,6-dichloro-4-(4-fluoro-2-methylphenylamino)nicotinic acid (1.18 g, 88%) was obtained. ESIMS m/z: 315 (M+H)+

(step 2) Using 5,6-dichloro-4-(4-fluoro-2-methylphenylamino)nicotinic acid (990 mg, 3.14 mmol) obtained in step 1, and in the same manner as in Example 1, step 1, [5,6-dichloro-4-(4-fluoro-2-methylphenylamino)pyridin-3-yl][4-(4-fluorophenyl)piperidin-1-yl]methanone (1.35 g, 90%) was obtained.

ESIMS m/z: 476 (M+H)+

(step 3) Using [5,6-dichloro-4-(4-fluoro-2-methylphenylamino)pyridin-3-yl][4-(4-fluorophenyl)piperidin-1-yl]methanone (8.89 g, 18.7 mmol) obtained in step 2, and in the same manner as in Example 1, step 3, [5-chloro-4-(4-fluoro-2-methylphenylamino)-6-mercaptopyridin-3-yl][4-(4-fluorophenyl)piperidin-1-yl]methanone (7.44 g, 84%) was obtained.

ESIMS m/z: 474 (M+H)+

(step 4) Using [5-chloro-4-(4-fluoro-2-methylphenylamino)-6-mercaptopyridin-3-yl][4-(4-fluorophenyl)piperidin-1-yl]methanone (9.90 g, 20.9 mmol) obtained in step 3, and in the same manner as in Example 1, step 4, compound 24 (7.78 g, 71%) was obtained.

ESIMS m/z: 522 (M+H)+; $^1$H NMR (400 MHz, DMSO-$d_5$, δ): 1.35-1.55 (m, 2H), 1.60-1.70 (m, 2H), 1.84-2.04 (m, 1H), 2.18 (s, 3H), 2.63-3.03 (m, 3H), 3.89-4.09 (m, 1H), 6.94-7.16 (m, 5H), 7.21-7.35 (m, 3H), 7.92 (s, 1H).

Example 25

3-chloro-4-(4-fluoro-2-methylphenylamino)-5-[4-(4-fluorophenyl)piperidine-1-carbonyl]pyridine-2-sulfonamide (compound 25)

Using compound 24 (3.00 g, 5.75 mmol), and in the same manner as in Example 2, compound 25 (2.24 g, 75%) was obtained. ESIMS m/z: 521 (M+H)+; $^1$H NMR (400 MHz, CDCl$_3$, δ): 1.39-1.57 (m, 2H), 1.76-1.83 (m, 2H), 2.02-2.24 (m, 1H), 2.33 (s, 3H), 2.60-2.99 (m, 2H), 3.57-3.64 (m, 1H), 4.23-4.32 (m, 1H), 5.68 (s, 2H), 6.72 (s, 1H), 6.85-6.92 (m, 1H), 6.97-7.06 (m, 4H), 7.11 (dd, J=4.9, 8.8 Hz, 2H), 8.00 (s, 1H).

Example 26

3-chloro-5-[4-(4-fluorophenyl)piperidine-1-carbonyl]-4-(m-tolylamino)pyridine-2-sulfonamide (compound 26)

(step 1) Using 4,5,6-trichloronicotinic acid (700 mg, 3.09 mmol) and m-toluidine (0.507 mL, 4.64 mmol), and in the same manner as in Example 1, step 2, 5,6-dichloro-4-(m-tolylamino)nicotinic acid (820 mg, 89%) was obtained.

ESIMS m/z: 297 (M+H)+

(step 2) Using 1 5,6-dichloro-4-(m-tolylamino)nicotinic acid (800 mg, 2.69 mmol) obtained in step 1, and in the same manner as in Example 1, step 1, [5,6-dichloro-4-(m-tolylamino)pyridin-3-yl][4-(4-fluorophenyl)piperidin-1-yl]methanone (1.10 g, 89%) was obtained.

ESIMS m/z: 458 (M+H)$^{30}$ (step 3) Using [5,6-dichloro-4-(m-tolylamino)pyridin-3-yl][4-(4-fluorophenyl)piperidin-1-yl]methanone (1.25 g, 2.73 mmol) obtained in step 2, and in the same manner as in Example 1, step 3, [5-chloro-6-mercapto-4-(m-tolylamino)pyridin-3-yl][4-(4-fluorophenyl)piperidin-1-yl]methanone (1.00 g, 80%) was obtained.

ESIMS m/z: 456 (M+H)+

(step 4) Using [5-chloro-6-mercapto-4-(m-tolylamino)pyridin-3-yl][4-(4-fluorophenyl)piperidin-1-yl]methanone (950 mg, 2.08 mmol) obtained in step 3, and in the same manner as in Example 1, step 4, 3-chloro-5-[4-(4-fluorophenyl)piperidine-1-carbonyl]-4-(m-tolylamino)pyridine-2-sulfonic acid (900 mg, 86%) was obtained.

ESIMS m/z: 504 (M+H)+

(step 5) Using 3-chloro-5-[4-(4-fluorophenyl)piperidine-1-carbonyl]-4-(m-tolylamino)pyridine-2-sulfonic acid (800 mg, 1.59 mmol) obtained in step 4, and in the same manner as in Example 2, compound 26 (250 mg, 31%) was obtained.

ESIMS m/z: 503 (M+H)+; $^1$H NMR (400 MHz, CD$_3$OD, δ): 1.60-1.95 (m, 4H), 2.35 (s, 3H), 2.61-2.73 (m, 1H), 2.94-3.10 (m, 1H), 3.45-3.58 (m, 2H), 3.93-4.15 (m, 1H), 6.93-7.09 (m, 6H), 7.14-7.33 (m, 4H), 8.18 (s, 1H).

Example 27

3-chloro-4-(2,4-difluorophenylamino)-5-[4-(4-fluorophenyl)piperidine-1-carbonyl]pyridine-2-sulfonamide (compound 27)

(step 1) Using 4,5,6-trichloronicotinic acid (500 mg, 2.21 mmol) and 2,4-difluoroaniline (371 mg, 2.87 mmol), and in the same manner as in Example 1, step 2, a crude product of 5,6-dichloro-4-(2,4-difluorophenylamino)nicotinic acid was obtained and used for the next reaction without purification.

ESIMS m/z: 319 (M+H)+

(step 2) Using a crude product of 5,6-dichloro-4-(2,4-difluorophenylamino)nicotinic acid obtained in step 1, and in the same manner as in Example 1, step 1, [5,6-dichloro-4-(2,4-difluorophenylamino)pyridin-3-yl][4-(4-fluorophenyl)piperidin-1-yl]methanone (1.00 g, yield of 2 steps 67%) was obtained.

ESIMS m/z: 480 (M+H)+

(step 3) Using [5,6-dichloro-4-(2,4-difluorophenylamino)pyridin-3-yl][4-(4-fluorophenyl)piperidin-1-yl]methanone (900 mg, 1.87 mmol) obtained in step 2, and in the same manner as in Example 1, step 3, a crude product of [5-chloro-4-(2,4-difluorophenylamino)-6-mercaptopyridin-3-yl][4-(4-fluorophenyl)piperidin-1-yl]methanone was obtained and used for the next reaction without purification.

ESIMS m/z: 478 (M+H)+

(step 4) Using a crude product of [5-chloro-4-(2,4-difluorophenylamino)-6-mercaptopyridin-3-yl][4-(4-fluorophenyl)piperidin-1-yl]methanone obtained in step 3, and in the same manner as in Example 1, step 4, 3-chloro-4-(2,4-difluorophenylamino)-5-[4-(4-fluorophenyl)piperidine-1-carbonyl]pyridine-2-sulfonic acid (630 mg, yield of 2 steps 64%) was obtained.

ESIMS m/z: 526 (M+H)+

(step 5) Using 3-chloro-4-(2,4-difluorophenylamino)-5-[4-(4-fluorophenyl)piperidine-1-carbonyl]pyridine-2-sulfonic acid (840 mg, 1.60 mmol) obtained in step 4, and in the same manner as in Example 2, compound 27 (92.1 mg, 11%) was obtained.

ESIMS m/z: 525 (M+H)+; $^1$H NMR (300 MHz, DMSO-$d_6$, D$_2$O, δ): 1.30-1.80 (m, 4H), 1.90-2.20 (m, 1H), 2.60-3.10 (m, 2H), 3.45-3.71 (m, 1H), 3.90-4.20 (m, 1H), 7.05-7.45 (m, 7H), 8.17 (s, 1H).

Example 28

3-chloro-4-(4-chloro-2-fluorophenylamino)-5-[4-(4-fluorophenyl)piperidine-1-carbonyl]pyridine-2-sulfonamide (compound 28)

(step 1) Using 4,5,6-trichloronicotinic acid (500 mg, 2.21 mmol) and 4-chloro-2-fluoroaniline (482 mg, 3.31 mmol), and in the same manner as in Example 1, step 2, a crude product of 5,6-dichloro-4-(4-chloro-2-fluorophenylamino) nicotinic acid was obtained and used for the next reaction without purification.

ESIMS m/z: 335 (M+H)$^+$ (step 2) Using a crude product of 5,6-dichloro-4-(4-chloro-2-fluorophenylamino)nicotinic acid obtained in step 1, and in the same manner as in Example 1, step 1, [5,6-dichloro-4-(4-chloro-2-fluorophenylamino)pyridin-3-yl][4-(4-fluorophenyl)piperidin-1-yl]methanone (900 mg, yield of 2 steps 82%) was obtained.

ESIMS m/z: 496 (M+H)$^+$ (step 3) Using [5,6-dichloro-4-(4-chloro-2-fluorophenylamino)pyridin-3-yl][4-(4-fluorophenyl)piperidin-1-yl]methanone (900 mg, 1.87 mmol) obtained in step 2, and in the same manner as in Example 1, step 3, a crude product of [5-chloro-4-(4-chloro-2-fluorophenylamino)-6-mercaptopyridin-3-yl][4-(4-fluorophenyl)piperidin-1-yl]methanone was obtained and used for the next reaction without purification.

ESIMS m/z: 494 (M+H)$^+$ (step 4) Using a crude product of [5-chloro-4-(4-chloro-2-fluorophenylamino)-6-mercaptopyridin-3-yl][4-(4-fluorophenyl)piperidin-1-yl]methanone obtained in step 3, and in the same manner as in Example 1, step 4, a crude product of 3-chloro-4-(4-chloro-2-fluorophenylamino)-5-[4-(4-fluorophenyl)piperidine-1-carbonyl]pyridine-2-sulfonic acid was obtained and used for the next reaction without purification.

ESIMS m/z: 542 (M+H)$^+$ (step 5) Using a crude product of 3-chloro-4-(4-chloro-2-fluorophenylamino)-5-[4-(4-fluorophenyl)piperidine-1-carbonyl]pyridine-2-sulfonic acid obtained in step 4, and in the same manner as in Example 2, compound 28 (50.1 mg, yield of 3 steps 5%) was obtained.

ESIMS m/z: 541 (M+H)$^+$; $^1$H NMR (300 MHz, DMSO-d$_6$, δ): 1.30-1.80 (m, 4H), 1.85-2.18 (m, 1H), 2.65-3.10 (m, 2H), 3.45-3.70 (m, 1H), 3.90-4.25 (m, 1H), 7.00-7.80 (m, 9H), 8.20 (s, 1H), 8.68 (s, 1H).

Example 29

3-chloro-5-[4-(4-fluorophenyl)piperidine-1-carbonyl]-4-(4-methoxyphenylamino)pyridine-2-sulfonamide (compound 29)

(step 1) Using 4,5,6-trichloronicotinic acid (500 mg, 2.21 mmol) and 4-methoxyaniline (354 mg, 2.87 mmol), and in the same manner as in Example 1, step 2, a crude product of 5,6-dichloro-4-(4-methoxyphenylamino)nicotinic acid was obtained and used for the next reaction without purification.

ESIMS m/z: 313 (M+H)$^+$ (step 2) Using a crude product of 5,6-dichloro-4-(4-methoxyphenylamino)nicotinic acid obtained in step 1, and in the same manner as in Example 1, step 1, [5,6-dichloro-4-(4-methoxyphenylamino)pyridin-3-yl][4-(4-fluorophenyl)piperidin-1-yl]methanone (870 mg, yield of 2 steps 80%) was obtained.

ESIMS m/z: 474 (M+H)$^+$ (step 3) Using [5,6-dichloro-4-(4-methoxyphenylamino)pyridin-3-yl][4-(4-fluorophenyl)piperidin-1-yl]methanone (870 mg, 1.76 mmol) obtained in step 2, and in the same manner as in Example 1, step 3, a crude product of [5-chloro-6-mercapto-4-(4-methoxyphenylamino)pyridin-3-yl][4-(4-fluorophenyl)piperidin-1-yl]methanone was obtained and used for the next reaction without purification.

ESIMS m/z: 472 (M+H)$^+$ (step 4) Using a crude product of [5-chloro-6-mercapto-4-(4-methoxyphenylamino)pyridin-3-yl][4-(4-fluorophenyl)piperidin-1-yl]methanone obtained in step 3, and in the same manner as in Example 1, step 4, a crude product of 3-chloro-5-(4-(4-fluorophenyl)piperidine-1-carbonyl)-4-(4-methoxyphenylamino)pyridine-2-sulfonic acid was obtained and used for the next reaction without purification.

ESIMS m/z: 520 (M+H)$^+$ (step 5) Using a crude product of 3-chloro-5-(4-(4-fluorophenyl)piperidine-1-carbonyl)-4-(4-methoxyphenylamino)pyridine-2-sulfonic acid obtained in step 4, and in the same manner as in Example 2, compound 29 (36.8 mg, yield of 3 steps 4%) was obtained.

ESIMS m/z: 519 (M+H)$^+$; $^1$H NMR (300 MHz, DMSO-d$_6$, δ): 1.35-1.95 (m, 4H), 2.55-3.10 (m, 3H), 3.55-3.70 (m, 1H), 3.75 (s, 3H), 3.88-4.20 (m, 1E), 6.85-7.45 (m, 8H), 7.59 (s, 1H).

Example 30

3-chloro-4-(2-fluoro-4-methoxyphenylamino)-5-[4-(4-fluorophenyl)piperidine-1-carbonyl]pyridine-2-sulfonamide (compound 30)

(step 1) Using 4,5,6-trichloronicotinic acid (500 mg, 2.21 mmol) and 2-fluoro-4-methoxyaniline (467 mg, 3.31 mmol), and in the same manner as in Example 1, step 2, a crude product of 5,6-dichloro-4-(2-fluoro-4-methoxyphenylamino)nicotinic acid was obtained and used for the next reaction without purification.

ESIMS m/z: 331 (M+H)$^+$ (step 2) Using a crude product of 5,6-dichloro-4-(2-fluoro-4-methoxyphenylamino)nicotinic acid obtained in step 1, and in the same manner as in Example 1, step 1, [5,6-dichloro-4-(2-fluoro-4-methoxyphenylamino)pyridin-3-yl][4-(4-fluorophenyl)piperidin-1-yl]methanone (700 mg, yield of 2 steps 64%) was obtained.

ESIMS m/z: 492 (M+H)$^+$ (step 3) Using [5,6-dichloro-4-(2-fluoro-4-methoxyphenylamino)pyridin-3-yl][4-(4-fluorophenyl)piperidin-1-yl]methanone (700 mg, 1.42 mmol) obtained in step 2, and in the same manner as in Example 1, step 3, a crude product of [5-chloro-4-(2-fluoro-4-methoxyphenylamino)-6-mercaptopyridin-3-yl][4-(4-fluorophenyl)piperidin-1-yl]methanone was obtained and used for the next reaction without purification.

ESIMS m/z: 490 (M+H)$^+$ (step 4) Using a crude product of [5-chloro-4-(2-fluoro-4-methoxyphenylamino)-6-mercaptopyridin-3-yl][4-(4-fluorophenyl)piperidin-1-yl]methanone obtained in step 3, and in the same manner as in Example 1, step 4, a crude product of 3-chloro-4-(2-fluoro-4-methoxyphenylamino)-5-[4-(4-fluorophenyl)piperidine-1-carbonyl]pyridine-2-sulfonic acid was obtained and used for the next reaction without purification.

ESIMS m/z: 538 (M+H)$^+$ (step 5) Using a crude product of 3-chloro-4-(2-fluoro-4-methoxyphenylamino)-5-[4-(4-fluorophenyl)piperidine-1-carbonyl]pyridine-2-sulfonic acid obtained in step 4, and in the same manner as in Example 2, compound 30 (89.9 mg, yield of 3 steps 12%) was obtained.

ESIMS m/z: 537 (M+H)$^+$; $^1$H NMR (300 MHz, DMSO-d$_6$, δ): 1.30-1.75 (m, 4H), 1.85-2.10 (m, 1H), 2.58-3.10 (m, 2H), 3.35-3.60 (m, 1H), 3.80 (s, 3H), 3.90-4.20 (m, 1H), 6.70-7.40 (m, 9H), 8.13 (s, 1H), 8.43 (s, 1H).

Example 31

3-chloro-4-(4-fluoro-3-methylphenylamino)-5-[4-(4-fluorophenyl)piperidine-1-carbonyl]pyridine-2-sulfonamide (compound 31)

(step 1) Using 4,5,6-trichloronicotinic acid (500 mg, 2.21 mmol) and 4-fluoro-3-methylaniline (414 mg, 3.31 mmol), and in the same manner as in Example 1, step 2, a crude product of 5,6-dichloro-4-(4-fluoro-3-methylphenylamino) nicotinic acid was obtained and used for the next reaction without purification.
ESIMS m/z: 315 (M+H)$^+$ (step 2) Using a crude product of 5,6-dichloro-4-(4-fluoro-3-methylphenylamino)nicotinic acid obtained in step 1, and in the same manner as in Example 1, step 1, [5,6-dichloro-4-(4-fluoro-3-methylphenylamino)pyridin-3-yl][4-(4-fluorophenyl)piperidin-1-yl]methanone (700 mg, yield of 2 steps 67%) was obtained.
ESIMS m/z: 476 (M+H)$^+$ (step 3) Using [5,6-dichloro-4-(4-fluoro-3-methylphenylamino)pyridin-3-yl][4-(4-fluorophenyl)piperidin-1-yl]methanone (700 mg, 1.47 mmol) obtained in step 2, and in the same manner as in Example 1, step 3, a crude product of [5-chloro-4-(4-fluoro-3-methylphenylamino)-6-mercaptopyridin-3-yl][4-(4-fluorophenyl)piperidin-1-yl]methanone was obtained and used for the next reaction without purification.
ESIMS m/z: 474 (M+H)$^+$ (step 4) Using a crude product of [5-chloro-4-(4-fluoro-3-methylphenylamino)-6-mercaptopyridin-3-yl][4-(4-fluorophenyl)piperidin-1-yl]methanone obtained in step 3, and in the same manner as in Example 1, step 4, a crude product of 3-chloro-4-(4-fluoro-3-methylphenylamino)-5-[4-(4-fluorophenyl)piperidine-1-carbonyl]pyridine-2-sulfonic acid was obtained and used for the next reaction without purification.
ESIMS m/z: 522 (M+H)$^+$ (step 5) Using a crude product of 3-chloro-4-(4-fluoro-3-methylphenylamino)-5-[4-(4-fluorophenyl)piperidine-1-carbonyl]pyridine-2-sulfonic acid obtained in step 4, and in the same manner as in Example 2, compound 31 (106 mg, yield of 3 steps 14%) was obtained.
ESIMS m/z: 521 (M+H)$^+$; $^1$H NMR (300 MHz, DMSO-d$_6$, δ): 1.30-1.75 (m, 4H), 1.78-2.00 (m, 1H), 2.07 (s, 3H), 2.58-3.05 (m, 2H), 3.39-3.57 (m, 1H), 3.90-4.12 (m, 1H), 6.88-7.40 (m, 7H), 7.60 (s, 2H), 8.20 (s, 1H), 8.85 (s, 1H).

Example 32

3-chloro-4-(3-fluoro-4-methoxyphenylamino)-5-[4-(4-fluorophenyl)piperidine-1-carbonyl]pyridine-2-sulfonamide (compound 32)

(step 1) Using 4,5,6-trichloronicotinic acid (500 mg, 2.21 mmol) and 3-fluoro-4-methoxyaniline (467 mg, 3.31 mmol), and in the same manner as in Example 1, step 2, a crude product of 5,6-dichloro-4-(3-fluoro-4-methoxyphenylamino)nicotinic acid was obtained and used for the next reaction without purification.
ESIMS m/z: 331 (M+H)$^+$ (step 2) Using a crude product of 5,6-dichloro-4-(3-fluoro-4-methoxyphenylamino)nicotinic acid obtained in step 1, and in the same manner as in Example 1, step 1, [5,6-dichloro-4-(3-fluoro-4-methoxyphenylamino)pyridin-3-yl][4-(4-fluorophenyl)piperidin-1-yl]methanone (940 mg, yield of 2 steps 86%) was obtained.
ESIMS m/z: 492 (M+H)$^+$ (step 3) Using [5,6-dichloro-4-(3-fluoro-4-methoxyphenylamino)pyridin-3-yl][4-(4-fluorophenyl)piperidin-1-yl]methanone (940 mg, 1.91 mmol) obtained in step 2, and in the same manner as in Example 1, step 3, a crude product of [5-chloro-4-(3-fluoro-4-methoxyphenylamino)-6-mercaptopyridin-3-yl][4-(4-fluorophenyl)piperidin-1-yl]methanone was obtained and used for the next reaction without purification.
ESIMS m/z: 490 (M+H)$^+$ (step 4) Using a crude product of [5-chloro-4-(3-fluoro-4-methoxyphenylamino)-6-mercaptopyridin-3-yl][4-(4-fluorophenyl)piperidin-1-yl]methanone obtained in step 3, and in the same manner as in Example 1, step 4, a crude product of 3-chloro-4-(3-fluoro-4-methoxyphenylamino)-5-[4-(4-fluorophenyl)piperidine-1-carbonyl]pyridine-2-sulfonic acid was obtained and used for the next reaction without purification.
ESIMS m/z: 538 (M+H)$^+$ (step 5) Using a crude product of 3-chloro-4-(3-fluoro-4-methoxyphenylamino)-5-[4-(4-fluorophenyl)piperidine-1-carbonyl]pyridine-2-sulfonic acid obtained in step 4, and in the same manner as in Example 2, compound 32 (81.1 mg, yield of 3 steps 8%) was obtained.
ESIMS m/z: 537 (M+H)$^+$, $^1$H NMR (300 MHz, DMSO-d$_5$, δ): 1.35-1.80 (m, 4H), 1.80-2.10 (m, 1H), 2.55-3.10 (m, 2H), 3.48-3.70 (m, 1H), 3.83 (s, 3H), 3.95-4.30 (m, 1H), 6.80-7.40 (m, 7H), 7.60 (s, 2H), 8.20 (s, 1H), 8.60 (s, 1H).

Example 33

3-chloro-5-[4-(4-fluorophenyl)piperidine-1-carbonyl]-4-(o-tolylamino)pyridine-2-sulfonamide (compound 33)

(step 1) Using 4,5,6-trichloronicotinic acid (500 mg, 2.21 mmol) and o-toluidine (355 mg, 3.31 mmol), and in the same manner as in Example 1, step 2, a crude product of 5,6-dichloro-4-(o-tolylamino)nicotinic acid was obtained and used for the next reaction without purification.
ESIMS m/z: 297 (M+H)$^+$ (step 2) Using a crude product of 5,6-dichloro-4-(o-tolylamino)nicotinic acid obtained in step 1, and in the same manner as in Example 1, step 1, [5,6-dichloro-4-(o-tolylamino)pyridin-3-yl][4-(4-fluorophenyl)piperidin-1-yl]methanone (900 mg, yield of 2 steps 88%) was obtained.
ESIMS m/z: 458 (M+H)$^+$ (step 3) Using [5,6-dichloro-4-(o-tolylamino)pyridin-3-yl][4-(4-fluorophenyl)piperidin-1-yl]methanone (900 mg, 1.96 mmol) obtained in step 2, and in the same manner as in Example 1, step 3, a crude product of [5-chloro-6-mercapto-4-(o-tolylamino)pyridin-3-yl][4-(4-fluorophenyl)piperidin-1-yl]methanone was obtained and used for the next reaction without purification.
ESIMS m/z: 456 (M+H)$^+$ (step 4) Using a crude product of [5-chloro-6-mercapto-4-(o-tolylamino)pyridin-3-yl][4-(4-fluorophenyl)piperidin-1-yl]methanone obtained in step 3, and in the same manner as in Example 1, step 4, a crude product of 3-chloro-5-[4-(4-fluorophenyl)piperidine-1-carbonyl]-4-(o-tolylamino)pyridine-2-sulfonic acid was obtained and used for the next reaction without purification.
ESIMS m/z: 504 (M+H)$^+$ (step 5) Using a crude product of 3-chloro-5-[4-(4-fluorophenyl)piperidine-1-carbonyl]-4-(o-tolylamino)pyridine-2-sulfonic acid obtained in step 4, and in the same manner as in Example 2, compound 33 (31.0 mg, yield of 3 steps 3%) was obtained.
ESIMS m/z: 503 (M+H)$^+$; $^1$H NMR (300 MHz, DMSO-d$_6$, D$_2$O, δ): 1.30-1.75 (m, 4H), 1.75-1.95 (m, 1H), 2.19 (s, 3H), 2.55-2.93 (m, 3H), 3.80-4.10 (m, 1H), 7.00-7.45 (m, 8H), 8.09 (s, 1H).

Example 34

3-chloro-5-[4-(4-fluorophenyl)piperidine-1-carbonyl]-4-(2,4,5-trifluorophenylamino)pyridine-2-sulfonamide (compound 34)

(step 1) Using 4,5,6-trichloronicotinic acid (500 mg, 2.21 mmol) and 2,4,5-trifluoroaniline (487 mg, 3.31 mmol), and in the same manner as in Example 1, step 2, a crude product of 5,6-dichloro-4-(2,4,5-trifluorophenylamino)nicotinic acid was obtained and used for the next reaction without purification.

ESIMS m/z: 337 (M+H)$^+$ (step 2) Using a crude product of 5,6-dichloro-4-(2,4,5-trifluorophenylamino)nicotinic acid obtained in step 1, and in the same manner as in Example 1, step 1, [5,6-dichloro-4-(2,4,5-trifluorophenylamino)pyridin-3-yl][4-(4-fluorophenyl)piperidin-1-yl]methanone (900 mg, yield of 2 steps 82%) was obtained.

ESIMS m/z: 498 (M+H)$^+$ (step 3) Using [5,6-dichloro-4-(2,4,5-trifluorophenylamino)pyridin-3-yl][4-(4-fluorophenyl)piperidin-1-yl]methanone (900 mg, 1.81 mmol) obtained in step 2, and in the same manner as in Example 1, step 3, a crude product of [5-chloro-6-mercapto-4-(2,4,5-trifluorophenylamino)pyridin-3-yl][4-(4-fluorophenyl)piperidin-1-yl]methanone was obtained and used for the next reaction without purification.

ESIMS m/z: 496 (M+H)$^+$ (step 4) Using a crude product of [5-chloro-6-mercapto-4-(2,4,5-trifluorophenylamino)pyridin-3-yl][4-(4-fluorophenyl)piperidin-1-yl]methanone obtained in step 3, and in the same manner as in Example 1, step 4, a crude product of 3-chloro-5-[4-(4-fluorophenyl)piperidine-1-carbonyl]-4-(2,4,5-trifluorophenylamino)pyridine-2-sulfonic acid was obtained and used for the next reaction without purification.

ESIMS m/z: 544 (M+H)$^+$ (step 5) Using a crude product of 3-chloro-5-[4-(4-fluorophenyl)piperidine-1-carbonyl]-4-(2,4,5-trifluorophenylamino)pyridine-2-sulfonic acid obtained in step 4, and in the same manner as in Example 2, compound 34 (40.0 mg, yield of 3 steps 4%) was obtained.

ESIMS m/z: 543 (M+H)$^+$; $^1$H NMR (300 MHz, DMSO-d$_6$, D$_2$O, δ): 1.30-1.85 (m, 4H), 1.95-2.25 (m, 1H), 2.60-3.15 (m, 2H), 3.40-3.75 (m, 1H), 4.05-4.25 (m, 1H), 7.05-7.80 (m, 6H), 8.24 (s, 1H).

Example 35

4-{3-chloro-4-(4-fluoro-2-methylphenylamino)-5-[4-(4-fluorophenyl)piperidine-1-carbonyl]pyridin-2-ylsulfonyl}-N-methylmorpholine-3-carboxamide (compound 35)

(step 1) Using compound 24 (193 mg, 0.370 mmol) and methyl morpholine-3-carboxylate (1343 mg, 9.25 mmol), and in the same manner as in Example 2, methyl 4-{3-chloro-4-(4-fluoro-2-methylphenylamino)-5-[4-(4-fluorophenyl)piperidine-1-carbonyl]pyridin-2-ylsulfonyl}morpholine-3-carboxylate (150.4 mg, 63%) was obtained.

ESIMS m/z: 649 (M+H)$^+$ (step 2) Using methyl 4-{3-chloro-4-(4-fluoro-2-methylphenylamino)-5-[4-(4-fluorophenyl)piperidine-1-carbonyl]pyridin-2-ylsulfonyl}morpholine-3-carboxylate (146 mg, 0.225 mmol) obtained in step 1, and in the same manner as in Example 6, step 2, 4-{3-chloro-4-(4-fluoro-2-methylphenylamino)-5-[4-(4-fluorophenyl)piperidine-1-carbonyl]pyridin-2-ylsulfonyl}morpholine-3-carboxylic acid (51 mg, 36%) was obtained.

ESIMS m/z: 635 (M+H)$^+$ (step 3) Using 4-{3-chloro-4-(4-fluoro-2-methylphenylamino)-5-[4-(4-fluorophenyl)piperidine-1-carbonyl]pyridin-2-ylsulfonyl}morpholine-3-carboxylic acid (50 mg, 0.079 mmol) obtained in step 2, and in the same manner as in Example 6, step 3, compound 35 (43.2 mg, 85%) was obtained.

ESIMS m/z: 648 (M+H)$^+$; $^1$H NMR (400 MHz, CDCl$_3$, δ): 1.25-1.70 (m, 4H), 1.71-1.90 (m, 1H), 2.32 (s, 3H), 2.55-2.73 (m, 1H), 2.73-3.05 (m, 5H), 3.38-3.99 (m, 5H), 4.10-4.62 (m, 2H), 4.69-4.91 (m, 1H), 6.70-7.18 (m, 6H), 7.18-7.40 (m, 2H), 8.01 (s, 1H), 8.60-8.92 (m, 1H).

Example 36

1-{3-chloro-4-(4-fluoro-2-methylphenylamino)-5-[4-(4-fluorophenyl)piperidine-1-carbonyl]pyridine-2-sulfonamide}-N-methylcyclopropanecarboxamide (compound 36)

(step 1) Using compound 24 (97 mg, 0.185 mmol) and ethyl 1-aminocyclopropanecarboxylate hydrochloride (306 mg, 1.85 mmol), and in the same manner as in Example 2, ethyl 1-{3-chloro-4-(4-fluoro-2-methylphenylamino)-5-[4-(4-fluorophenyl)piperidine-1-carbonyl]pyridine-2-sulfonamide}cyclopropanecarboxylate (71 mg, 61%) was obtained.

ESIMS m/z: 633 (M+H)$^+$ (step 2) Using ethyl 1-{3-chloro-4-(4-fluoro-2-methylphenylamino)-5-[4-(4-fluorophenyl)piperidine-1-carbonyl]pyridine-2-sulfonamide}cyclopropanecarboxylate (68 mg, 0.107 mmol) obtained in step 1, and in the same manner as in Example 6, step 2, a crude product of 1-{3-chloro-4-(4-fluoro-2-methylphenylamino)-5-[4-(4-fluorophenyl)piperidine-1-carbonyl]pyridine-2-sulfonamide}cyclopropanecarboxylic acid was obtained and used for the next reaction without purification.

ESIMS m/z: 605 (M+H)$^+$ (step 3) Using a crude product of 1-{3-chloro-4-(4-fluoro-2-methylphenylamino)-5-[4-(4-fluorophenyl)piperidine-1-carbonyl]pyridine-2-sulfonamide}cyclopropanecarboxylic acid obtained in step 2, and in the same manner as in Example 6, step 3, compound 36 (50.7 mg, yield of 2 steps 70%) was obtained.

ESIMS m/z: 618 (M+H)$^+$; $^1$H NMR (400 MHz, CDCl$_3$, δ): 1.19-1.31 (m, 2H), 1.35-1.50 (m, 2H), 1.59-1.69 (m, 2H), 1.75-1.87 (m, 2H), 2.31 (s, 3H), 2.28-2.40 (m, 1H), 2.59-2.70 (m, 1H), 2.78-3.00 (m, 4H), 3.48-3.64 (m, 1H), 4.21-4.35 (m, 1H), 5.71 (s, 1H), 6.78 (s, 1H), 6.87-7.08 (m, 4H), 7.08-7.15 (m, 2H), 7.24-7.31 (m, 1H), 7.36-7.42 (m, 1H), 8.02 (s, 1H).

Example 37

(2S,3R)-2-{3-chloro-4-(4-fluoro-2-methylphenylamino)-5-[4-(4-fluorophenyl)piperidine-1-carbonyl]pyridine-2-sulfonamide}-3-hydroxy-N-methylbutanamide (compound 37)

(step 1) Using compound 24 (193 mg, 0.370 mmol) and methyl (2S,3R)-2-amino-3-hydroxybutanoate hydrochloride (1699 mg, 9.25 mmol), and in the same manner as in Example 2, methyl (2S,3R)-2-{3-chloro-4-(4-fluoro-2-methylphenylamino)-5-[4-(4-fluorophenyl)piperidine-1-carbonyl]pyridine-2-sulfonamide}-3-hydroxybutanoate (189.4 mg, 80%) was obtained.

ESIMS m/z: 637 (M+H)$^+$ (step 2) Using methyl (2S,3R)-2-{3-chloro-4-(4-fluoro-2-methylphenylamino)-5-[4-(4-fluorophenyl)piperidine-1-carbonyl]pyridine-2-sulfonamide}-3-hydroxybutanoate (189 mg, 0.297 mmol) obtained in step 1, and in the same manner as in Example 6, step 2, a crude product of (2S,3R)-2-{3-chloro-4-(4-fluoro-2-methylphenylamino)-5-[4-(4-fluorophenyl)piperidine-1-carbonyl]pyridine-2-sulfonamide}-3-hydroxybutanoic acid was obtained and used for the next reaction without purification.

ESIMS m/z: 623 (M+H)$^+$ (step 3) Using a crude product of (2S,3R)-2-{3-chloro-4-(4-fluoro-2-methylphenylamino)-5-[4-(4-fluorophenyl)piperidine-1-carbonyl]pyridine-2-sulfonamide}-3-hydroxybutanoic acid obtained in step 2, and in the same manner as in Example 6, step 3, compound 37 (97.6 mg, yield of 2 steps 52%) was obtained.

ESIMS m/z: 636 (M+H)$^+$; $^1$H NMR (400 MHz, CDCl$_3$, δ): 1.29 (d, J=6.5 Hz, 3H), 1.32-1.52 (m, 2H), 1.73-1.82 (m, 2H), 2.30 (s, 3H), 2.59-2.70 (m, 1H), 2.76-3.20 (m, 5H), 3.48-3.62 (m, 1H), 3.95-4.05 (m, 1H), 4.17-4.32 (m, 1H), 4.48-4.60 (m, 1H), 5.97-6.04 (m, 1H), 6.78 (s, 1H), 6.85-6.95 (m, 1H), 6.96-7.14 (m, 6H), 7.76-7.88 (m, 1H), 8.02 (s, 1H).

Example 38

3-chloro-4-(4-fluoro-2-methylphenylamino)-5-[4-(4-fluorophenyl)piperidine-1-carbonyl]-N-(4-methoxyphenyl)pyridine-2-sulfonamide (compound 38)

Using compound 24 (80.0 mg, 0.153 mmol) and 4-methoxyaniline (365 mg, 2.96 mmol), and in the same manner as in Example 11, compound 38 (52.7 mg, 57%) was obtained. ESIMS m/z: 627 (M+H)$^+$; $^1$H NMR (300 MHz, CDCl$_3$, δ): 1.38-1.44 (m, 2H), 1.75-1.81 (m, 2H), 2.03-2.26 (m, 1H), 2.28 (s, 3H), 2.59-2.70 (m, 1H), 2.79-2.98 (m, 1H), 3.53-3.63 (m, 1H), 3.76 (s, 3H), 4.20-4.32 (m, 1H), 6.68 (s, 1H), 6.78-6.92 (m, 3H), 6.96-7.05 (m, 4H), 7.07-7.13 (m, 3H), 7.26-7.31 (m, 2H), 8.07 (s, 1H).

Example 39

3-chloro-4-(4-fluoro-2-methylphenylamino)-5-[4-(4-fluorophenyl)piperidine-1-carbonyl]-N-(1-methyl-1H-pyrazol-3-yl)pyridine-2-sulfonamide (compound 39)

Using compound 24 (80.0 mg, 0.153 mmol) and 1-methyl-1H-pyrazole-3-amine (431 mg 4.44 mmol), and in the same manner as in Example 11, compound 39 (43.5 mg, 49%) was obtained.

ESIMS m/z: 601 (M+H)$^+$; $^1$H NMR (400 MHz, CDCl$_3$, δ): 1.35-1.55 (m, 2H), 1.73-1.82 (m, 2H), 2.03-2.26 (m, 1H), 2.29 (s, 3H), 2.55-2.70 (m, 1H), 2.75-2.94 (m, 1H), 3.53-3.63 (m, 1H), 3.81 (s, 3H), 4.20-4.32 (m, 1H), 6.22 (d, J=2.0 Hz, 1H), 6.67 (s, 1H), 6.83-6.90 (m, 1H), 6.95-7.04 (m, 4H), 7.10 (dd, J=4.9, 8.8 Hz, 2H), 7.16 (d, J=2.0 Hz, 1H), 8.09 (s, 1H), 9.32 (s, 1H).

Example 40

3-chloro-4-(4-fluoro-2-methylphenylamino)-5-[4-(4-fluorophenyl)piperidine-1-carbonyl]-N-(5-methylisoxazol-3-yl)pyridine-2-sulfonamide (compound 40)

Using compound 24 (100 mg, 0.205 mmol) and 5-methylisoxazol-3-amine (545 mg 5.55 mmol), and in the same manner as in Example 11, compound 40 (62.0 mg, 56%) was obtained.

ESIMS m/z: 602 (M+H)$^+$; $^1$H NMR (300 MHz, CDCl$_3$, δ): 1.38-1.57 (m, 2H), 1.75-1.82 (m, 2H), 2.03-2.26 (m, 1H), 2.31 (s, 3H), 2.35 (s, 3H), 2.58-2.68 (m, 1H), 2.81-2.90 (m, 1H), 3.53-3.63 (m, 1H), 4.20-4.32 (m, 1H), 6.22 (s, 1H), 6.70 (s, 1H), 6.84-6.93 (m, 1H), 6.96-7.04 (m, 5H), 7.07-7.13 (m, 2H), 8.04 (s, 1H).

Example 41

3-chloro-4-(4-fluoro-2-methylphenylamino)-5-[4-(4-fluorophenyl)piperidine-1-carbonyl]-N-(3-methylisoxazol-5-yl)pyridine-2-sulfonamide (compound 41)

Using compound 24 (100 mg, 0.205 mmol) and 3-methylisoxazol-5-amine (545 mg, 5.55 mmol), and in the same manner as in Example 11, compound 41 (41.5 mg, 37%) was obtained.

ESIMS m/z: 602 (M+H)$^+$; $^1$H NMR (300 MHz, CDCl$_3$, δ): 1.35-1.55 (m, 2H), 1.70-1.80 (m, 2H), 2.03-2.26 (m, 1H), 2.14 (s, 3H), 2.31 (s, 3H), 2.55-2.70 (m, 1H), 2.75-2.94 (m, 1H), 3.53-3.63 (m, 1H), 4.20-4.32 (m, 1H), 5.66 (s, 1H), 6.70 (s, 1H), 6.82-6.91 (m, 1H), 6.95-7.04 (m, 5H), 7.07-7.14 (m, 2H), 7.98 (s, 1H).

Example 42

N-(5-tert-butylisoxazol-3-yl)-3-chloro-4-(4-fluoro-2-methylphenylamino)-5-[4-(4-fluorophenyl)piperidine-1-carbonyl]pyridine-2-sulfonamide (compound 42)

Using compound 24 (100 mg, 0.205 mmol) and 5-tert-butylisoxazol-3-amine (778 mg 5.55 mmol), and in the same manner as in Example 11, compound 42 (71.2 mg, 60%) was obtained.

ESIMS m/z: 644 (M+H)$^+$; $^1$H NMR (400 MHz, CDCl$_3$, δ): 1.29 (s, 9H), 1.35-1.55 (m, 2H), 1.73-1.82 (m, 2H), 2.03-2.26 (m, 1H), 2.32 (s, 3H), 2.55-2.70 (m, 1H), 2.75-2.94 (m, 1H), 3.53-3.63 (m, 1H), 4.20-4.32 (m, 1H), 6.00 (s, 1H), 6.18 (s, 1H), 6.71 (s, 1H), 6.84-6.92 (m, 1H), 6.97-7.04 (m, 4H), 7.07-7.13 (m, 2H), 8.06 (s, 1H).

Example 43

3-chloro-N-(ethylcarbamoyl)-4-(4-fluoro-2-methylphenylamino)-5-[4-(4-fluorophenyl)piperidine-1-carbonyl]pyridine-2-sulfonamide (compound 43)

Using compound 25 (41.1 mg, 0.0790 mmol) and ethyl isocyanate (0.0069 mL, 0.087 mmol), and in the same manner as in Example 16, compound 43 (30.0 mg, 64%) was obtained.

ESIMS m/z: 592 (M+H)$^+$; $^1$H NMR (300 MHz, DMSO-d$_6$, δ): 0.99 (t, J=7.1 Hz, 3H), 1.39-1.51 (m, 1H), 1.56-1.71 (m, 3H), 1.82-2.01 (m, 1H), 2.20 (s, 3H), 2.59-2.91 (m, 2H), 2.99-3.08 (m, 2H), 3.48-3.59 (m, 1H), 3.89-4.04 (m, 1H), 6.47-6.54 (m, 1H), 6.96-7.20 (m, 5H), 7.21-7.36 (m, 2H), 8.11 (s, 1H), 8.43 (s, 1H), 10.78 (s, 1H).

Example 44

4-(benzylamino)-3-chloro-5-[4-(4-fluorophenyl)piperidine-1-carbonyl]pyridine-2-sulfonamide (compound 44)

(step 1) 4,5,6-Trichloronicotinic acid (500 mg, 2.21 mmol) was dissolved in acetonitrile (20 mL), benzylamine (237 mg, 2.21 mmol) and triethylamine (0.90 mL, 4.4 mmol) were added, and the mixture was stirred at 80° C. for 6 hr. To the reaction mixture was added saturated aqueous sodium chloride solution, and the mixture was extracted with ethyl acetate. The organic layer was dried over anhydrous magnesium sulfate, and the solvent was evaporated under reduced pressure. A crude product of 4-(benzylamino)-5,6-dichloronicotinic acid was obtained and used for the next reaction without purification.

ESIMS m/z: 297 (M+H)+

(step 2) Using a crude product of 4-(benzylamino)-5,6-dichloronicotinic acid obtained in step 1, and in the same manner as in Example 1, step 1, [4-(benzylamino)-5,6-dichloropyridin-3-yl][4-(4-fluorophenyl)piperidin-1-yl]methanone (520 mg, yield of 2 steps 51%) was obtained.

ESIMS m/z: 458 (M+H)+

(step 3) Using [4-(benzylamino)-5,6-dichloropyridin-3-yl][4-(4-fluorophenyl)piperidin-1-yl]methanone (520 mg, 1.13 mmol) obtained in step 2, and in the same manner as in Example 1, step 3, a crude product of [4-(benzylamino)-5-chloro-6-mercaptopyridin-3-yl][4-(4-fluorophenyl) piperidin-1-yl]methanone was obtained and used for the next reaction without purification.

ESIMS m/z: 456 (M+H)+

(step 4) Using a crude product of [4-(benzylamino)-5-chloro-6-mercaptopyridin-3-yl][4-(4-fluorophenyl) piperidin-1-yl]methanone obtained in step 3, and in the same manner as in Example 1, step 4, 4-(benzylamino)-3-chloro-5-[4-(4-fluorophenyl)piperidine-1-carbonyl]pyridine-2-sulfonic acid (140 mg, yield of 2 steps 13%) was obtained.

ESIMS m/z: 504 (M+H)+

(step 5) Using 4-(benzylamino)-3-chloro-5-[4-(4-fluorophenyl)piperidine-1-carbonyl]pyridine-2-sulfonic acid (490 mg, 0.97 mmol) obtained in step 4, and in the same manner as in Example 2, compound 44 (7.8 mg, 2%) was obtained.

ESIMS m/z: 503 (M+H)+; 1H NMR (300 MHz, DMSO-d6, D2O, δ): 1.45-1.70 (m, 2H), 1.70-1.95 (m, 2H), 2.35-2.60 (m, 1H), 2.70-3.40 (m, 2H), 3.90-4.20 (m, 1H), 4.48-4.70 (m, 3H), 7.00-7.55 (m, 9H), 8.06 (s, 1H).

Example 45

3-chloro-4-(cyclohexylamino)-5-[4-(4-fluorophenyl) piperidine-1-carbonyl]pyridine-2-sulfonamide (compound 45)

(step 1) Using 4,5,6-trichloronicotinic acid (500 mg, 2.21 mmol) and cyclohexylamine (350 mg, 3.53 mmol), and in the same manner as in Example 44, step 1, a crude product of 5,6-dichloro-4-(cyclohexylamino)nicotinic acid was obtained and used for the next reaction without purification.

ESIMS m/z: 289 (M+H)+

(step 2) Using a crude product of 5,6-dichloro-4-(cyclohexylamino)nicotinic acid obtained in step 1, and in the same manner as in Example 1, step 1, a crude product of [5,6-dichloro-4-(cyclohexylamino)pyridin-3-yl][4-(4-fluorophenyl)piperidin-1-yl]methanone was obtained and used for the next reaction without purification.

ESIMS m/z: 450 (M+H)+

(step 3) Using a crude product of [5,6-dichloro-4-(cyclohexylamino)pyridin-3-yl][4-(4-fluorophenyl)piperidin-1-yl]methanone obtained in step 2, and in the same manner as in Example 1, step 3, a crude product of [5-chloro-4-(cyclohexylamino)-6-mercaptopyridin-3-yl][4-(4-fluorophenyl) piperidin-1-yl]methanone was obtained and used for the next reaction without purification.

ESIMS m/z: 448 (M+H)+

(step 4) Using a crude product of [5-chloro-4-(cyclohexylamino)-6-mercaptopyridin-3-yl][4-(4-fluorophenyl)piperidin-1-yl]methanone obtained in step 3, and in the same manner as in Example 1, step 4, a crude product of 3-chloro-4-(cyclohexylamino)-5-[4-(4-fluorophenyl)piperidine-1-carbonyl]pyridine-2-sulfonic acid was obtained and used for the next reaction without purification.

ESIMS m/z: 496 (M+H)+

(step 5) Using a crude product of 3-chloro-4-(cyclohexylamino)-5-[4-(4-fluorophenyl)piperidine-1-carbonyl]pyridine-2-sulfonic acid obtained in step 4, and in the same manner as in Example 2, compound 45 (77.7 mg, yield of 5 steps 4%) was obtained.

ESIMS m/z: 495 (M+H)+; 1H NMR (300 MHz, DMSO-d6, D2O, δ): 1.05-2.15 (m, 14H), 2.75-3.05 (m, 2H), 3.05-3.75 (m, 3H), 4.59-4.81 (m, 1H), 7.10-7.50 (m, 4H), 7.90-8.20 (m, 1H).

Example 46

4-(4-chloro-2-methylphenylamino)-5-(3H-spiro [isobenzofuran-1,4'-piperidine]-1'-ylcarbonyl]pyridine-2-sulfonamide (compound 46)

(step 1) Using 6-chloro-(4-chloro-2-methylphenylamino) nicotinic acid (0.75 g, 2.52 mmol) obtained in Example 20, step 2, and 3H-spiro[isobenzofuran-1,4'-piperidine]hydrochloride (0.684 g, 3.03 mmol), and in the same manner as in Example 1, step 1, [6-chloro-4-(4-chloro-2-methylphenylamino)pyridin-3-yl](3H-spiro[isobenzofuran-1,4'-piperidine]-1'-yl)methanone (1.18 g, quantitative) was obtained.

ESIMS m/z: 468 (M+H)+

(step 2) Using [6-chloro-4-(4-chloro-2-methylphenylamino)pyridin-3-yl](3H-spiro[isobenzofuran-1,4'-piperidine]-1'-yl)methanone (1.08 g, 2.31 mmol) obtained in step 1, and in the same manner as in Example 1, step 3, [4-(4-chloro-2-methylphenylamino)-6-mercaptopyridin-3-yl](3H-spiro[isobenzofuran-1,4'-piperidine]-1'-yl)methanone (1.10 g, 93%) was obtained.

ESIMS m/z: 466 (M+H)+

(step 3) [4-(4-Chloro-2-methylphenylamino)-6-mercaptopyridin-3-yl](3H-spiro[isobenzofuran-1,4'-piperidine]-1'-yl) methanone (0.2 g, 0.43 mmol) obtained in step 2 was dissolved in acetonitrile (2.15 mL), benzyltrimethylammonium chloride (0.32 g, 1.72 mmol), water (0.019 mL, 1.07 mmol) and N-chlorosuccinimide (0.17 g, 1.29 mmol) were added under ice-cooling, and the mixture was stirred for 30 min. To the reaction mixture was added 25% aqueous ammonia (0.146 g 2.15 mmol), and the mixture was stirred at 0° C. for 30 min. 10% Aqueous citric acid solution was added to the reaction mixture, and the mixture was extracted with ethyl acetate. The organic layer was dried over anhydrous magnesium sulfate, and the solvent was evaporated under reduced pressure. The residue was purified by silica gel column chromatography (chloroform/methanol=100/0-92/8) to give compound 46 (0.2 g, 91%).

ESIMS m/z: 513 (M+H)+; 1H NMR (300 MHz, CDCl3, δ): 1.85-2.00 (m, 4H), 2.26 (s, 3H), 3.46-3.63 (m, 2H), 5.00 (s, 2H), 5.09 (br s, 2H), 7.10-7.13 (m, 1H), 7.19-7.35 (m, 9H), 8.25 (s, 1H), 8.36 (s, 1H).

Example 47

4-(4-chloro-2-methylphenylamino)-N-cyclopropyl-carbamoyl-5-(3E-spiro[isobenzofuran-1,4'-piperidine]-1'-ylcarbonyl]pyridine-2-sulfonamide (compound 47)

Using compound 46 (80 mg, 0.16 mmol) and cyclopropyl isocyanate (16 mg, 0.19 mmol), and in the same manner as in Example 16, compound 47 (27 mg, 29%) was obtained.

ESIMS m/z: 596 (M+H)+; 1H NMR (300 MHz, CDCl3, δ): 0.48-0.52 (m, 2H), 0.72-0.78 (m, 2H), 1.86-1.97 (m, 4H), 2.25 (s, 3H), 2.59-2.65 (m, 1H), 3.46-3.63 (m, 2H), 5.12 (s, 2H), 6.81 (br s, 1E), 7.11-7.13 (m, 1H), 7.16-7.33 (m, 9H), 8.34 (s, 1H), 8.36 (s, 1E).

Example 48

3-chloro-4-(3-chlorophenylamino)-5-[4-(4-fluorophenyl)piperidine-1-carbonyl]pyridine-2-sulfonamide (compound 176)

(step 1) Using 4,5,6-trichloronicotinic acid (400 mg, 1.77 mmol), and in the same manner as in Example 1, step 1, [4-(4-fluorophenyl)piperidin-1-yl](4,5,6-trichloropyridin-3-yl)methanone (650 mg, 95%) was obtained.
ESIMS m/z: 387 (M+H)$^+$
(step 2) Using [4-(4-fluorophenyl)piperidin-1-yl](4,5,6-trichloropyridin-3-yl)methanone (400 mg, 1.03 mmol) obtained in step 1, and 3-chloroaniline (0.14 mL, 1.3 mmol), and in the same manner as in Example 1, step 2, [5,6-dichloro-4-(3-chlorophenylamino)pyridin-3-yl][4-(4-fluorophenyl)piperidin-1-yl]methanone (250 mg, 51%) was obtained.
ESIMS m/z: 478 (M+H)$^+$
(step 3) [5,6-Dichloro-4-(3-chlorophenylamino)pyridin-3-yl][4-(4-fluorophenyl)piperidin-1-yl]methanone (250 mg, 0.522 mmol) obtained in step 2 was dissolved in DMF (2.61 mL), sodium hydrogen sulfide n hydrate (146 mg, 1.83 mmol) was added, and the mixture was stirred at 80° C. for 2 hr. Saturated brine was added to the residue, and the mixture was extracted with ethyl acetate. The organic layer was washed with saturated brine, and dried over anhydrous magnesium sulfate. The solvent was evaporated under reduced pressure. The residue was purified by silica gel column chromatography (chloroform/methanol=100/0-95/5) to give [5-chloro-4-(3-chlorophenylamino)-6-mercaptopyridin-3-yl][4-(4-fluorophenyl)piperidin-1-yl]methanone (259 mg, quantitative).
ESIMS m/z: 476 (M+H)$^+$
(step 4) Using [5-chloro-4-(3-chlorophenylamino)-6-mercaptopyridin-3-yl][4-(4-fluorophenyl)piperidin-1-yl]methanone (259 mg, 0.544 mmol) obtained in step 3, and in the same manner as in Example 1, step 4, 3-chloro-4-(3-chlorophenylamino)-5-[4-(4-fluorophenyl)piperidine-1-carbonyl]pyridine-2-sulfonic acid (196 mg, 69%) was obtained.
ESIMS m/z: 524 (M+H)$^+$
(step 5) Using 3-chloro-4-(3-chlorophenylamino)-5-[4-(4-fluorophenyl)piperidine-1-carbonyl]pyridine-2-sulfonic acid (196 mg, 0.374 mmol) obtained in step 4, and in the same manner as in Example 2, compound 176 (20.0 mg, 10%) was obtained.
ESIMS m/z: 523 (M+H)$^+$; $^1$H NMR (300 MHz, CDCl$_3$, δ): 1.48-1.58 (m, 3H), 1.75-1.87 (m, 2H), 2.66 (t, J=11.7 Hz, 1H), 3.07 (t, 12.5 Hz, 1E), 3.61 (d, J=11.7 Hz, 1E), 4.29 (d, J=12.5 Hz, 1H), 5.46 (s, 2H), 6.99-7.07 (m, 3H), 7.08-7.12 (m, 2H), 7.12-7.15 (m, 2H), 7.21 (d, J=8.0 Hz, 1H), 7.32 (t, J=8.0 Hz, 1H), 8.19 (s, 1H).

Example 49

3-chloro-4-(4-chloro-2-methylphenylamino)-5-[4-(4-fluorophenyl)piperidine-1-carbonyl]pyridine-2-sulfonamide (compound 177)

(step 1) Using [4-(4-fluorophenyl)piperidin-1-yl](4,5,6-trichloropyridin-3-yl)methanone (900 mg, 2.32 mmol) obtained in Example 48, step 1, and 4-chloro-2-methylaniline (427 mg, 3.02 mmol), and in the same manner as in Example 1, step 2, [5,6-dichloro-4-(4-chloro-2-methylphenylamino)pyridin-3-yl][4-(4-fluorophenyl)piperidin-1-yl]methanone (1.25 g, quantitative) was obtained.
ESIMS m/z: 492 (M+H)$^+$
(step 2) Using [5,6-dichloro-4-(4-chloro-2-methylphenylamino)pyridin-3-yl][4-(4-fluorophenyl)piperidin-1-yl]methanone (500 mg, 1.01 mmol) obtained in step 1, and in the same manner as in Example 1, step 3, [5-chloro-4-(4-chloro-2-methylphenylamino)-6-mercaptopyridin-3-yl][4-(4-fluorophenyl)piperidin-1-yl]methanone (350 mg, 70%) was obtained.
ESIMS m/z: 490 (M+H)$^+$
(step 3) Using [5-chloro-4-(4-chloro-2-methylphenylamino)-6-mercaptopyridin-3-yl][4-(4-fluorophenyl)piperidin-1-yl]methanone (250 mg, 0.510 mmol) obtained in step 2, and in the same manner as in Example 1, step 4, a crude product of 3-chloro-4-(4-chloro-2-methylphenylamino)-5-[4-(4-fluorophenyl)piperidine-1-carbonyl]pyridine-2-sulfonic acid was obtained and used for the next reaction without purification.
ESIMS m/z: 538 (M+H)$^+$
(step 4) Using a crude product of 3-chloro-4-(4-chloro-2-methylphenylamino)-5-[4-(4-fluorophenyl)piperidine-1-carbonyl]pyridine-2-sulfonic acid obtained in step 3, and in the same manner as in Example 2, compound 177 (25.9 mg, yield of 2 steps 12%) was obtained.
ESIMS m/z: 537 (M+H)$^+$; $^1$H NMR (300 MHz, DMSO-d$_6$, δ): 1.30-1.75 (m, 4H), 1.80-2.10 (m, 1H), 2.09-2.30 (s, 3H), 2.60-2.95 (m, 2H), 3.40-3.70 (s, 1H), 3.80-4.15 (s, 1H), 7.00-7.40 (m, 7H), 8.10 (s, 1H).

Example 50

3-chloro-4-(4-fluoro-2-methylphenylamino)-5-[4-(4-fluorophenyl)piperidine-1-carbonyl]-N'-benzoylpyridine-2-sulfonimidamide (compound 194)

(step 1) [5-Chloro-4-(4-fluoro-2-methylphenylamino)-6-mercaptopyridin-3-yl][4-(4-fluorophenyl)piperidin-1-yl]methanone (258 mg, 0.544 mmol) obtained in Example 24, step 3 was dissolved in methanol (7.8 mL), N-bromosuccinimide (203 mg, 1.143 mmol) was added, and the mixture was stirred at room temperature for 1 hr. To the reaction mixture was added water was added, and extracted with chloroform. The organic layer was washed with saturated brine, and dried over anhydrous magnesium sulfate. The solvent was evaporated under reduced pressure, and a crude product of methyl 3-chloro-4-(4-fluoro-2-methylphenylamino)-5-[4-(4-fluorophenyl)piperidine-1-carbonyl]pyridine-2-sulfinate was obtained and used for the next step without purification.
ESIMS m/z: 520 (M+H)$^+$
(step 2) A crude product of methyl 3-chloro-4-(4-fluoro-2-methylphenylamino)-5-[4-(4-fluorophenyl)piperidine-1-carbonyl]pyridine-2-sulfinate obtained in step 1 was dissolved in THF (5.4 mL), and lithium bis(trimethylsilyl)amide (1.0 mol/L, THF solution, 2.42 mL, 2.42 mmol) was added dropwise at −78° C. After stirring for 20 min under ice-cooling, saturated aqueous ammonium chloride solution was added, and the mixture was stirred at room temperature for 15 min. The reaction mixture was extracted with ethyl acetate, and the solvent was evaporated under reduced pressure. The residue was purified by silica gel column chromatography (heptane/ethyl acetate=1/5) to give 3-chloro-4-(4-fluoro-2-methylphenylamino)-5-[4-(4-fluorophenyl)piperidine-1-carbonyl]pyridine-2-sulfinamide (168 mg, yield of 2 steps 62%).
ESIMS m/z: 505 (M+H)$^+$
(step 3) 3-Chloro-4-(4-fluoro-2-methylphenylamino)-5-[4-(4-fluorophenyl)piperidine-1-carbonyl]pyridine-2-sulfinamide (168 mg, 0.344 mmol) obtained in step 2 was dissolved in THF (3.3 mL), n-butyllithium (1.64 mol/L, hexane solution, 0.428 mL, 0.701 mmol) and benzoic anhydride (79 mg, 0.351 mmol) were added at −78° C., and the mixture was stirred for 15 min. To the reaction mixture was added saturated aqueous ammonium chloride solution, and the mixture was extracted with ethyl acetate.

The solvent was evaporated under reduced pressure, and the residue was purified by silica gel column chromatography (heptane/ethyl acetate=1/2) to give N-{3-chloro-4-(4-fluoro-2-methylphenylamino)-5-[4-(4-fluorophenyl)piperidine-1-carbonyl]pyridin-2-ylsulfinyl}benzamide (100 mg, 49%).

ESIMS m/z: 609 (M+H)$^+$ (step 4) N-{3-Chloro-4-(4-fluoro-2-methylphenylamino)-5-[4-(4-fluorophenyl)piperidine-1-carbonyl]pyridin-2-ylsulfinyl}benzamide (87.0 mg, 0.143 mmol) obtained in step 3 was dissolved in acetonitrile (1.4 mL), N-chlorosuccinimide (22.9 mg, 0.171 mmol) was added, and the mixture was stirred at room temperature for 1 hr. To the reaction mixture was added hexamethyldisilasane (0.060 mL, 0.286 mmol), and the mixture was stirred at room temperature for 1 hr. To the reaction mixture was added water, the mixture was extracted with ethyl acetate, and the solvent was evaporated under reduced pressure. The residue was purified by silica gel column chromatography (chloroform/methanol=20/1) and reslurried with acetonitrile to give 3-chloro-4-(4-fluoro-2-methylphenylamino)-5-[4-(4-fluorophenyl)piperidine-1-carbonyl]-N'-benzoylpyridine-2-sulfonimidamide (50.6 mg, 57%).

ESIMS m/z: 624 (M+H)$^+$; $^1$H NMR (400 MHz, CDCl$_3$, δ): 1.36-1.52 (m, 2H), 1.74-1.85 (m, 2H), 1.91-2.25 (m, 1H), 2.25-2.35 (m, 1H), 2.56-2.70 (m, 3H), 2.75-3.04 (m, 1H), 3.54-3.72 (m, 1H), 4.18-4.38 (m, 1H), 6.57-6.72 (m, 3H), 6.83-6.90 (m, 1H), 6.94-7.04 (m, 4H), 7.06-7.15 (m, 2H), 7.43 (t, J=7.7 Hz, 2H), 7.51-7.58 (m, 1H), 8.06 (s, 1H), 8.18-8.21 (m, 1H), 8.21 (s, 1H).

Example 51

3-chloro-5-(4-cyano-4-phenylpiperidine-1-carbonyl)-4-(4-fluoro-2-methylphenylamino)pyridine-2-sulfonamide (compound 195)

(step 1) Using ethyl 4,5,6-trichloronicotinate (2.0 g, 7.86 mmol) and 4-fluoro-2-methylaniline (1.48 g, 11.8 mmol), and in the same manner as in Example 1, step 2, ethyl 5,6-dichloro-4-(4-fluoro-2-methylphenylamino)nicotinate (1.64 g, 61%) was obtained.

ESIMS m/z: 343 (M+H)$^+$ (step 2) Ethyl 5,6-dichloro-4-(4-fluoro-2-methylphenylamino)nicotinate (1.00 g, 2.91 mmol) obtained in step 1 was dissolved in DMF (B mL), sodium hydrogen sulfide n hydrate (0.467 g, 5.83 mmol) was added, and the mixture was stirred at room temperature for 2 hr. To the reaction mixture was added saturated aqueous sodium chloride solution, and the mixture was extracted with ethyl acetate. The organic layer was washed with water, and dried over anhydrous magnesium sulfate. The solvent was evaporated under reduced pressure to give ethyl 5-chloro-4-(4-fluoro-2-methylphenylamino)-6-mercaptonicotinate (900 mg, 91%) was obtained.

ESIMS m/z: 341 (M+H)$^+$ (step 3) Ethyl 5-chloro-4-(4-fluoro-2-methylphenylamino)-6-mercaptonicotinate (0.60 g, 1.76 mmol) obtained in step 2 was dissolved in acetonitrile (10 mL), 30% aqueous hydrogen peroxide solution (8.99 mL, 88 mmol) was added, and the mixture was stirred at room temperature for 2 hr. To the reaction mixture was added 12 mol/L hydrochloric acid (0.44 mL, 5.28 mmol), and the mixture was stirred at room temperature for 2 hr. To the reaction mixture was added saturated aqueous sodium chloride solution, and the mixture was extracted with ethyl acetate. The organic layer was dried over anhydrous magnesium sulfate, and the solvent was evaporated under reduced pressure. The residue was purified by silica gel column chromatography (chloroform/methanol=1/4) to give 3-chloro-5-(ethoxycarbonyl)-4-(4-fluoro-2-methylphenylamino)pyridine-2-sulfonic acid (500 mg, 73%).

ESIMS m/z: 389 (M+H)$^+$ (step 4) Using 3-chloro-5-(ethoxycarbonyl)-4-(4-fluoro-2-methylphenylamino)pyridine-2-sulfonic acid (500 mg, 1.29 mmol) obtained in step 3, and in the same manner as in Example 2, ethyl 5-chloro-4-(4-fluoro-2-methylphenylamino)-6-sulfamoylnicotinate (280 mg, 56%) was obtained.

ESIMS m/z: 388 (M+H)$^+$ (step 5) Ethyl 5-chloro-4-(4-fluoro-2-methylphenylamino)-6-sulfamoylnicotinate (250 mg, 0.645 mmol) obtained in step 4 was dissolved in THF (4 mL), 1 mol/L aqueous sodium hydroxide solution (2.58 mL, 2.58 mmol) was added, and the mixture was stirred at room temperature for 2 hr. To the reaction mixture was added 1 mol/L hydrochloric acid, and the mixture was extracted with ethyl acetate. The organic layer was washed with saturated aqueous sodium chloride solution, and dried over anhydrous magnesium sulfate. The solvent was evaporated under reduced pressure to give 5-chloro-4-(4-fluoro-2-methylphenylamino)-6-sulfamoylnicotinic acid (220 mg, 95%) was obtained.

ESIMS m/z: 360 (M+H)$^+$ (step 6) Using 5-chloro-4-(4-fluoro-2-methylphenylamino)-6-sulfamoylnicotinic acid (25 mg, 0.069 mmol) obtained in step 5 and 4-phenylpiperidine-4-carbonitrile hydrochloride (31 mg, 0.139 mmol), and in the same manner as in Example 1, step 1, compound 195 (30 mg, 82%) was obtained.

ESIMS m/z: 528 (M+H)$^+$; $^1$H NMR (400 MHz, DMSO-$_6$, δ): 2.00-2.15 (m, 4H), 2.22 (s, 3H), 2.69 (s, 2H), 2.98-3.07 (m, 1H), 3.62-3.71 (m, 1H), 4.04-4.12 (m, 1H), 6.94-7.01 (m, 1H), 7.10-7.22 (m, 2H), 7.38-7.62 (m, 6H), 8.20 (s, 1H), 8.41 (br s, 1H).

Example 52

4-(4-chloro-2-methylphenylamino)-5-[4-(4-fluorophenyl)piperidine-1-carbonyl]-3-methylpyridine-2-sulfonamide (compound 196)

(step 1) Using 4,6-dichloro-5-methylnicotinic acid (1.00 g, 4.85 mmol) obtained by the method described in a document (Journal of Heterocyclic Chemistry, 1999, 36, p. 953), and in the same manner as in Example 1, step 1, (4,6-dichloro-5-methylpyridin-3-yl)[4-(4-fluorophenyl)piperidin-1-yl]methanone (1.60 g, 90%) was obtained.

ESIMS m/z: 367 (M+H)$^+$ (step 2) Using (4,6-dichloro-5-methylpyridin-3-yl) [4-(4-fluorophenyl)piperidin-1-yl]methanone (236 mg, 0.643 mmol), and 4-chloro-2-methylaniline (227 mg, 1.61 mmol) obtained in step 1, and in the same manner as in Example 1, step 2, [6-chloro-4-(4-chloro-2-methylphenylamino)-5-methylpyridin-3-yl][4-(4-fluorophenyl)piperidin-1-yl] methanone (273 mg, 90%) was obtained.

ESIMS m/z: 472 (M+H)$^+$ (step 3) Using [6-chloro-4-(4-chloro-2-methylphenylamino)-5-methylpyridin-3-yl][4-(4-fluorophenyl)piperidin-1-yl]methanone (270 mg, 0.572 mmol) obtained in step 2, and in the same manner as in Example 1, step 3, [4-(4-chloro-2-methylphenylamino)-6-mercapto-5-methylpyridin-3-yl][4-(4-fluorophenyl)piperidin-1-yl]methanone (164 mg, 61%) was obtained.

ESIMS m/z: 470 (M+H)$^+$ (step 4) Using [4-(4-chloro-2-methylphenylamino)-6-mercapto-5-methylpyridin-3-yl][4-(4-fluorophenyl)piperidin-1-yl]methanone (163 mg, 0.347 mmol) obtained in step 3, and in the same manner as in Example 1, step 4, 4-(4-chloro-2-methylphenylamino)-5-[4-(4-fluorophenyl)piperidine-1-carbonyl]-3-methylpyridine-2-sulfonic acid (167 mg, 93%) was obtained.

ESIMS m/z: 518 (M+H)$^+$ (step 5) Using 4-(4-chloro-2-methylphenylamino)-5-[4-(4-fluorophenyl)piperidine-1-carbonyl]-3-methylpyridine-2-sulfonic acid (164 mg, 0.317 mmol) obtained in step 4, and in the same manner as in Example 2, compound 196 (25.1 mg, 15%) was obtained.

ESIMS m/z: 517 (M+H)$^+$; $^1$H NMR (400 MHz, CDCl$_3$, δ); 1.34-1.62 (m, 2H), 1.69-1.99 (m, 2H), 2.33 (s, 3H), 2.38 (s, 3H), 2.52-2.83 (m, 2H), 2.93-3.27 (m, 1H), 3.66-3.96 (m, 1H), 4.56-4.78 (m, 1H), 5.51 (s, 2H), 6.52 (d, J=8.2 Hz, 1H), 6.72 (s, 1H), 6.94-7.04 (m, 4H), 7.06 (dd, J=8.6, 2.3 Hz, 1H), 7.24 (d, J 2.3 Hz, 1H), 8.16 (s, 1H).

Example 53

4-(3-chlorophenylamino)-5-[4-(4-fluorophenyl)piperidine-1-carbonyl]-3-methylpyridine-2-sulfonamide (compound 197)

(step 1) Using (4,6-dichloro-5-methylpyridin-3-yl) [4-(4-fluorophenyl)piperidin-1-yl]methanone (236 mg, 0.643 mmol) obtained in Example 52, step 1, and 3-chloroaniline (205 mg, 1.61 mmol), and in the same manner as in Example 1, step 2, [6-chloro-4-(3-chlorophenylamino)-5-methylpyridin-3-yl][4-(4-fluorophenyl)piperidin-1-yl]methanone (223 mg, 76%) was obtained.

ESIMS m/z: 458 (M+H)$^+$ (step 2) Using [6-chloro-4-(3-chlorophenylamino)-5-methylpyridin-3-yl][4-(4-fluorophenyl)piperidin-1-yl]methanone (220 mg, 0.480 mmol) obtained in step 1, and in the same manner as in Example 1, step 3, [4-(3-chlorophenylamino)-6-mercapto-5-methylpyridin-3-yl][4-(4-fluorophenyl)piperidin-1-yl]methanone (182 mg, 83%) was obtained.

ESIMS m/z: 456 (M+H)$^+$ (step 3) Using [4-(3-chlorophenylamino)-6-mercapto-5-methylpyridin-3-yl][4-(4-fluorophenyl)piperidin-1-yl]methanone (180 mg, 0.395 mmol) obtained in step 2, and in the same manner as in Example 1, step 4, 4-(3-chlorophenylamino)-5-[4-(4-fluorophenyl)piperidine-1-carbonyl]-3-methylpyridine-2-sulfonic acid (174 mg, 87%) was obtained.

ESIMS m/z: 504 (M+H)$^+$ (step 4) Using 4-(3-chlorophenylamino)-5-[4-(4-fluorophenyl)piperidine-1-carbonyl]-3-methylpyridine-2-sulfonic acid (164 mg, 0.317 mmol) obtained in step 3, and in the same manner as in Example 2, compound 197 (9.2 mg, 5.4%) was obtained.

ESIMS m/z: 503 (M+H)$^+$; $^1$H NMR (400 MHz, CDCl$_3$, δ): 1.35-1.69 (m, 2H), 1.69-1.96 (m, 2H), 2.39 (s, 3H), 2.48-2.66 (m, 1H), 2.66-2.82 (m, 1H), 3.06-3.30 (m, 1H), 3.68-3.90 (m, 1H), 4.51-4.72 (m, 1H), 5.53-5.76 (m, 2H), 6.74 (d, J=7.7 Hz, 1H), 6.83 (t, J=1.8 Hz, 1H), 6.93-7.10 (m, 5H), 7.14 (s, 1H), 7.21 (t, J 7.9 Hz, 1H), 8.19 (s, 1H).

Example 54

3-chloro-N'-(ethylcarbamoyl)-4-(4-fluoro-2-methylphenylamino)-5-[4-(4-fluorophenyl)piperidine-1-carbonyl]pyridine-2-sulfonamide (compound 198)

(step 1) Using 3-chloro-4-(4-fluoro-2-methylphenylamino)-5-[4-(4-fluorophenyl)piperidine-1-carbonyl]pyridine-2-sulfinamide (102 mg, 0.202 mmol) obtained in Example 50, step 2, and ethyl isocyanate (0.017 mL, 0.212 mmol), and in the same manner as in Example 50, step 3, 3-chloro-N-(ethylcarbamoyl)-4-(4-fluoro-2-methylphenylamino)-5-[4-(4-fluorophenyl)piperidine-1-carbonyl]pyridine-2-sulfinamide (33.4 mg, 29%) was obtained.

ESIMS m/z: 576 (M+H)$^+$ (step 2) Using 3-chloro-N-(ethylcarbamoyl)-4-(4-fluoro-2-methylphenylamino)-5-[4-(4-fluorophenyl)piperidine-1-carbonyl]pyridine-2-sulfinamide (31.0 mg, 0.054 mmol) obtained in step 1, and in the same manner as in Example 50, step 4, compound 198 (12.6 mg, 40%) was obtained.

ESIMS m/z: 591 (M+H)$^+$; $^1$H NMR (400 MHz, CDCl$_3$, δ): 1.13 (t, J=7.2 Hz, 3H), 1.36-1.50 (m, 2H), 1.74-1.84 (m, 2H), 1.92-2.26 (m, 1H), 2.32 (s, 3H), 2.57-2.71 (m, 1H), 2.74-3.02 (m, 1H), 3.11-3.32 (m, 2H), 3.56-3.73 (m, 1H), 4.19-4.37 (m, 1H), 5.20 (br s, 1H), 6.71 (s, 1H), 6.74 (br s, 2H), 6.89 (dt, J=2.7, 8.2 Hz, 1H), 6.96-7.04 (m, 4H), 7.11 (dd, J=8.4, 5.2 Hz, 2H), 8.04 (s, 1H).

Example 55

3-chloro-4-(4-fluoro-2-methylphenylamino)-5-[4-(4-fluorophenyl)piperidine-1-carbonyl]pyridine-2-sulfonimidamide (compound 200)

(step 1) Using 3-chloro-4-(4-fluoro-2-methylphenylamino)-5-[4-(4-fluorophenyl)piperidine-1-carbonyl]pyridine-2-sulfinamide (126 mg, 0.250 mmol) obtained in Example 50, step 2, and di-tert-butyl dicarbonate (57.2 mg, 0.262 mmol), and in the same manner as in Example 50, step 3, tert-butyl 3-chloro-4-(4-fluoro-2-methylphenylamino)-5-[4-(4-fluorophenyl)piperidine-1-carbonyl]pyridin-2-ylsulfinylcarbamate (96.0 mg, 64%) was obtained.

ESIMS m/z: 605 (M+H)$^+$ (step 2) Using tert-butyl 3-chloro-4-(4-fluoro-2-methylphenylamino)-5-[4-(4-fluorophenyl)piperidine-1-carbonyl]pyridin-2-ylsulfinylcarbamate (93.0 mg, 0.154 mmol) obtained in step 1, and in the same manner as in Example 50, step 4, 3-chloro-4-(4-fluoro-2-methylphenylamino)-5-[4-(4-fluorophenyl)piperidine-1-carbonyl]-N'-tert-butoxycarbonylpyridine-2-sulfonimidamide (22.5 mg, 24%) was obtained.

ESIMS m/z: 620 (M+H)$^+$ (step 3) 3-Chloro-4-(4-fluoro-2-methylphenylamino)-5-[4-(4-fluorophenyl)piperidine-1-carbonyl]-N'-tert-butoxycarbonylpyridine-2-sulfonimidamide (20.0 mg, 0.032 mmol) obtained in step 2 was dissolved in dichloromethane (1 mL), trifluoroacetic acid (0.248 mL, 3.23 mmol) was added, and the mixture was stirred at room temperature for 30 min. The solvent was evaporated under reduced pressure to give and the residue was purified by silica gel column chromatography (chloroform/methanol=10/1) to give compound 200 (16.6 mg, 99%). ESIMS m/z: 520 (M+H)$^+$; $^1$H NMR (400 MHz, CDCl$_3$, δ): 1.37-1.54 (m, 2H), 1.74-1.84 (m, 2H), 2.32 (s, 3H), 2.37-2.46 (m, 1H), 2.64 (tt, J=3.6, 12.2

Hz, 1H), 2.78-3.04 (m, 1H), 3.53-3.70 (m, 1H), 4.21-4.36 (m, 1H), 6.72 (br s, 1H), 6.89 (td, J=8.2, 2.9 Hz, 1H), 6.96-7.05 (m, 4H), 7.07-7.14 (m, 2H), 8.03 (s, 1H).

Example 56

[5-chloro-6-(ethylsulfonyl)-4-(o-tolylamino)pyridin-3-yl][4-(4-fluorophenyl)piperidin-1-yl]methanone (compound 204)

(step 1) [5,6-Dichloro-4-(o-tolylamino)pyridin-3-yl][4-(4-fluorophenyl)piperidin-1-yl]methanone (148 mg, 0.323 mmol) obtained in Example 33, step 2 was dissolved in DMF (1.5 mL), sodium ethanethiolate (102 mg, 0.969 mmol) was added, and the mixture was stirred at room temperature for 1.5 hr. To the reaction mixture was added water was added, and the mixture was extracted with ethyl acetate. The solvent was evaporated under reduced pressure to give and the residue was purified by silica gel column chromatography (heptane/ethyl acetate=2/1) to give [5-chloro-6-(ethylthio)-4-(o-tolylamino)pyridin-3-yl][4-(4-fluorophenyl)piperidin-1-yl]methanone (100 mg, 64%).
ESIMS m/z: 484 (M+H)$^+$ (step 2) [5-Chloro-6-(ethylthio)-4-(o-tolylamino)pyridin-3-yl][4-(4-fluorophenyl)piperidin-1-yl]methanone (47 mg, 0.097 mmol) obtained in step 1 was dissolved in dichloromethane (1.0 mL), m-chloroperbenzoic acid (36.9 mg, 0.214 mmol) was added under ice-cooling, and the mixture was stirred at room temperature for 3 hr. To the reaction mixture was added saturated aqueous sodium hydrogen carbonate solution, and the mixture was extracted with chloroform. The solvent was evaporated under reduced pressure and the residue was purified by silica gel column chromatography (heptane/ethyl acetate-2/1) to give compound 204 (26.1 mg, 52%).
ESIMS m/z: 516 (M+H)$^+$; $^1$H NMR (400 MHz, CDCl$_3$, δ): 1.36-1.46 (m, 2H), 1.49 (t, J=7.2 Hz, 3H), 1.69-1.83 (m, 2H), 1.88-2.12 (m, 1H), 2.33 (s, 3H), 2.60 (tt, J=3.6, 0.5 Hz, 1H), 2.76-3.01 (m, 1H), 3.52-3.76 (m, 3H), 4.16-4.27 (m, 1H), 6.84 (br s, 1H), 6.95-7.05 (m, 3H), 7.05-7.12 (m, 2H), 7.20 (dt, J=9.7, 3.9 Hz, 2H), 7.27-7.32 (m, 1H), 8.10 (s, 1H).

Example 57

3-chloro-5-[4-(4-fluorophenyl)piperidine-1-carbonyl]-4-(m-tolylthio)pyridine-2-sulfonamide (compound 210)

(step 1) 60% Sodium hydride (203 mg, 5.08 mmol) was dissolved in THF (10 mL), 2-propanol (0.19 mL, 2.4 mmol) and a solution of 4,5,6-trichloronicotinic acid (500 mg, 2.21 mmol) in THF (2 mL) were added under ice-cooling, and the mixture was stirred at room temperature for 2 hr. To the reaction mixture was added 1 mol/L hydrochloric acid (5.5 mL, 5.5 mmol), and the mixture was extracted with ethyl acetate. The organic layer was dried over anhydrous magnesium sulfate, and the solvent was evaporated under reduced pressure to give a crude product of 5,6-dichloro-4-isopropoxynicotinic acid, which was used for the next reaction without purification.
ESIMS m/z: 250 (M+H)$^+$ (step 2) Using a crude product of 5,6-dichloro-4-isopropoxynicotinic acid obtained in step 1, and in the same manner as in Example 1, step 1, (5,6-dichloro-4-isopropoxypyridin-3-yl) [4-(4-fluorophenyl)piperidin-1-yl)methanone (780 mg, yield of 2 steps 86%) was obtained.
ESIMS m/z: 411 (M+H)$^+$ (step 3) (5,6-Dichloro-4-isopropoxypyridin-3-yl)[4-(4-fluorophenyl)piperidin-1-yl)methanone (760 mg, 1.85 mmol) obtained in step 2 was dissolved in DMF (9.0 mL), sodium hydrogen sulfide n hydrate (518 mg, 6.47 mmol) was added, and the mixture was stirred at 80° C. for 1 hr. To the reaction mixture was added saturated aqueous sodium chloride solution, and the mixture was extracted with ethyl acetate. The organic layer was washed with saturated aqueous sodium chloride solution, and dried over anhydrous magnesium sulfate. The solvent was evaporated under reduced pressure. The residue was purified by silica gel column chromatography (chloroform/methanol=20/1) to give (5-chloro-4-isopropoxy-6-mercaptopyridin-3-yl)[4-(4-fluorophenyl)piperidin-1-yl]methanone (626 mg, 83%).
ESIMS m/z: 409 (M+H)$^+$ (step 4) Using (5-chloro-4-isopropoxy-6-mercaptopyridin-3-yl)[4-(4-fluorophenyl)piperidin-1-yl]methanone (149 mg, 0.364 mmol) obtained in step 3, and in the same manner as in Example 46, step 3, 3-chloro-5-[4-(4-fluorophenyl)piperidine-1-carbonyl]-4-isopropoxypyridine-2-sulfonamide (138 mg, 83%) was obtained.
ESIMS m/z: 456 (M+H)$^+$ (step 5) 3-Chloro-5-[4-(4-fluorophenyl)piperidine-1-carbonyl]-4-isopropoxypyridine-2-sulfonamide (143 mg, 0.314 mmol) obtained in step 4 was dissolved in toluene (6.3 mL), aluminum chloride (209 mg, 1.57 mmol) was added, and the mixture was stirred at 70° C. for 1 hr. To the reaction mixture was added water was added, and the mixture was extracted with ethyl acetate. The organic layer was dried over anhydrous magnesium sulfate, and the solvent was evaporated under reduced pressure. The residue was purified by silica gel column chromatography (ethyl acetate/methanol-6/1) to give 3-chloro-5-[4-(4-fluorophenyl)piperidine-1-carbonyl]-4-hydroxypyridine-2-sulfonamide (121 mg, 93%).
ESIMS m/z: 414 (M+H)$^+$ (step 6) 3-Chloro-5-[4-(4-fluorophenyl)piperidine-1-carbonyl]-4-hydroxypyridine-2-sulfonamide (217 mg, 0.524 mmol) obtained in step 5 was dissolved in acetonitrile (2.6 mL), phosphorus oxychloride (0.22 mL, 2.4 mmol) was added, and the mixture was stirred under reflux for 7.5 hr. The reaction mixture was added to saturated aqueous sodium hydrogen carbonate solution, and the mixture was extracted with ethyl acetate. The organic layer was dried over anhydrous magnesium sulfate, and the solvent was evaporated under reduced pressure. The residue was purified by silica gel column chromatography (ethyl acetate) to give 3,4-dichloro-5-[4-(4-fluorophenyl)piperidine-1-carbonyl]pyridine-2-sulfonamide (208 mg, 92%).
ESIMS m/z: 432 (M+H)$^+$ (step 7) Using 3,4-dichloro-5-[4-(4-fluorophenyl)piperidine-1-carbonyl]pyridine-2-sulfonamide (25.9 mg, 0.060 mmol) obtained in step 6, and 3-methylbenzenethiol (0.011 mL, 0.096 mmol), and in the same manner as in Example 1, step 2, compound 210 (29.8 mg, 96%) was obtained.
ESIMS m/z: 520 (M+H)$^+$; $^1$H NMR (400 MHz, CDCl$_3$, δ): 1.42-1.98 (m, 5H), 2.30-2.38 (m, 3H), 2.43-3.19 (m, 2H), 3.36-3.45 (m, 1H), 4.55-4.83 (m, 1H), 5.26-5.30 (m, 2H), 6.96-7.02 (m, 2H), 7.05-7.25 (m, 6H), 8.30-8.35 (s, 1H).

Example 58

N-{3-chloro-5-[4-(4-fluorophenyl)piperidine-1-carbonyl]-2-sulfamoylpyridin-4-yl}benzamide (compound 211)

(step 1) Using [4-(4-fluorophenyl)piperidin-1-yl](4,5,6-trichloropyridin-3-yl)methanone (123 mg, 0.317 mmol) obtained in Example 48, step 1, and (4-methoxyphenyl)methanamine (0.053 mL, 0.41 mmol), and in the same manner as in Example 44, step 1, a crude product of

[5,6-dichloro-4-(4-methoxybenzylamino)pyridin-3-yl][4-(4-fluorophenyl)piperidin-1-yl]methanone was obtained and used for the next reaction without purification.

ESIMS m/z: 488 (M+H)+

(step 2) The crude product of [5,6-dichloro-4-(4-methoxybenzylamino)pyridin-3-yl][4-(4-fluorophenyl)piperidin-1-yl]methanone obtained in step 1 was dissolved in dichloromethane (2.0 mL), trifluoroacetic acid (0.50 mL, 6.5 mmol) was added, and the mixture was stirred at room temperature for 11 hr. The solvent of the reaction mixture was evaporated under reduced pressure and the residue was purified by silica gel column chromatography (heptane/ethyl acetate=1/0-1/1) to give (4-amino-5,6-dichloropyridin-3-yl)[4-(4-fluorophenyl)piperidin-1-yl]methanone (90.3 mg, yield of 2 steps 77%).

ESIMS m/z: 368 (M+H)+

(step 3) (4-Amino-5,6-dichloropyridin-3-yl) [4-(4-fluorophenyl)piperidin-1-yl]methanone (77.0 mg, 0.209 mmol) obtained in step 2 was dissolved in dichloromethane (3.0 mL), triethylamine (0.61 mL, 4.4 mmol), benzoyl chloride (1.3 mL, 1.3 mmol) and DMAP (25.6 mg, 0.208 mmol) were added under ice-cooling, and the mixture was stirred at room temperature for 16 hr. To the reaction mixture were added water and saturated aqueous ammonium chloride solution, and the mixture was extracted with ethyl acetate. The organic layer was dried over anhydrous magnesium sulfate, and the solvent was evaporated under reduced pressure. The residue was purified by silica gel column chromatography (hexane/ethyl acetate=1/0-1/1) to give N-benzoyl-N-({2,3-dichloro-5-[4-(4-fluorophenyl)piperidine-1-carbonyl]pyridin-4-yl}benzamide (117 mg, 97%).

ESIMS m/z: 576 (M+H)+

(step 4) Using N-benzoyl-N-{2,3-dichloro-5-[4-(4-fluorophenyl)piperidine-1-carbonyl]pyridin-4-yl}benzamide (117 mg, 0.202 mmol) obtained in step 3, and in the same manner as in Example 57, step 3, N-benzoyl-N-(3-chloro-5-[4-(4-fluorophenyl)piperidine-1-carbonyl]-2-mercaptopyridin-4-yl)benzamide (49.3 mg, 42%) was obtained.

ESIMS m/z: 574 (M+H)+

(step 5) N-benzoyl-N-{3-chloro-5-[4-(4-fluorophenyl)piperidine-1-carbonyl]-2-mercaptopyridin-4-yl}benzamide (49.3 mg, 0.086 mmol) obtained in step 4 was dissolved in methanol (3.0 mL), potassium carbonate (11.9 mg, 0.086 mmol) was added, and the mixture was stirred at room temperature for 1.5 hr and under reflux for 22.5 hr. To the reaction mixture was added saturated aqueous ammonium chloride solution, and the mixture was extracted with ethyl acetate. The organic layer was dried over anhydrous magnesium sulfate, and the solvent was evaporated under reduced pressure. The residue was purified by silica gel column chromatography (heptane/ethyl acetate=1/0-1/1) to give N-{3-chloro-5-[4-(4-fluorophenyl)piperidine-1-carbonyl]-2-mercaptopyridin-4-yl}benzamide (27.6 mg, 68%).

ESIMS m/z: 470 (M+H)+

(step 6) Using N-{3-chloro-5-[4-(4-fluorophenyl)piperidine-1-carbonyl]-2-mercaptopyridin-4-yl}benzamide (117 mg, 0.202 mmol) obtained in step 5, and in the same manner as in Example 46, step 3, compound 211 (2.9 mg, 16%) was obtained.

ESIMS m/z: 517 (M+H)+; 1H NMR (300 MHz, CDCl3, δ): 1.58-1.78 (m, 2H), 1.96-2.06 (m, 2H), 2.81 (d, J=11.7 Hz, 2H), 3.29-3.45 (m, 1H), 3.94 (d, J=15.4 Hz, 1H), 4.53-4.81 (m, 1H), 6.37 (br s, 2H), 7.02 (t, J=8.4 Hz, 2H), 7.19 (dd, J=5.5, 8.4 Hz, 2H), 7.52-7.62 (m, 3H), 8.03 (d, J=7.0 Hz, 2H), 8.17 (s, 1H), 8.82 (s, 1H).

Example 59

4-benzyl-3-chloro-5-[4-(4-fluorophenyl)piperidine-1-carbonyl]pyridine-2-sulfonamide (compound 212)

3,4-Dichloro-5-[4-(4-fluorophenyl)piperidine-1-carbonyl]pyridine-2-sulfonamide (20.0 mg, 0.0460 mmol) obtained in Example 57, step 6, and [1,3-bis(2,6-diisopropylphenyl)imidazol-2-ylidene](3-chloropyridyl)palladium (II) dichloride (PEPPSI™, 9.4 mg, 0.014 mmol) were dissolved in THF (1.0 mL), 0.5 mol/L benzyl zinc bromide/THF solution (0.28 mL, 0.14 mmol) was added, and the mixture was stirred at room temperature for 12 hr. To the reaction mixture was added saturated aqueous ammonium chloride solution, and the mixture was extracted with ethyl acetate. The organic layer was washed with saturated aqueous sodium chloride solution, and dried over anhydrous magnesium sulfate. The solvent was evaporated under reduced pressure. The residue was purified by silica gel column chromatography (heptane/ethyl acetate=1/0-0/1) and preparative HPLC (XBridge™ manufactured by Waters) (acetonitrile/0.05% aqueous trifluoroacetic acid solution) to give compound 212 (3.0 mg, 13%).

ESIMS m/z: 488 (M+H)+; 1H NMR (400 MHz, CDCl3, δ): 1.53-1.74 (m, 2H), 1.77-2.07 (m, 2H), 2.46-2.64 (m, 2H), 2.69-3.27 (m, 2H), 4.08-4.48 (m, 1H), 4.50-4.64 (m, 1H), 4.69-4.93 (m, 1H), 5.26 (br s, 2H), 6.94-7.01 (m, 3H), 7.08-7.21 (m, 4H), 7.27-7.34 (m, 2H), 8.24-8.28 (m, 1H).

Example 60

3-chloro-5-[5-(4-fluorophenyl)octahydropyrrolo[3,4-c]pyrrole-2-carbonyl]-4-(m-tolylamino)pyridine-2-sulfonamide (compound 213)

(step 1) tert-Butyl hexahydropyrrolo[3,4-c]pyrrole-2(1H)-carboxylate (300 mg, 1.41 mmol) was dissolved in toluene (10 mL), 1-bromo-4-fluorobenzene (0.20 mL, 1.84 mmol), 2,2'-bis(diphenylphosphino)-1,1'-binaphthyl (35 mg, 0.057 mmol), tert-butoxy sodium (217 mg, 2.26 mmol) and tris(dibenzylideneacetone)dipalladium(0) (26 mg, 0.028 mmol) were added, and the mixture was stirred at 85° C. for 12 hr. The reaction mixture was filtered through celite (registered trade mark), saturated aqueous sodium hydrogen carbonate solution was added, and the mixture was extracted with ethyl acetate. The organic layer was washed with saturated aqueous sodium chloride solution, and dried over anhydrous magnesium sulfate. The solvent was evaporated under reduced pressure. The residue was purified by silica gel column chromatography (heptane/ethyl acetate=3/2) to give tert-butyl 5-(4-fluorophenyl)hexahydropyrrolo[3,4-c]pyrrole-2(1H)-carboxylate (140 mg, 32%).

ESIMS m/z: 307 (M+H)+.

(step 2) tert-Butyl 5-(4-fluorophenyl)hexahydropyrrolo[3,4-c]pyrrole-2(1H)-carboxylate (130 mg, 0.424 mmol) obtained in step 1 was dissolved in ethyl acetate (1 mL), 4 mol/L hydrochloric acid/ethyl acetate solution (0.530 mL, 2.12 mmol) was added, and the mixture was stirred at room temperature for 2 hr. The reaction mixture was concentrates under reduced pressure to give 2-(4-fluorophenyl)octahydropyrrolo[3,4-c]pyrrole hydrochloride (100 mg, 97%).

ESIMS m/z: 207 (M+H)+

(step 3) Using ethyl 4,5,6-trichloronicotinate (1.50 g, 5.89 mmol) and m-toluidine (0.695 g, 6.48 mmol), and in the same manner as in Example 1, step 2, ethyl 5,6-dichloro-4-(m-tolylamino)nicotinate (1.00 g, 52%) was obtained.

ESIMS m/z: 325 (M+H)+.

(step 4) Using ethyl 5,6-dichloro-4-(m-tolylamino)nicotinate (0.95 g, 2.92 mmol) obtained in step 3, and in the same manner as in Example 51, step 2, ethyl 5-chloro-6-mercapto-4-(m-tolylamino)nicotinate (0.9 g, 95%) was obtained.

ESIMS m/z: 323 (M+H)$^+$ (step 5) Using ethyl 5-chloro-6-mercapto-4-(m-tolylamino)nicotinate (0.8 g, 2.48 mmol) obtained in step 4, and in the same manner as in Example 51, step 3, a crude product of 3-chloro-5-(ethoxycarbonyl)-4-(m-tolylamino)pyridine-2-sulfonic acid was obtained and used for the next reaction without purification.

ESIMS m/z: 371 (M+H)$^+$ (step 6) Using a crude product of 3-chloro-5-(ethoxycarbonyl)-4-(m-tolylamino)pyridine-2-sulfonic acid obtained in step 5, and in the same manner as in Example 2, ethyl 5-chloro-6-sulfamoyl-4-(m-tolylamino)nicotinate (370 mg, yield of 2 steps 40%) was obtained.

ESIMS m/z: 370 (M+H)$^+$ (step 7) Using ethyl 5-chloro-6-sulfamoyl-4-(m-tolylamino)nicotinate (350 mg, 0.946 mmol) obtained in step 6, and in the same manner as in Example 51, step 5, 5-chloro-6-sulfamoyl-4-(m-tolylamino)nicotinic acid (320 mg, 99%) was obtained.

ESIMS m/z: 342 (M+H)$^+$ (step 8) Using 2-(4-fluorophenyl)octahydropyrrolo[3,4-c]pyrrole hydrochloride (27 mg, 0.110 mmol) obtained in step 2, and 5-chloro-6-sulfamoyl-4-(m-tolylamino)nicotinic acid (25 mg, 0.073 mmol) obtained in step 7, and in the same manner as in Example 1, step 1, compound 213 (33 mg, 85%) was obtained.

ESIMS m/z: 530 (M+H)$^+$; $^1$H NMR (400 MHz, DMSO-d$_6$, δ): 2.22 (s, 3H), 2.70-2.77 (m, 2H), 2.88-2.96 (m, 2H), 3.02-3.10 (m, 2H), 3.24-3.32 (m, 2H), 3.44-3.51 (m, 2H), 6.46-6.52 (m, 2H), 6.77-6.93 (m, 3H), 7.02 (t, J=8.8 Hz, 2H), 7.13 (t, J=8.8 Hz, 1H), 7.62 (br s, 2H), 8.21 (s, 1H), 8.70 (s, 1H).

Example 61

3-chloro-5-[2',4'-dihydro-1'H-spiro[piperidine-4,3'-quinoline]-1-ylcarbonyl]-4-(m-tolylamino)pyridine-2-sulfonamide (compound 218)

(step 1) tert-Butyl 2',4'-dihydro-1'H-spiro[piperidine-4,3'-quinoline]-1-carboxylate (200 mg, 0.661 mmol) was dissolved in THF (3 mL), benzyloxycarbonyl chloride (0.208 mL, 1.45 mmol) and potassium carbonate (274 mg, 1.98 mmol) were added, and the mixture was stirred at room temperature for 3 hr. To the reaction mixture was added saturated aqueous ammonium chloride solution, and the mixture was extracted with ethyl acetate. The organic layer was washed with saturated aqueous sodium chloride solution, and dried over anhydrous magnesium sulfate. The solvent was evaporated under reduced pressure to give a crude product of 1'-benzyl 1-tert-butyl 1'H-spiro[piperidine-4,3'-quinoline]-1,1'(2'H,4'H)-dicarboxylate, which was used for the next reaction without purification.

ESIMS m/z: 437 (M+H)$^+$ (step 2) Using a crude product of 1'-benzyl 1-tert-butyl 1'H-spiro[piperidine-4,3'-quinoline]-1,1' (2'H,4'H)-dicarboxylate obtained in step 1, and in the same manner as in Example 60, step 2, benzyl 2',4'-dihydro-1'H-spiro[piperidine-4,3'-quinoline]-1'-carboxylate (100 mg, yield of 2 steps 45%) was obtained.

ESIMS m/z: 337 (M+H)$^+$ (step 3) Using benzyl 2',4'-dihydro-1'H-spiro[piperidine-4,3'-quinoline]-1'-carboxylate (74 mg, 0.219 mmol) obtained in step 2, and 5-chloro-6-sulfamoyl-4-(m-tolylamino)nicotinic acid (50 mg, 0.146 mmol) obtained in Example 60, step 7, and in the same manner as in Example 1, step 1, benzyl 1-[5-chloro-6-sulfamoyl-4-(m-tolylamino)nicotinoyl]-2',4'-dihydro-1'H-spiro[piperidine-4,3'-quinoline]-1'-carboxylate (70 mg, 73%) was obtained.

ESIMS m/z: 660 (M+H)$^+$ (step 4) Benzyl 1-[5-Chloro-6-sulfamoyl-4-(m-tolylamino)nicotinoyl]-2',4'-dihydro-1'H-spiro[piperidine-4,3'-quinoline]-1'-carboxylate (50 mg, 0.076 mmol) obtained in step 3 was dissolved in methanol (4 mL), and passed through a ThalesNano inc., H-Cube (registered trade mark) flow type hydrogenation reaction apparatus. As the cartridge, 10% Pd/C Cat Cart 30 was used, and full H2 mode, temperature 30° C., flow rate 1 ml/min were employed. After completion of the reaction, the reaction mixture was concentrated under reduced pressure, and the residue was purified by preparative HPLC (XBridge™ manufactured by Waters) (acetonitrile/0.05% aqueous trifluoroacetic acid solution) to give compound 218 (11 mg, 28%).

ESIMS m/z: 526 (M+H)$^+$; $^1$H NMR (400 MHz, CDCl$_3$, δ): 1.23-1.34 (m, 7H), 2.38 (s, 3H), 2.50-2.57 (m, 2H), 2.93-3.00 (m, 2H), 3.06-3.14 (m, 2H), 5.75 (br s, 2H), 6.48 (d, J=7.8 Hz, 1H), 6.63 (t, J=7.3 Hz, 1H), 6.90-6.95 (m, 2H), 6.96-7.00 (m, 2H), 7.02-7.07 (m, 2H), 7.24 (s, 1H), 8.11 (s, 1H).

Example 62

5-[4-(4-fluorophenyl)piperidine-1-carbonyl]-3-methyl-4-(1-phenylethylamino)pyridine-2-sulfonamide (compound 220)

(step 1) Using (4,6-dichloro-5-methylpyridin-3-yl)[4-(4-fluorophenyl)piperidin-1-yl]methanone (450 mg, 1.23 mmol) obtained in Example 52, step 1, and 1-phenylethan-1-amine (595 mg, 4.91 mmol), and in the same manner as in Example 44, step 1, [6-chloro-5-methyl-4-(1-phenylethylamino)pyridin-3-yl][4-(4-fluorophenyl)piperidin-1-yl]methanone (460 mg, 83%) was obtained.

ESIMS m/z: 452 (M+H)$^+$ (step 2) Using [6-chloro-5-methyl-4-(1-phenylethylamino)pyridin-3-yl][4-(4-fluorophenyl)piperidin-1-yl]methanone (340 mg, 0.750 mmol) obtained in step 1, and in the same manner as in Example 1, step 3, [4-(4-fluorophenyl)piperidin-1-yl][6-mercapto-5-methyl-4-(1-phenylethylamino)pyridin-3-yl]methanone (310 mg, 92%) was obtained.

ESIMS m/z: 450 (M+H)$^+$ (step 3) [4-(4-Fluorophenyl)piperidin-1-yl][6-mercapto-5-methyl-4-(1-phenylethylamino)pyridin-3-yl]methanone (150 mg, 0.330 mmol), and 3 mol/L hydrochloric acid (0.6 mL, 2.0 mmol) obtained in step 2 were dissolved in acetonitrile (3.0 mL), 5% aqueous sodium hypochlorite solution (2.00 g, 1.35 mmol) was added dropwise under ice-cooling, and the mixture was stirred at 0° C. for 15 min. To the reaction mixture was added saturated aqueous ammonia solution (1.0 mL), and the mixture was stirred at room temperature for 20 min. The reaction mixture was extracted with ethyl acetate, dried over anhydrous sodium sulfate, and the solvent was evaporated under reduced pressure. The residue was purified by preparative HPLC (XBridge™ manufactured by Waters) (acetonitrile/50 mmol/L aqueous ammonium carbonate solution) to give compound 220 (30.2 mg, 18%).

ESIMS m/z: 497 (M+H)$^+$; $^1$H NMR (300 MHz, DMSO-d$_6$, δ): 1.43 (d, J=13 Hz, 3H), 1.44-1.50 (m, 4H), 2.10-2.47 (m, 1H), 2.48-2.51 (m, 2H), 2.52 (s, 3H), 2.52-2.80 (m, 1H), 4.80-4.98 (m, 1H), 5.60-5.78 (m, 1H), 6.99-7.08 (m, 4H), 7.26-7.34 (m, 8H), 7.96 (s, 1H).

Example 63

4-(benzylamino)-3-fluoro-5-[4-(4-fluorophenyl)piperidine-1-carbonyl]-N-(isoxazol-3-yl)pyridine-2-sulfonamide (compound 225)

(step 1) Benzylamine (0.542 mL, 4.96 mmol) was dissolved in THF (10 mL), 2.0 mol/L lithiumdiisopropylamide/THF solution (45 mL, 45 mmol) was added dropwise at −78° C., and the mixture was stirred at −78° C. for 30 min. To the reaction mixture was added 4-chloro-5,6-difluoronicotinic acid (600 mg, 3.10 mmol), and the mixture was stirred at −78° C. for 30 min. To the reaction mixture was added saturated aqueous ammonium chloride solution, and the mixture was extracted with ethyl acetate. The organic layer was dried over anhydrous magnesium sulfate, and the solvent was evaporated under reduced pressure to give a crude product of 4-(benzylamino)-5,6-difluoronicotinic acid, which was used for the next reaction without purification.

ESIMS m/z: 265 (M+H)+

(step 2) Using a crude product of 4-(benzylamino)-5,6-difluoronicotinic acid obtained in step 1, and in the same manner as in Example 1, step 1, [4-(benzylamino)-5,6-difluoropyridin-3-yl][4-(4-fluorophenyl)piperidin-1-yl]methasone (480 mg, yield of 2 steps 36%) was obtained.

ESIMS m/z: 426 (M+H)+

(step 3) Using [4-(benzylamino)-5,6-difluoropyridin-3-yl][4-(4-fluorophenyl)piperidin-1-yl]methanone (480 mg, 1.13 mmol) obtained in step 2, and in the same manner as in Example 57, step 3, [4-(benzylamino)-5-fluoro-6-mercaptopyridin-3-yl][4-(4-fluorophenyl)piperidin-1-yl]methanone (370 mg, 75%) was obtained.

ESIMS m/z: 440 (M+H)+

(step 4) [4-(Benzylamino)-5-fluoro-6-mercaptopyridin-3-yl][4-(4-fluorophenyl)piperidin-1-yl]methanone (150 mg, 0.341 mmol) obtained in step 3 was dissolved in acetonitrile (3.41 mL), benzyltrimethylammonium chloride (253 mg, 1.365 mmol), water (0.015 mL, 0.853 mmol) and N-chlorosuccinimide (137 mg, 1.024 mmol) were added at −25° C., and the mixture was stirred for 20 min while raising the temperature to −10° C. To the reaction mixture was added 3-aminoisoxazole (0.504 mL, 6.83 mmol), and the mixture was stirred for 10 min while raising the temperature to 0° C. To the reaction mixture was added saturated aqueous sodium chloride solution, and the mixture was extracted with ethyl acetate. The organic layer was dried over anhydrous magnesium sulfate, and the solvent was evaporated under reduced pressure. The residue was purified by silica gel column chromatography (chloroform/methanol-9/1) to give compound 225 (120 mg, 64%).

ESIMS m/z: 554 (M+H)+; 1H NMR (400 MHz, DMSO-d5, δ): 1.41-1.57 (m, 3H), 1.67-1.83 (m, 1H), 2.54-2.70 (m, 3H), 4.45-4.58 (m, 4H), 6.28 (s, 1H), 7.09 (t, J=8.8 Hz, 2H), 7.18-7.37 (m, 9H), 7.85 (s, 1H), 8.42 (br s, 1H).

Example 64

5-(4-fluoro-2-methylphenylamino)-6-[4-(4-fluorophenyl)piperidine-1-carbonyl]pyridazine-3-sulfonamide (compound 229)

(step 1) Methyl 4,6-dichloropyridazine-3-carboxylate (100 mg, 0.483 mmol) was dissolved in THF (3 mL), and the mixture was stirred at 0° C. for 15 min. To the reaction mixture was added 4 mol/L aqueous sodium hydroxide solution (0.362 mL, 1.449 mmol), and the mixture was stirred at 0° C. for 1 hr. To the reaction mixture was added 1 mol/L hydrochloric acid, and the mixture was extracted with chloroform. The organic layer was washed with saturated aqueous sodium chloride solution, and dried over anhydrous magnesium sulfate. The solvent was evaporated under reduced pressure to give a crude product of 4,6-dichloropyridazine-3-carboxylic acid, which was used for the next reaction without purification.

ESIMS m/z: 193 (M+H)+

(step 2) Using a crude product of 4,6-dichloropyridazine-3-carboxylic acid obtained in step 1, and 4-fluoro-2-methylaniline, and in the same manner as in Example 1, step 2, a crude product of 6-chloro-4-(4-fluoro-2-methylphenylamino)pyridazine-3-carboxylic acid was obtained and used for the next reaction without purification.

ESIMS m/z: 282 (M+H)+

(step 3) Using a crude product of 6-chloro-4-(4-fluoro-2-methylphenylamino)pyridazine-3-carboxylic acid obtained in step 2, and in the same manner as in Example 1, step 1, [6-chloro-4-(4-fluoro-2-methylphenylamino)pyridazin-3-yl][4-(4-fluorophenyl)piperidin-1-yl]methanone (42 mg, yield of 3 steps 20%) was obtained.

ESIMS m/z: 443 (M+H)+

(step 4) Using [6-chloro-4-(4-fluoro-2-methylphenylamino)pyridazin-3-yl][4-(4-fluorophenyl)piperidin-1-yl]methanone (80 mg, 0.181 mmol) obtained in step 3, and in the same manner as in Example 1, step 3, [4-(4-fluoro-2-methylphenylamino)-6-mercaptopyridazin-3-yl][4-(4-fluorophenyl)piperidin-1-yl]methanone (68 mg, 85%) was obtained.

ESIMS m/z: 441 (M+H)+

(step 5) [4-(4-Fluoro-2-methylphenylamino)-6-mercaptopyridazin-3-yl][4-(4-fluorophenyl)piperidin-1-yl]methanone (30 mg, 0.068 mmol) obtained in step 4 was dissolved in acetonitrile (1 ml), benzyltrimethylammonium chloride (51 mg, 0.272 mmol), water (0.005 mL, 0.278 mmol) and N-chlorosuccinimide (27 mg, 0.204 mmol) were added at −25° C., and the mixture was stirred for 30 min while raising the temperature to −5° C. To the reaction mixture was added 25% aqueous ammonia solution (0.295 mL, 3.41 mmol), and the mixture was stirred at room temperature for 1 hr. To the reaction mixture was added saturated aqueous sodium chloride solution, and the mixture was extracted with ethyl acetate. The organic layer was dried over anhydrous magnesium sulfate, and the solvent was evaporated under reduced pressure. The residue was purified by silica gel column chromatography (chloroform/methanol=9/1) and preparative HPLC (manufactured by Waters XBridge™) (acetonitrile/0.05% aqueous trifluoroacetic acid solution) to give compound 229 (10 mg, 30%) was obtained.

ESIMS m/z: 488 (M+H)+; 1H NMR (400 MHz, CD3OD, δ): 1.80-1.90 (m, 4H), 1.97-2.03 (m, 1H), 2.24 (s, 3H), 2.90-3.07 (m, 2H), 3.32-3.41 (m, 1H), 3.87-3.93 (m, 1H), 6.92 (s, 1H), 6.99-7.10 (m, 4H), 7.17 (dd, J=8.8, 2.9 Hz, 2H), 7.28 (dd, J=8.8, 5.4 Hz, 4H).

Example 65

3-chloro-5-[4-(4-fluorophenyl)piperidine-1-carbonyl]-4-(thiophen-2-ylmethylamino)pyridine-2-sulfonamide (compound 231)

(step 1) Using (4,6-dichloro-5-methylpyridin-3-yl)[4-(4-fluorophenyl)piperidin-1-yl]methanone (450 mg, 1.23 mmol) obtained in Example 52, step 1, and thiophen-2-ylmethanamine (595 mg, 4.91 mmol), and in the same manner as in Example 44, step 1, [5,6-dichloro-4-(thiophen-2-ylmethylamino)pyridin-3-yl][4-(4-fluorophenyl)piperidin-1-yl]methanone (387 mg, 81%) was obtained.

ESIMS m/z: 464 (M+H)+

(step 2) Using [5,6-dichloro-4-(thiophen-2-ylmethylamino)pyridin-3-yl][4-(4-fluorophenyl)piperidin-1-yl]methanone (378 mg, 0.810 mmol) obtained in step 1, and in the same manner as in Example 1, step 3, [5-chloro-6-mercapto-4-(thiophen-2-ylmethylamino)pyridin-3-yl][4-(4-fluorophenyl)piperidin-1-yl]methanone (182 mg, 48%) was obtained.

ESIMS m/z: 462 (M+H)+

(step 3) Using [5-chloro-6-mercapto-4-(thiophen-2-ylmethylamino)pyridin-3-yl][4-(4-fluorophenyl)piperidin-1-yl]methanone (100 mg, 0.220 mmol) obtained in step 2, and in the same manner as in Example 46, step 3, compound 231 (17.6 mg, 16%) was obtained.

ESIMS m/z: 509 (M+H)+; $^1$H NMR (300 MHz, DMSO-$d_6$, δ): 1.20-1.90 (m, 4H), 2.10-2.30 (m, 1H), 2.50-2.90 (m, 2H), 3.10-3.30 (m, 1H), 4.50-5.00 (m, 3H), 6.50-7.70 (m, 10H), 8.03-8.30 (m, 1H).

Example 66

4-(5-chloro-2-methylphenylamino)-5-[4-(4-fluorophenyl)piperidine-1-carbonyl]-N-(isoxazol-3-yl)-3-methylpyridine-2-sulfonamide (compound 232)

(step 1) Using (4,6-dichloro-5-methylpyridin-3-yl)[4-(4-fluorophenyl)piperidin-1-yl]methanone (150 mg, 0.408 mmol) obtained in Example 52, step 1, and 5-chloro-2-methylaniline (156 mg, 1.10 mmol), and in the same manner as in Example 1, step 2, [6-chloro-4-(5-chloro-2-methylphenylamino)-5-methylpyridin-3-yl][4-(4-fluorophenyl)piperidin-1-yl]methanone (192 mg, 99%) was obtained.

ESIMS m/z: 472 (M+H)+

(step 2) Using [6-chloro-4-(5-chloro-2-methylphenylamino)-5-methylpyridin-3-yl][4-(4-fluorophenyl)piperidin-1-yl]methanone (191 mg, 0.404 mmol) obtained in step 1, and in the same manner as in Example 1, step 3, [4-(5-chloro-2-methylphenylamino)-6-mercapto-5-methylpyridin-3-yl][4-(4-fluorophenyl)piperidin-1-yl]methanone (182 mg, 96%) was obtained.

ESIMS m/z: 470 (M+H)+

(step 3) Using [4-(5-chloro-2-methylphenylamino)-6-mercapto-5-methylpyridin-3-yl][4-(4-fluorophenyl)piperidin-1-yl]methanone (4.36 g, 9.28 mmol) obtained in step 2, and in the same manner as in Example 1, step 4, 4-(5-chloro-2-methylphenylamino)-5-[4-(4-fluorophenyl)piperidine-1-carbonyl]-3-methylpyridine-2-sulfonic acid (4.29 g, 89%) was obtained.

ESIMS m/z: 518 (M+H)+

(step 4) Using 4-(5-chloro-2-methylphenylamino)-5-[4-(4-fluorophenyl)piperidine-1-carbonyl]-3-methylpyridine-2-sulfonic acid (3.48 g, 6.49 mmol) obtained in step 3, and in the same manner as in Example 11, compound 232 (2.66 g, 70%) was obtained.

ESIMS m/z: 584 (M+H)+; $^1$H NMR (400 MHz, DMSO-$d_6$, δ): 1.18-1.77 (m, 4H), 1.93-2.11 (m, 1H), 2.16 (s, 3H), 2.51 (s, 3H), 2.59-2.71 (m, 1H), 2.84-3.09 (m, 1H), 3.51-3.66 (m, 1H), 4.00-4.15 (m, 1H), 6.35 (d, J=1.8 Hz, 1H), 6.92-7.03 (m, 1H), 7.05-7.15 (m, 3H), 7.19-7.34 (m, 3H), 7.80 (br s, 1H), 8.09 (s, 1H), 8.67 (d, J=1.4 Hz, 1H), 11.80 (br s, 1H).

Example 67

5-[4-(4-fluorophenyl)piperidine-1-carbonyl]-4-(3-fluorophenylamino)-N-(isoxazol-3-yl)-3-methylpyridine-2-sulfonamide (compound 233)

(step 1) Using (4,6-dichloro-5-methylpyridin-3-yl)[4-(4-fluorophenyl)piperidin-1-yl]methanone (150 mg, 0.408 mmol) obtained in Example 52, step 1, and 3-fluoroaniline (0.106 mL, 1.10 mmol), and in the same manner as in Example 1, step 2, [6-chloro-4-(3-fluorophenylamino)-5-methylpyridin-3-yl][4-(4-fluorophenyl)piperidin-1-yl]methanone (182 mg, quantitative) was obtained.

ESIMS m/z: 442 (M+H)+

(step 2) Using [6-chloro-4-(3-fluorophenylamino)-5-methylpyridin-3-yl][4-(4-fluorophenyl)piperidin-1-yl]methanone (182 mg, 0.412 mmol) obtained in step 1, and in the same manner as in Example 1, step 3, [4-(4-fluorophenyl)piperidin-1-yl][4-(3-fluorophenylamino)-6-mercapto-5-methylpyridin-3-yl]methanone (169 mg, 94%) was obtained.

ESIMS m/z: 440 (M+H)+

(step 3) Using [4-(4-fluorophenyl)piperidin-1-yl][4-(3-fluorophenylamino)-6-mercapto-5-methylpyridin-3-yl]methanone (168 mg, 0.382 mmol) obtained in step 2, and in the same manner as in Example 1, step 4, 5-[4-(4-fluorophenyl)piperidine-1-carbonyl]-4-(3-fluorophenylamino)-3-methylpyridine-2-sulfonic acid (156 mg, 84%) was obtained.

ESIMS m/z: 488 (M+H)+

(step 4) Using 5-[4-(4-fluorophenyl)piperidine-1-carbonyl]-4-(3-fluorophenylamino)-3-methylpyridine-2-sulfonic acid (168 mg, 0.345 mmol) obtained in step 3, and in the same manner as in Example 11, compound 233 (46.6 mg, 24%) was obtained.

ESIMS m/z: 554 (M+H)+; $^1$H NMR (400 MHz, DMSO-$d_6$, δ): 1.22-1.80 (m, 4H), 2.48 (s, 3H), 2.59-2.81 (m, 2H), 2.84-3.17 (m, 1H), 3.40-3.60 (m, 1H), 4.06-4.43 (m, 1H), 6.37 (s, 1H), 6.60-6.81 (m, 3H), 7.09 (t, J=8.4 Hz, 3H), 7.26 (dd, J=15.0, 7.7 Hz, 2H), 8.24 (s, 1H), 8.51 (s, 1H), 8.70 (s, 1H), 11.87 (s, 1H).

Example 68

4-(2-fluoro-4-methylphenylamino)-5-[4-(4-fluorophenyl)piperidine-1-carbonyl]-N-(isoxazol-3-yl)-3-methylpyridine-2-sulfonamide (compound 235)

(step 1) Using (4,6-dichloro-5-methylpyridin-3-yl)[4-(4-fluorophenyl)piperidin-1-yl]methanone (300 mg, 0.817 mmol) obtained in Example 52, step 1, and 2-fluoro-4-methylaniline (0.249 mL, 2.21 mmol), and in the same manner as in Example 1, step 2, [6-chloro-4-(2-fluoro-4-methylphenylamino)-5-methylpyridin-3-yl][4-(4-fluorophenyl)piperidin-1-yl]methanone (330 mg, 89%) was obtained.

ESIMS m/z: 456 (M+H)+

(step 2) Using [6-chloro-4-(2-fluoro-4-methylphenylamino)-5-methylpyridin-3-yl][4-(4-fluorophenyl)piperidin-1-yl]methanone (330 mg, 0.724 mmol) obtained in step 1, and in the same manner as in Example 1, step 3, [4-(2-fluoro-4-methylphenylamino)-6-mercapto-5-methylpyridin-3-yl][4-(4-fluorophenyl)piperidin-1-yl]methanone (300 mg, 91%) was obtained.

ESIMS m/z: 454 (M+H)+

(step 3) Using [4-(2-fluoro-4-methylphenylamino)-6-mercapto-5-methylpyridin-3-yl][4-(4-fluorophenyl)piperidin-1-yl]methanone (163 mg, 0.347 mmol) obtained in step 2, and in the same manner as in Example 1, step 4, a crude product of 4-(2-fluoro-4-methylphenylamino)-5-[4-(4-fluorophenyl)piperidine-1-carbonyl]-3-methylpyridine-2-sulfonic acid was obtained and used for the next reaction without purification.

ESIMS m/z: 502 (M+H)$^+$ (step 4) Using a crude product of 4-(2-fluoro-4-methylphenylamino)-5-[4-(4-fluorophenyl)piperidine-1-carbonyl]-3-methylpyridine-2-sulfonic acid obtained in step 3, and in the same manner as in Example 11, compound 235 (153 mg, yield of 2 steps 41%) was obtained.

ESIMS m/z: 568 (M+H)$^+$; $^1$H NMR (400 MHz, DMSO-d$_6$, δ): 1.14-1.71 (m, 5H), 2.28 (s, 3H), 2.49 (s, 3H), 2.62-2.76 (m, 1H), 2.83-2.99 (m, 1H), 3.42-3.52 (m, 1H), 3.94-4.15 (m, 1H), 6.31 (s, 1H), 6.85-7.34 (m, 8H), 7.96 (br s, 1H), 8.04 (s, 1H), 8.60 (br s, 1H).

Example 69

4-(2-ethylphenylamino)-5-[4-(4-fluorophenyl)piperidine-1-carbonyl]-N-(isoxazol-3-yl)-3-methylpyridine-2-sulfonamide (compound 239)

(step 1) Using (4,6-dichloro-5-methylpyridin-3-yl)[4-(4-fluorophenyl)piperidin-1-yl]methanone (250 mg, 0.681 mmol) obtained in Example 52, step 1, and 2-ethylaniline (223 mg, 1.84 mmol), and in the same manner as in Example 1, step 2, [6-chloro-4-(2-ethylphenylamino)-5-methylpyridin-3-yl][4-(4-fluorophenyl)piperidin-1-yl]methanone (278 mg, 90%) was obtained.

ESIMS m/z: 452 (M+H)$^+$ (step 2) Using [6-chloro-4-(2-ethylphenylamino)-5-methylpyridin-3-yl][4-(4-fluorophenyl)piperidin-1-yl]methanone (278 mg, 0.615 mmol) obtained in step 1, and in the same manner as in Example 1, step 3, [4-(2-ethylphenylamino)-6-mercapto-5-methylpyridin-3-yl][4-(4-fluorophenyl)piperidin-1-yl]methanone (236 mg, 85%) was obtained.

ESIMS m/z: 450 (M+H)$^+$ (step 3) Using [4-(2-ethylphenylamino)-6-mercapto-5-methylpyridin-3-yl][4-(4-fluorophenyl)piperidin-1-yl]methanone (236 mg, 0.525 mmol) obtained in step 2, and in the same manner as in Example 1, step 4, 4-(2-ethylphenylamino)-5-[4-(4-fluorophenyl)piperidine-1-carbonyl]-3-methylpyridine-2-sulfonic acid (235 mg, 90%) was obtained.

ESIMS m/z: 498 (M+H)$^+$ (step 4) Using 4-(2-ethylphenylamino)-5-[4-(4-fluorophenyl)piperidine-1-carbonyl]-3-methylpyridine-2-sulfonic acid (235 mg, 0.472 mmol) obtained in step 3, and in the same manner as in Example 11, compound 239 (78.9 mg, 30%) was obtained.

ESIMS m/z: 564 (M+H)$^+$; $^1$H NMR (400 MHz, DMSO-d$_6$, δ): 1.05-1.48 (m, 5H), 1.48-1.75 (m, 2H), 2.40 (s, 3H), 2.59 (q, J=7.6 Hz, 2H), 2.63-2.74 (m, 2H), 2.80-3.10 (m, 1H), 3.47-3.63 (m, 1H), 4.08-4.40 (m, 1H), 6.18 (s, 1H), 6.48-6.73 (m, 1H), 6.93-7.35 (m, 8H), 8.07 (s, 1H), 8.11-8.37 (m, 1H).

Example 70

4-chloro-5-(4-fluoro-2-methylphenylamino)-6-[4-(4-fluorophenyl)piperidine-1-carbonyl]pyridazine-3-sulfonamide (compound 240)

(step 1) [6-Chloro-4-(4-fluoro-2-methylphenylamino)pyridazin-3-yl][4-(4-fluorophenyl)piperidin-1-yl]methanone (100 mg, 0.226 mmol) obtained in Example 64, step 3, was dissolved in DMF (2 mL), N-chlorosuccinimide (32 mg, 0.237 mmol) was added under ice-cooling, and the mixture was stirred at room temperature for 3 hr. To the reaction mixture was added saturated aqueous ammonium chloride solution, and the mixture was extracted with ethyl acetate. The organic layer was washed with saturated aqueous sodium chloride solution, and dried over anhydrous magnesium sulfate. The solvent was evaporated under reduced pressure. The residue was purified by preparative HPLC (XBridge™ manufactured by Waters) (acetonitrile/0.05% aqueous trifluoroacetic acid solution) to give [5,6-dichloro-4-(4-fluoro-2-methylphenylamino)pyridazin-3-yl][4-(4-fluorophenyl)piperidin-1-yl]methanone (45 mg, 42%).

ESIMS m/z: 477 (M+H)$^+$ (step 2) Using [5,6-dichloro-4-(4-fluoro-2-methylphenylamino)pyridazin-3-yl][4-(4-fluorophenyl)piperidin-1-yl]methanone (40 mg, 0.084 mmol) obtained in step 1, and in the same manner as in Example 51, step 2, a crude product of [5-chloro-4-(4-fluoro-2-methylphenylamino)-6-mercaptopyridazin-3-yl][4-(4-fluorophenyl)piperidin-1-yl]methanone was obtained and used for the next reaction without purification.

ESIMS m/z: 475 (M+H)$^+$ (step 3) Using a crude product of [5-chloro-4-(4-fluoro-2-methylphenylamino)-6-mercaptopyridazin-3-yl][4-(4-fluorophenyl)piperidin-1-yl]methanone obtained in step 2, and in the same manner as in Example 64, step 5, compound 240 (4 mg, yield of 2 steps 9%) was obtained.

ESIMS m/z: 522 (M+H)$^+$; $^1$H NMR (400 MHz, CD$_3$OD, δ): 1.67-1.86 (m, 3H), 1.95-2.13 (m, 1H), 2.25-2.39 (m, 4H), 2.69-2.88 (m, 1H), 2.91-3.08 (m, 1H), 3.77-3.91 (m, 1H), 4.02-4.20 (m, 1H), 6.91-7.17 (m, 6H), 7.18-7.32 (m, 3H).

Example 71

5-[4-(4-fluorophenyl)piperidine-1-carbonyl]-3-methyl-N-(3-methylisothiazol-5-yl)-4-(o-tolylamino)pyridine-2-sulfonamide (compound 241)

(step 1) Using (4,6-dichloro-5-methylpyridin-3-yl)[4-(4-fluorophenyl)piperidin-1-yl]methanone (250 mg, 0.681 mmol) obtained in Example 52, step 1, and o-toluidine (182 mg, 1.70 mmol), and in the same manner as in Example 1, step 2, [6-chloro-5-methyl-4-(o-tolylamino)pyridin-3-yl][4-(4-fluorophenyl)piperidin-1-yl]methanone (289 mg, 97%) was obtained.

ESIMS m/z: 438 (M+H)$^+$ (step 2) Using [6-chloro-5-methyl-4-(o-tolylamino)pyridin-3-yl][4-(4-fluorophenyl)piperidin-1-yl]methanone (285 mg, 0.651 mmol) obtained in step 1, and in the same manner as in Example 1, step 3, [4-(4-fluorophenyl)piperidin-1-yl][6-mercapto-5-methyl-4-(o-tolylamino)pyridin-3-yl]methanone (243 mg, 86%) was obtained.

ESIMS m/z: 436 (M+H)$^+$ (step 3) Using [4-(4-fluorophenyl)piperidin-1-yl][6-mercapto-5-methyl-4-(o-tolylamino)pyridin-3-yl]methanone (239 mg, 0.549 mmol) obtained in step 2, and in the same manner as in Example 1, step 4, 5-[4-(4-fluorophenyl)piperidine-1-carbonyl]-3-methyl-4-(o-tolylamino)pyridine-2-sulfonic acid (213 mg, 80%) was obtained.

ESIMS m/z: 484 (M+H)$^+$ (step 4) Using 5-[4-(4-fluorophenyl)piperidine-1-carbonyl]-3-methyl-4-(o-tolylamino)pyridine-2-sulfonic acid (102 mg, 0.210 mmol) obtained in step 3, and 3-methylisothiazole-5-amine hydrochloride, and in the same manner as in Example 11, compound 241 (47.1 mg, 39%) was obtained.

ESIMS m/z: 580 (M+H)$^+$; $^1$H NMR (400 MHz, DMSO-d$_6$, δ): 1.13-1.51 (m, 2H), 1.51-1.71 (m, 2H), 2.00-2.31 (m, 1H), 2.10 (s, 3H), 2.19 (s, 3H), 2.41 (s, 3H), 2.60-2.71 (m, 1H), 2.78-3.06 (m, 1H), 3.47-3.63 (m, 1H), 3.99-4.27 (m, 1H), 6.04 (s, 1H), 6.60-6.77 (m, 1H), 6.98 (t, J=7.2 Hz, 1H), 7.02-7.42 (m, 7H), 8.03 (s, 1H).

Example 72

4-(3-chlorophenylamino)-5-[4-(4-fluorophenyl)piperidine-1-carbonyl]-N-(isoxazol-3-yl)-3-methylpyridine-2-sulfonamide (compound 244)

(step 1) Using (4,6-dichloro-5-methylpyridin-3-yl) [4-(4-fluorophenyl)piperidin-1-yl]methanone (300 mg, 0.817 mmol) obtained in Example 52, step 1, and 3-chloroaniline (231 mg, 2.21 mmol), and in the same manner as in Example 1, step 2, [6-chloro-4-(3-chlorophenylamino)-5-methylpyridin-3-yl][4-(4-fluorophenyl)piperidin-1-yl]methanone (408 mg, quantitative) was obtained.

ESIMS m/z: 458 (M+H)$^+$ (step 2) Using [6-chloro-4-(3-chlorophenylamino)-5-methylpyridin-3-yl][4-(4-fluorophenyl)piperidin-1-yl]methanone (374 mg, 0.817 mmol) obtained in step 1, and in the same manner as in Example 1, step 3, [4-(3-chlorophenylamino)-6-mercapto-5-methylpyridin-3-yl][4-(4-fluorophenyl)piperidin-1-yl]methanone (292 mg, 78%) was obtained.

ESIMS m/z: 456 (M+H)$^+$ (step 3) Using [4-(3-chlorophenylamino)-6-mercapto-5-methylpyridin-3-yl][4-(4-fluorophenyl)piperidin-1-yl]methanone (292 mg, 0.640 mmol) obtained in step 2, and in the same manner as in Example 1, step 4, 4-(3-chlorophenylamino)-5-[4-(4-fluorophenyl)piperidine-1-carbonyl]-3-methylpyridine-2-sulfonic acid (262 mg, 81%) was obtained.

ESIMS m/z: 504 (M+H)$^+$ (step 4) Using 4-(3-chlorophenylamino)-5-[4-(4-fluorophenyl)piperidine-1-carbonyl]-3-methylpyridine-2-sulfonic acid (154 mg, 0.306 mmol) obtained in step 3, and in the same manner as in Example 11, compound 244 (70.5 mg, 41%) was obtained.

ESIMS m/z: 570 (M+H)$^+$; $^1$H NMR (400 MHz, CDCl$_3$, δ): 1.20-1.36 (m, 1H), 1.70-1.96 (m, 2H), 2.43 (s, 3H), 2.64-2.76 (m, 2H), 3.07-3.19 (m, 1H), 3.43-3.82 (m, 2H), 4.62-4.77 (m, 1H), 6.58 (d, J=2.0 Hz, 1H), 6.66 (d, J=7.8 Hz, 1H), 6.81 (s, 1H), 6.93-7.10 (m, 6H), 7.21 (dd, J=7.8, 15.6 Hz, 2H), 8.23 (s, 2H).

Example 73

4-(benzylamino)-5-[4-(4-fluorophenyl)piperidine-1-carbonyl]-3-methyl-N-(1-methyl-1H-pyrazol-3-yl)pyridine-2-sulfonamide (compound 250)

(step 1) Using (4,6-dichloro-5-methylpyridin-3-yl)[4-(4-fluorophenyl)piperidin-1-yl]methanone (2.00 g, 5.45 mmol) obtained in Example 52, step 1, and benzylamine (5.84 g, 54.5 mmol), and in the same manner as in Example 1, step 2, [4-(benzylamino)-6-chloro-5-methylpyridin-3-yl][4-(4-fluorophenyl)piperidin-1-yl]methanone (2.23 g, 94%) was obtained.

ESIMS m/z: 438 (M+H)$^+$ (step 2) Using [4-(benzylamino)-6-chloro-5-methylpyridin-3-yl][4-(4-fluorophenyl)piperidin-1-yl]methanone (2.20 g, 5.02 mmol) obtained in step 1, and in the same manner as in Example 1, step 3, [4-(benzylamino)-6-mercapto-5-methylpyridin-3-yl][4-(4-fluorophenyl)piperidin-1-yl]methanone (2.20 g, quantitative) was obtained.

ESIMS m/z: 436 (M+H)$^+$ (step 3) Using [4-(benzylamino)-6-mercapto-5-methylpyridin-3-yl][4-(4-fluorophenyl)piperidin-1-yl]methanone (1.13 g, 2.59 mmol) obtained in step 2, and in the same manner as in Example 1, step 4, 4-(benzylamino)-5-[4-(4-fluorophenyl)piperidine-1-carbonyl]-3-methylpyridine-2-sulfonic acid (870 mg, 70%) was obtained.

ESIMS m/z: 484 (M+H)$^+$ (step 4) Using 4-(benzylamino)-5-[4-(4-fluorophenyl)piperidine-1-carbonyl]-3-methylpyridine-2-sulfonic acid (125 mg, 0.257 mmol) obtained in step 3, and in the same manner as in Example 39, compound 250 (80.4 mg, 56%) was obtained.

ESIMS m/z: 563 (M f H)$^+$; $^1$H NMR (400 MHz, DMSO-d$_6$, δ): 1.33-1.44 (m, 1H), 1.44-1.64 (m, 1H), 1.64-1.85 (m, 2H), 2.29-2.42 (m, 1H), 2.49 (s, 3H), 2.58-2.86 (m, 1H), 2.90-3.21 (m, 1H), 3.31-3.34 (m, 1H), 3.66 (s, 3H), 4.32-4.77 (m, 3H), 5.81 (s, 1H), 6.55-6.93 (m, 1H), 6.96-7.12 (m, 2H), 7.12-7.19 (m, 2H), 7.19-7.26 (m, 2H), 7.26-7.39 (m, 3H), 7.42 (s, 1H), 7.79-8.05 (m, 1H), 10.50 (s, 1H).

Example 74

4-(benzylamino)-5-[4-(4-fluorophenyl)piperidine-1-carbonyl]-3-methyl-N-(3-methylisothiazol-5-yl)pyridine-2-sulfonamide (compound 251)

Using 4-(benzylamino)-5-[4-(4-fluorophenyl)piperidine-1-carbonyl]-3-methylpyridine-2-sulfonic acid (125 mg, 0.257 mmol) obtained in Example 73, step 3, and in the same manner as in Example 71, step 4, compound 251 (78.3 mg, 52%) was obtained.

ESIMS m/z: 580 (M+H)$^+$; $^1$H NMR (400 MHz, DMSO-d$_5$, δ): 1.36-1.60 (m, 2H), 1.68-1.88 (m, 2H), 2.07 (s, 3H), 2.31-2.43 (m, 1H), 2.47 (s, 3H), 2.53-2.89 (m, 2H), 2.94-3.17 (m, 1H), 4.28-4.74 (m, 3H), 5.92 (s, 1H), 6.17-6.63 (m, 1H), 6.97-7.11 (m, 3H), 7.11-7.25 (m, 3H), 7.25-7.41 (m, 3H), 7.69-7.90 (m, 1H).

Example 75

4-(2,5-difluorophenylamino)-5-[4-(4-fluorophenyl)piperidine-1-carbonyl]-N-(isoxazol-3-yl)-3-methylpyridine-2-sulfonamide (compound 252)

(step 1) Using (4,6-dichloro-5-methylpyridin-3-yl)[4-(4-fluorophenyl)piperidin-1-yl]methanone (300 mg, 0.817 mmol) obtained in Example 52, step 1, and 2,5-difluoroaniline (0.12 mL, 1.3 mmol), and in the same manner as in Example 1, step 2, [6-chloro-4-(2,5-difluorophenylamino)-5-methylpyridin-3-yl][4-(4-fluorophenyl)piperidin-1-yl]methanone (331 mg, 88%) was obtained.

ESIMS m/z: 460 (M+H)$^+$ (step 2) Using [6-chloro-4-(2,5-difluorophenylamino)-5-methylpyridin-3-yl][4-(4-fluorophenyl)piperidin-1-yl]methanone (359 mg, 0.781 mmol) obtained in step 1, and in the same manner as in Example 1, step 3, [4-(2,5-difluorophenylamino)-6-mercapto-5-methylpyridin-3-yl][4-(4-fluorophenyl)piperidin-1-yl]methanone (311 mg, 87%) was obtained.

ESIMS m/z: 458 (M+H)$^+$ (step 3) Using [4-(2,5-difluorophenylamino)-6-mercapto-5-methylpyridin-3-yl][4-(4-fluorophenyl)piperidin-1-yl]methanone (318 mg, 0.695 mmol) obtained in step 2, and in the same manner as in Example 1, step 4, 4-(2,5-difluorophenylamino)-5-[4-(4-fluorophenyl)piperidine-1-carbonyl]-3-methylpyridine-2-sulfonic acid (191 mg, 54%) was obtained.

ESIMS m/z: 504 (M−H)+

(step 4) Using 4-(2,5-difluorophenylamino)-5-[4-(4-fluorophenyl)piperidine-1-carbonyl]-3-methylpyridine-2-sulfonic acid (191 mg, 0.378 mmol) obtained in step 3, and in the same manner as in Example 11, compound 252 (165 mg, 76%) was obtained.

ESIMS m/z: 572 (M+H)+; $^1$H NMR (400 MHz, DMSO-$d_6$, δ): 1.34-1.73 (m, 4H), 1.93-2.31 (m, 1H), 2.53 (s, 3H), 2.64-2.76 (m, 1H), 2.86-3.09 (m, 1H), 3.54 (d, J=12.7 Hz, 1H), 4.07-4.24 (m, 1H), 6.36 (s, 1H), 6.82-6.94 (m, 2H), 7.10 (t, J 8.3 Hz, 2H), 7.21-7.30 (m, 3H), 8.19 (s, 1H), 8.31 (br s, 1H), 8.69 (s, 1H), 11.86 (br s, 1H).

Example 76

4-(2,3-difluorophenylamino)-5-[4-(4-fluorophenyl)piperidine-1-carbonyl]-N-(isoxazol-3-yl)-3-methylpyridine-2-sulfonamide (compound 254)

(step 1) Using (4,6-dichloro-5-methylpyridin-3-yl)[4-(4-fluorophenyl)piperidin-1-yl]methanone (300 mg, 0.817 mmol) obtained in Example 52, step 1, and 2,3-difluoroaniline (0.221 mL, 2.21 mmol), and in the same manner as in Example 1, step 2, [6-chloro-4-(2,3-difluorophenylamino)-5-methylpyridin-3-yl][4-(4-fluorophenyl)piperidin-1-yl]methanone (332 mg, 88%) was obtained.

ESIMS m/z: 460 (M+H)+

(step 2) Using [6-chloro-4-(2,3-difluorophenylamino)-5-methylpyridin-3-yl][4-(4-fluorophenyl)piperidin-1-yl]methanone (332 mg, 0.722 mmol) obtained in step 1, and in the same manner as in Example 1, step 3, [4-(2,3-difluorophenylamino)-6-mercapto-5-methylpyridin-3-yl][4-(4-fluorophenyl)piperidin-1-yl]methanone (320 mg, 97%) was obtained.

ESIMS m/z: 458 (M+H)+

(step 3) Using [4-(2,3-difluorophenylamino)-6-mercapto-5-methylpyridin-3-yl][4-(4-fluorophenyl)piperidin-1-yl]methanone (320 mg, 0.699 mmol) obtained in step 2, and in the same manner as in Example 1, step 4, 4-(2,3-difluorophenylamino)-5-[4-(4-fluorophenyl)piperidine-1-carbonyl]-3-methylpyridine-2-sulfonic acid (352 mg, quantitative) was obtained.

ESIMS m/z: 506 (M+H)+

(step 4) Using 4-(2,3-difluorophenylamino)-5-[4-(4-fluorophenyl)piperidine-1-carbonyl]-3methylpyridine-2-sulfonic acid (176 mg, 0.348 mmol) obtained in step 3, and in the same manner as in Example 11, compound 254 (72.0 mg, 37%) was obtained.

ESIMS m/z: 572 (M+H)+; $^1$H NMR (400 MHz, DMSO-$d_6$, δ): 1.28-1.77 (m, 4H), 1.94-2.16 (m, 1H), 2.53 (s, 3H), 2.63-2.76 (m, 1H), 2.81-3.07 (m, 1H), 3.45-3.56 (m, 1H), 3.98-4.20 (m, 1H), 6.35 (d, J=1.8 Hz, 1H), 6.79-6.91 (m, 1H), 7.01-7.17 (m, 4H), 7.17-7.38 (m, 2H), 8.17 (s, 1H), 8.35 (s, 1H), 8.68 (s, 1H), 11.85 (s, 1H).

Example 77

5-[4-(4-fluorophenyl)piperidine-1-carbonyl]-4-(2-fluorophenylamino)-N-(isoxazol-3-yl)-3-methylpyridine-2-sulfonamide (compound 255)

(step 1) Using (4,6-dichloro-5-methylpyridin-3-yl)[4-(4-fluorophenyl)piperidin-1-yl]methanone (300 mg, 0.817 mmol) obtained in Example 52, step 1, and 2-fluoroaniline (0.213 mL, 2.21 mmol), and in the same manner as in Example 1, step 2, [6-chloro-4-(2-fluorophenylamino)-5-methylpyridin-3-yl][4-(4-fluorophenyl)piperidin-1-yl]methanone (361 mg, quantitative) was obtained.

ESIMS m/z: 442 (M+H)+

(step 2) Using [6-chloro-4-(2-fluorophenylamino)-5-methylpyridin-3-yl][4-(4-fluorophenyl)piperidin-1-yl]methanone (372 mg, 0.842 mmol) obtained in step 1, and in the same manner as in Example 1, step 3, [4-(4-fluorophenyl)piperidin-1-yl][4-(2-fluorophenylamino)-6-mercapto-5-methylpyridin-3-yl]methanone (347 mg, 94%) was obtained.

ESIMS m/z: 440 (M+H)+

(step 3) Using [4-(4-fluorophenyl)piperidin-1-yl][4-(2-fluorophenylamino)-6-mercapto-5-methylpyridin-3-yl]methanone (347 mg, 0.789 mmol) obtained in step 2, and in the same manner as in Example 1, step 4, 5-[4-(4-fluorophenyl)piperidine-1-carbonyl]-4-(2-fluorophenylamino)-3-methylpyridine-2-sulfonic acid (385 mg, quantitative) was obtained.

ESIMS m/z: 488 (M+H)+

(step 4) Using 5-[4-(4-fluorophenyl)piperidine-1-carbonyl]-4-(2-fluorophenylamino)-3-methylpyridine-2-sulfonic acid (199 mg, 0.408 mmol) obtained in step 3, and in the same manner as in Example 11, compound 255 (120 mg, 54%) was obtained.

ESIMS m/z: 554 (M+H)+; $^1$H NMR (400 MHz, DMSO-$d_6$, δ): 1.27-1.73 (m, 4H), 1.84-2.10 (m, 1H), 2.51 (s, 3H), 2.60-2.74 (m, 1H), 2.77-3.04 (m, 1H), 3.44-3.56 (m, 1H), 3.92-4.17 (m, 1H), 6.35 (d, J=1.8 Hz, 1H), 6.99-7.17 (m, 5H), 7.17-7.37 (m, 3H), 8.10 (s. 1H), 8.14 (s. 1H), 8.67 (s, 1H), 11.82 (s, 1H).

Example 78

3-chloro-4-[2-cyano-4-(trifluoromethoxy)phenylamino]-5-[4-(4-fluorophenyl)piperidine-1-carbonyl]pyridine-2-sulfonamide (compound 256)

(step 1) 3,4-Dichloro-5-[4-(4-fluorophenyl)piperidine-1-carbonyl]pyridine-2-sulfonamide (847 mg, 1.96 mmol) obtained in Example 57, step 6 was dissolved in DMF (15 mL), 4-methoxybenzyl chloride (0.800 mL, 5.88 mmol) and potassium carbonate (1.36 g, 9.80 mmol) were added, and the mixture was stirred at 60° C. for 4 hr. The reaction mixture was allowed to cool to room temperature, saturated aqueous ammonium chloride solution was added, and the mixture was extracted with ethyl acetate. The organic layer was washed with water and saturated brine, and dried over anhydrous magnesium sulfate. The solvent was evaporated under reduced pressure. The residue was purified by silica gel column chromatography (heptane/ethyl acetate=80/20-50/50) to give 3,4-dichloro-5-[4-(4-fluorophenyl)piperidine-1-carbonyl]-N,N-bis(4-methoxybenzyl)pyridine-2-sulfonamide (1.18 g, 90%).

ESIMS m/z: 672 (M+H)+

(step 2) 3,4-Dichloro-5-[4-(4-fluorophenyl)piperidine-1-carbonyl]-N,N-bis(4-methoxybenzyl)pyridine-2-sulfonamide (74.2 mg, 0.110 mmol) obtained in step 1, 2-amino-5-(trifluoromethoxy)benzonitrile (33.4 mg, 0.165 mmol), 4,5-bis(diphenylphosphino)-9,9-dimethylxanthene (25.5 mg, 0.044 mmol) and cesium carbonate (53.9 mg, 0.165 mmol) were suspended in toluene (2.0 mL), tris(dibenzylideneacetone)dipalladium(0) (20.2 mg, 0.022 mmol) was added, and the mixture was stirred at 80° C. for 8 hr. The reaction mixture was allowed to cool to room temperature, saturated aqueous ammonium chloride solution was added, and the mixture was extracted with ethyl acetate. The organic layer was washed with saturated brine, and dried over anhydrous magnesium sulfate. The solvent was evaporated under reduced pressure. The residue was purified by silica gel column chromatography (heptane/ethyl acetate=80/20-40/60) to give 3-chloro-4-[2-cyano-4-(trifluoromethoxy)phenylamino]-5-[4-(4-fluorophenyl)piperidine-1-carbonyl]-N,N-bis(4-methoxybenzyl)pyridine-2-sulfonamide (71.9 mg, 78%).

ESIMS m/z: 838 (M+H)$^+$ (step 3) 3-Chloro-4-[2-cyano-4-(trifluoromethoxy)phenylamino]-5-[4-(4-fluorophenyl)piperidine-1-carbonyl]-N,N-bis(4-methoxybenzyl)pyridine-2-sulfonamide (70.2 mg, 0.084 mmol) obtained in step 2, and anisole (0.055 mL, 0.502 mmol) were dissolved in trifluoroacetic acid (2.0 mL), and the mixture was stirred at 60° C. for 2 hr. The reaction mixture was allowed to cool to room temperature, and the solvent was evaporated under reduced pressure. Water was added to the residue, and the mixture was extracted with ethyl acetate. The organic layer was washed with saturated brine, and dried over anhydrous magnesium sulfate. The solvent was evaporated under reduced pressure. The residue was purified by silica gel column chromatography (heptane/ethyl acetate-50/50-20/80) to give compound 256 (43.4 mg, 87%).

ESIMS m/z: 598 (M+H)$^+$; $^1$H NMR (400 MHz, CDCl$_3$, δ): 1.41-1.61 (m, 2H), 1.81-1.90 (m, 2H), 2.30-2.45 (m, 1H), 2.66-2.77 (m, 1H), 3.06-3.22 (m, 1H), 3.55-3.70 (m, 1H), 4.27-4.43 (m, 1H), 5.44 (br s, 2H), 6.96-7.03 (m, 2H), 7.07-7.13 (m, 2H), 7.21 (d, J=8.8 Hz, 1H), 7.37 (br s, 1H), 7.43 (dd, J=2.0, 8.8 Hz, 1H), 7.51 (d, J=2.0 Hz, 1H), 8.33 (s, 1H).

Example 79

3-chloro-4-[2-cyano-5-(trifluoromethyl)phenylamino]-5-[4-(4-fluorophenyl)piperidine-1-carbonyl]pyridine-2-sulfonamide (compound 257)

(step 1) Using 3,4-dichloro-5-[4-(4-fluorophenyl)piperidine-1-carbonyl]-N,N-bis(4-methoxybenzyl)pyridine-2-sulfonamide (57.6 mg, 0.086 mmol) obtained in Example 78, step 1, and 2-amino-4-(trifluoromethyl)benzonitrile (23.9 mg, 0.128 mmol), and in the same manner as in Example 78, step 2, 3-chloro-4-[2-cyano-5-(trifluoromethyl)phenylamino]-5-[4-(4-fluorophenyl)piperidine-1-carbonyl]-N,N-bis(4-methoxybenzyl)pyridine-2-sulfonamide (58.7 mg, 83%) was obtained.

ESIMS m/z: 622 (M+H)$^+$ (step 2) Using 3-chloro-4-[2-cyano-5-(trifluoromethyl)phenylamino]-5-[4-(4-fluorophenyl)piperidine-1-carbonyl]-N,N-bis(4-methoxybenzyl)pyridine-2-sulfonamide (55.9 mg, 0.068 mmol) obtained in step 1, and in the same manner as in Example 78, step 3, compound 257 (33.2 mg, 84%) was obtained.

ESIMS m/z: 582 (M+H)$^+$; $^1$H NMR (400 MHz, CDCl$_3$, δ): 1.42-1.60 (m, 2H), 1.79-1.92 (m, 2H), 2.27-2.51 (m, 1H), 2.64-2.78 (m, 1H), 3.05-3.21 (m, 1H), 3.63-3.76 (m, 1H), 4.35-4.49 (m, 1H), 5.54 (br s, 2H), 6.94-7.03 (m, 2H), 7.06-7.14 (m, 2H), 7.38 (s, 1H), 7.47 (d, J=8.8 Hz, 1H), 7.63 (br s, 1H), 7.77 (d, J=8.8 Hz, 1H), 8.35 (s, 1H).

Example 80

4-(3,4-difluorophenylamino)-5-[4-(4-fluorophenyl)piperidine-1-carbonyl]-N-(isoxazol-3-yl)-3-methylpyridine-2-sulfonamide (compound 258)

(step 1) Using (4,6-dichloro-5-methylpyridin-3-yl)[4-(4-fluorophenyl)piperidin-1-yl]methanone (300 mg, 0.817 mmol) obtained in Example 52, step 1, and 3,4-difluoroaniline (0.122 mL, 1.23 mmol), and in the same manner as in Example 1, step 2, [6-chloro-4-(3,4-difluorophenylamino)-5-methylpyridin-3-yl][4-(4-fluorophenyl)piperidin-1-yl]methanone (377 mg, quantitative) was obtained.

ESIMS m/z: 460 (M+H)$^+$ (step 2) Using [6-chloro-4-(3,4-difluorophenylamino)-5-methylpyridin-3-yl][4-(4-fluorophenyl)piperidin-1-yl]methanone (377 mg, 0.820 mmol) obtained in step 1, and in the same manner as in Example 1, step 3, [4-(3,4-difluorophenylamino)-6-mercapto-5-methylpyridin-3-yl][4-(4-fluorophenyl)piperidin-1-yl]methanone (335 mg, 89%) was obtained.

ESIMS m/z: 458 (M+H)$^+$ (step 3) Using [4-(3,4-difluorophenylamino)-6-mercapto-5-methylpyridin-3-yl][4-(4-fluorophenyl)piperidin-1-yl]methanone (335 mg, 0.732 mmol) obtained in step 2, and in the same manner as in Example 1, step 4, 4-(3,4-difluorophenylamino)-5-[4-(4-fluorophenyl)piperidine-1-carbonyl]-3-methylpyridine-2-sulfonic acid (279 mg, 75%) was obtained.

ESIMS m/z: 506 (M+H)$^+$ (step 4) Using 4-(3,4-difluorophenylamino)-5-[4-(4-fluorophenyl)piperidine-1-carbonyl]-3-methylpyridine-2-sulfonic acid (273 mg, 0.540 mmol) obtained in step 3, and in the same manner as in Example 11, compound 258 (177 mg, 57%) was obtained.

ESIMS m/z: 572 (M+H)$^+$; $^1$H NMR (400 MHz, DMSO-d$_6$, δ): 1.31-1.76 (m, 4H), 2.00-2.19 (m, 1H), 2.48 (s, 3H), 2.60-2.78 (m, 1H), 2.82-3.14 (m, 1H), 3.43-3.62 (m, 1H), 4.06-4.40 (m, 1H), 6.36 (d, J=1.4 Hz, 1H), 6.68-6.76 (m, 1H), 6.90-7.00 (m, 1H), 7.09 (t, J=8.4 Hz, 2H), 7.16-7.39 (m, 3H), 8.19 (s, 1H), 8.43 (s, 1H), 8.65-8.71 (m, 1H), 11.85 (s, 1H).

Example 81

4-(4-chlorophenylamino)-5-[4-(4-fluorophenyl)piperidine-1-carbonyl]-N-(isoxazol-3-yl)-3-methylpyridine-2-sulfonamide (compound 259)

(step 1) Using (4,6-dichloro-5-methylpyridin-3-yl) [4-(4-fluorophenyl)piperidin-1-yl]methanone (300 mg, 0.817 mmol) obtained in Example 52, step 1, and 4-chloroaniline (156 mg, 1.23 mmol), and in the same manner as in Example 1, step 2, [6-chloro-4-(4-chlorophenylamino)-5-methylpyridin-3-yl][4-(4-fluorophenyl)piperidin-1-yl]methanone (356 mg, 95%) was obtained.

ESIMS m/z: 458 (M+H)$^+$ (step 2) Using [6-chloro-4-(4-chlorophenylamino)-5-methylpyridin-3-yl][4-(4-fluorophenyl)piperidin-1-yl]methanone (356 mg, 0.777 mmol) obtained in step 1, and in the same manner as in Example 1, step 3, [4-(4-chlorophenylamino)-6-mercapto-5-methylpyridin-3-yl][4-(4-fluorophenyl)piperidin-1-yl]methanone (348 mg, 98%) was obtained.

ESIMS m/z: 456 (M+H)$^+$ (step 3) Using [4-(4-chlorophenylamino)-6-mercapto-5-methylpyridin-3-yl][4-(4-fluorophenyl)piperidin-1-yl]methanone (348 mg, 0.763 mmol) obtained in step 2, and in the same manner as in Example 1, step 4, 4-(4-chlorophenylamino)-5-[4-(4-fluorophenyl)piperidine-1-carbonyl]-3-methylpyridine-2-sulfonic acid (282 mg, 73%) was obtained.

ESIMS m/z: 504 (M+H)$^+$ (step 4) Using 4-(4-chlorophenylamino)-5-[4-(4-fluorophenyl)piperidine-1-carbonyl]-3-methylpyridine-2-sulfonic acid (274 mg, 0.577 mmol) obtained in step 3, and in the same manner as in Example 11, compound 259 (177 mg, 57%) was obtained.

ESIMS m/z: 570 (M+H)$^+$; $^1$H NMR (400 MHz, DMSO-d$_6$, δ): 1.24-1.75 (m, 4H), 1.93-2.15 (m, 1H), 2.47 (s, 3H), 2.60-2.78 (m, 1H), 2.85-3.13 (m, 1H), 3.41-3.54 (m, 1H), 3.99-4.43 (m, 1H), 6.36 (d, J=1.4 Hz, 1H), 6.89 (d, J=8.6 Hz, 2H), 7.09 (t, J=8.6 Hz, 2H), 7.15-7.35 (m, 4H), 8.19 (s, 1H), 8.41 (s, 1H), 8.66-8.72 (m, 1H), 11.85 (s, 1H).

Example 82

4-(4-bromophenylamino)-5-[4-(4-fluorophenyl)piperidine-1-carbonyl]-N-(isoxazol-3-yl)-3-methylpyridine-2-sulfonamide (compound 260)

(step 1) Using (4,6-dichloro-5-methylpyridin-3-yl)[4-(4-fluorophenyl)piperidin-1-yl]methanone (3.00 g, 8.17 mmol) obtained in Example 52, step 1, and 4-bromoaniline (1.69 g, 9.81 mmol), and in the same manner as in Example 1, step 2, [4-(4-bromophenylamino)-6-chloro-5-methylpyridin-3-yl][4-(4-fluorophenyl)piperidin-1-yl]methanone (4.03 g, 98%) was obtained.

ESIMS m/z: 502 (M+H)$^+$ (step 2) Using [4-(4-bromophenylamino)-6-chloro-5-methylpyridin-3-yl][4-(4-fluorophenyl)piperidin-1-yl]methanone (4.03 g, 8.01 mmol) obtained in step 1, and in the same manner as in Example 1, step 3, a crude product of [4-(4-bromophenylamino)-6-mercapto-5-methylpyridin-3-yl][4-(4-fluorophenyl)piperidin-1-yl]methanone was obtained and used for the next reaction without purification.

ESIMS m/z: 500 (M+H)$^+$ (step 3) Using a crude product of [4-(4-bromophenylamino)-6-mercapto-5-methylpyridin-3-yl][4-(4-fluorophenyl)piperidin-1-yl]methanone obtained in step 2, and in the same manner as in Example 1, step 4, 4-(4-bromophenylamino)-5-[4-(4-fluorophenyl)piperidine-1-carbonyl]-3-methylpyridine-2-sulfonic acid (3.97 g, yield of 2 steps 77%) was obtained.

ESIMS m/z: 548 (M+H)$^+$ (step 4) Using 4-(4-bromophenylamino)-5-[4-(4-fluorophenyl)piperidine-1-carbonyl]-3-methylpyridine-2-sulfonic acid (159 mg, 0.280 mmol) obtained in step 3, and in the same manner as in Example 11, compound 260 (115 mg, 67%) was obtained.

ESIMS m/z: 614 (M+H)$^+$; $^1$H NMR (400 MHz, DMSO-d$_6$, δ): 1.22-1.77 (m, 4H), 1.93-2.16 (m, 1H), 2.46 (s, 3H), 2.59-2.79 (m, 1H), 2.81-3.14 (m, 1H), 3.41-3.55 (m, 1H), 3.94-4.46 (m, 1H), 6.36 (d, J=1.4 Hz, 1H), 6.83 (d, J=8.6 Hz, 2H), 7.00-7.19 (m, 3H), 7.19-7.35 (m, 1H), 7.41 (d, J=8.6 Hz, 2H), 8.20 (s, 1H), 8.41 (s, 1H), 8.68 (s, 1H), 11.85 (s, 1H).

Example 83

4-(benzylamino)-3-methyl-5-(2H-spiro[benzofuran-3,4'-piperidine]-1'-yl carbonyl)pyridine-2-sulfonamide (compound 261)

(step 1) Using ethyl 4,6-dichloro-5-methylnicotinate (200 mg, 0.854 mmol) obtained by the method described in a document (Journal of Heterocyclic Chemistry, 1999, 36, p. 953), and benzylamine (0.14 mL, 1.3 mmol), and in the same manner as in Example 44, step 1, ethyl 4-(benzylamino)-6-chloro-5-methylnicotinate (251 mg, 96%) was obtained.

ESIMS m/z: 305 (M+H)$^+$ (step 2) Using ethyl 4-(benzylamino)-6-chloro-5-methylnicotinate (251 mg, 0.824 mmol) obtained in step 1, and in the same manner as in Example 57, step 3, ethyl 4-(benzylamino)-6-mercapto-5-methylnicotinate (192 mg, 77%) was obtained.

ESIMS m/z: 303 (M+H)$^+$ (step 3) Using ethyl 4-(benzylamino)-6-mercapto-5-methylnicotinate (192 mg, 0.635 mmol) obtained in step 2, and in the same manner as in Example 46, step 3, ethyl 4-(benzylamino)-5-methyl-6-sulfamoylnicotinate (112 mg, 51%) was obtained.

ESIMS m/z: 350 (M+H)$^+$ (step 4) Using ethyl 4-(benzylamino)-5-methyl-6-sulfamoylnicotinate (110 mg, 0.315 mmol) obtained in step 3, and in the same manner as in Example 51, step 5, 4-(benzylamino)-5-methyl-6-sulfamoylnicotinic acid (105 mg, quantitative) was obtained.

ESIMS m/z: 322 (M+H)$^+$ (step 5) Using 4-(benzylamino)-5-methyl-6-sulfamoylnicotinic acid (45.7 mg, 0.142 mmol) obtained in step 4, and 2H-spiro[benzofuran-3,4'-piperidine](32.3 mg, 0.171 mmol), and in the same manner as in Example 1, step 1, compound 261 (41.7 mg, 60%) was obtained.

ESIMS m/z: 493 (M+H)$^+$; $^1$H NMR (300 MHz, CDCl$_3$, δ): 1.52-1.93 (m, 3H), 2.51 (s, 3H), 2.86-3.45 (m, 7H), 4.19-4.55 (m, 3H), 4.58-4.62 (br m, 2H), 6.80 (d, J=8.1 Hz, 1H), 6.87 (t, J=7.7 Hz, 1H), 6.95-7.05 (m, 1H), 7.15 (t, J=7.7 Hz, 1H), 7.24-7.28 (m, 2H), 7.34-7.48 (m, 3H), 8.07 (s, 1H).

Example 84

4-(3,4-dimethylphenylamino)-5-[4-(4-fluorophenyl) piperidine-1-carbonyl]-N-(isoxazol-3-yl)-3-methyl-pyridine-2-sulfonamide (compound 263)

(step 1) Using (4,6-dichloro-5-methylpyridin-3-yl)[4-(4-fluorophenyl)piperidin-1-yl]methanone (1.00 g, 2.72 mmol) obtained in Example 52, step 1, and 3,4-dimethylaniline (495 mg, 4.08 mmol), and in the same manner as in Example 1, step 2, [6-chloro-4-(3,4-dimethylphenylamino)-5-methyl-pyridin-3-yl][4-(4-fluorophenyl)piperidin-1-yl]methanone (1.13 g, 92%) was obtained.

ESIMS m/z: 452 (M+H)$^+$ (step 2) Using [6-chloro-4-(3,4-dimethylphenylamino)-5-methylpyridin-3-yl][4-(4-fluorophenyl)piperidin-1-yl]methanone (1.13 g, 2.50 mmol) obtained in step 1, and in the same manner as in Example 1, step 3, [4-(3,4-dimethylphenylamino)-6-mercapto-5-methylpyridin-3-yl][4-(4-fluorophenyl)piperidin-1-yl]methanone (1.11 g, 99%) was obtained.

ESIMS m/z: 450 (M+H)$^+$ (step 3) Using [4-(3,4-dimethylphenylamino)-6-mercapto-5-methylpyridin-3-yl][4-(4-fluorophenyl)piperidin-1-yl]methanone (1.11 g, 2.47 mmol) obtained in step 2, and in the same manner as in Example 1, step 4, 4-(3,4-dimethylphenylamino)-5-[4-(4-fluorophenyl)piperidine-1-carbonyl]-3-methylpyridine-2-sulfonic acid (500 mg, 42%) was obtained.

ESIMS m/z: 498 (M+H)$^+$ (step 4) Using 4-(3,4-dimethylphenylamino)-5-[4-(4-fluorophenyl)piperidine-1-carbonyl]-3-methylpyridine-2-sulfonic acid (200 mg, 0.40 mmol) obtained in step 3, and in the same manner as in Example 11, compound 263. (70.7 mg, 31%) was obtained.

ESIMS m/z: 564 (M+H)$^+$; $^1$H NMR (300 MHz, DMSO-d$_5$, δ): 1.10-1.70 (m, 4H), 2.00-2.20 (m, 7H), 2.50 (s, 3H), 2.60-2.80 (m, 1H), 2.80-3.00 (m, 1H), 3.30-3.50 (m, 1H), 4.00-4.30 (m, 1H), 6.25 (s, 1H), 6.45-6.63 (m, 1H), 6.68 (s, 1H), 6.90-7.40 (m, 5H), 7.90 (s, 1H), 8.10 (s, 1H), 8.50 (s, 1H), 11.80 (s, 1H).

Example 85

4-(2-fluoro-3-methylphenylamino)-5-[4-(4-fluorophenyl)piperidine-1-carbonyl]-N-(isoxazol-3-yl)-3-methylpyridine-2-sulfonamide (compound 264)

(step 1) Using (4,6-dichloro-5-methylpyridin-3-yl) [4-(4-fluorophenyl)piperidin-1-yl]methanone (1.00 g, 2.72 mmol) obtained in Example 52, step 1, and 2-fluoro-3-methylaniline (511 mg, 4.08 mmol), and in the same manner as in Example 1, step 2, [6-chloro-4-(2-fluoro-3-methylphenylamino)-5-methylpyridin-3-yl][4-(4-fluorophenyl)piperidin-1-yl]methanone (1.08 g, 87%) was obtained.

ESIMS m/z: 456 (M+H)$^+$ (step 2) Using [6-chloro-4-(2-fluoro-3-methylphenylamino)-5-methylpyridin-3-yl][4-(4-fluorophenyl)piperidin-1-yl]methanone (1.08 g, 2.37 mmol) obtained in step 1, and in the same manner as in Example 1, step 3, [4-(2-fluoro-3-methylphenylamino)-6-mercapto-5-methylpyridin-3-yl][4-(4-fluorophenyl)piperidin-1-yl]methanone (1.18 g, quantitative) was obtained.

ESIMS m/z: 454 (M+H)$^+$ (step 3) Using [4-(2-fluoro-3-methylphenylamino)-6-mercapto-5-methylpyridin-3-yl][4-(4-fluorophenyl)piperidin-1-yl]methanone (1.18 g, 2.60 mmol) obtained in step 2, and in the same manner as in Example 1, step 4, 4-(2-fluoro-3-methylphenylamino)-5-[4-(4-fluorophenyl)piperidine-1-carbonyl]-3-methylpyridine-2-sulfonic acid (550 mg, 42%) was obtained.

ESIMS m/z: 502 (M+H)$^+$ (step 4) Using 4-(2-fluoro-3-methylphenylamino)-5-[4-(4-fluorophenyl)piperidine-1-carbonyl]-3-methylpyridine-2-sulfonic acid (200 mg, 0.40 mmol) obtained in step 3, and in the same manner as in Example 11, compound 264 (75.1 mg, 33%) was obtained.

ESIMS m/z: 568 (M+H)$^+$; $^1$H NMR (300 MHz, DMSO-d$_6$, δ): 1.10-1.70 (m, 4H), 2.00-2.30 (m, 1H), 2.21 (s, 3H), 2.50 (s, 3H), 2.60-2.80 (m, 1H), 2.80-3.10 (m, 1H), 3.40-3.50 (m, 1H), 3.90-4.20 (m, 1H), 6.30 (d, J=1.5 Hz, 1H), 6.81 (br s, 1H), 6.90-7.15 (m, 4H), 7.22 (br s, 2H), 7.97 (br s, 1H), 8.10 (s, 1H), 8.59 (br s, 1H), 11.8 (br s, 1H).

Example 86

4-(3-chloro-2-fluorophenylamino)-5-[4-(4-fluorophenyl)piperidine-1-carbonyl]-N-(isoxazol-3-yl)-3-methylpyridine-2-sulfonamide (compound 265)

(step 1) Using (4,6-dichloro-5-methylpyridin-3-yl)[4-(4-fluorophenyl)piperidin-1-yl]methanone (432 mg, 1.14 mmol) obtained in Example 52, step 1, and 3-chloro-2-fluoroaniline (215 mg, 1.48 mmol), and in the same manner as in Example 1, step 2, [6-chloro-4-(3-chloro-2-fluorophenylamino)-5-methylpyridin-3-yl][4-(4-fluorophenyl)piperidin-1-yl]methanone (543 mg, quantitative) was obtained.

ESIMS m/z: 476 (M+H)$^+$ (step 2) Using [6-chloro-4-(3-chloro-2-fluorophenylamino)-5-methylpyridin-3-yl][4-(4-fluorophenyl)piperidin-1-yl]methanone (543 mg, 1.13 mmol) obtained in step 1, and in the same manner as in Example 1, step 3, a crude product of [4-(3-chloro-2-fluorophenylamino)-6-mercapto-5-methylpyridin-3-yl][4-(4-fluorophenyl)piperidin-1-yl]methanone was obtained and used for the next reaction without purification.

ESIMS m/z: 474 (M+H)$^+$ (step 3) Using a crude product of [4-(3-chloro-2-fluorophenylamino)-6-mercapto-5-methylpyridin-3-yl][4-(4-fluorophenyl)piperidin-1-yl]methanone obtained in step 2, and in the same manner as in Example 1, step 4, 4-(3-chloro-2-fluorophenylamino)-5-[4-(4-fluorophenyl)piperidine-1-carbonyl]-3-methylpyridine-2-sulfonic acid (422 mg, yield of 2 steps 71%) was obtained.

ESIMS m/z: 522 (M+H)$^+$ (step 4) Using 4-(3-chloro-2-fluorophenylamino)-5-[4-(4-fluorophenyl)piperidine-1-carbonyl]-3-methylpyridine-2-sulfonic acid (422 mg, 0.803 mmol) obtained in step 3, and in the same manner as in Example 11, compound 265 (80.2 mg, 17%) was obtained.

ESIMS m/z: 588 (M+H)$^+$; $^1$H NMR (400 MHz, DMSO-d$_6$, δ): 1.15-1.76 (m, 4H), 1.85-2.15 (m, 1H), 2.49 (s, 3H), 2.60-2.74 (m, 1H), 2.80-3.10 (m, 1H), 3.40-3.60 (m, 1H), 4.00-4.28 (m, 1H), 6.33 (s, 1H), 6.80-7.50 (m, 7H), 8.10-8.35 (m, 2H), 8.55 (br s, 1H), 11.85 (br s, 1H).

Example 87

5-[4-(4-fluorophenyl)piperidine-1-carbonyl]-4-(3-fluorophenylamino)-3-methyl-N-(3-methylisothiazol-5-yl)pyridine-2-sulfonamide (compound 267)

Using 5-[4-(4-fluorophenyl)piperidine-1-carbonyl]-4-(3-fluorophenylamino)-3-methylpyridine-2-sulfonic acid (357 mg, 0.732 mmol) obtained in Example 67, step 3, and in the same manner as in Example 71, step 4, compound 267 (38 mg, 8.9%) was obtained.

ESIMS m/z: 584 (M+H)$^+$; $^1$H NMR (400 MHz, DMSO-d$_6$, δ): 1.25-1.82 (m, 4H), 2.08 (s, 3H), 2.11-2.31 (m, 1H), 2.42 (s, 3H), 2.61-2.78 (m, 1H), 2.84-3.12 (m, 1H), 3.40-3.59 (m, 1H), 4.12-4.49 (m, 1H), 5.97 (s, 1H), 6.48-6.57 (m, 2H), 6.58-6.68 (m, 1H), 6.95-7.34 (m, 6H), 8.19 (s, 1H), 8.23 (s, 1H).

Example 88

4-(2-fluoro-5-methoxyphenylamino)-5-[4-(4-fluorophenyl)piperidine-1-carbonyl]-N-(isoxazol-3-yl)-3-methylpyridine-2-sulfonamide (compound 268)

(step 1) Using (4,6-dichloro-5-methylpyridin-3-yl) [4-(4-fluorophenyl)piperidin-1-yl]methanone (1.00 g, 2.72 mmol) obtained in Example 52, step 1, and 2-fluoro-5-methoxyaniline (575 mg, 4.08 mmol), and in the same manner as in Example 1, step 2, [6-chloro-4-(2-fluoro-5-methoxyphenylamino)-5-methylpyridin-3-yl][4-(4-fluorophenyl)piperidin-1-yl]methanone (1.35 g, quantitative) was obtained.

ESIMS m/z: 472 (M+H)$^+$ (step 2) Using [6-chloro-4-(2-fluoro-5-methoxyphenylamino)-5-methylpyridin-3-yl][4-(4-fluorophenyl)piperidin-1-yl]methanone (1.35 g, 2.87 mmol) obtained in step 1, and in the same manner as in Example 1, step 3, [4-(2-fluoro-5-methoxyphenylamino)-6-mercapto-5-methylpyridin-3-yl][4-(4-fluorophenyl)piperidin-1-yl]methanone (1.10 g, 82%) was obtained.

ESIMS m/z: 470 (M+H)$^+$ (step 3) Using [4-(2-fluoro-5-methoxyphenylamino)-6-mercapto-5-methylpyridin-3-yl][4-(4-fluorophenyl)piperidin-1-yl]methanone (1.10 g, 2.34 mmol) obtained in step 2, and in the same manner as in Example 1, step 4, 4-(2-fluoro-5-methoxyphenylamino)-5-[4-(4-fluorophenyl)piperidine-1-carbonyl]-3-methylpyridine-2-sulfonic acid (500 mg, 41%) was obtained.

ESIMS m/z: 518 (M+H)$^+$ (step 4) Using 4-(2-fluoro-5-methoxyphenylamino)-5-[4-(4-fluorophenyl)piperidine-1-carbonyl]-3-methylpyridine- 2-sulfonic acid (250 mg, 0.480 mmol) obtained in step 3, and in the same manner as in Example 11, compound 268 (118 mg, 42%) was obtained.

ESIMS m/z: 584 (M+H)$^+$; $^1$H NMR (400 MHz, DMSO-d$_6$, D$_2$O, δ): 1.10-1.70 (m, 4H), 1.90-2.30 (m, 1H), 2.50 (s, 3H), 2.60-2.80 (m, 1H), 2.90-3.10 (m, 1H), 3.40-3.60 (m, 1H), 3.67 (s, 3H), 4.05-4.30 (m, 1H), 6.27 (s, 1H), 6.30-6.70 (m, 2H), 7.00-7.40 (m, 5H), 8.13 (s, 1H), 8.46 (br s, 1H).

Example 89

4-(4-fluoro-3-methoxyphenylamino)-5-[4-(4-fluorophenyl)piperidine-1-carbonyl]-N-(isoxazol-3-yl)-3-methylpyridine-2-sulfonamide (compound 269)

(step 1) Using (4,6-dichloro-5-methylpyridin-3-yl) [4-(4-fluorophenyl)piperidin-1-yl]methanone (1.50 g, 4.09 mmol) obtained in Example 52, step 1, and 4-fluoro-3-methoxyaniline (865 mg, 6.13 mmol), and in the same manner as in Example 1, step 2, [6-chloro-4-(4-fluoro-3-methoxyphenylamino)-5-methylpyridin-3-yl][4-(4-fluorophenyl)piperidin-1-yl]methanone (1.35 mg, 70%) was obtained.

ESIMS m/z: 472 (M+H)$^+$ (step 2) Using [6-chloro-4-(4-fluoro-3-methoxyphenylamino)-5-methylpyridin-3-yl][4-(4-fluorophenyl)piperidin-1-yl]methanone (1.35 g, 2.85 mmol) obtained in step 1, and in the same manner as in Example 1, step 3, a crude product of [4-(4-fluoro-3-methoxyphenylamino)-6-mercapto-5-methylpyridin-3-yl][4-(4-fluorophenyl)piperidin-1-yl]methanone was obtained and used for the next reaction without purification.

ESIMS m/z: 470 (M+H)$^+$ (step 3) Using a crude product of [4-(4-fluoro-3-methoxyphenylamino)-6-mercapto-5-methylpyridin-3-yl][4-(4-fluorophenyl)piperidin-1-yl]methanone obtained in step 2, and in the same manner as in Example 1, step 4, a crude product of 4-(4-fluoro-3-methoxyphenylamino)-5-[4-(4-fluorophenyl)piperidine-1-carbonyl]-3-methylpyridine-2-sulfonic acid was obtained and used for the next reaction without purification.

ESIMS m/z: 518 (M+H)$^+$ (step 4) Using a crude product of 4-(4-fluoro-3-methoxyphenylamino)-5-[4-(4-fluorophenyl)piperidine-1-carbonyl]-3-methylpyridine-2-sulfonic acid obtained in step 3, and in the same manner as in Example 11, compound 269 (61 mg, yield of 3 steps 22%) was obtained.

ESIMS m/z: 584 (M+H)$^+$; $^1$H NMR (300 MHz, DMSO-d$_6$, D$_2$O, δ): 1.20-1.80 (m, 4H), 1.88-2.28 (m, 1H), 2.52 (s, 3H), 2.60-3.19 (m, 2H), 3.40-3.68 (m, 1H), 3.77 (s, 3H), 3.87-4.39 (m, 1H), 6.33 (s, 1H), 6.46 (br s, 1H), 6.65-6.80 (m, 1H), 7.04-7.34 (m, 5H), 8.13 (s, 1H), 8.23 (s, 1H), 8.59 (br s, 1H), 11.81 (br s, 1H).

Example 90

4-(4-chloro-2-fluorophenylamino)-5-[4-(4-fluorophenyl)piperidine-1-carbonyl]-N-(isoxazol-3-yl)-3-methylpyridine-2-sulfonamide (compound 270)

(step 1) Using (4,6-dichloro-5-methylpyridin-3-yl)[4-(4-fluorophenyl)piperidin-1-yl]methanone (1.00 g, 2.72 mmol) obtained in Example 52, step 1, and 4-chloro-2-fluoroaniline (594 mg, 4.08 mmol), and in the same manner as in Example 1, step 2, [6-chloro-4-(4-chloro-2-fluorophenylamino)-5-methylpyridin-3-yl][4-(4-fluorophenyl)piperidin-1-yl]methanone (920 mg, 71%) was obtained.

ESIMS m/z: 476 (M+H)$^+$ (step 2) Using [6-chloro-4-(4-chloro-2-fluorophenylamino)-5-methylpyridin-3-yl][4-(4-fluorophenyl)piperidin-1-yl]methanone (1.28 g, 2.70 mmol) obtained in step 1, and in the same manner as in Example 1, step 3, a crude product of [4-(4-chloro-2-fluorophenylamino)-6-mercapto-5-methylpyridin-3-yl][4-(4-fluorophenyl)piperidin-1-yl]methanone was obtained and used for the next reaction without purification.

ESIMS m/z: 474 (M+H)$^+$ (step 3) Using a crude product of [4-(4-chloro-2-fluorophenylamino)-6-mercapto-5-methylpyridin-3-yl][4-(4-fluorophenyl)piperidin-1-yl]methanone obtained in step 2, and in the same manner as in Example 1, step 4, 4-(4-chloro-2-fluorophenylamino)-5-[4-(4-fluorophenyl)piperidine-1-carbonyl]-3-methylpyridine-2-sulfonic acid (500 mg, yield of 2 steps 35%) was obtained.

ESIMS m/z: 522 (M+H)$^+$ (step 4) Using 4-(4-chloro-2-fluorophenylamino)-5-[4-(4-fluorophenyl)piperidine-1-carbonyl]-3-methylpyridine-2-sulfonic acid (250 mg, 0.480 mmol) obtained in step 3, and in the same manner as in Example 11, compound 270 (53.9 mg, 19%) was obtained.

ESIMS m/z: 588 (M+H)$^+$; $^1$H NMR (400 MHz, DMSO-d$_6$, D$_2$O, δ):

1.20-1.80 (m, 4H), 1.90-2.30 (m, 1H), 2.50 (s, 3H), 2.60-2.80 (m, 1H), 2.80-3.10 (m, 1H), 3.40-3.60 (m, 1H), 4.00-4.30 (m, 1H), 6.27 (m, 1H) 6.80-7.60 (m, 7H), 8.12 (s, 1H), 8.48 (br s, 1H).

Example 91

4-(5-chloro-2-fluorophenylamino)-5-[4-(4-fluorophenyl)piperidine-1-carbonyl]-N-(isoxazol-3-yl)-3-methylpyridine-2-sulfonamide (compound 271)

(step 1) Using (4,6-dichloro-5-methylpyridin-3-yl) [4-(4-fluorophenyl)piperidin-1-yl]methanone (1.00 g, 2.72 mmol) obtained in Example 52, step 1, and 5-chloro-2-fluoroaniline (594 mg, 4.08 mmol), and in the same manner as in Example 1, step 2, [6-chloro-4-(5-chloro-2-fluorophenylamino)-5-methylpyridin-3-yl][4-(4-fluorophenyl)piperidin-1-yl]methanone (890 mg, 69%) was obtained.

ESIMS m/z: 476 (M+H)$^+$ (step 2) Using [6-chloro-4-(5-chloro-2-fluorophenylamino)-5-methylpyridin-3-yl][4-(4-fluorophenyl)piperidin-1-yl]methanone (920 mg, 1.93 mmol) obtained in step 1, and in the same manner as in Example 1, step 3, a crude product of [4-(5-chloro-2-fluorophenylamino)-6-mercapto-5-methylpyridin-3-yl][4-(4-fluorophenyl)piperidin-1-yl]methanone was obtained and used for the next reaction without purification.

ESIMS m/z: 474 (M+H)$^+$ (step 3) Using a crude product of [4-(5-chloro-2-fluorophenylamino)-6-mercapto-5-methylpyridin-3-yl][4-(4-fluorophenyl)piperidin-1-yl]methanone obtained in step 2, and in the same manner as in Example 1, step 4, 4-(5-chloro-2-fluorophenylamino)-5-[4-(4-fluorophenyl)piperidine-1-carbonyl]-3-methylpyridine-2-sulfonic acid (500 mg, yield of 2 steps 50%) was obtained.

ESIMS m/z: 522 (M+H)$^+$ (step 4) Using 4-(5-chloro-2-fluorophenylamino)-5-[4-(4-fluorophenyl)piperidine-1-carbonyl]-3-methylpyridine-2-sulfonic acid (250 mg, 0.480 mmol) obtained in step 3, and in the same manner as in Example 11, compound 271 (95.4 mg, 34%) was obtained.

ESIMS m/z: 588 (M+H)$^+$; $^1$H NMR (300 MHz, DMSO-d$_6$, δ): 1.20-1.80 (m, 4H), 2.00-2.30 (m, 1H), 2.51 (s, 3H), 2.60-2.80 (m, 1H), 2.90-3.15 (m, 1H), 3.40-3.60 (m, 1H), 4.15-4.30 (m, 1H), 6.23 (s, 1H), 6.70-7.40 (m, 7E), 8.37 (s, 1H), 8.47 (br s, 1H).

Example 92

4-(2-chloro-3-fluorophenylamino)-5-[4-(4-fluorophenyl)piperidine-1-carbonyl]-N-(isoxazol-3-yl)-3-methylpyridine-2-sulfonamide (compound 272)

(step 1) Using (4,6-dichloro-5-methylpyridin-3-yl)[4-(4-fluorophenyl)piperidin-1-yl]methanone (1.50 g, 4.09 mmol) obtained in Example 52, step 1, and 2-chloro-3-fluoroaniline (892 mg, 6.13 mmol), and in the same manner as in Example 1, step 2, [6-chloro-4-(2-chloro-3-fluorophenylamino)-5-methylpyridin-3-yl][4-(4-fluorophenyl)piperidin-1-yl]methanone (1.24 g, 64%) was obtained.

ESIMS m/z: 476 (M+H)$^+$ (step 2) Using [6-chloro-4-(2-chloro-3-fluorophenylamino)-5-methylpyridin-3-yl][4-(4-fluorophenyl)piperidin-1-yl]methanone (1.24 mg, 2.59 mmol) obtained in step 1, and in the same manner as in Example 1, step 3, a crude product of [4-(2-chloro-3-fluorophenylamino)-6-mercapto-5-methylpyridin-3-yl][4-(4-fluorophenyl)piperidin-1-yl]methanone was obtained and used for the next reaction without purification.

ESIMS m/z: 474 (M+H)$^+$ (step 3) Using a crude product of [4-(2-chloro-3-fluorophenylamino)-6-mercapto-5-methylpyridin-3-yl][4-(4-fluorophenyl)piperidin-1-yl]methanone obtained in step 2, and in the same manner as in Example 1, step 4, a crude product of 4-(2-chloro-3-fluorophenylamino)-5-[4-(4-fluorophenyl)piperidine-1-carbonyl]-3-methylpyridine-2-sulfonic acid was obtained and used for the next reaction without purification.

ESIMS m/z: 522 (M+H)$^+$ (step 4) Using a crude product of 4-(2-chloro-3-fluorophenylamino)-5-[4-(4-fluorophenyl)piperidine-1-carbonyl]-3-methylpyridine-2-sulfonic acid obtained in step 3, and in the same manner as in Example 11, compound 272 (89.9 mg, yield of 3 steps 32%) was obtained.

ESIMS m/z: 588 (M+H)$^+$; $^1$H NMR (300 MHz, DMSO-d$_6$, δ): 1.05-1.80 (m, 4H), 2.10-2.45 (m, 1H), 2.53 (s, 3H), 2.65-2.80 (m, 1H), 2.90-3.20 (m, 1H), 3.49-3.65 (m, 1H), 4.15-4.35 (m, 1H), 6.33 (s, 1H), 6.50-6.75 (m, 1H), 7.01-7.45 (m, 6H), 7.85-8.12 (m, 1H), 8.28 (s, 1H), 8.57 (br s, 1H), 11.86 (br s, 1H).

Example 93

4-(2-chloro-4-fluorophenylamino)-5-[4-(4-fluorophenyl)piperidine-1-carbonyl]-N-(isoxazol-3-yl)-3-methylpyridine-2-sulfonamide (compound 273)

(step 1) Using (4,6-dichloro-5-methylpyridin-3-yl)[4-(4-fluorophenyl)piperidin-1-yl]methanone (1.00 g, 2.72 mmol) obtained in Example 52, step 1, and 2-chloro-4-fluoroaniline (594 mg, 4.08 mmol), and in the same manner as in Example 1, step 2, [6-chloro-4-(2-chloro-4-fluorophenylamino)-5-methylpyridin-3-yl][4-(4-fluorophenyl)piperidin-1-yl]methanone (930 mg, 72%) was obtained.

ESIMS m/z: 476 (M+H)$^+$ (step 2) Using [6-chloro-4-(2-chloro-4-fluorophenylamino)-5-methylpyridin-3-yl][4-(4-fluorophenyl)piperidin-1-yl]methanone (1.05 g, 2.20 mmol) obtained in step 1, and in the same manner as in Example 1, step 3, a crude product of [4-(2-chloro-4-fluorophenylamino)-6-mercapto-5-methylpyridin-3-yl][4-(4-fluorophenyl)piperidin-1-yl]methanone was obtained and used for the next reaction without purification.

ESIMS m/z: 474 (M+H)$^+$ (step 3) Using a crude product of [4-(2-chloro-4-fluorophenylamino)-6-mercapto-5-methylpyridin-3-yl][4-(4-fluorophenyl)piperidin-1-yl]methanone obtained in step 2, and in the same manner as in Example 1, step 4, 4-(2-chloro-4-fluorophenylamino)-5-[4-(4-fluorophenyl)piperidine-1-carbonyl]-3-methylpyridine-2-sulfonic acid (900 mg, yield of 2 steps 78%) was obtained.

ESIMS m/z: 522 (M+H)$^+$ (step 4) Using 4-(2-chloro-4-fluorophenylamino)-5-[4-(4-fluorophenyl)piperidine-1-carbonyl]-3-methylpyridine-2-sulfonic acid (250 mg, 0.480 mmol) obtained in step 3, and in the same manner as in Example 11, compound 273 (67.8 mg, 24%) was obtained.

ESIMS m/z: 588 (M+H)$^+$; $^1$H NMR (300 MHz, DMSO-d$_6$, δ): 1.15-1.79 (m, 4H), 2.05-2.40 (m, 1H), 2.50 (s, 3H), 2.60-2.80 (m, 1H), 2.82-3.10 (m, 1H), 3.45-3.63 (m, 1H), 4.05-4.25 (m, 1H), 6.30 (s, 1H), 7.06-7.24 (m, 7H), 7.40-7.58 (m, 1H), 7.78-8.00 (m, 1H), 8.10 (s, 1H), 8.54 (br s, 1H).

Example 94

4-(2-chloro-5-fluorophenylamino)-5-[4-(4-fluorophenyl)piperidine-1-carbonyl]-N-(isoxazol-3-yl)-3-methylpyridine-2-sulfonamide (compound 274)

(step 1) Using (4,6-dichloro-5-methylpyridin-3-yl)[4-(4-fluorophenyl)piperidin-1-yl]methanone (1.00 g, 2.72 mmol) obtained in Example 52, step 1, and 2-chloro-5-fluoroaniline (594 mg, 4.08 mmol), and in the same manner as in Example 1, step 2, [6-chloro-4-(2-chloro-5-fluorophenylamino)-5-methylpyridin-3-yl][4-(4-fluorophenyl)piperidin-1-yl]methanone (910 mg, 70%) was obtained.

ESIMS m/z: 476 (M+H)$^+$ (step 2) Using [6-chloro-4-(2-chloro-5-fluorophenylamino)-5-methylpyridin-3-yl][4-(4-fluorophenyl)piperidin-1-yl]methanone (643 mg, 1.35 mmol) obtained in step 1, and in the same manner as in Example 1, step 3, a crude product of [4-(2-chloro-5-fluorophenylamino)-6-mercapto-5-methylpyridin-3-yl][4-(4-fluorophenyl)piperidin-1-yl]methanone was obtained and used for the next reaction without purification.

ESIMS m/z: 474 (M+H)$^+$ (step 3) Using a crude product of [4-(2-chloro-5-fluorophenylamino)-6-mercapto-5-methylpyridin-3-yl][4-(4-fluorophenyl)piperidin-1-yl]methanone obtained in step 2, and in the same manner as in Example 1, step 4, 4-(2-chloro-5-fluorophenylamino)-5-[4-(4-fluorophenyl)piperidine-1-carbonyl]-3-methylpyridine-2-sulfonic acid (600 mg, yield of 2 steps 80%) was obtained.

ESIMS m/z: 522 (M+H)$^+$ (step 4) Using 4-(2-chloro-5-fluorophenylamino)-5-[4-(4-fluorophenyl)piperidine-1-carbonyl]-3-methylpyridine-2-sulfonic acid (250 mg, 0.480 mmol) obtained in step 3, and in the same manner as in Example 11, compound 274 (53.7 mg, 19%) was obtained.

ESIMS m/z: 588 (M+H)$^+$; $^1$H NMR (300 MHz, DMSO-d$_6$, δ): 1.10-1.80 (m, 4H), 2.20-2.45 (m, 1H), 2.50 (s, 3H), 2.62-2.82 (m, 1H), 2.90-3.15 (m, 1H), 3.48-3.68 (m, 1H), 4.18-4.42 (m, 1H), 6.31 (s, 1H), 6.50-6.75 (m, 1H), 6.80-7.00 (m, 1H), 7.00-7.38 (m, 5H), 7.45-7.65 (m, 1H), 7.75-8.05 (m, 1H), 8.28 (s, 1H), 8.59 (br s, 1H).

Example 95

5-[4-(4-fluorophenyl)piperidine-1-carbonyl]-N-(isoxazol-3-yl)-3-methyl-4-(2,3,5-trifluorophenylamino)pyridine-2-sulfonamide (compound 275)

(step 1) Using (4,6-dichloro-5-methylpyridin-3-yl)[4-(4-fluorophenyl)piperidin-1-yl]methanone (1.20 g, 3.27 mmol)

obtained in Example 52, step 1, and 2,3,5-trifluoroaniline (721 mg, 4.90 mmol), and in the same manner as in Example 1, step 2, [6-chloro-5-methyl-4-(2,3,5-trifluorophenylamino)pyridin-3-yl][4-(4-fluorophenyl)piperidin-1-yl]methanone (663 mg, 42%) was obtained.

ESIMS m/z: 478 (M+H)$^+$ (step 2) Using [6-chloro-5-methyl-4-(2,3,5-trifluorophenylamino)pyridin-3-yl][4-(4-fluorophenyl)piperidin-1-yl]methanone (663 mg, 1.39 mmol) obtained in step 1, and in the same manner as in Example 1, step 3, [4-(4-fluorophenyl)piperidin-1-yl][6-mercapto-5-methyl-4-(2,3,5-trifluorophenylamino)pyridin-3-yl]methanone (610 mg, 92%) was obtained.

ESIMS m/z: 476 (M+H)$^+$ (step 3) Using [4-(4-fluorophenyl)piperidin-1-yl][6-mercapto-5-methyl-4-(2,3,5-trifluorophenylamino)pyridin-3-yl]methanone (610 mg, 1.28 mmol) obtained in step 2, and in the same manner as in Example 1, step 4, 5-[4-(4-fluorophenyl)piperidine-1-carbonyl]-3-methyl-4-(2,3,5-trifluorophenylamino)pyridine-2-sulfonic acid (300 mg, 45%) was obtained.

ESIMS m/z: 524 (M+H)$^+$ (step 4) Using 5-[4-(4-fluorophenyl)piperidine-1-carbonyl]-3-methyl-4-(2,3,5-trifluorophenylamino)pyridine-2-sulfonic acid (250 mg, 0.480 mmol) obtained in step 3, and in the same manner as in Example 11, compound 275 (81.8 mg, 30%) was obtained. ESIMS m/z: 590 (M+H)$^+$; $^1$H NMR (300 MHz, DMSO-d$_6$, D$_2$O, δ): 1.00-1.80 (m, 4H), 2.10-2.30 (m, 1H), 2.51 (s, 3H), 2.60-2.80 (m, 1H), 2.80-3.20 (m, 1H), 3.40-3.60 (m, 1H), 4.10-4.30 (m, 1H), 6.29 (s, 1H), 6.50-6.80 (m, 1H), 7.00-7.40 (m, 5H), 8.32 (br s, 1H), 8.51 (br s, 1H).

Example 96

5-[4-(4-fluorophenyl)piperidine-1-carbonyl]-3-methyl-N-(3-methylisothiazol-5-yl)-4-(phenylamino)pyridine-2-sulfonamide (compound 277)

(step 1) Using (4,6-dichloro-5-methylpyridin-3-yl)[4-(4-fluorophenyl)piperidin-1-yl]methanone (300 mg, 0.817 mmol) obtained in Example 52, step 1, and aniline (0.112 mh, 1.23 mmol), and in the same manner as in Example 1, step 2, [6-chloro-5-methyl-4-(phenylamino)pyridin-3-yl][4-(4-fluorophenyl)piperidin-1-yl]methanone (290 mg, 84%) was obtained.

ESIMS m/z: 424 (M+H)$^+$ (step 2) Using [6-chloro-5-methyl-4-(phenylamino)pyridin-3-yl][4-(4-fluorophenyl)piperidin-1-yl]methanone (290 mg, 0.684 mmol) obtained in step 1, and in the same manner as in Example 1, step 3, [4-(4-fluorophenyl)piperidin-1-yl][6-mercapto-5-methyl-4-(phenylamino)pyridin-3-yl]methanone (262 mg, 91%) was obtained.

ESIMS m/z: 422 (M+H)$^+$ (step 3) Using [4-(4-fluorophenyl)piperidin-1-yl][6-mercapto-5-methyl-4-(phenylamino)pyridin-3-yl]methanone (260 mg, 0.617 mmol) obtained in step 2, and in the same manner as in Example 1, step 4, 5-[4-(4-fluorophenyl)piperidine-1-carbonyl]-3-methyl-4-(phenylamino)pyridine-2-sulfonic acid (250 mg, 86%) was obtained.

ESIMS m/z: 470 (M+H)$^+$ (step 4) Using 5-[4-(4-fluorophenyl)piperidine-1-carbonyl]-3-methyl-4-(phenylamino)pyridine-2-sulfonic acid (250 mg, 0.532 mmol) obtained in step 3, and in the same manner as in Example 71, step 4, compound 277 (102 mg, 34%) was obtained.

ESIMS m/z: 566 (M+H)$^+$; $^1$H NMR (400 MHz, DMSO-d$_6$, δ): 1.22-1.76 (m, 4H), 1.80-2.03 (m, 1H), 2.28 (s, 3H), 2.47 (s, 3H), 2.57-2.76 (m, 1H), 2.78-3.11 (m, 1H), 3.48-3.68 (m, 1H), 3.86-4.42 (m, 1H), 6.66 (s, 1H), 6.90 (d, J=7.7 Hz, 2H), 6.93-7.35 (m, 7H), 8.17 (s, 1H), 8.35 (s, 1H), 12.09 (br s, 1H).

Example 97

4-(2,5-dichlorophenylamino)-5-[4-(4-fluorophenyl)piperidine-1-carbonyl]-N-(isoxazol-3-yl)-3-methylpyridine-2-sulfonamide (compound 281)

(step 1) Using (4,6-dichloro-5-methylpyridin-3-yl)[4-(4-fluorophenyl)piperidin-1-yl]methanone (1.20 g, 3.27 mmol) obtained in Example 52, step 1, and 2,5-dichloroaniline (6BB mg, 4.25 mmol), and in the same manner as in Example 1, step 2, [6-chloro-4-(2,5-dichlorophenylamino)-5-methylpyridin-3-yl][4-(4-fluorophenyl)piperidin-1-yl]methanone (874 mg, 54%) was obtained.

ESIMS m/z: 492 (M+H)$^+$ (step 2) Using [6-chloro-4-(2,5-dichlorophenylamino)-5-methylpyridin-3-yl][4-(4-fluorophenyl)piperidin-1-yl]methanone (874 mg, 1.77 mmol) obtained in step 1, and in the same manner as in Example 1, step 3, a crude product of [4-(2,5-dichlorophenylamino)-6-mercapto-5-methylpyridin-3-yl][4-(4-fluorophenyl)piperidin-1-yl]methanone was obtained and used for the next reaction without purification.

ESIMS m/z: 490 (M+H)$^+$ (step 3) Using a crude product of [4-(2,5-dichlorophenylamino)-6-mercapto-5-methylpyridin-3-yl][4-(4-fluorophenyl)piperidin-1-yl]methanone obtained in step 2, and in the same manner as in Example 1, step 4, a crude product of 4-(2,5-dichlorophenylamino)-5-[4-(4-fluorophenyl)piperidine-1-carbonyl]-3-methylpyridine-2-sulfonic acid was obtained and used for the next reaction without purification.

ESIMS m/z: 538 (M+H)$^+$ (step 4) Using a crude product of 4-(2,5-dichlorophenylamino)-5-[4-(4-fluorophenyl)piperidine-1-carbonyl]-3-methylpyridine-2-sulfonic acid obtained in step 3, and in the same manner as in Example 11, compound 281 (59.5 mg, yield of 3 steps 12%) was obtained.

ESIMS m/z: 604 (M+H)$^+$; $^1$H NMR (300 MHz, DMSO-d$_6$, δ): 1.10-1.80 (m, 4H), 2.10-2.45 (m, 1H), 2.53 (s, 3H), 2.70-2.83 (m, 1H), 2.98-3.19 (m, 1H), 3.50-3.65 (m, 1H), 4.15-4.40 (m, 1H), 6.34 (s, 1H), 6.70-7.45 (m, 6H), 7.46-7.60 (m, 1H), 7.80-8.10 (m, 1H), 8.29 (s, 1H), 8.59 (br s, 1H), 11.89 (br s, 1H).

Example 98

4-(benzylamino)-5-[3-(4-fluorophenyl)azetidine-1-carbonyl]-3-methylpyridine-2-sulfonamide (compound 284)

(step 1) Using 4,6-dichloro-5-methylnicotinic acid (1.00 g, 4.85 mmol) obtained by the method described in a document (Journal of Heterocyclic Chemistry, 1999, 36, p. 953), and in the same manner as in Example 44, step 1, 4-(benzylamino)-6-chloro-5-methylnicotinic acid (433 mg, 32%) was obtained.

ESIMS m/z: 277 (M+H)$^+$ (step 2) Using 4-(benzylamino)-6-chloro-5-methylnicotinic acid (433 mg, 1.55 mmol) obtained in step 1, and 3-(4-fluorophenyl)azetidine hydrochloride (441 mg, 2.34 mmol), and in the same manner as in Example 1, step 1,

[4-(benzylamino)-6-chloro-5-methylpyridin-3-yl][3-(4-fluorophenyl)azetidin-1-yl]methanone (220 mg, 35%) was obtained.

ESIMS m/z: 410 (M+H)$^+$ (step 3) Using [4-(benzylamino)-6-chloro-5-methylpyridin-3-yl][3-(4-fluorophenyl)azetidin-1-yl]methanone (85.6 mg, 1.07 mmol) obtained in step 2, and in the same manner as in Example 1, step 3, a crude product of [4-(benzylamino)-6-mercapto-5-methylpyridin-3-yl][3-(4-fluorophenyl)azetidin-1-yl]methanone was obtained and used for the next reaction without purification.

ESIMS m/z: 408 (M+H)$^+$ (step 4) Using a crude product of [4-(benzylamino)-6-mercapto-5-methylpyridin-3-yl][3-(4-fluorophenyl)azetidin-1-yl]methanone obtained in step 3, and in the same manner as in Example 1, step 4, 4-(benzylamino)-5-[3-(4-fluorophenyl)azetidine-1-carbonyl]-3-methylpyridine-2-sulfonic acid (208 mg, yield of 2 steps 85%) was obtained.

ESIMS m/z: 456 (M+H)$^+$ (step 5) Using 4-(benzylamino)-5-[3-(4-fluorophenyl)azetidine-1-carbonyl]-3-methylpyridine-2-sulfonic acid (180 mg, 0.390 mmol) obtained in step 4, and in the same manner as in Example 2, compound 284 (54.8 mg, 31%) was obtained.

ESIMS m/z: 455 (M+H)$^+$; $^1$H NMR (400 MHz, DMSO-d$_6$, δ): 2.53 (s, 3H), 3.30-3.53 (m, 3H), 3.80-3.95 (m, 1H), 4.23-4.35 (m, 1H), 4.50-4.73 (m, 2H), 6.95-7.48 (m, 12H), 8.05 (s, 1H).

Example 99

4-(3-chlorophenylamino)-5-[3-(4-fluorophenyl)azetidine-1-carbonyl]-3-methylpyridine-2-sulfonamide (compound 285)

(step 1) Using 4,6-dichloro-5-methylnicotinic acid (480 mg, 2.34 mmol) obtained by the method described in a document (Journal of Heterocyclic Chemistry, 1999, 36, p. 953), and 3-chloroaniline (300 mg, 2.34 mmol), and in the same manner as in Example 1, step 2, a crude product of 6-chloro-4-(3-chlorophenylamino)-5-methylnicotinic acid was obtained and used for the next reaction without purification.

ESIMS m/z: 297 (M+H)$^+$ (step 2) Using a crude product of 6-chloro-4-(3-chlorophenylamino)-5-methylnicotinic acid obtained in step 1, and in the same manner as in Example 98, step 2, [6-chloro-4-(3-chlorophenylamino)-5-methylpyridin-3-yl][3-(4-fluorophenyl)azetidin-1-yl]methanone (302 mg, yield of 2 steps 30%) was obtained.

ESIMS m/z: 430 (M+H)$^+$ (step 3) Using [6-chloro-4-(3-chlorophenylamino)-5-methylpyridin-3-yl][3-(4-fluorophenyl)azetidin-1-yl]methanone (302 mg, 0.700 mmol) obtained in step 2, and in the same manner as in Example 1, step 3, a crude product of [4-(3-chlorophenylamino)-6-mercapto-5-methylpyridin-3-yl][3-(4-fluorophenyl)azetidin-1-yl]methanone was obtained and used for the next reaction without purification.

ESIMS m/z: 428 (M+H)$^+$ (step 4) Using a crude product of [4-(3-chlorophenylamino)-6-mercapto-5-methylpyridin-3-yl][3-(4-fluorophenyl)azetidin-1-yl]methanone obtained in step 3, and in the same manner as in Example 1, step 4, 4-(3-chlorophenylamino)-5-[3-(4-fluorophenyl)azetidine-1-carbonyl]-3-methylpyridine-2-sulfonic acid (226, mg, yield of 2 steps 68%) was obtained.

ESIMS m/z: 476 (M+H)$^+$ (step 5) Using 4-(3-chlorophenylamino)-5-[3-(4-fluorophenyl)azetidine-1-carbonyl]-3-methylpyridine-2-sulfonic acid (200 mg, 0.420 mmol) obtained in step 4, and in the same manner as in Example 2, compound 285 (70.4 mg, 35%) was obtained.

ESIMS m/z: 475 (M+H)$^+$; $^1$H NMR (400 MHz, CDCl$_3$, δ): 2.46 (s, 3H), 3.50-3.70 (m, 1H), 3.78-3.94 (m, 1H), 4.00-4.18 (m, 2H), 4.42 (t, J=6.6 Hz, 1H), 6.75-6.89 (m, 1H), 6.90-7.00 (m, 1H), 7.00-7.08 (m, 1H), 7.15-7.60 (m, 7H), 8.42 (s, 1H), 8.61 (s, 1E).

Example 100

3-ethyl-5-[4-(4-fluorophenyl)piperidine-1-carbonyl]-N-(isoxazol-3-yl)-4-(o-tolylamino)pyridine-2-sulfonamide (compound 287)

(step 1) Using diethyl 2-ethyl-3-oxopentanedioate (10.7 g, 44.2 mmol) obtained by the method described in a document (Nippon Nogeikagaku Kaishi, 1974, 48, p. 507), and in the same manner as in the method described in a document (Journal of Heterocyclic Chemistry, 1999, 36, p. 953), 4,6-dichloro-5-ethylnicotinic acid (5.50 g, 54%) was obtained.

ESIMS m/z: 220 (M+H)$^+$ (step 2) Using 4,6-dichloro-5-ethylnicotinic acid (5.5 g, 23.7 mmol) obtained in step 1, and in the same manner as in Example 1, step 1, (4,6-dichloro-5-ethylpyridin-3-yl)[4-(4-fluorophenyl)piperidin-1-yl]methanone (10.0 g, quantitative) was obtained.

ESIMS m/z: 381 (M+H)$^+$ (step 3) Using (4,6-dichloro-5-ethylpyridin-3-yl)[4-(4-fluorophenyl)piperidin-1-yl]methanone (432 mg, 1.14 mmol), and o-toluidine (159 mg, 1.48 mmol) obtained in step 2, and in the same manner as in Example 1, step 2, a crude product of [6-chloro-5-ethyl-4-(o-tolylamino)pyridin-3-yl][4-(4-fluorophenyl)piperidin-1-yl]methanone was obtained and used for the next reaction without purification.

ESIMS m/z: 452 (M+H)$^+$ (step 4) Using a crude product of [6-chloro-5-ethyl-4-(o-tolylamino)pyridin-3-yl][4-(4-fluorophenyl)piperidin-1-yl]methanone obtained in step 3, and in the same manner as in Example 1, step 3, a crude product of [5-ethyl-6-mercapto-4-(o-tolylamino)pyridin-3-yl][4-(4-fluorophenyl)piperidin-1-yl]methanone was obtained and used for the next reaction without purification.

ESIMS m/z: 450 (M+H)$^+$ (step 5) Using a crude product of [5-ethyl-6-mercapto-4-(o-tolylamino)pyridin-3-yl][4-(4-fluorophenyl)piperidin-1-yl]methanone obtained in step 4, and in the same manner as in Example 1, step 4, 3-ethyl-5-[4-(4-fluorophenyl)piperidine-1-carbonyl]-4-(o-tolylamino)pyridine-2-sulfonic acid (400 mg, yield of 3 steps 71%) was obtained.

ESIMS m/z: 498 (M+H)$^+$ (step 6) Using 3-ethyl-5-[4-(4-fluorophenyl)piperidine-1-carbonyl]-4-(o-tolylamino)pyridine-2-sulfonic acid (400 mg, 0.803 mmol) obtained in step 5, and in the same manner as in Example 11, compound 287 (191 mg, 42%) was obtained.

ESIMS m/z: 564 (M+H)$^+$; $^1$H NMR (400 MHz, DMSO-d$_6$, δ): 1.21 (t, J=5.1 Hz, 3H), 1.30-1.70 (m, 5H), 2.24 (s, 3H), 2.60-2.90 (m, 2H), 3.11-3.28 (m, 2H), 3.50-3.60 (m, 1H), 3.80-4.08 (m, 1H), 6.31 (s, 1H), 6.75-7.00 (m, 1H), 7.00-7.80 (m, 9H), 7.97 (s, 1H), 8.52 (br s, 1H).

Example 101

5-[4-(4-fluorophenyl)piperidine-1-carbonyl]-3-methyl-4-(p-tolyloxy)pyridine-2-sulfonamide (compound 289)

(step 1) (4,6-Dichloro-5-methylpyridin-3-yl)[4-(4-fluorophenyl)piperidin-1-yl]methanone (3.00 g, 8.17 mmol) obtained in Example 52, step 1 was dissolved in 1,4-dioxane (41 mL), methyl 3-mercaptopropionate (1.1 mL, 9.8 mmol), tris(dibenzylideneacetone)dipalladium(0) (374 mg, 0.408 mmol), 4,5-bis(diphenylphosphino)-9,9-dimethylxanthene (473 mg, 0.817 mmol) and cesium carbonate (5.32 g, 16.3 mmol) were added, and the mixture was stirred under reflux for 6.5 hr. To the reaction mixture was added saturated aqueous ammonium chloride solution, and the mixture was extracted with ethyl acetate. The organic layer was dried over anhydrous magnesium sulfate, and the solvent was evaporated under reduced pressure to give a crude product of methyl 3-(4-chloro-5-[4-(4-fluorophenyl)piperidine-1-carbonyl]-3-methylpyridin-2-ylthio)propionate, which was used for the next reaction without purification.

ESIMS m/z: 451 (M+H)$^+$ (step 2) The crude product of methyl 3-(4-chloro-5-[4-(4-fluorophenyl)piperidine-1-carbonyl]-3-methylpyridin-2-ylthio)propionate obtained in step 1 was dissolved in THF (30 mL), potassium tert-butoxide (917 mg, 8.17 mmol) was added under ice-cooling, and the mixture was stirred for 15 min under ice-cooling. To the reaction mixture was added saturated aqueous ammonium chloride solution, and the mixture was extracted with ethyl acetate. The organic layer was dried over anhydrous magnesium sulfate, and the solvent was evaporated under reduced pressure. The residue was purified by silica gel column chromatography (chloroform/methanol-4/0-10/1) to give (4-chloro-6-mercapto-5-methylpyridin-3-yl)[4-(4-fluorophenyl)piperidin-1-yl]methanone (2.71 g, yield of 2 steps 91%).

ESIMS m/z: 365 (M+H)$^+$ (step 3) Using (4-chloro-6-mercapto-5-methylpyridin-3-yl)[4-(4-fluorophenyl)piperidin-1-yl]methanone (2.23 g, 6.11 mmol) obtained in step 2, and in the same manner as in Example 46, step 3, 4-chloro-5-[4-(4-fluorophenyl)piperidine-1-carbonyl]-3-methylpyridine-2-sulfonamide (633 mg, 25%) was obtained.

ESIMS m/z: 412 (M+H)$^+$ (step 4) Using 4-chloro-5-[4-(4-fluorophenyl)piperidine-1-carbonyl]-3-methylpyridine-2-sulfonamide (326 mg, 0.791 mmol) obtained in step 3, and in the same manner as in Example 78, step 1, 4-chloro-5-[4-(4-fluorophenyl)piperidine-1-carbonyl]-N,N-bis(4-methoxybenzyl)-3-methylpyridine-2-sulfonamide (299 mg, 58%) was obtained.

ESIMS m/z: 652 (M+H)$^+$ (step 5) 4-Chloro-5-[4-(4-fluorophenyl)piperidine-1-carbonyl]-N,N-bis(4-methoxybenzyl)-3-methylpyridine-2-sulfonamide (22.9 mg, 0.0350 mmol) obtained in step 4 was dissolved in DMA (0.70 mL), p-cresol (19.0 mg, 0.176 mmol) and cesium carbonate (34.3 mg, 0.105 mmol) were added, and the mixture was stirred at 80° C. for 8 hr. To the reaction mixture was added saturated aqueous sodium chloride solution, and the mixture was extracted with ethyl acetate. The organic layer was dried over anhydrous magnesium sulfate, and the solvent was evaporated under reduced pressure. The residue was purified by preparative HPLC (XBridge™ manufactured by Waters) (acetonitrile/0.05% aqueous trifluoroaceticacid solution) to give 5-[4-(4-fluorophenyl)piperidine-1-carbonyl]-N,N-bis(4-methoxybenzyl)-3-methyl-4-(p-tolyloxy)pyridine-2-sulfonamide (14.0 mg, 55%).

ESIMS m/z: 724 (M (step 6) Using 5-[4-(4-fluorophenyl)piperidine-1-carbonyl]-N,N-bis(4-methoxybenzyl)-3-methyl-4-(p-tolyloxy)pyridine-2-sulfonamide (17.9 mg, 0.025 mmol) obtained in step 5, and in the same manner as in Example 78, step 3, compound 289 (8.6 mg, 72%) was obtained.

ESIMS m/z: 484 (M+H)$^+$; $^1$H NMR (400 MHz, CDCl$_3$, δ): 1.24-1.53 (m, 2H), 1.65-1.88 (m, 2H), 2.29-2.31 (m, 3H), 2.40 (t, J=12.2 Hz, 1H), 2.52-2.56 (m, 3H), 2.62-2.80 (m, 1H), 2.98-3.17 (m, 1H), 3.52 (t, J=10.7 Hz, 1H), 4.53-4.70 (m, 1H), 5.37 (s, 2H), 6.76 (d, J=6.8 Hz, 2H), 6.96-7.07 (m, 3H), 7.09-7.15 (m, 3H), 8.34-8.39 (m, 1H).

Example 102

3-chloro-5-[4-(4-fluorophenyl)piperidine-1-carbonyl]-4-[4-(trifluoromethyl)phenylamino]pyridine-2-sulfonamide (compound 291)

(step 1) Using 3,4-dichloro-5-[4-(4-fluorophenyl)piperidine-1-carbonyl]-N,N-bis(4-methoxybenzyl)pyridine-2-sulfonamide (114 mg, 0.169 mmol) obtained in Example 78, step 1, and 4-(trifluoromethyl)aniline (41.0 mg, 0.254 mmol), and in the same manner as in Example 78, step 2, 3-chloro-5-[4-(4-fluorophenyl)piperidine-1-carbonyl]-N,N-bis(4-methoxybenzyl)-4-[4-(trifluoromethyl)phenylamino]pyridine-2-sulfonamide (112 mg, 83%) was obtained.

ESIMS m/z: 797 (M+H)$^+$ (step 2) Using 3-chloro-5-[4-(4-fluorophenyl)piperidine-1-carbonyl]-N,N-bis(4-methoxybenzyl)-4-[4-(trifluoromethyl)phenylamino]pyridine-2-sulfonamide (112 mg, 0.140 mmol) obtained in step 1, and in the same manner as in Example 78, step 3, compound 291 (59.4 mg, 76%) was obtained.

ESIMS m/z: 557 (M+H)$^+$; $^1$H NMR (400 MHz, CDCl$_3$, δ): 1.28-1.52 (m, 2H), 1.73-1.85 (m, 2H), 2.58-2.69 (m, 1H), 2.92-3.07 (m, 1H), 3.48-3.63 (m, 2H), 4.22-4.36 (m, 1H), 5.26 (s, 2H), 6.99 (t, J 8.8 Hz, 2H), 7.03-7.09 (m, 2H), 7.16 (d, J=8.8 Hz, 2H), 7.19-7.22 (m, 1H), 7.63 (d, J=7.8 Hz, 2H), 8.29 (s, 1H).

Example 103

5-[3-(4-fluorophenyl)azetidine-1-carbonyl]-N-(isoxazol-3-yl)-3-methyl-4-(o-tolylamino)pyridine-2-sulfonamide (compound 292)

(step 1) Using 4,6-dichloro-5-methylnicotinic acid (2.00 g, 9.66 mmol) obtained by the method described in a document (Journal of Heterocyclic Chemistry, 1999, 36, p. 953), and o-toluidine (1.55 g, 14.5 mmol), and in the same manner as in Example 1, step 2, a crude product of 6-chloro-5-methyl-4-(o-tolylamino)nicotinic acid was obtained and used for the next reaction without purification.

ESIMS m/z: 277 (M+H)$^+$ (step 2) The crude product of 6-chloro-5-methyl-4-(o-tolylamino)nicotinic acid obtained in step 1 was dissolved in THF (30 mL), diazomethane (4.5 mol/L diethylether solution, 20 mL, 90 mmol) was added under ice-cooling, and the mixture was stirred for 2 hr under ice-cooling. To the reaction mixture was added acetic acid (3 mL), and the solvent was evaporated under reduced pressure to give a crude product of methyl 6-chloro-5-methyl-4-(o-tolylamino)nicotinate, which was used for the next reaction without purification.

ESIMS m/z: 291 (M+H)+

(step 3) Using a crude product of methyl 6-chloro-5-methyl-4-(o-tolylamino)nicotinate obtained in step 2, and in the same manner as in Example 1, step 3, a crude product of methyl 6-mercapto-5-methyl-4-(o-tolylamino)nicotinate was obtained and used for the next reaction without purification.

ESIMS m/z: 289 (M+H)+

(step 4) Using a crude product of methyl 6-mercapto-5-methyl-4-(o-tolylamino)nicotinate obtained in step 3, and in the same manner as in Example 1, step 4, 5-(methoxycarbonyl)-3-methyl-4-(o-tolylamino)pyridine-2-sulfonic acid (1.80 g, yield of 4 steps 55%) was obtained.

ESIMS m/z: 337 (M+H)+

(step 5) Using 5-(methoxycarbonyl)-3-methyl-4-(o-tolylamino)pyridine-2-sulfonic acid (520 mg, 1.55 mmol) obtained in step 4, and in the same manner as in Example 11, methyl 6-(N-isoxazol-3-ylsulfamoyl)-5-methyl-4-(o-tolylamino)nicotinate (500 mg, 80%) was obtained.

ESIMS m/z: 403 (M+H)+

(step 6) Using methyl 6-(N-isoxazol-3-ylsulfamoyl)-5-methyl-4-(o-tolylamino)nicotinate (1.00 g, 2.48 mmol) obtained in step 5, and in the same manner as in Example 51, step 5, 6-(N-isoxazol-3-ylsulfamoyl)-5-methyl-4-(o-tolylamino)nicotinic acid (126 mg, 13%) was obtained.

ESIMS m/z: 389 (M+H)+

(step 7) Using 6-(N-isoxazol-3-ylsulfamoyl)-5-methyl-4-(o-tolylamino)nicotinic acid (100 mg, 0.27 mmol) obtained in step 6, and in the same manner as in Example 98, step 2, compound 292 (33.3 mg, 25%) was obtained.

ESIMS m/z: 552 (M+H)+; $^1$H NMR (300 MHz, CD$_3$OD, δ): 2.29 (s, 3E), 2.50 (s, 3H), 3.70-3.90 (m, 2H), 4.00-4.27 (m, 2H), 4.40-4.60 (m, 1H), 6.25 (s, 1H), 6.80-6.90 (m, 1H), 7.00-7.18 (m, 4H), 7.20-7.40 (m, 3H), 8.20-8.35 (m, 2E).

Example 104

3-ethyl-5-[4-(4-fluorophenyl)piperidine-1-carbonyl]-N-isoxazol-3-yl)-4-(phenylamino)pyridine-2-sulfonamide (compound 293)

(step 1) Using (4,6-dichloro-5-ethylpyridin-3-yl)[4-(4-fluorophenyl)piperidin-1-yl]methanone (800 mg, 2.10 mmol) obtained in Example 100, step 2, and aniline (293 mg, 3.15 mmol), and in the same manner as in Example 1, step 2, [6-chloro-5-ethyl-4-(phenylamino)pyridin-3-yl][4-(4-fluorophenyl)piperidin-1-yl]methanone (761 mg, 83%) was obtained.

ESIMS m/z: 438 (M+H)+

(step 2) Using [6-chloro-5-ethyl-4-(phenylamino)pyridin-3-yl][4-(4-fluorophenyl)piperidin-1-yl]methanone (761 mg, 1.53 mmol) obtained in step 1, and in the same manner as in Example 1, step 3, a crude product of [5-ethyl-6-mercapto-4-(phenylamino)pyridin-3-yl][4-(4-fluorophenyl)piperidin-1-yl]methanone was obtained and used for the next reaction without purification.

ESIMS m/z: 436 (M+1)+

(step 3) Using a crude product of [5-ethyl-6-mercapto-4-(phenylamino)pyridin-3-yl][4-(4-fluorophenyl)piperidin-1-yl]methanone obtained in step 2, and in the same manner as in Example 1, step 4, a crude product of 3-ethyl-5-[4-(4-fluorophenyl)piperidine-1-carbonyl]-4-(phenylamino)pyridine-2-sulfonic acid was obtained and used for the next reaction without purification.

ESIMS m/z: 484 (M+H)+

(step 4) Using a crude product of 3-ethyl-5-[4-(4-fluorophenyl)piperidine-1-carbonyl]-4-(phenylamino)pyridine-2-sulfonic acid obtained in step 3, and in the same manner as in Example 11, compound 293 (23.3 mg, yield of 3 steps 6%) was obtained.

ESIMS m/z: 550 (M+H)+; $^1$H NMR (300 MHz, DMSO-d$_5$, D$_2$O, δ): 0.80-2.10 (m, 8H), 2.50-2.80 (m, 1H), 2.90-3.80 (m, 4H), 3.90-4.30 (m, 1H), 6.30 (s, 1H), 6.90-7.50 (m, 9H), 8.10 (s, 1H), 8.30 (s, 1H).

Example 105

3-ethyl-4-(3-fluoro-2-methylphenylamino)-5-[4-(4-fluorophenyl)piperidine-1-carbonyl]-N-(isoxazol-3-yl)pyridine-2-sulfonamide (compound 294)

(step 1) Using (4,6-dichloro-5-ethylpyridin-3-yl)[4-(4-fluorophenyl)piperidin-1-yl]methanone (800 mg, 2.10 mmol) obtained in Example 100, step 2, and 3-fluoro-2-methylaniline (394 mg, 3.15 mmol), and in the same manner as in Example 1, step 2, [6-chloro-5-ethyl-4-(3-fluoro-2-methylphenylamino)pyridin-3-yl][4-(4-fluorophenyl)piperidin-1-yl]methanone (750 mg, 83%) was obtained.

ESIMS m/z: 470 (M+H)+

(step 2) Using [6-chloro-5-ethyl-4-(3-fluoro-2-methylphenylamino)pyridin-3-yl][4-(4-fluorophenyl)piperidin-1-yl]methanone (750 mg, 1.60 mmol) obtained in step 1, and in the same manner as in Example 1, step 3, a crude product of [5-ethyl-4-(3-fluoro-2-methylphenylamino)-6-mercaptopyridin-3-yl][4-(4-fluorophenyl)piperidin-1-yl]methanone was obtained and used for the next reaction without purification.

ESIMS m/z: 468 (M+H)+

(step 3) Using a crude product of [5-ethyl-4-(3-fluoro-2-methylphenylamino)-6-mercaptopyridin-3-yl][4-(4-fluorophenyl)piperidin-1-yl]methanone obtained in step 2, and in the same manner as in Example 1, step 4, a crude product of 3-ethyl-4-(3-fluoro-2-methylphenylamino)-5-[4-(4-fluorophenyl)piperidine-1-carbonyl]pyridine-2-sulfonic acid was obtained and used for the next reaction without purification.

ESIMS m/z: 516 (M+H)+

(step 4) Using a crude product of 3-ethyl-4-(3-fluoro-2-methylphenylamino)-5-[4-(4-fluorophenyl)piperidine-1-carbonyl]pyridine-2-sulfonic acid obtained in step 3, and in the same manner as in Example 11, compound 294 (28.2 mg, yield of 3 steps 6%) was obtained.

ESIMS m/z: 582 (M+H)+; $^1$H NMR (300 MHz, CD$_3$OD, δ): 1.10-2.30 (m, 8H), 2.27 (s, 3H), 2.55-3.30 (m, 4H), 3.55-3.70 (m, 1H), 4.05-4.30 (m, 1H), 6.31 (s, 1H), 6.70-6.85 (m, 1H), 6.97-7.10 (m, 3H), 7.11-7.30 (m, 3H), 8.01 (s, 1H), 8.31 (s, 1H).

Example 106

3-chloro-5-[4-(4-fluorophenyl)-4-methoxypiperidine-1-carbonyl]-4-(1-phenylcyclopropylamino)pyridine-2-sulfonamide (compound 295)

(step 1) Using ethyl 4,5,6-trichloronicotinate (0.400 g, 1.57 mmol) and 1-phenylcyclopropanamine (0.291 mL, 2.36 mmol), and in the same manner as in Example 44, step 1, ethyl 5,6-dichloro-4-(1-phenylcyclopropylamino)nicotinate (0.438 mg, 79%) was obtained.

ESIMS m/z: 351 (M+H)+

(step 2) Using ethyl 5,6-dichloro-4-(1-phenylcyclopropylamino)nicotinate (0.438 g, 1.25 mmol) obtained in step 1, and in the same manner as in Example 51, step 2, ethyl 5-chloro-6-mercapto-4-(1-phenylcyclopropylamino)nicotinate (370 mg, 85%) was obtained.

ESIMS m/z: 349 (M+H)+

(step 3) Using ethyl 5-chloro-6-mercapto-4-(1-phenylcyclopropylamino)nicotinate (0.370 g, 1.06 mmol) obtained in step 2, and in the same manner as in Example 51, step 3, 3-chloro-5-(ethoxycarbonyl)-4-(1-phenylcyclopropylamino)pyridine-2-sulfonic acid (285 mg, 68%) was obtained.

ESIMS m/z: 397 (M+H)$^+$ (step 4) Using 3-chloro-5-(ethoxycarbonyl)-4-(1-phenylcyclopropylamino)pyridine-2-sulfonic acid (280 mg, 0.706 mmol) obtained in step 3, and in the same manner as in Example 2, ethyl 5-chloro-4-(1-phenylcyclopropylamino)-6-sulfamoylnicotinate (226 mg, 81%) was obtained.

ESIMS m/z: 396 (M+H)$^+$ (step 5) Using ethyl 5-chloro-4-(1-phenylcyclopropylamino)-6-sulfamoylnicotinate (225 mg, 0.568 mmol) obtained in step 4, and in the same manner as in Example 51, step 5, 5-chloro-4-(1-phenylcyclopropylamino)-6-sulfamoylnicotinic acid (210 mg, quantitative) was obtained.

ESIMS m/z: 368 (M+14)$^+$ (step 6) Using 5-chloro-4-(1-phenylcyclopropylamino)-6-sulfamoylnicotinic acid (53.0 mg, 0.144 mmol) obtained in step 5, and 4-(4-fluorophenyl)-4-methoxypiperidine hydrochloride (49.6 mg, 0.202 mmol) obtained by the method described in WO2003/053361, and in the same manner as in Example 1, step 1, compound 295 (38.6 mg, 48%) was obtained.

ESIMS m/z: 559 (M+H)$^+$; $^1$H NMR (400 MHz, CDCl$_3$, δ): 0.93-1.15 (m, 1H), 1.34-1.60 (m, 3H), 1.60-1.76 (m, 3H), 1.90-2.01 (m, 2H), 2.21-2.55 (m, 1H), 2.63-2.78 (m, 1H), 2.80 (s, 3H), 4.16-4.46 (m, 1H), 5.28 (s, 2H), 6.34 (s, 1H), 7.02 (t, J=8.6 Hz, 2H), 7.06-7.14 (m, 2H), 7.16-7.25 (m, 3H), 7.28-7.42 (m, 2H), 7.90 (s, 1H).

Example 107

3-chloro-4-(1-phenylcyclopropylamino)-5-(4-phenylpiperidine-1-carbonyl)pyridine-2-sulfonamide (compound 296)

Using 5-chloro-4-(1-phenylcyclopropylamino)-6-sulfamoylnicotinic acid (53.0 mg, 0.144 mmol) obtained in Example 106, step 5, and 4-phenylpiperidine (32.5 mg, 0.202 mmol), and in the same manner as in Example 1, step 1, compound 296 (15.1 mg, 21%) was obtained.

ESIMS m/z: 511 (M+H)$^+$; $^1$H NMR (400 MHz, CDCl$_3$, δ): 0.94-1.12 (m, 1H), 1.18-1.35 (m, 1H), 1.35-1.47 (m, 1H), 1.47-1.65 (m, 3H), 1.65-1.85 (m, 3H), 1.99-2.15 (m, 1H), 2.37-2.51 (m, 1H), 2.92-3.08 (m, 1H), 4.45-4.61 (m, 1H), 5.26 (s, 2H), 6.34 (s, 1H), 7.06-7.15 (m, 4H), 7.17-7.24 (m, 2H), 7.27-7.31 (m, 1H), 7.35 (t, J=7.7 Hz, 2H), 7.96 (s, 1H).

Example 108

3-chloro-4-(1-phenylcyclopropylamino)-5-(2H-spiro[benzofuran-3,4'-piperidin]-1'-ylcarbonyl)pyridine-2-sulfonamide (compound 297)

Using 5-chloro-4-(1-phenylcyclopropylamino)-6-sulfamoylnicotinic acid (53.0 mg, 0.144 mmol) obtained in Example 106, step 5, and 2H-spiro[benzofuran-3,4'-piperidine](38.2 mg, 0.202 mmol), and in the same manner as in Example 1, step 1, compound 297 (27.4 mg, 35%) was obtained. ESIMS m/z: 539 (M+H)$^+$; $^1$H NMR (400 MHz, CDCl$_3$, δ): 0.85-1.08 (m, 1H), 1.30-1.96 (m, 9H), 2.67-3.00 (m, 1H), 3.94-4.17 (m, 2H), 4.32-4.59 (m, 1H), 5.29 (s, 2H), 6.35 (s, 1H), 6.78 (d, J=8.2 Hz, 1H), 6.87 (t, J=7.0 Hz, 1H), 6.96 (d, J=7.2 Hz, 1H), 7.09-7.19 (m, 3H), 7.29 (d, J=7.7 Hz, 1H), 7.38 (t, J=7.7 Hz, 2H), 7.99 (s, 1H).

Example 109

4-(4-cyanophenylamino)-5-[4-(4-fluorophenyl)piperidine-1-carbonyl]-N-(isoxazol-3-yl)-3-methylpyridine-2-sulfonamide (compound 298)

(step 1) Using (4,6-dichloro-5-methylpyridin-3-yl)[4-(4-fluorophenyl)piperidin-1-yl]methanone (300 mg, 0.817 mmol) obtained in Example 52, step 1, and 4-aminobenzonitrile (193 mg, 1.63 mmol), and in the same manner as in Example 1, step 2, 4-{2-chloro-5-[4-(4-fluorophenyl)piperidine-1-carbonyl]-3-methylpyridin-4-ylamino}benzonitrile (232 mg, 63%) was obtained.

ESIMS m/z: 449 (M+H)$^+$ (step 2) Using 4-{2-chloro-5-[4-(4-fluorophenyl)piperidine-1-carbonyl]-3-methylpyridin-4-ylamino}benzonitrile (179 mg, 0.399 mmol) obtained in step 1, and in the same manner as in Example 1, step 3, 4-{5-[4-(4-fluorophenyl)piperidine-1-carbonyl]-2-mercapto-3-methylpyridin-4-ylamino}benzonitrile (150 mg, 84%) was obtained.

ESIMS m/z: 447 (M+H)$^+$ (step 3) Using 4-{5-[4-(4-fluorophenyl)piperidine-1-carbonyl]-2-mercapto-3-methylpyridin-4-ylamino}benzonitrile (150 mg, 0.336 mmol) obtained in step 2, and in the same manner as in Example 1, step 4, 4-(4-cyanophenylamino)-5-[4-(4-fluorophenyl)piperidine-1-carbonyl]-3-methylpyridine-2-sulfonic acid (130 mg, 78%) was obtained.

ESIMS m/z: 495 (M+H)$^+$ (step 4) Using 4-(4-cyanophenylamino)-5-[4-(4-fluorophenyl)piperidine-1-carbonyl]-3-methylpyridine-2-sulfonic acid (84 mg, 0.170 mmol) obtained in step 3, and in the same manner as in Example 11, compound 298 (86.1 mg, 90%) was obtained.

ESIMS m/z: 561 (M+H)$^+$; $^1$H NMR (400 MHz, DMSO-d$_6$, δ): 0.89-1.12 (m, 1H), 1.31-1.80 (m, 3H), 2.17-2.37 (m, 1H), 2.43 (s, 3H), 2.60-2.82 (m, 2H), 2.84-3.15 (m, 1H), 4.19-4.53 (m, 1H), 6.14 (s, 1H), 6.73 (d, J=8.2 Hz, 2H), 6.83-7.03 (m, 1H), 7.09 (t, J=8.8 Hz, 2H), 7.17-7.38 (m, 1H), 7.58 (d, J=8.6 Hz, 2H), 8.11-8.22 (m, 1H), 8.22-8.37 (m, 1H), 8.63-8.83 (m, 1H).

Example 110

5-[4-(4-fluorophenyl)piperidine-1-carbonyl]-4-(4-fluorophenylamino)-3-methyl-N-(3-methylisothiazol-5-yl)pyridine-2-sulfonamide (compound 299)

(step 1) Using (4,6-dichloro-5-methylpyridin-3-yl)[4-(4-fluorophenyl)piperidin-1-yl]methanone (400 mg, 1.09 mmol) obtained in Example 52, step 1, and 4-fluoroaniline (181 mg, 1.63 mmol), and in the same manner as in Example 1, step 2, [6-chloro-4-(4-fluorophenylamino)-5-methylpyridin-3-yl][4-(4-fluorophenyl)piperidin-1-yl]methanone (420 mg, 87%) was obtained.

ESIMS m/z: 442 (M+H)$^+$ (step 2) Using [6-chloro-4-(4-fluorophenylamino)-5-methylpyridin-3-yl][4-(4-fluorophenyl)piperidin-1-yl]methanone (420 mg, 0.950 mmol) obtained in step 1, and in the same manner as in Example 1, step 3, a crude product of [4-(4-fluorophenyl)piperidin-1-yl][4-(4-fluorophenylamino)-6-mercapto-5-methylpyridin-3-yl]methanone was obtained and used for the next reaction without purification.

ESIMS m/z: 440 (M+H)$^+$ (step 3) Using a crude product of [4-(4-fluorophenyl)piperidin-1-yl][4-(4-fluorophenylamino)-6-mercapto-5- methylpyridin-3-yl]methanone obtained in step 2, and in the same manner as in Example 1, step 4, a crude product of 5-[4-(4-fluorophenyl)piperidine-1-carbonyl]-4-(4-fluorophenylamino)-3-methylpyridine-2-sulfonic acid was obtained and used for the next reaction without purification.

ESIMS m/z: 488 (M+H)+

(step 4) Using a crude product of 5-[4-(4-fluorophenyl)piperidine-1-carbonyl]-4-(4-fluorophenylamino)-3-methylpyridine-2-sulfonic acid obtained in step 3, and in the same manner as in Example 71, step 4, compound 299 (46.9 mg, yield of 3 steps 14%) was obtained.

ESIMS m/z: 584 (M+H)+; $^1$H NMR (300 MHz, DMSO-$d_6$, $D_2O$, δ): 1.20-1.80 (m, 4H), 2.10 (s, 3H), 2.40 (s, 3H), 2.60-2.80 (m, 1H), 2.90-3.10 (m, 1H), 3.30-3.50 (m, 1H), 4.00-4.20 (m, 2H), 6.00 (m, 1H), 6.80-6.90 (m, 2H), 7.00-7.40 (m, 6H), 8.10 (s, 1H).

Example 111

5-[4-(4-fluorophenyl)piperidine-1-carbonyl]-3-methyl-N-(3-methylisothiazol-5-yl)-4-(p-tolylamino)pyridine-2-sulfonamide (compound 300)

(step 1) Using (4,6-dichloro-5-methylpyridin-3-yl)[4-(4-fluorophenyl)piperidin-1-yl]methanone (400 mg, 1.09 mmol) obtained in Example 52, step 1, and p-toluidine (174 mg, 1.62 mmol), and in the same manner as in Example 1, step 2, [6-chloro-5-methyl-4-(p-tolylamino)pyridin-3-yl][4-(4-fluorophenyl)piperidin-1-yl]methanone (440 mg, 91%) was obtained.

ESIMS m/z: 438 (M+H)+

(step 2) Using [6-chloro-5-methyl-4-(p-tolylamino)pyridin-3-yl][4-(4-fluorophenyl)piperidin-1-yl]methanone (440 mg, 1.00 mmol) obtained in step 1, and in the same manner as in Example 1, step 3, a crude product of [4-(4-fluorophenyl)piperidin-1-yl][6-mercapto-5-methyl-4-(p-tolylamino)pyridin-3-yl]methanone was obtained and used for the next reaction without purification.

ESIMS m/z: 436 (M+H)+

(step 3) Using a crude product of [4-(4-fluorophenyl)piperidin-1-yl][6-mercapto-5-methyl-4-(p-tolylamino)pyridin-3-yl]methanone obtained in step 2, and in the same manner as in Example 1, step 4, a crude product of 5-[4-(4-fluorophenyl)piperidine-1-carbonyl]-3-methyl-4-(p-tolylamino)pyridine-2-sulfonic acid was obtained and used for the next reaction without purification.

ESIMS m/z: 484 (M+H)+

(step 4) Using a crude product of 5-[4-(4-fluorophenyl)piperidine-1-carbonyl]-3-methyl-4-(p-tolylamino)pyridine-2-sulfonic acid obtained in step 3, and in the same manner as in Example 71, step 4, compound 300 (39.7 mg, yield of 3 steps 10%) was obtained.

ESIMS m/z: 580 (M+H)+; $^1$H NMR (300 MHz, DMSO-$d_6$, $D_2O$, δ): 1.10-1.80 (m, 4H), 2.10-2.30 (m, 1H), 2.13 (s, 3H), 2.22 (s, 3H), 2.42 (s, 3H), 2.50-2.70 (m, 1H), 2.90-3.10 (m, 1H), 3.30-3.50 (m, 1H), 3.90-4.30 (m, 1H), 6.15 (s, 1H) 6.70-6.80 (m, 2H), 7.00-7.30 (m, 6H), 8.10 (s, 1H).

Example 112

4-(3,4-difluorophenylamino)-5-[4-(4-fluorophenyl)piperidine-1-carbonyl]-3-methyl-N-(3-methylisothiazol-5-yl)pyridine-2-sulfonamide (compound 301)

Using 4-(3,4-difluorophenylamino)-5-[4-(4-fluorophenyl)piperidine-1-carbonyl]-3-methylpyridine-2-sulfonic acid (240 mg, 0.48 mmol) obtained in Example 80, step 3, and in the same manner as in Example 71, step 4, compound 301 (57.0 mg, 20%) was obtained.

ESIMS m/z: 602 (M+H)+; $^1$H NMR (300 MHz, DMSO-$d_6$, $D_2O$, δ): 1.25-1.85 (m, 4H), 1.92-2.00 (m, 1H), 2.28 (s, 3H), 2.48 (s, 3H), 2.62-2.80 (m, 1H), 2.80-3.21 (m, 1H), 3.42-3.59 (m, 1H), 3.95-4.36 (m, 1H), 6.68 (s, 1H), 6.70-6.82 (m, 1H), 6.90-7.04 (m, 1H), 7.04-7.49 (m, 5H), 8.50 (s, 1H).

Example 113

3-chloro-4-(4-chlorophenylamino)-5-[4-(4-fluorophenyl)piperidine-1-carbonyl]pyridine-2-sulfonamide (compound 302)

(step 1) Using 3,4-dichloro-5-[4-(4-fluorophenyl)piperidine-1-carbonyl]-N,N-bis(4-methoxybenzyl)pyridine-2-sulfonamide (90.0 mg, 0.134 mmol) obtained in Example 78, step 1, and 4-chloroaniline (25.6 mg, 0.201 mmol), and in the same manner as in Example 78, step 2, a crude product of 3-chloro-4-(4-chlorophenylamino)-5-[4-(4-fluorophenyl)piperidine-1-carbonyl]-N,N-bis(4-methoxybenzyl)pyridine-2-sulfonamide was obtained and used for the next reaction without purification.

ESIMS m/z: 763 (M+H)+

(step 2) Using a crude product of 3-chloro-4-(4-chlorophenylamino)-5-[4-(4-fluorophenyl)piperidine-1-carbonyl]-N,N-bis(4-methoxybenzyl)pyridine-2-sulfonamide obtained in step 1, and in the same manner as in Example 78, step 3, compound 302 (41.8 mg, yield of 2 steps 60%) was obtained.

ESIMS m/z: 523 (M+H)+; $^1$H NMR (400 MHz, CDCl$_3$, δ): 1.26-1.36 (m, 1H), 1.41-1.55 (m, 1H), 1.75-1.84 (m, 3H), 2.59-2.69 (m, 1H), 2.86-3.00 (m, 1H), 3.47-3.56 (m, 1H), 4.22-4.33 (m, 1H), 5.32 (s, 2H), 6.97-7.04 (m, 3H), 7.05-7.12 (m, 4H), 7.36 (d, J=8.8 Hz, 2H), 8.19 (s, 1H).

Example 114

4-(5-acetyl-2-methylphenylamino)-3-chloro-3-[4-(4-fluorophenyl)piperidine-1-carbonyl]pyridine-2-sulfonamide (compound 303)

(step 1) Using 3,4-dichloro-5-[4-(4-fluorophenyl)piperidine-1-carbonyl]-N,N-bis(4-methoxybenzyl)pyridine-2-sulfonamide (60.0 mg, 0.089 mmol) obtained in Example 78, step 1, and 1-(3-amino-4-methylphenyl)ethanone (20.0 mg, 0.134 mmol), and in the same manner as in Example 78, step 2, 4-(5-acetyl-2-methylphenylamino)-3-chloro-5-[4-(4-fluorophenyl)piperidine-1-carbonyl]-N,N-bis(4-methoxybenzyl)pyridine-2-sulfonamide (59.1 mg, 84%) was obtained.

ESIMS m/z: 785 (M+H)+

(step 2) Using 4-(5-acetyl-2-methylphenylamino)-3-chloro-5-[4-(4-fluorophenyl)piperidine-1-carbonyl]-N,N-bis(4-methoxybenzyl)pyridine-2-sulfonamide (59.1 mg, 0.075 mmol) obtained in step 1, and in the same manner as in Example 78, step 3, compound 303 (28.5 mg, 70%) was obtained.

ESIMS m/z: 545 (M+H)+; $^1$H NMR (400 MHz, CDCl$_3$, δ): 1.25-1.31 (m, 1H), 1.36-1.58 (m, 1H), 1.70-1.84 (m, 2H), 1.88-2.10 (m, 1H), 2.43 (s, 3H), 2.54-2.62 (m, 1H), 2.58 (s, 3H), 2.98 (br s, 1H), 3.68 (d, J=12.7 Hz, 1H), 4.15 (d, J=12.7 Hz, 1H), 6.88 (br s, 1H), 6.98 (t, J=8.8 Hz, 2H), 7.10 (dd, J=5.9, 7.8 Hz, 2H), 7.37 (d, J=7.8 Hz, 1H), 7.59 (s, 1H), 7.74 (d, J=7.8 Hz, 1H), 8.05 (s, 1H).

Example 115

5-[4-(4-fluorophenyl)-4-methoxypiperidine-1-carbonyl]-3-methyl-4-(o-tolylamino)pyridine-2-sulfonamide (compound 304)

(step 1) Using 5-(methoxycarbonyl)-3-methyl-4-(o-tolylamino)pyridine-2-sulfonic acid (0.220 g, 0.650 mmol) obtained in Example 103, step 4, and in the same manner as in Example 2, a crude product of methyl 5-methyl-6-sulfamoyl-4-(o-tolylamino)nicotinate was obtained and used for the next step without purification.
ESIMS m/z: 336 (M+H)$^+$ (step 2) Using a crude product of methyl 5-methyl-6-sulfamoyl-4-(o-tolylamino)nicotinate obtained in step 1, and in the same manner as in Example 51, step 5, 5-methyl-6-sulfamoyl-4-(o-tolylamino)nicotinic acid (0.133 g, yield of 2 steps 63%) was obtained.
ESIMS m/z: 322 (M+H)$^+$ (step 3) Using 5-methyl-6-sulfamoyl-4-(o-tolylamino) nicotinic acid (44.0 mg, 0.137 mmol) obtained in step 2, and 4-(4-fluorophenyl)-4-methoxypiperidine hydrochloride (44.0 mg, 0.178 mmol) obtained by the method described in WO2003/053361, and in the same manner as in Example 1, step 1, compound 304 (38.0 mg, 54%) was obtained.
ESIMS m/z: 513 (M+H)$^+$; $^1$H NMR (400 MHz, DMSO-d$_6$, δ): 1.40-1.94 (m, 4H), 2.17 (s, 3H), 2.39-2.64 (m, 1H), 2.41 (s, 3H), 2.84 (s, 3H), 3.04-3.22 (m, 1H), 3.22-3.30 (m, 1H), 3.75-3.94 (m, 1H), 6.78-6.92 (m, 1H), 6.96-7.12 (m, 2H), 7.12-7.26 (m, 3H), 7.29-7.44 (m, 4H), 7.50-7.69 (m, 1H), 8.08 (s, 1H).

Example 116

3-methyl-5-(2H-spiro[benzofuran-3,4'-piperidin]-1'-yl carbonyl)-4-(o-tolylamino)pyridine-2-sulfonamide (compound 305)

Using 5-chloro-6-sulfamoyl-4-(o-tolylamino)nicotinic acid (44.0 mg, 0.137 mmol) obtained in Example 115, step 2, and in the same manner as in Example 83, step 5, compound 305 (42.7 mg, 63%) was obtained.
ESIMS m/z: 493 (M+H)$^+$; $^1$H NMR (400 MHz, DMSO-d$_6$, δ): 1.43-1.87 (m, 4H), 2.20 (s, 3H), 2.43 (s, 3H), 2.78-3.15 (m, 1H), 3.36-3.47 (m, 2H), 3.79-3.95 (m, 1H), 4.37 (dd, J=25.4, 9.1 Hz, 2H), 6.76 (d, J=8.2 Hz, 1H), 6.82-6.94 (m, 2H), 7.05-7.14 (m, 2H), 7.14-7.29 (m, 3H), 7.38 (s, 2H), 7.56-7.73 (m, 1H), 8.12 (s, 1H).

Example 117

3-chloro-4-(3-chlorophenylamino)-5-[4-(4-fluorophenyl)-4-methoxypiperidine-1-carbonyl]pyridine-2-sulfonamide (compound 306)

(step 1) Using 4,5,6-trichloronicotinic acid (2.00 g, 8.83 mmol), and 3-chloroaniline (1.70 g, 12.0 mmol), and in the same manner as in Example 1, step 2, a crude product of 5,6-dichloro-4-(3-chlorophenylamino)nicotinic acid was obtained and used for the next reaction without purification.
ESIMS m/z: 317 (M+H)$^+$ (step 2) Using a crude product of 5,6-dichloro-4-(3-chlorophenylamino)nicotinic acid obtained in step 1, and in the same manner as in Example 103, step 2, a crude product of methyl 5,6-dichloro-4-(3-chlorophenylamino)nicotinate was obtained and used for the next reaction without purification.
ESIMS m/z: 331 (M+H)$^+$ (step 3) Using a crude product of methyl 5,6-dichloro-4-(3-chlorophenylamino)nicotinate obtained in step 2, and in the same manner as in Example 1, step 3, a crude product of methyl 5-chloro-4-(3-chlorophenylamino)-6-mercaptonicotinate was obtained and used for the next reaction without purification.
ESIMS m/z: 329 (M+H)$^+$ (step 4) Using a crude product of methyl 5-chloro-4-(3-chlorophenylamino)-6-mercaptonicotinate obtained in step 3, and in the same manner as in Example 1, step 4, a crude product of 3-chloro-4-(3-chlorophenylamino)-5-(methoxycarbonyl)pyridine-2-sulfonic acid was obtained and used for the next reaction without purification.
ESIMS m/z: 377 (M+H)$^+$ (step 5) Using a crude product of 3-chloro-4-(3-chlorophenylamino)-5-(methoxycarbonyl)pyridine-2-sulfonic acid obtained in step 4, and in the same manner as in Example 2, a crude product of methyl 5-chloro-4-(3-chlorophenylamino)-6-sulfamoylnicotinate was obtained and used for the next step without purification.
ESIMS m/z: 376 (M+H)$^+$ (step 6) Using a crude product of methyl 5-chloro-4-(3-chlorophenylamino)-6-sulfamoylnicotinate obtained in step 5, and in the same manner as in Example 51, step 5, 5-chloro-4-(3-chlorophenylamino)-6-sulfamoylnicotinic acid (0.105 g, yield of 6 steps 12%) was obtained.
ESIMS m/z: 362 (M+H)$^+$ (step 7) Using 5-chloro-4-(3-chlorophenylamino)-6-sulfamoylnicotinic acid (52.0 mg, 0.144 mmol) obtained in step 6, and 4-(4-fluorophenyl)-4-methoxypiperidin hydrochloride (45.9 mg, 0.187 mmol) obtained by the method described in WO2003/053361, and in the same manner as in Example 1, step 1, compound 306 (32.6 mg, 41%) was obtained.
ESIMS m/z: 553 (M+H)$^+$; $^1$H NMR (400 MHz, CDCl$_3$, δ): 1.64-1.85 (m, 2H), 1.90-2.04 (m, 2H), 2.23-2.71 (m, 1H), 2.94 (s, 3H), 3.31-3.51 (m, 2H), 3.98-4.09 (m, 1H), 5.57-5.67 (m, 2H), 7.00-7.11 (m, 4H), 7.14 (s, 1H), 7.17-7.23 (m, 1H), 7.25-7.34 (m, 3H), 8.12 (s, 1H).

Example 118

3-chloro-4-(3-chlorophenylamino)-5-(2H-spiro[benzofuran-3,4'-piperidine]-1'-yl carbonyl)pyridine-2-sulfonamide (compound 307)

Using 5-chloro-4-(3-chlorophenylamino)-6-sulfamoylnicotinic acid (52.0 mg, 0.144 mmol) obtained in Example 117, step 6, and in the same manner as in Example 83, step 5, compound 307 (16.1 mg, 21%) was obtained.
ESIMS m/z: 533 (M+H)$^+$; $^1$H NMR (400 MHz, CDCl$_3$, δ): 1.46-1.91 (m, 4H), 2.08-2.53 (m, 1H), 3.02-3.19 (m, 1H), 3.48-3.61 (m, 1H), 3.87-4.23 (m, 1H), 4.29-4.41 (m, 2H), 5.44 (s, 2H), 6.82 (d, J=8.2 Hz, 1H), 6.92 (t, J=7.0 Hz, 1H), 7.02-7.15 (m, 4H), 7.15-7.21 (m, 1H), 7.22-7.28 (m, 1H), 7.35 (t, J=7.9 Hz, 1H), 8.21 (s, 1H).

Example 119

3-chloro-4-(3-chlorophenylamino)-5-(4-phenylpiperidine-1-carbonyl)pyridine-2-sulfonamide (compound 308)

Using 5-chloro-4-(3-chlorophenylamino)-6-sulfamoylnicotinic acid (110 mg, 0.310 mmol) obtained in Example 117, step 6, and 4-phenylpiperidine (58.9 mg, 0.370 mmol), and in the same manner as in Example 1, step 1, compound 308 (43.0 mg, 28%) was obtained.

ESIMS m/z: 505 (M+H)+; ¹H NMR (300 MHz, CD₃OD, δ): 1.45-2.20 (m, 5H), 2.60-2.80 (m, 1H), 3.00-3.20 (m, 1H), 3.50-3.70 (m, 1H), 4.00-4.30 (m, 1H), 6.95-7.12 (m, 1H), 7.13-7.40 (m, 8H), 8.28 (s, 1H).

Example 120

3-chloro-4-(5-chloro-2-methylphenylamino)-5-(4-phenylpiperidine-1-carbonyl)pyridine-2-sulfonamide (compound 309)

(step 1) Using 4,5,6-trichloronicotinic acid (2.50 g, 11.0 m=1), and 5-chloro-2-methylaniline (2.37 g, 16.6 mmol), and in the same manner as in Example 1, step 2, a crude product of 5,6-dichloro-4-(5-chloro-2-methylphenylamino)nicotinic acid was obtained and used for the next reaction without purification.
ESIMS m/z: 331 (M+H)+
(step 2) Using a crude product of 5,6-dichloro-4-(5-chloro-2-methylphenylamino)nicotinic acid obtained in step 1, and in the same manner as in Example 103, step 2, a crude product of methyl 5,6-dichloro-4-(5-chloro-2-methylphenylamino)nicotinate was obtained and used for the next reaction without purification.
ESIMS m/z: 345 (M+H)+
(step 3) Using a crude product of methyl 5,6-dichloro-4-(5-chloro-2-methylphenylamino)nicotinate obtained in step 2, and in the same manner as in Example 1, step 3, a crude product of methyl 5-chloro-4-(5-chloro-2-methylphenylamino)-6-mercaptonicotinate was obtained and used for the next reaction without purification.
ESIMS m/z: 343 (M+H)+
(step 4) Using a crude product of methyl 5-chloro-4-(5-chloro-2-methylphenylamino)-6-mercaptonicotinate obtained in step 3, and in the same manner as in Example 1, step 4, a crude product of 3-chloro-4-(5-chloro-2-methylphenylamino)-5-(methoxycarbonyl)pyridine-2-sulfonic acid was obtained and used for the next reaction without purification.
ESIMS m/z: 391 (M+H)+
(step 5) Using a crude product of 3-chloro-4-(5-chloro-2-methylphenylamino)-5-(methoxycarbonyl)pyridine-2-sulfonic acid obtained in step 4, and in the same manner as in Example 2, methyl 5-chloro-4-(5-chloro-2-methylphenylamino)-6-sulfamoylnicotinate (1.00 g, yield of 5 steps 35%) was obtained.
ESIMS m/z: 390 (M+H)+
(step 6) Using methyl 5-chloro-4-(5-chloro-2-methylphenylamino)-6-sulfamoylnicotinate (1.00 g, 2.56 mmol) obtained in step 5, and in the same manner as in Example 51, step 5, 5-chloro-4-(5-chloro-2-methylphenylamino)-6-sulfamoylnicotinic acid (220 mg, 23%) was obtained.
ESIMS m/z: 376 (M+H)+
(step 7) Using 5-chloro-4-(5-chloro-2-methylphenylamino)-6-sulfamoylnicotinic acid (90 mg, 0.240 mmol) obtained in step 6, and in the same manner as in Example 119, compound 309 (29.2 mg, 23%) was obtained.
ESIMS m/z: 519 (M+H)+; ¹H NMR (300 MHz, CD₃OD, δ): 1.40-2.00 (m, 4H), 2.01-2.30 (m, 1H), 2.27 (s, 3H), 2.60-2.85 (m, 1H), 3.00-3.30 (m, 1H), 3.60-3.85 (m, 1H), 4.10-4.25 (m, 1H), 7.10-7.45 (m, 8H), 8.12 (s, 1H).

Example 121

3-chloro-4-(4-ethylphenylamino)-5-[4-(4-fluorophenyl)piperidine-1-carbonyl]pyridine-2-sulfonamide (compound 310)

(step 1) Using [4-(4-fluorophenyl)piperidin-1-yl](4,5,6-trichloropyridin-3-yl)methanone (400 mg, 1.03 mmol) obtained in Example 48, step 1, and 4-ethylaniline (186 mg, 1.53 mmol), and in the same manner as in Example 1, step 2, [5,6-dichloro-4-(4-ethylphenylamino)pyridin-3-yl][4-(4-fluorophenyl)piperidin-1-yl]methanone (387 mg, 79%) was obtained.
ESIMS m/z: 472 (M+H)+
(step 2) Using [5,6-dichloro-4-(4-ethylphenylamino)pyridin-3-yl][4-(4-fluorophenyl)piperidin-1-yl]methanone (387 mg, 0.820 mmol) obtained in step 1, and in the same manner as in Example 1, step 3, a crude product of [5-chloro-4-(4-ethylphenylamino)-6-mercaptopyridin-3-yl][4-(4-fluorophenyl)piperidin-1-yl]methanone was obtained and used for the next reaction without purification.
ESIMS m/z: 470 (M+H)+
(step 3) Using a crude product of [5-chloro-4-(4-ethylphenylamino)-6-mercaptopyridin-3-yl][4-(4-fluorophenyl)piperidin-1-yl]methanone obtained in step 2, and in the same manner as in Example 1, step 4, a crude product of 3-chloro-4-(4-ethylphenylamino)-5-[4-(4-fluorophenyl)piperidine-1-carbonyl]pyridine-2-sulfonic acid was obtained and used for the next reaction without purification.
ESIMS m/z: 518 (M+H)+
(step 4) Using a crude product of 3-chloro-4-(4-ethylphenylamino)-5-[4-(4-fluorophenyl)piperidine-1-carbonyl]pyridine-2-sulfonic acid (196 mg, 0.374 mmol) obtained in step 3, and in the same manner as in Example 2, compound 310 (5.8 mg, yield of 3 steps 3%) was obtained.
ESIMS m/z: 517 (M+H)+; ¹H NMR (300 MHz, DMSO-d₆, δ): 1.05-1.20 (m, 3H), 1.31-1.91 (m, 5H), 2.56-2.73 (m, 3H), 2.75-3.05 (m, 1H), 3.75-4.20 (m, 2H), 6.96-7.31 (m, 8H), 7.60 (br s, 2H), 8.19 (s, 1H), 8.65 (br s, 1H).

Example 122

3-chloro-5-[4-(4-fluorophenyl)piperidine-1-carbonyl]-4-[2-methyl-5-(trifluoromethyl)phenylamino]pyridine-2-sulfonamide (compound 311)

(step 1) Using [4-(4-fluorophenyl)piperidin-1-yl](4,5,6-trichloropyridin-3-yl)methanone (400 mg, 1.03 mmol) obtained in Example 48, step 1, and 2-methyl-5-(trifluoromethyl)aniline (276 mg, 1.54 mmol), and in the same manner as in Example 1, step 2, {5,6-dichloro-4-[2-methyl-5-(trifluoromethyl)phenylamino]pyridin-3-yl}[4-(4-fluorophenyl)piperidin-1-yl]methanone (400 mg, 74%) was obtained.
ESIMS m/z: 526 (M+H)+
(step 2) Using {5,6-dichloro-4-[2-methyl-5-(trifluoromethyl)phenylamino]pyridin-3-yl}[4-(4-fluorophenyl)piperidin-1-yl]methanone (400 mg, 0.762 mmol) obtained in step 1, and in the same manner as in Example 1, step 3, a crude product of {5-chloro-6-mercapto-4-[2-methyl-5-(trifluoromethyl)phenylamino]pyridin-3-yl}[4-(4-fluorophenyl)piperidin-1-yl]methanone was obtained and used for the next reaction without purification.
ESIMS m/z: 524 (M+H)+
(step 3) Using a crude product of {5-chloro-6-mercapto-4-[2-methyl-5-(trifluoromethyl)phenylamino]pyridin-3-yl}[4-(4-fluorophenyl)piperidin-1-yl]methanone obtained in step 2, and in the same manner as in Example 1, step 4, a crude product of 3-chloro-5-[4-(4-fluorophenyl)piperidine-1-carbonyl]-4-[2-methyl-5-(trifluoromethyl)phenylamino]pyridine-2-sulfonic acid was obtained and used for the next reaction without purification.
ESIMS m/z: 572 (M+H)+
(step 4) Using a crude product of 3-chloro-5-[4-(4-fluorophenyl)piperidine-1-carbonyl]-4-[2-methyl-5-(trifluoromethyl)phenylamino]pyridine-2-sulfonic acid obtained in step 3, and in the same manner as in Example 2, compound 311 (10.0 mg, yield of 3 steps 4%) was obtained.

ESIMS m/z: 571 (M+H)⁺; ¹H NMR (400 MHz, CD₃OD, D₂O, δ): 1.40-2.10 (m, 5H), 2.34 (s, 3H), 2.60-2.78 (m, 1H), 2.80-3.10 (m, 1H), 3.50-3.70 (m, 1H), 4.00-4.20 (m, 1H), 6.90-7.10 (m, 2H), 7.15-7.30 (m, 2H), 7.48-7.65 (m, 3H), 8.13 (s, 1H).

Example 123

3-chloro-4-[4-(difluoromethoxy)phenylamino]-5-[4-(4-fluorophenyl)piperidine-1-carbonyl]pyridine-2-sulfonamide (compound 312)

(step 1) Using [4-(4-fluorophenyl)piperidin-1-yl](4,5,6-trichloropyridin-3-yl)methanone (400 mg, 1.03 mmol) obtained in Example 48, step 1, and 4-(difluoromethoxy)aniline (245 mg, 1.54 mmol), and in the same manner as in Example 1, step 2, {5,6-dichloro-4-[4-(difluoromethoxy)phenylamino]pyridin-3-yl}[4-(4-fluorophenyl)piperidin-1-yl]methanone (415 mg, 79%) was obtained.

ESIMS m/z: 510 (M+H)⁺

(step 2) Using {5,6-dichloro-4-[4-(difluoromethoxy)phenylamino]pyridin-3-yl}[4-(4-fluorophenyl)piperidin-1-yl]methanone (415 mg, 0.840 mmol) obtained in step 1, and in the same manner as in Example 1, step 3, a crude product of {5-chloro-4-[4-(difluoromethoxy)phenylamino]-6-mercaptopyridin-3-yl}[4-(4-fluorophenyl)piperidin-1-yl]methanone was obtained and used for the next reaction without purification.

ESIMS m/z: 508 (M+H)⁺

(step 3) Using a crude product of {5-chloro-4-[4-(difluoromethoxy)phenylamino]-6-mercaptopyridin-3-yl}[4-(4-fluorophenyl)piperidin-1-yl]methanone obtained in step 2, and in the same manner as in Example 1, step 4, a crude product of 3-chloro-4-[4-(difluoromethoxy)phenylamino]-5-[4-(4-fluorophenyl)piperidine-1-carbonyl]pyridine-2-sulfonic acid was obtained and used for the next reaction without purification.

ESIMS m/z: 556 (M+H)⁺

(step 4) Using a crude product of 3-chloro-4-[4-(difluoromethoxy)phenylamino]-5-[4-(4-fluorophenyl)piperidine-1-carbonyl]pyridine-2-sulfonic acid obtained in step 3, and in the same manner as in Example 2, compound 312 (62.0 mg, yield of 3 steps 21%) was obtained.

ESIMS m/z: 555 (M+H)⁺; ¹H NMR (300 MHz, DMSO-d₅, δ): 1.35-1.98 (m, 5H), 2.60-2.80 (m, 1H), 2.83-3.25 (m, 1H), 3.45-3.55 (m, 1H), 3.89-4.23 (m, 1H), 7.05-7.40 (m, 9H), 7.50-7.70 (m, 2H), 8.24 (s, 1H), 8.76 (br s, 1H).

Example 124

3-chloro-4-(5-chloro-2-methylphenylamino)-5-[4-(4-fluorophenyl)-4-methoxypiperidine-1-carbonyl]pyridine-2-sulfonamide (compound 313)

Using 5-chloro-4-(5-chloro-2-methylphenylamino)-6-sulfamoylnicotinic acid (58.0 mg, 0.154 mmol) obtained in Example 120, step 6, and in the same manner as in Example 106, step 6, compound 313 (42.3 mg, 48%) was obtained.

ESIMS m/z: 567 (M+H)⁺; ¹H NMR (400 MHz, CDCl₃, δ): 1.64-1.85 (m, 2H), 1.96-2.04 (m, 2H), 2.32 (s, 3H), 2.45-2.82 (m, 1H), 2.95 (s, 3H), 3.43-3.58 (m, 2H), 3.97-4.09 (m, 1H), 5.46-5.64 (m, 2H), 6.76 (s, 1H), 6.96 (s, 1H), 7.06 (t, J=8.6 Hz, 2H), 7.11-7.24 (m, 2H), 7.31 (dd, J=8.6, 5.4 Hz, 2H), 8.02 (s, 1H).

Example 125

3-chloro-4-(5-chloro-2-methylphenylamino)-5-[3-(4-fluorophenyl)azetidine-1-carbonyl]pyridine-2-sulfonamide (compound 314)

Using 5-chloro-4-(5-chloro-2-methylphenylamino)-6-sulfamoylnicotinic acid (90 mg, 0.24 mmol) obtained in Example 120, step 6, and in the same manner as in Example 98, step 2, compound 314 (4.9 mg, 4%) was obtained.

ESIMS m/z: 509 (M+H)⁺; ¹H NMR (300 MHz, DMSO-d₆, δ): 2.29 (s, 3H), 3.70-3.80 (m, 1H), 3.85-4.00 (m, 2H), 4.10-4.20 (m, 1H), 4.40-4.60 (m, 1H), 7.00-7.20 (m, 2H), 7.20-7.32 (m, 3H), 7.33-7.43 (m, 2H), 8.22 (s, 1H).

Example 126

4-(2,5-difluorophenylamino)-5-[4-(4-fluorophenyl)piperidine-1-carbonyl]-3-methyl-N-(3-methylisothiazol-5-yl)pyridine-2-sulfonamide (compound 315)

Using 4-(2,5-difluorophenylamino)-5-[4-(4-fluorophenyl)piperidine-1-carbonyl]-3-methylpyridine-2-sulfonic acid (240 mg, 0.470 mmol) obtained in Example 75, step 3, and in the same manner as in Example 71, step 4, compound 315 (19.7 mg, 7%) was obtained.

ESIMS m/z: 602 (M+H)⁺; ¹H NMR (400 MHz, CD₃OD, δ): 1.30-1.70 (m, 4H), 2.10-2.35 (m, 1H), 2.28 (s, 3H), 2.49 (s, 3H), 2.50-2.70 (m, 1H), 2.90-3.10 (m, 1H), 3.40-3.60 (m, 1H), 4.10-4.30 (m, 1H), 6.56 (s, 1H), 6.60-6.80 (m, 2H), 6.80-6.90 (m, 2H), 7.00-7.20 (m, 3H), 8.07 (s, 1H).

Example 127

4-(2,4-difluorophenylamino)-5-[4-(4-fluorophenyl)piperidine-1-carbonyl]-3-methyl-N-(3-methylisothiazol-5-yl)pyridine-2-sulfonamide (compound 316)

(step 1) Using (4,6-dichloro-5-methylpyridin-3-yl)[4-(4-fluorophenyl)piperidin-1-yl]methanone (400 mg, 1.09 mmol) obtained in Example 52, step 1, and 2,4-difluoroaniline (169 mg, 1.31 mmol), and in the same manner as in Example 1, step 2, [6-chloro-4-(2,4-difluorophenylamino)-5-methylpyridin-3-yl][4-(4-fluorophenyl)piperidin-1-yl]methanone (385 mg, 77%) was obtained.

ESIMS m/z: 460 (M+H)⁺

(step 2) Using [6-chloro-4-(2,4-difluorophenylamino)-5-methylpyridin-3-yl][4-(4-fluorophenyl)piperidin-1-yl]methanone (385 mg, 0.840 mmol) obtained in step 1, and in the same manner as in Example 1, step 3, a crude product of [4-(2,4-difluorophenylamino)-6-mercapto-5-methylpyridin-3-yl][4-(4-fluorophenyl)piperidin-1-yl]methanone was obtained and used for the next reaction without purification.

ESIMS m/z: 458 (M+H)⁺

(step 3) Using a crude product of [4-(2,4-difluorophenylamino)-6-mercapto-5-methylpyridin-3-yl][4-(4-fluorophenyl)piperidin-1-yl]methanone obtained in step 2, and in the same manner as in Example 1, step 4, 4-(2,4-difluorophenylamino)-5-[4-(4-fluorophenyl)piperidine-1-carbonyl]-3-methylpyridine-2-sulfonic acid (180 mg, yield of 2 steps 53%) was obtained.

ESIMS m/z: 506 (M+H)⁺

(step 4) Using 4-(2,4-difluorophenylamino)-5-[4-(4-fluorophenyl)piperidine-1-carbonyl]-3-methylpyridine-2-sulfonic acid (180 mg, 0.360 mmol) obtained in step 3, and in the same manner as in Example 71, step 4, compound 316 (19.3 mg, 9%) was obtained.

ESIMS m/z: 602 (M+H)⁺; ¹H NMR (300 MHz, CD₃OD, δ): 0.40-0.80 (m, 4H), 2.00-2.10 (m, 1H), 2.23 (s, 3H), 2.49 (s, 3H), 2.60-2.70 (m, 1H), 2.80-2.90 (m, 1H), 3.40-3.50 (m, 1H), 4.00-4.10 (m, 1H), 6.52 (s, 1H), 6.86-7.09 (m, 4H), 7.10-7.12 (m, 3H), 7.96 (s, 1H).

Example 128

3-chloro-5-[4-(4-fluorophenyl)piperidine-1-carbonyl]-N-(1-methyl-1H-pyrazol-3-yl)-4-(o-tolylamino)pyridine-2-sulfonamide (compound 317)

(step 1) Using [4-(4-fluorophenyl)piperidin-1-yl](4,5,6-trichloropyridin-3-yl)methanone (400 mg, 1.03 mmol) obtained in Example 48, step 1, and o-toluidine (165 mg, 1.54 mmol), and in the same manner as in Example 1, step 2, [5,6-dichloro-4-(o-tolylamino)pyridin-3-yl][4-(4-fluorophenyl)piperidin-1-yl]methanone (430 mg, 91%) was obtained.

ESIMS m/z: 458 (M+H)⁺

(step 2) Using [5,6-dichloro-4-(o-tolylamino)pyridin-3-yl][4-(4-fluorophenyl)piperidin-1-yl]methanone (430 mg, 0.940 mmol) obtained in step 1, and in the same manner as in Example 1, step 3, [5-chloro-6-mercapto-4-(o-tolylamino)pyridin-3-yl][4-(4-fluorophenyl)piperidin-1-yl]methanone (360 mg, 84%) was obtained.

ESIMS m/z: 456 (M+H)⁺

(step 3) Using [5-chloro-6-mercapto-4-(o-tolylamino)pyridin-3-yl][4-(4-fluorophenyl)piperidin-1-yl]methanone (360 mg, 0.790 mmol) obtained in step 2, and in the same manner as in Example 1, step 4, a crude product of 3-chloro-5-[4-(4-fluorophenyl)piperidine-1-carbonyl]-4-(o-tolylamino)pyridine-2-sulfonic acid was obtained and used for the next reaction without purification.

ESIMS m/z: 504 (M+H)⁺

(step 4) Using a crude product of 3-chloro-5-[4-(4-fluorophenyl)piperidine-1-carbonyl]-4-(o-tolylamino)pyridine-2-sulfonic acid obtained in step 3, and in the same manner as in Example 39, compound 317 (40.3 mg, yield of 2 steps 11%) was obtained.

ESIMS m/z: 583 (M+H)⁺; ¹H NMR (300 MHz, DMSO-d₆, δ): 1.20-2.00 (m, 5H), 2.15 (s, 3H), 2.50-2.70 (m, 1H), 2.70-2.90 (m, 1H), 3.40-3.60 (m, 1H), 3.70 (s, 3H), 4.00-4.20 (m, 1H), 5.90 (s, 1H), 7.00-7.50 (m, 9H), 8.05 (s, 1H).

Example 129

3-chloro-5-[4-(4-fluorophenyl)piperidine-1-carbonyl]-4-(2-methyl-4-nitrophenylamino)pyridine-2-sulfonamide (compound 318)

(step 1) Using 3,4-dichloro-5-[4-(4-fluorophenyl)piperidine-1-carbonyl]-N,N-bis(4-methoxybenzyl)pyridine-2-sulfonamide (150 mg, 0.225 mmol) obtained in Example 78, step 1, and 2-methyl-4-nitroaniline (34.2 mg, 0.225 mmol), and in the same manner as in Example 78, step 2, 3-chloro-5-[4-(4-fluorophenyl)piperidine-1-carbonyl]-N,N-bis(4-methoxybenzyl)-4-(2-methyl-4-nitrophenylamino)pyridine-2-sulfonamide (64.0 mg, 36%) was obtained.

ESIMS m/z: 788 (M+H)⁺

(step 2) Using 3-chloro-5-[4-(4-fluorophenyl)piperidine-1-carbonyl]-N,N-bis(4-methoxybenzyl)-4-(2-methyl-4-nitrophenylamino)pyridine-2-sulfonamide (64.0 mg, 0.081 mmol) obtained in step 1, and in the same manner as in Example 78, step 3, compound 318 (14.7 mg, 33%) was obtained.

ESIMS m/z: 548 (M+H)⁺; ¹H NMR (300 MHz, CD₃OD, δ): 1.30-1.69 (m, 2H), 1.70-1.95 (m, 2H), 1.95-2.40 (m, 1H), 2.43 (s, 3H), 2.65-2.85 (m, 1H), 3.05-3.25 (m, 1H), 3.65-3.85 (m, 1H), 4.10-4.35 (m, 1H), 6.90-7.10 (m, 2H), 7.11-7.30 (m, 3H), 8.00-8.10 (m, 1H), 8.20 (s, 1H), 8.30 (s, 1E).

Example 130

4-(3-bromophenylamino)-3-chloro-5-[4-(4-fluorophenyl)piperidine-1-carbonyl]pyridine-2-sulfonamide (compound 319)

(step 1) Using [4-(4-fluorophenyl)piperidin-1-yl](4,5,6-trichloropyridin-3-yl)methanone (400 mg, 1.03 mmol) obtained in Example 48, step 1, and 3-bromoaniline (265 mg, 1.54 mmol), and in the same manner as in Example 1, step 2, [4-(3-bromophenylamino)-5,6-dichloropyridin-3-yl][4-(4-fluorophenyl)piperidin-1-yl]methanone (430 mg, 80%) was obtained.

ESIMS m/z: 522 (M+H)⁺

(step 2) Using [4-(3-bromophenylamino)-5,6-dichloropyridin-3-yl][4-(4-fluorophenyl)piperidin-1-yl]methanone (430 mg, 0.820 mmol) obtained in step 1, and in the same manner as in Example 1, step 3, a crude product of [4-(3-bromophenylamino)-5-chloro-6-mercaptopyridin-3-yl][4-(4-fluorophenyl)piperidin-1-yl]methanone was obtained and used for the next reaction without purification.

ESIMS m/z: 520 (M+H)⁺

(step 3) Using a crude product of [4-(3-bromophenylamino)-5-chloro-6-mercaptopyridin-3-yl][4-(4-fluorophenyl)piperidin-1-yl]methanone obtained in step 2, and in the same manner as in Example 1, step 4, a crude product of 4-(3-bromophenylamino)-3-chloro-5-[4-(4-fluorophenyl)piperidine-1-carbonyl]pyridine-2-sulfonic acid was obtained and used for the next reaction without purification.

ESIMS m/z: 568 (M+H)⁺

(step 4) Using a crude product of 4-(3-bromophenylamino)-3-chloro-5-[4-(4-fluorophenyl)piperidine-1-carbonyl]pyridine-2-sulfonic acid obtained in step 3, and in the same manner as in Example 2, compound 319 (23.3 mg, yield of 3 steps 9%) was obtained.

ESIMS m/z: 567 (M+H)⁺; ¹H NMR (300 MHz, DMSO-d$_E$, δ): 1.40-1.72 (m, 4H), 1.85-2.10 (m, 1H), 2.60-2.80 (m, 1H), 2.91-3.12 (m, 1H), 3.41-3.69 (m, 1H), 4.01-4.23 (m, 1H), 6.95-7.35 (m, 8H), 7.65 (br s, 2H), 8.32 (s, 1H), 8.86 (br s, 1H).

Example 131

3-chloro-4-(2-cyano-4,5-dimethylphenylamino)-5-[4-(4-fluorophenyl)piperidine-1-carbonyl]pyridine-2-sulfonamide (compound 320)

(step 1) Using 3,4-dichloro-5-[4-(4-fluorophenyl)piperidine-1-carbonyl]-N,N-bis(4-methoxybenzyl)pyridine-2-sulfonamide (150 mg, 0.225 mmol) obtained in Example 78, step 1, and 2-amino-4,5-dimethylbenzonitrile (32.9 mg, 0.225 mmol), and in the same manner as in Example 78, step 2, 3-chloro-4-(2-cyano-4,5-dimethylphenylamino)-5-[4-(4-fluorophenyl)piperidine-1-carbonyl]-N,N-bis(4-methoxybenzyl)pyridine-2-sulfonamide (71.0 mg, 40%) was obtained.

ESIMS m/z: 782 (M+H)⁺

(step 2) Using 3-chloro-4-(2-cyano-4,5-dimethylphenylamino)-5-[4-(4-fluorophenyl)piperidine-1-carbonyl]-N,N-bis(4-methoxybenzyl)pyridine-2-sulfonamide (71.0 mg, 0.091 mmol) obtained in step 1, and in the same manner as in Example 78, step 3, compound 320 (2.4 mg, 5%) was obtained.

ESIMS m/z: 542 (M+H)$^+$; $^1$H NMR (400 MHz, CD$_3$OD, δ): 1.30-1.59 (m, 3H), 1.60-1.80 (m, 2H), 2.21 (s, 3H), 2.23 (s, 3H), 2.10-2.35 (m, 1H), 2.50-2.70 (m, 1H), 3.40-3.60 (m, 1H), 3.90-4.10 (m, 1H), 6.80-6.95 (m, 2H), 7.00 (s, 1E), 7.05-7.20 (m, 2H), 7.40 (s, 1H), 8.10 (s, 1H).

Example 132

3-chloro-4-(2-cyano-5-methoxyphenylamino)-5-[4-(4-fluorophenyl)piperidine-1-carbonyl]pyridine-2-sulfonamide (compound 321)

(step 1) Using 3,4-dichloro-5-[4-(4-fluorophenyl)piperidine-1-carbonyl]-N,N-bis(4-methoxybenzyl)pyridine-2-sulfonamide (150 mg, 0.225 mmol) obtained in Example 78, step 1, and 2-amino-4-methoxybenzonitrile (32.9 mg, 0.225 mmol), and in the same manner as in Example 78, step 2, 3-chloro-4-(2-cyano-5-methoxyphenylamino)-5-[4-(4-fluorophenyl)piperidine-1-carbonyl]-N,N-bis(4-methoxybenzyl)pyridine-2-sulfonamide (72.0 mg, 61%) was obtained.

ESIMS m/z: 784 (M+H)$^+$ (step 2) Using 3-chloro-4-(2-cyano-5-methoxyphenylamino)-5-[4-(4-fluorophenyl)piperidine-1-carbonyl]-N,N-bis(4-methoxybenzyl)pyridine-2-sulfonamide (72.0 mg, 0.092 mmol) obtained in step 1, and in the same manner as in Example 78, step 3, compound 321 (12.5 mg, 25%) was obtained.

ESIMS m/z: 544 (M+H)$^+$; $^1$H NMR (300 MHz, CDCl$_3$, δ): 1.20-2.40 (m, 5H), 2.50-2.80 (m, 1H), 3.00-3.20 (m, 1H), 3.40-3.60 (m, 1H), 3.85 (s, 3H), 4.20-4.40 (m, 1H), 5.29 (s, 2H), 6.60 (s, 1H), 6.70-6.80 (m, 1H), 6.90-7.02 (m, 2H), 7.05-7.15 (m, 2H), 7.21 (s, 1H), 7.50-7.60 (m, 1H), 8.37 (s, 1H).

Example 133

3-chloro-4-(2-cyano-5-nitrophenylamino)-5-[4-(4-fluorophenyl)piperidine-1-carbonyl]pyridine-2-sulfonamide (compound 322)

(step 1) Using 3,4-dichloro-5-[4-(4-fluorophenyl)piperidine-1-carbonyl]-N,N-bis(4-methoxybenzyl)pyridine-2-sulfonamide (150 mg, 0.225 mmol) obtained in Example 78, step 1, and 2-amino-4-nitrobenzonitrile (37.0 mg, 0.225 mmol), and in the same manner as in Example 78, step 2, 3-chloro-4-(2-cyano-5-nitrophenylamino)-5-[4-(4-fluorophenyl)piperidine-1-carbonyl]-N,N-bis(4-methoxybenzyl)pyridine-2-sulfonamide (65.0 mg, 36%) was obtained.

ESIMS m/z: 799 (M+H)$^+$ (step 2) Using 3-chloro-4-(2-cyano-5-nitrophenylamino)-5-[4-(4-fluorophenyl)piperidine-1-carbonyl]-N,N-bis(4-methoxybenzyl)pyridine-2-sulfonamide (65.0 mg, 0.081 mmol) obtained in step 1, and in the same manner as in Example 78, step 3, compound 322 (6.0 mg, 13%) was obtained.

ESIMS m/z: 559 (M+H)$^+$; $^1$H NMR (400 MHz, CD$_3$OD, δ): 1.40-2.40 (m, 5H), 2.70-2.90 (m, 1H), 3.20-3.30 (m, 1H), 3.70-3.80 (m, 1H), 4.10-4.30 (m, 1H), 6.95-7.12 (m, 2H), 7.20-7.38 (m, 2H), 7.95-8.24 (m, 3H), 8.40 (s, 1H).

Example 134

3-chloro-4-(5-chloro-2-methylphenylamino)-5-(2H-spiro[benzofuran-3,4'-piperidin]-1'-ylcarbonyl)pyridine-2-sulfonamide (compound 323)

Using 5-chloro-4-(5-chloro-2-methylphenylamino)-6-sulfamoylnicotinic acid (58.0 mg, 0.154 mmol) obtained in Example 120, step 6, and in the same manner as in Example 83, step 5, compound 323 (20.0 mg, 24%) was obtained.

ESIMS m/z: 547 (M+H)$^+$; $^1$H NMR (400 MHz, CDCl$_3$, δ): 1.66-1.91 (m, 4H), 2.19-2.54 (m, 1H), 2.33 (s, 3H), 3.10-3.29 (m, 1H), 3.60-3.75 (m, 1H), 3.89-4.20 (m, 1H), 4.39 (s, 2H), 5.41 (s, 2H), 6.76 (s, 1H), 6.83 (d, J=8.2 Hz, 1H), 6.92 (t, J=7.2 Hz, 1H), 6.97 (s, 1H), 7.07-7.14 (m, 1H), 7.14-7.32 (m, 3H), 8.08 (s, 1H).

Example 135

3-chloro-4-(2-chloro-5-methoxyphenylamino)-5-[4-(4-fluorophenyl)piperidine-1-carbonyl]pyridine-2-sulfonamide (compound 324)

(step 1) Using 3,4-dichloro-5-[4-(4-fluorophenyl)piperidine-1-carbonyl]-N,N-bis(4-methoxybenzyl)pyridine-2-sulfonamide (100 mg, 0.149 mmol) obtained in Example 78, step 1, and 2-chloro-5-methoxyaniline hydrochloride (43.3 mg, 0.223 mmol), and in the same manner as in Example 78, step 2, 3-chloro-4-(2-chloro-5-methoxyphenylamino)-5-[4-(4-fluorophenyl)piperidine-1-carbonyl]-N,N-bis(4-methoxybenzyl)pyridine-2-sulfonamide (59.0 mg, 50%) was obtained.

ESIMS m/z: 793 (M+H)$^+$ (step 2) Using 3-chloro-4-(2-chloro-5-methoxyphenylamino)-5-[4-(4-fluorophenyl)piperidine-1-carbonyl]-N,N-bis(4-methoxybenzyl)pyridine-2-sulfonamide (59.0 mg, 0.074 mmol) obtained in step 1, and in the same manner as in Example 78, step 3, compound 324 (35.9 mg, 87%) was obtained.

ESIMS m/z: 553 (M+H)$^+$; $^1$H NMR (400 MHz, CDCl$_3$, δ): 1.22-1.35 (m, 2H), 1.38-1.49 (m, 1H), 1.71-1.81 (m, 2H), 2.56-2.64 (m, 1H), 2.99 (t, J=12.7 Hz, 1H), 3.42 (d, J=12.7 Hz, 1H), 3.81 (s, 3H), 4.28 (d, J=10.7 Hz, 1H), 5.28 (s, 2H), 6.70 (d, J=6.8 Hz, 2H), 6.92-7.13 (m, 5H), 7.34 (d, J=8.8 Hz, 1H), 8.30 (s, 1H).

Example 136

3-chloro-4-(2-chloro-5-fluorophenylamino)-5-[4-(4-fluorophenyl)piperidine-1-carbonyl]pyridine-2-sulfonamide (compound 325)

(step 1) Using 3,4-dichloro-5-[4-(4-fluorophenyl)piperidine-1-carbonyl]-N,N-bis(4-methoxybenzyl)pyridine-2-sulfonamide (100 mg, 0.149 mmol) obtained in Example 78, step 1, and 2-chloro-5-fluoroaniline (32.5 mg, 0.223 mmol), and in the same manner as in Example 78, step 2, 3-chloro-4-(2-chloro-5-fluorophenylamino)-5-[4-(4-fluorophenyl)piperidine-1-carbonyl]-N,N-bis(4-methoxybenzyl)pyridine-2-sulfonamide (80.8 mg, 70%) was obtained.

ESIMS m/z: 781 (M+H)$^+$ (step 2) Using 3-chloro-4-(2-chloro-5-fluorophenylamino)-5-[4-(4-fluorophenyl)piperidine-1-carbonyl]-N,N-bis(4-methoxybenzyl)pyridine-2-sulfonamide (80.8 mg, 0.103 mmol) obtained in step 1, and in the same manner as in Example 78, step 3, compound 325 (48.0 mg, 86%) was obtained.

ESIMS m/z: 541 (M+H)+; 1H NMR (400 MHz, CDCl3, δ): 1.23-1.35 (m, 2H), 1.40-1.54 (m, 1H), 1.81 (d, J=12.7 Hz, 2H), 2.66 (t, J=12.2 Hz, 1H), 3.09 (t, J=12.7 Hz, 1H), 3.59 (d, J=11.7 Hz, 1H), 4.40 (d, J=13.7 Hz, 1H), 5.34 (s, 2H), 6.81-6.90 (m, 2H), 6.97-7.11 (m, 5H), 7.43 (dd, J=8.8, 4.9 Hz, 1H), 8.29 (s, 1H).

Example 137

3-chloro-4-(2,5-dimethylpyridin-3-ylamino)-5-[4-(4-fluorophenyl)piperidine-1-carbonyl]pyridine-2-sulfonamide (compound 326)

(step 1) Using 3,4-dichloro-3-[4-(4-fluorophenyl)piperidine-1-carbonyl]-N,N-bis(4-methoxybenzyl)pyridine-2-sulfonamide (80 mg, 0.119 mmol) obtained in Example 78, step 1, and 2,5-dimethylpyridin-3-amine (14.5 mg, 0.119 mmol), and in the same manner as in Example 78, step 2, 3-chloro-4-(2,5-dimethylpyridin-3-ylamino)-5-[4-(4-fluorophenyl)piperidine-1-carbonyl]-N,N-bis(4-methoxybenzyl)pyridine-2-sulfonamide (54.3 mg, 60%) was obtained.

ESIMS m/z: 758 (M+H)+

(step 2) Using 3-chloro-4-(2,5-dimethylpyridin-3-ylamino)-5-[4-(4-fluorophenyl)piperidine-1-carbonyl]-N,N-bis(4-methoxybenzyl)pyridine-2-sulfonamide (54.3 mg, 0.072 mmol) obtained in step 1, and in the same manner as in Example 78, step 3, compound 326 (30.0 mg, 81%) was obtained.

ESIMS m/z: 518 (M+H)+; 1HNMR (400 MHz, CDCl3, δ): 1.30-1.48 (m, 2H), 1.70-1.83 (m, 2H), 1.95-2.24 (m, 1H), 2.32 (s, 3H), 2.52 (s, 3H), 2.54-2.65 (m, 1H), 2.76-2.97 (m, 1H), 3.44-3.59 (m, 1H), 4.18-4.32 (m, 1H), 5.41 (s, 2H), 6.84 (s, 1H), 6.99 (t, J=8.6 Hz, 2H), 7.09 (dd, J=8.6, 5.4 Hz, 2H), 7.22-7.33 (m, 1H), 8.12 (s, 1H), 8.25 (s, 1H).

Example 138

3-chloro-4-(2,6-dichloropyridin-3-ylamino)-5-[4-(4-fluorophenyl)piperidine-1-carbonyl]pyridine-2-sulfonamide (compound 327)

(step 1) Using 3,4-dichloro-5-[4-(4-fluorophenyl)piperidine-1-carbonyl]-N,N-bis(4-methoxybenzyl)pyridine-2-sulfonamide (80.0 mg, 0.119 mmol) obtained in Example 78, step 1, and 2,6-dichloropyridin-3-amine (19.4 mg, 0.119 mmol), and in the same manner as in Example 78, step 2, 3-chloro-4-(2,6-dichloropyridin-3-ylamino)-5-[4-(4-fluorophenyl)piperidine-1-carbonyl]-N,N-bis(4-methoxybenzyl)pyridine-2-sulfonamide (40.6 mg, 43%) was obtained.

ESIMS m/z: 798 (M+H)+

(step 2) Using 3-chloro-4-(2,6-dichloropyridin-3-ylamino)-5-[4-(4-fluorophenyl)piperidine-1-carbonyl]-N,N-bis(4-methoxybenzyl)pyridine-2-sulfonamide (40.6 mg, 0.051 mmol) obtained in step 1, and in the same manner as in Example 78, step 3, compound 327 (24.0 mg, 85%) was obtained.

ESIMS m/z: 558 (M+H)+; 1H NMR (400 MHz, CDCl3, δ): 1.33-1.53 (m, 2H), 1.75-1.91 (m, 2H), 2.25-2.51 (m, 1H), 2.61-2.73 (m, 1H), 3.02-3.16 (m, 1H), 3.49-3.62 (m, 1H), 4.30-4.42 (m, 1H), 5.44 (s, 2H), 6.96-7.05 (m, 3H), 7.08-7.16 (m, 2H), 7.29 (d, J=8.2 Hz, 1H), 7.53 (d, J=8.2 Hz, 1H), 8.22 (s, 1E).

Example 139

3-chloro-4-(2-fluoro-4-methylphenylamino)-5-[4-(4-fluorophenyl)piperidine-1-carbonyl]pyridine-2-sulfonamide (compound 328)

(step 1) Using 4,5,6-trichloronicotinic acid (500 mg, 2.21 mmol) and 2-fluoro-4-methylaniline (415 mg, 3.32 mmol), and in the same manner as in Example 1, step 2, a crude product of 5,6-dichloro-4-(2-fluoro-4-methylphenylamino) nicotinic acid was obtained and used for the next reaction without purification.

ESIMS m/z: 315 (M+H)+

(step 2) Using a crude product of 5,6-dichloro-4-(2-fluoro-4-methylphenylamino)nicotinic acid obtained in step 1, and in the same manner as in Example 1, step 1, [5,6-dichloro-4-(2-fluoro-4-methylphenylamino)pyridin-3-yl][4-(4-fluorophenyl)piperidin-1-yl]methanone (850 mg, yield of 2 steps 87%) was obtained.

ESIMS m/z: 476 (M H)+

(step 3) Using [5,6-dichloro-4-(2-fluoro-4-methylphenylamino)pyridin-3-yl][4-(4-fluorophenyl)piperidin-1-yl] methanone (850 mg, 1.79 mmol) obtained in step 2, and in the same manner as in Example 1, step 3, [5-chloro-4-(2-fluoro-4-methylphenylamino)-6-mercaptopyridin-3-yl][4-(4-fluorophenyl)piperidin-1-yl]methanone (710 mg, B4%) was obtained.

ESIMS m/z: 474 (M+H)+

(step 4) Using [5-chloro-4-(2-fluoro-4-methylphenylamino)-6-mercaptopyridin-3-yl][4-(4-fluorophenyl)piperidin-1-yl]methanone (710 mg, 1.50 mmol) obtained in step 3, and in the same manner as in Example 1, step 4, a crude product of 3-chloro-4-(2-fluoro-4-methylphenylamino)-5-[4-(4-fluorophenyl)piperidine-1-carbonyl]pyridine-2-sulfonic acid was obtained and used for the next reaction without purification.

ESIMS m/z: 522 (M+H)+

(step 5) Using a crude product of 3-chloro-4-(2-fluoro-4-methylphenylamino)-5-[4-(4-fluorophenyl)piperidine-1-carbonyl]pyridine-2-sulfonic acid obtained in step 4, and in the same manner as in Example 2, compound 328 (73.6 mg, yield of 2 steps 25%) was obtained.

ESIMS m/z: 521 (M+H)+; 1H NMR (300 MHz, DMSO-d6, δ): 1.20-1.80 (m, 4H), 1.80-2.10 (m, 1H), 2.31 (s, 3H), 2.60-2.75 (m, 1H), 2.80-3.00 (m, 1H), 3.35-3.62 (m, 1H), 3.85-4.20 (m, 1H), 6.90-7.00 (m, 1H), 7.00-7.20 (m, 4H), 7.20-7.55 (m, 2H), 7.60 (br s, 2H), 8.16 (s, 15), 8.51 (br s, 1H).

Example 140

4-(4-fluoro-2-methylphenylamino)-5-[4-(4-fluorophenyl)piperidine-1-carbonyl]-3-methyl-N-(3-methylisothiazol-5-yl)pyridine-2-sulfonamide (compound 266)

(step 1) Using (4,6-dichloro-5-methylpyridin-3-yl) [4-(4-fluorophenyl)piperidin-1-yl]methanone (300 mg, 0.817 mmol) obtained in Example 52, step 1, and 4-fluoro-2-methylaniline (261 mg, 2.04 mmol), and in the same manner as in Example 1, step 2, [6-chloro-4-(4-fluoro-2-methylphenylamino)-5-methylpyridin-3-yl][4-(4-fluorophenyl)piperidin-1-yl]methanone (355 mg, 95%) was obtained.

ESIMS m/z: 456 (M+H)+

(step 2) Using [6-chloro-4-(4-fluoro-2-methylphenylamino)-5-methylpyridin-3-yl][4-(4-fluorophenyl)piperidin-1-yl]methanone (555 mg, 1.22 mmol) obtained in step 1, and in the same manner as in Example 1, step 3, [4-(4-fluoro-2-methylphenylamino)-6-mercapto-5-methylpyridin-3-yl][4-(4-fluorophenyl)piperidin-1-yl]methanone (430 mg, 78%) was obtained.

ESIMS m/z: 454 (M+H)+

(step 3) Using [4-(4-fluoro-2-methylphenylamino)-6-mercapto-5-methylpyridin-3-yl][4-(4-fluorophenyl)piperidin-1-yl]methanone (102 mg, 0.225 mmol) obtained in step. 2, and in the same manner as in Example 1, step 4, 4-(4-fluoro-2-methylphenylamino)-5-[4-(4-fluorophenyl)piperidine-1-carbonyl]-3-methylpyridine-2-sulfonic acid (113 mg, quantitative) was obtained.

ESIMS m/z: 502 (M+H)+

(step 4) Using 4-(4-fluoro-2-methylphenylamino)-5-[4-(4-fluorophenyl)piperidine-1-carbonyl]-3-methylpyridine-2-sulfonic acid (400 mg, 0.798 mmol) obtained in step 3, and in the same manner as in Example 11, compound 266 (190 mg, 40%) was obtained.

ESIMS m/z: 598 (M+H)+; $^1$H NMR (400 MHz, DMSO-$d_6$, δ): 1.21-1.75 (m, 4H), 2.09 (s, 3H), 2.17 (s, 3H), 2.44 (s, 3H), 2.61-2.75 (m, 1H), 2.76-3.03 (m, 1H), 3.46-3.59 (m, 2H), 3.98-4.24 (m, 1H), 5.98 (s, 1H), 6.75-6.87 (m, 1H), 6.87-6.98 (m, 1H), 6.99-7.06 (m, 1H), 7.09 (t, J=8.8 Hz, 2H), 7.14-7.44 (m, 3H), 7.95 (s, 1H).

Example 141

5-[4-(4-fluorophenyl)piperidine-1-carbonyl]-3-methyl-N-(3-methylisothiazol-5-yl)-4-(m-tolylamino)pyridine-2-sulfonamide (compound 276)

(step 1) Using (4,6-dichloro-5-methylpyridin-3-yl)[4-(4-fluorophenyl)piperidin-1-yl]methanone (750 mg, 2.04 mmol) obtained in Example 52, step 1, and m-toluidine (591 mg, 5.51 mmol), and in the same manner as in Example 1, step 2, [6-chloro-5-methyl-4-(m-tolylamino)pyridin-3-yl][4-(4-fluorophenyl)piperidin-1-yl]methanone (795 mg, 89%) was obtained.

ESIMS m/z: 438 (M+H)+

(step 2) Using [6-chloro-5-methyl-4-(m-tolylamino)pyridin-3-yl][4-(4-fluorophenyl)piperidin-1-yl]methanone (795 mg, 1.82 mmol) obtained in step 1, and in the same manner as in Example 1, step 3, [4-(4-fluorophenyl)piperidin-1-yl][6-mercapto-5-methyl-4-(m-tolylamino)pyridin-3-yl]methanone (762 mg, 96%) was obtained.

ESIMS m/z: 436 (M+H)+

(step 3) Using [4-(4-fluorophenyl)piperidin-1-yl][6-mercapto-5-methyl-4-(m-tolylamino)pyridin-3-yl]methanone (745 mg, 1.71 mmol) obtained in step 2, and in the same manner as in Example 1, step 4, 5-[4-(4-fluorophenyl)piperidine-1-carbonyl]-3-methyl-4-(m-tolylamino)pyridine-2-sulfonic acid (653 mg, 79%) was obtained.

ESIMS m/z: 484 (M+H)+

(step 4) Using 5-[4-(4-fluorophenyl)piperidine-1-carbonyl]-3-methyl-4-(m-tolylamino)pyridine-2-sulfonic acid (318 mg, 0.658 mmol) obtained in step 3, and in the same manner as in Example 11, compound 276 (124 mg, 33%) was obtained.

ESIMS m/z: 580 (M+H)+; $^1$H NMR (400 MHz, DMSO-$d_6$, δ): 1.27-1.71 (m, 4H), 1.81-2.03 (m, 1H), 2.24 (s, 3H), 2.27 (s, 3H), 2.46 (s, 3H), 2.56-2.73 (m, 2H), 2.81-3.07 (m, 1E), 3.92-4.35 (m, 1H), 6.62-6.72 (m, 2H), 6.74 (s, 1H), 6.76-6.86 (m, 1H), 7.04-7.17 (m, 4H), 7.17-7.36 (m, 1H), 8.17 (s, 1E), 8.28 (s, 1H), 11.81-12.38 (m, 1H).

Example 142

5-[4-(4-fluorophenyl)piperidine-1-carbonyl]-3-methyl-4-(o-tolylamino)pyridine-2-sulfonamide (compound 331)

Using 5-[4-(4-fluorophenyl)piperidine-1-carbonyl]-3-methyl-4-(o-tolylamino)pyridine-2-sulfonic acid (63.0 mg, 0.125 mmol) obtained in Example 71, step 3, and in the same manner as in Example 2, compound 331 (47.6 mg, 79%) was obtained.

ESIMS m/z: 483 (M+H)+; $^1$H NMR (400 MHz, CDCl$_3$, δ): 1.37-1.65 (m, 2H), 1.68-1.99 (m, 2H), 2.35 (s, 3H), 2.37 (s, 3H), 2.48-2.81 (m, 2H), 2.95-3.27 (m, 1H), 3.68-4.00 (m, 1H), 4.47-4.80 (m, 1H), 5.45 (s, 2H), 6.62 (d, J=7.7 Hz, 1H), 6.74-6.85 (m, 1H), 6.91-7.07 (m, 5H), 7.10 (t, J=6.8 Hz, 1H), 7.22-7.26 (m, 1H), 8.16 (s, 1H).

Example 143

The following compounds were synthesized based on Example 2.

4-(2-chloro-5-methylphenylamino)-5-[4-(4-fluorophenyl)piperidine-1-carbonyl]pyridine-2-sulfonamide (compound 50); ESIMS m/z: 503 (M+H)+

4-(2,4-dichloro-5-methylphenylamino)-5-[4-(4-fluorophenyl)piperidine-1-carbonyl]pyridine-2-sulfonamide (compound 51); ESIMS m/z: 537 (M+H)+

4-(2-chloro-4-fluoro-5-methylphenylamino)-5-[4-(4-fluorophenyl)piperidine-1-carbonyl]pyridine-2-sulfonamide (compound 52); ESIMS m/z: 521 (M+H)+

4-(2,5-dimethylphenylamino)-5-[4-(4-fluorophenyl)piperidine-1-carbonyl]pyridine-2-sulfonamide (compound 53); ESIMS m/z: 483 (M+H)+

4-(2,6-dimethylphenylamino)-5-[4-(4-fluorophenyl)piperidine-1-carbonyl]pyridine-2-sulfonamide (compound 54); ESIMS m/z: 483 (M+H)+

4-(2,4-dimethylphenylamino)-5-[4-(4-fluorophenyl)piperidine-1-carbonyl]pyridine-2-sulfonamide (compound 55); ESIMS m/z: 483 (M+H)+

4-(2-fluoro-4-methylphenylamino)-5-[4-(4-fluorophenyl)piperidine-1-carbonyl]pyridine-2-sulfonamide (compound 56); ESIMS m/z: 487 (M+H)+

4-(3-chloro-2-methylphenylamino)-5-[4-(4-fluorophenyl)piperidine-1-carbonyl]pyridine-2-sulfonamide (compound 57); ESIMS m/z: 503 (M+H)+

4-(2-chloro-4-methylphenylamino)-5-[4-(4-fluorophenyl)piperidine-1-carbonyl]pyridine-2-sulfonamide (compound 58); ESIMS m/z: 503 (M+H)+

4-(4-chloro-3-fluoro-2-methylphenylamino)-5-[4-(4-fluorophenyl)piperidine-1-carbonyl]pyridine-2-sulfonamide (compound 59); ESIMS m/z: 521 (M+H)+

4-(3-fluoro-2-methylphenylamino)-5-[4-(4-fluorophenyl)piperidine-1-carbonyl]pyridine-2-sulfonamide (compound 60); ESIMS m/z: 487 (M+H)+

5-[4-(4-fluorophenyl)piperidine-1-carbonyl]-4-[2-methyl-3-(trifluoromethyl)phenylamino]pyridine-2-sulfonamide (compound 61); ESIMS m/z: 537 (M+H)+

4-(5-fluoro-2-methylphenylamino)-5-[4-(4-fluorophenyl)piperidine-1-carbonyl]pyridine-2-sulfonamide (compound 62); ESIMS m/z: 487 (M+H)+

4-(2-chloro-4-fluorophenylamino)-5-[4-(4-fluorophenyl)piperidine-f-carbonyl]pyridine-2-sulfonamide (compound 63); ESIMS m/z: 507 (M+H)+

4-(3-fluoro-4-methylphenylamino)-5-[4-(4-fluorophenyl)piperidine-1-carbonyl]pyridine-2-sulfonamide (compound 64); ESIMS m/z: 487 (M+H)+

4-(2,3-dimethylphenylamino)-5-[4-(4-fluorophenyl)piperidine-1-carbonyl]pyridine-2-sulfonamide (compound 65); ESIMS m/z: 483 (M+H)+

4-(4-chloro-2,3-dimethylphenylamino)-5-[4-(4-fluorophenyl)piperidine-1-carbonyl]pyridine-2-sulfonamide (compound 66); ESIMS m/z: 517 (M+H)+

4-(4-chloro-2-fluoro-5-methylphenylamino)-5-[4-(4-fluorophenyl)piperidine-1-carbonyl]pyridine-2-sulfonamide (compound 67); ESIMS m/z: 521 (M+H)+

4-(2-fluoro-5-methylphenylamino)-5-[4-(4-fluorophenyl)piperidine-1-carbonyl]pyridine-2-sulfonamide (compound 68); ESIMS m/z: 487 (M+H)+

4-(5-chloro-2-methoxyphenylamino)-5-[4-(4-fluorophenyl)piperidine-1-carbonyl]pyridine-2-sulfonamide (compound 69); ESIMS m/z: 519 (M+H)+

4-(2-chloro-5-fluorophenylamino)-5-[4-(4-fluorophenyl)piperidine-1-carbonyl]pyridine-2-sulfonamide (compound 70); ESIMS m/z: 507 (M+H)+

4-(2,4-dichloro-5-fluorophenylamino)-5-[4-(4-fluorophenyl)piperidine-1-carbonyl]pyridine-2-sulfonamide (compound 71); ESIMS m/z: 541 (M+H)+

4-(2-fluoro-6-methylphenylamino)-5-[4-(4-fluorophenyl)piperidine-1-carbonyl]pyridine-2-sulfonamide (compound 72); ESIMS m/z: 487 (M+H)+

4-(2,6-difluorophenylamino)-5-[4-(4-fluorophenyl)piperidine-1-carbonyl]pyridine-2-sulfonamide (compound 73); ESIMS m/z: 491 (M+H)+

4-(2-chloro-3-fluorophenylamino)-5-[4-(4-fluorophenyl)piperidine-1-carbonyl]pyridine-2-sulfonamide (compound 74); ESIMS m/z: 507 (M+H)+

4-(2,4-dichloro-3-fluorophenylamino)-5-[4-(4-fluorophenyl)piperidine-1-carbonyl]pyridine-2-sulfonamide (compound 75); ESIMS m/z: 541 (M+H)+

4-(2-fluoro-3-methylphenylamino)-5-[4-(4-fluorophenyl)piperidine-1-carbonyl]pyridine-2-sulfonamide (compound 76); ESIMS m/z: 487 (M+H)+

4-(4-chloro-2-fluoro-3-methylphenylamino)-5-[4-(4-fluorophenyl)piperidine-1-carbonyl]pyridine-2-sulfonamide (compound 77); ESIMS m/z: 521 (M+H)+

5-[4-(4-fluorophenyl)piperidine-1-carbonyl]-4-(4-methoxy-2-methylphenylamino)pyridine-2-sulfonamide (compound 78); ESIMS m/z: 499 (M+H)+

4-(3-chloro-4-methylphenylamino)-5-[4-(4-fluorophenyl)piperidine-1-carbonyl]pyridine-2-sulfonamide (compound 79); ESIMS m/z: 503 (M+H)+

4-(4-chloro-2-fluorophenylamino)-5-[4-(4-fluorophenyl)piperidine-1-carbonyl]pyridine-2-sulfonamide (compound 80); ESIMS m/z: 507 (M+H)+

4-(2,4-dichlorophenylamino)-5-[4-(4-fluorophenyl)piperidine-1-carbonyl]pyridine-2-sulfonamide (compound 81); ESIMS m/z: 523 (M+H)+

4-(4-chlorophenylamino)-5-[4-(4-fluorophenyl)piperidine-1-carbonyl]pyridine-2-sulfonamide (compound 82); ESIMS m/z: 489 (M+H)+

4-(4-fluoro-3-methylphenylamino)-5-[4-(4-fluorophenyl)piperidine-1-carbonyl]pyridine-2-sulfonamide (compound 83); ESIMS m/z: 487 (M+H)+

5-[4-(4-fluorophenyl)piperidine-1-carbonyl]-4-(4-methoxyphenylamino)pyridine-2-sulfonamide (compound 84); ESIMS m/z: 485 (M+H)+

5-[4-(4-fluorophenyl)piperidine-1-carbonyl]-4-(0-tolylamino)pyridine-2-sulfonamide (compound 85); ESIMS m/z: 469 (M+H)+

4-(3-fluoro-4-methoxyphenylamino)-5-[4-(4-fluorophenyl)piperidine-1-carbonyl]pyridine-2-sulfonamide (compound 86); ESIMS m/z: 503 (M+H)+

4-(2-fluoro-4-methoxyphenylamino)-5-[4-(4-fluorophenyl)piperidine-1-carbonyl]pyridine-2-sulfonamide (compound 87); ESIMS m/z: 503 (M+H)+

5-[4-(4-fluorophenyl)piperidine-1-carbonyl]-4-(4-methoxy-3-methylphenylamino)pyridine-2-sulfonamide (compound 88); ESIMS m/z: 499 (M+H)+

5-[4-(4-fluorophenyl)piperidine-1-carbonyl]-4-[4-methoxy-3-(trifluoromethyl)phenylamino]pyridine-2-sulfonamide (compound 89); ESIMS m/z: 553 (M+H)+

4-(4-bromo-2-chlorophenylamino)-5-[4-(4-fluorophenyl)piperidine-1-carbonyl]pyridine-2-sulfonamide (compound 90); ESIMS m/z: 567 (M+H)+

4-(4-bromo-2-fluorophenylamino)-5-[4-(4-fluorophenyl)piperidine-1-carbonyl]pyridine-2-sulfonamide (compound 91); ESIMS m/z: 551 (M+H)+

4-(2-chloro-4-methoxyphenylamino)-5-[4-(4-fluorophenyl)piperidine-1-carbonyl]pyridine-2-sulfonamide (compound 92); ESIMS m/z: 519 (M+H)+

5-[4-(4-fluorophenyl)piperidine-1-carbonyl]-4-(5-methoxy-2-methylphenylamino)pyridine-2-sulfonamide (compound 93); ESIMS m/z: 499 (M+H)+

4-(2,3-dihydrobenzofuran-5-ylamino)-5-[4-(4-fluorophenyl)piperidine-1-carbonyl]pyridine-2-sulfonamide (compound 94); ESIMS m/z: 497 (M+H)+

5-[4-(4-fluorophenyl)piperidine-1-carbonyl]-4-(phenylamino)pyridine-2-sulfonamide (compound 95); ESIMS m/z: 455 (M+H)+

5-[4-(4-fluorophenyl)piperidine-1-carbonyl]-4-(m-tolylamino)pyridine-2-sulfonamide (compound 96); ESIMS m/z: 469 (M+H)+

5-[4-(4-fluorophenyl)piperidine-1-carbonyl]-4-(2-methoxyphenylamino)pyridine-2-sulfonamide (compound 97); ESIMS m/z: 485 (M+H)+

5-[4-(4-fluorophenyl)piperidine-1-carbonyl]-4-(p-tolylamino)pyridine-2-sulfonamide (compound 98); ESIMS m/z: 469 (M+H)+

4-(4-fluoro-2-methoxyphenylamino)-5-[4-(4-fluorophenyl)piperidine-1-carbonyl]pyridine-2-sulfonamide (compound 99); ESIMS m/z: 503 (M+H)+

5-[4-(4-fluorophenyl) piperidine-1-carbonyl]-4-[2-methyl-4-(trifluoromethyl)phenylamino]pyridine-2-sulfonamide (compound 100); ESIMS m/z: 537 (M+H)+

5-[4-(4-fluorophenyl)piperidine-1-carbonyl]-4-[2-(trifluoromethyl)phenylamino]pyridine-2-sulfonamide (compound 101); ESIMS m/z: 523 (M+H)+5-[4-(4-fluorophenyl)piperidine-1-carbonyl]-4-(2-fluorophenylamino)pyridine-2-sulfonamide (compound 102); ESIMS m/z: 473 (M+H)+

4-(3-chlorophenylamino)-5-[4-(4-fluorophenyl)piperidine-1-carbonyl]pyridine-2-sulfonamide (compound 103); ESIMS m/z: 489 (M+H)+

4-(5-chloro-4-methoxy-2-methylphenylamino)-5-[4-(4-fluorophenyl)piperidine-1-carbonyl]pyridine-2-sulfonamide (compound 104); ESIMS m/z: 533 (M+H)+

4-(5-chloro-4-hydroxy-2-methylphenylamino)-5-[4-(4-fluorophenyl)piperidine-1-carbonyl]pyridine-2-sulfonamide (compound 105); ESIMS m/z: 519 (M+H)+

4-[4-(difluoromethoxy)phenylamino]-5-[4-(4-fluorophenyl)piperidine-1-carbonyl]pyridine-2-sulfonamide (compound 106); ESIMS m/z: 521 (M+H)+

4-(3,4-dimethylphenylamino)-5-[4-(4-fluorophenyl)piperidine-1-carbonyl]pyridine-2-sulfonamide (compound 107); ESIMS m/z: 483 (M+H)+

5-[4-(4-fluorophenyl)piperidine-1-carbonyl]-4-(4-isopropylphenylamino)pyridine-2-sulfonamide (compound 108); ESIMS m/z: 497 (M+H)+

4-(5-chloro-2-methylphenylamino)-5-[4-(4-fluorophenyl)piperidine-1-carbonyl]pyridine-2-sulfonamide (compound 109); ESIMS m/z: 503 (M+H)+

4-(3,5-dimethylphenylamino)-5-[4-(4-fluorophenyl)piperidine-1-carbonyl]pyridine-2-sulfonamide (compound 110); ESIMS m/z: 483 (M+H)+

4-(4-fluoro-2-methylphenylamino)-5-[4-(4-fluorophenyl)piperidine-1-carbonyl]-N-methylpyridine-2-sulfonamide (compound 111); ESIMS m/z: 501 (M+H)+

4-(4-fluoro-2-methylphenylamino)-5-[4-(4-fluorophenyl)piperidine-1-carbonyl]-N-(2-methoxyethyl)pyridine-2-sulfonamide (compound 112); ESIMS m/z: 545 (M+H)+ diethyl 2,2'-{4-(4-fluoro-2-methylphenylamino)-5-[4-(4-fluorophenyl)piperidine-1-carbonyl]pyridin-2-ylsulfonylazanediyl}diacetate (compound 114); ESIMS m/z: 659 (M+H)+

2-{4-(4-fluoro-2-methylphenylamino)-5-[4-(4-fluorophenyl)piperidine-1-carbonyl]pyridine-2-sulfonamide}acetamide (compound 115); ESIMS m/z: 544 (M+H)+ methyl 1-{4-(4-fluoro-2-methylphenylamino)-5-[4-(4-fluorophenyl)piperidine-1-carbonyl]pyridin-2-ylsulfonyl}pyrrolidine-2-carboxylate (compound 116); ESIMS m/z: 599 (M+H)+

[4-(4-fluoro-2-methylphenylamino)-6-(pyrrolidin-1-ylsulfonyl)pyridin-3-yl][4-(4-fluorophenyl)piperidin-1-yl]methanone (compound 119); ESIMS m/z: 541 (M+H)+

[4-(4-fluoro-2-methylphenylamino)-6-(piperidin-1-ylsulfonyl)pyridin-3-yl][4-(4-fluorophenyl)piperidin-1-yl]methanone (compound 121); ESIMS m/z: 555 (M+H)+

[4-(4-fluoro-2-methylphenylamino)-6-(morpholinosulfonyl)pyridin-3-yl][4-(4-fluorophenyl)piperidin-1-yl]methanone (compound 122); ESIMS m/z: 557 (M+H)+

1-{4-{4-(4-fluoro-2-methylphenylamino)-5-[4-(4-fluorophenyl)piperidine-1-carbonyl]pyridin-2-ylsulfonyl}piperazin-1-yl}ethanone (compound 124); ESIMS m/z: 598 (M+H)+

4-(4-fluoro-2-methylphenylamino)-5-[4-(4-fluorophenyl)piperidine-1-carbonyl]-N,N-dimethylpyridine-2-sulfonamide (compound 125); ESIMS m/z: 515 (M+H)+

4-(4-fluoro-2-methylphenylamino)-5-[4-(4-fluorophenyl)piperidine-1-carbonyl]-N-(2-oxopropyl)pyridine-2-sulfonamide (compound 131); ESIMS m/z: 543 (M+H)+

4-(4-fluoro-2-methylphenylamino)-5-[4-(4-fluorophenyl)piperidine-1-carbonyl]-N-[(5-methylpyrazin-2-yl)methyl]pyridine-2-sulfonamide (compound 134); ESIMS m/z: 593 (M+H)+

N-(cyanomethyl)-4-(4-fluoro-2-methylphenylamino)-5-[4-(4-fluorophenyl)piperidine-1-carbonyl]pyridine-2-sulfonamide (compound 135); ESIMS m/z: 526 (M+H)+

N-{1-{4-(4-fluoro-2-methylphenylamino)-5-[4-(4-fluorophenyl)piperidine-1-carbonyl]pyridin-2-ylsulfonyl}piperidin-4-yl}acetamide (compound 136); ESIMS m/z: 612 (M+H)+

1-{4-(4-fluoro-2-methylphenylamino)-5-[4-(4-fluorophenyl)piperidine-1-carbonyl]pyridin-2-ylsulfonyl}piperidine-4-carboxamide (compound 138); ESIMS m/z: 598 (M+H)+

4-(4-fluoro-2-methylphenylamino)-5-[4-(4-fluorophenyl)piperidine-1-carbonyl]-N-(2-oxopyrrolidin-3-yl)pyridine-2-sulfonamide (compound 142); ESIMS m/z: 570 (M+H)+

3-{4-(4-fluoro-2-methylphenylamino)-5-[4-(4-fluorophenyl)piperidine-1-carbonyl]pyridin-2-ylsulfonyl}oxazolidin-2-one (compound 143); ESIMS m/z: 557 (M+H)+

1-{4-(4-fluoro-2-methylphenylamino)-5-[4-(4-fluorophenyl)piperidine-1-carbonyl]pyridin-2-ylsulfonyl}imidazolidin-2-one (compound 144); ESIMS m/z: 556 (M+H)+

4-(4-fluoro-2-methylphenylamino)-5-[4-(4-fluorophenyl)piperidine-1-carbonyl]-N-(pyrimidin-2-yl)pyridine-2-sulfonamide (compound 145); ESIMS m/z: 565 (M+H)+

4-(4-fluoro-2-methylphenylamino)-5-[4-(4-fluorophenyl)piperidine-1-carbonyl]-N-(pyridin-2-yl)pyridine-2-sulfonamide (compound 146); ESIMS m/z: 564 (M+H)+

N-(5-bromopyrimidin-2-yl)-4-(4-fluoro-2-methylphenylamino)-5-[4-(4-fluorophenyl)piperidine-1-carbonyl]pyridine-2-sulfonamide (compound 147); ESIMS m/z: 643 (M+H)+

4-(4-fluoro-2-methylphenylamino)-5-[4-(4-fluorophenyl)piperidine-1-carbonyl]-N-(thiazol-2-yl)pyridine-2-sulfonamide (compound 148); ESIMS m/z: 570 (M+H)+

4-(4-fluoro-2-methylphenylamino)-5-[4-(4-fluorophenyl)piperidine-1-carbonyl]-N-(1-methyl-1H-imidazol-2-yl)pyridine-2-sulfonamide (compound 149); ESIMS m/z: 567 (M+H)+

4-(4-fluoro-2-methylphenylamino)-5-[4-(4-fluorophenyl)piperidine-1-carbonyl]-N-[2-(methylthio)pyrimidin-4-yl]pyridine-2-sulfonamide (compound 150); ESIMS m/z: 611 (M+H)+

N-(3,5-dimethylisoxazol-4-yl)-4-(4-fluoro-2-methylphenylamino)-5-[4-(4-fluorophenyl)piperidine-1-carbonyl]pyridine-2-sulfonamide (compound 151); ESIMS m/z: 582 (M+H)+

4-(4-fluoro-2-methylphenylamino)-5-[4-(4-fluorophenyl)piperidine-1-carbonyl]-N-(1,3,5-trimethyl-1H-pyrazol-4-yl)pyridine-2-sulfonamide (compound 152); ESIMS m/z: 595 (M+H)+

4-(4-fluoro-2-methylphenylamino)-5-[4-(4-fluorophenyl)piperidine-1-carbonyl]-N-(1-methyl-1H-pyrazol-3-yl)pyridine-2-sulfonamide (compound 153); ESIMS m/z: 567 (M+H)+

4-(4-fluoro-2-methylphenylamino)-5-[4-(4-fluorophenyl)piperidine-1-carbonyl]-N-(thiazol-4-yl)pyridine-2-sulfonamide (compound 154); ESIMS m/z: 570 (M+H)+

4-(4-fluoro-2-methylphenylamino)-5-[4-(4-fluorophenyl)piperidine-1-carbonyl]-N-(thiazol-5-yl)pyridine-2-sulfonamide (compound 155); ESIMS m/z: 570 (M+H)+

4-(4-fluoro-2-methylphenylamino)-5-[4-(4-fluorophenyl)piperidine-1-carbonyl]-N-(pyrimidin-5-yl)pyridine-2-sulfonamide (compound 156); ESIMS m/z: 565 (M+H)+

4-(4-fluoro-2-methylphenylamino)-5-[4-(4-fluorophenyl)piperidine-1-carbonyl]-N-(5-methylisoxazol-3-yl)pyridine-2-sulfonamide (compound 157); ESIMS m/z: 568 (M+H)+

N-(3,4-dimethylisoxazol-5-yl)-4-(4-fluoro-2-methylphenylamino)-5-[4-(4-fluorophenyl)piperidine-1-carbonyl]pyridine-2-sulfonamide (compound 158); ESIMS m/z: 582 (M+H)+

N-(5-tert-butylisoxazol-3-yl)-4-(4-fluoro-2-methylphenylamino)-5-[4-(4-fluorophenyl)piperidine-1-carbonyl]pyridine-2-sulfonamide (compound 159); ESIMS m/z: 610 (M+H)+

5-[4-(4-fluorophenyl)piperidine-1-carbonyl]-N-(isoxazol-3-yl)-4-(4-methoxy-2-methylphenylamino)-3-methylpyridine-2-sulfonamide (compound 234); ESIMS m/z: 580 (M+H)+

5-[4-(4-fluorophenyl)piperidine-1-carbonyl]-3-methyl-4-[2-methyl-6-(trifluoromethyl)pyridin-3-ylamino]pyridine-2-sulfonamide (compound 245); ESIMS m/z: 552 (M+H)+

5-[4-(4-fluorophenyl)piperidine-1-carbonyl]-N-(isoxazol-3-yl)-3-methyl-4-(2,4,5-trifluorophenylamino)pyridine-2-sulfonamide (compound 246); ESIMS m/z: 590 (M+H)+

4-(1,3-dihydroisobenzofuran-5-ylamino)-5-[4-(4-fluorophenyl)piperidine-1-carbonyl]-N-(isoxazol-3-yl)-3-methylpyridine-2-sulfonamide (compound 247); ESIMS m/z: 578 (M+H)$^+$ 4-(4-fluoro-2-methylphenylamino)-5-[4-(4-fluorophenyl)piperidine-1-carbonyl]-3-methyl-N-(3-methylisothiazol-5-yl)pyridine-2-sulfonamide (compound 266); ESIMS m/z: 598 (M+H)$^+$ 5-[4-(4-fluorophenyl)piperidine-1-carbonyl]-3-methyl-N-(3-methylisothiazol-5-yl)-4-(m-tolylamino)pyridine-2-sulfonamide (compound 276); ESIMS m/z: 580 (M+H)$^+$ 4-(3,4-dichlorophenylamino)-5-[4-(4-fluorophenyl)piperidine-1-carbonyl]-N-(isoxazol-3-yl)-3-methylpyridine-2-sulfonamide (compound 279); ESIMS m/z: 604 (M+H)$^+$ 4-(2,4-dichlorophenylamino)-5-[4-(4-fluorophenyl)piperidine-1-carbonyl]-N-(isoxazol-3-yl)-3-methylpyridine-2-sulfonamide (compound 280); ESIMS m/z: 604 (M+H)$^+$ Example 144

The following compounds were synthesized according to Example 6, step 1.

1-{4-(4-fluoro-2-methylphenylamino)-5-[4-(4-fluorophenyl)piperidine-1-carbonyl]pyridin-2-ylsulfonyl}-N-methylpyrrolidine-2-carboxamide (compound 117); ESIMS m/z: 598 (M+H)$^+$ 1-{4-(4-fluoro-2-methylphenylamino)-5-[4-(4-fluorophenyl)piperidine-1-carbonyl]pyridin-2-ylsulfonyl}pyrrolidine-2-carboxamide (compound 123); ESIMS m/z: 584 (M+H)$^+$ 2-{4-(4-fluoro-2-methylphenylamino)-5-[4-(4-fluorophenyl)piperidine-1-carbonyl]pyridine-2-sulfonamide}-N,N-dimethylacetamide (compound 126); ESIMS m/z: 572 (M+H)$^+$ N-cyclopropyl-2-{4-(4-fluoro-2-methylphenylamino)-5-[4-(4-fluorophenyl)piperidine-1-carbonyl]pyridine-2-sulfonamide}acetamide (compound 127); ESIMS m/z: 584 (M+H)$^+$ N-ethyl-2-{4-(4-fluoro-2-methylphenylamino)-5-[4-(4-fluorophenyl)piperidine-1-carbonyl]pyridine-2-sulfonamide}acetamide (compound 128); ESIMS m/z: 572 (M+H)$^+$ 2-{4-(4-fluoro-2-methylphenylamino)-5-[4-(4-fluorophenyl)piperidine-1-carbonyl]pyridine-2-sulfonamide}-N-methoxy-N-methylacetamide (compound 129); ESIMS m/z: 588 (M+H)$^+$ 4-(4-fluoro-2-methylphenylamino)-5-[4-(4-fluorophenyl)piperidine-1-carbonyl]-N-(2-morpholino-2-oxoethyl)pyridine-2-sulfonamide (compound 130); ESIMS m/z: 614 (M+H)$^+$ 2-{4-(4-fluoro-2-methylphenylamino)-5-[4-(4-fluorophenyl)piperidine-1-carbonyl]-N-methylpyridine-2-sulfonamide}-N-methylacetamide (compound 132); ESIMS m/z: 572 (M+H)$^+$ 2-{4-(4-fluoro-2-methylphenylamino)-5-[4-(4-fluorophenyl)piperidine-1-carbonyl]pyridine-2-sulfonamide}-3-hydroxy-N-methylpropaneamide (compound 137); ESIMS m/z: 588 (M+H)$^+$ 2-{4-(4-fluoro-2-methylphenylamino)-5-[4-(4-fluorophenyl)piperidine-1-carbonyl]pyridine-2-sulfonamide}-N-methylpropaneamide (compound 139); ESIMS m/z: 572 (M+H)$^+$ 2-{4-(4-fluoro-2-methylphenylamino)-5-[4-(4-fluorophenyl)piperidine-1-carbonyl]pyridine-2-sulfonamide}-N,2-dimethylpropaneamide (compound 140); ESIMS m/z: 586 (M+H)$^+$ (2S,4R)-1-{4-(4-fluoro-2-methylphenylamino)-5-[4-(4-fluorophenyl)piperidine-1-carbonyl]pyridin-2-ylsulfonyl}-4-hydroxy-N-methylpyrrolidine-2-carboxamide (compound 141); ESIMS m/z: 614 (M+H)$^+$ 4-(cyclohexylamino)-5-[4-(4-fluorophenyl)piperidine-1-carbonyl]-3-methylpyridine-2-sulfonamide (compound 207); ESIMS m/z: 475 (M+H)$^+$ 5-[4-(4-fluorophenyl)piperidine-1-carbonyl]-3-methyl-4-[(tetrahydro-2H-pyran-4-yl)methylamino]pyridine-2-sulfonamide (compound 214); ESIMS m/z: 491 (M+H)$^+$ 4-(cyclohexylamino)-5-[4-(4-fluorophenyl)piperidine-1-carbonyl]-N-(isoxazol-3-yl)-3-methylpyridine-2-sulfonamide (compound 215); ESIMS m/z: 542 (M+H)$^+$ 5-[4-(4-fluorophenyl)piperidine-1-carbonyl]-3-methyl-4-(pyridin-3-ylmethylamino)pyridine-2-sulfonamide (compound 221); ESIMS m/z: 484 (M+H)$^+$ 5-[4-(4-fluorophenyl)piperidine-1-carbonyl]-N-(isoxazol-3-yl)-3-methyl-4-(phenethylamino)pyridine-2-sulfonamide (compound 222); ESIMS m/z: 564 (M+H)$^+$ 5-[4-(4-fluorophenyl)piperidine-1-carbonyl]-N-(isoxazol-3-yl)-3-methyl-4-(pyridin-2-ylmethylamino)pyridine-2-sulfonamide (compound 223); ESIMS m/z: 551 (M+H)$^+$ 5-[4-(4-fluorophenyl)piperidine-1-carbonyl]-N-(isoxazol-3-yl)-3-methyl-4-(2-morpholinoethylamino)pyridine-2-sulfonamide (compound 224); ESIMS m/z: 573 (M+H)$^+$ 4-(cyclobutylmethylamino)-5-[4-(4-fluorophenyl)piperidine-1-carbonyl]-N-(isoxazol-3-yl)-3-methylpyridine-2-sulfonamide (compound 227); ESIMS m/z: 528 (M+H)$^+$ 4-(3-cyanobenzylamino)-5-[4-(4-fluorophenyl)piperidine-1-carbonyl]-3-methylpyridine-2-sulfonamide (compound 228); ESIMS m/z: 508 (M+H)$^+$ 3-chloro-5-[4-(4-fluorophenyl)piperidine-1-carbonyl]-4-(1-phenylcyclopropylamino)pyridine-2-sulfonamide (compound 230); ESIMS m/z: 529 (M+H)$^+$ 3-chloro-4-(3-fluorophenoxy)-5-[4-(4-fluorophenyl)piperidine-1-carbonyl]pyridine-2-sulfonamide (compound 238); ESIMS m/z: 508 (M+H)$^+$ 3-chloro-5-[4-(4-fluorophenyl)piperidine-1-carbonyl]-4-(1-oxo-2,3-dihydro-1H-inden-5-ylamino)pyridine-2-sulfonamide (compound 243); ESIMS m/z: 543 (M+H)$^+$ 4-(5-chloro-2-methylpyridin-3-ylamino)-5-[4-(4-fluorophenyl)piperidine-1-carbonyl]-N-(isoxazol-3-yl)-3-methylpyridine-2-sulfonamide (compound 248); ESIMS m/z: 585 (M+H)$^+$ 5-[4-(4-fluorophenyl)piperidine-1-carbonyl]-N-(isoxazol-3-yl)-3-methyl-4-(m-tolyloxy)pyridine-2-sulfonamide (compound 249); ESIMS m/z: 551 (M+H)$^+$ 4-(benzylamino)-5-[4-(4-fluorophenyl)-3-oxopiperazine-1-carbonyl]-3-methylpyridine-2-sulfonamide (compound 253); ESIMS m/z: 498 (M+H)$^+$ Example 145

The following compounds were synthesized based on Example 6, step 2.

1-{4-(4-fluoro-2-methylphenylamino)-5-[4-(4-fluorophenyl)piperidine-1-carbonyl]pyridin-2-ylsulfonyl}pyrrolidine-2-carboxylic acid (compound 120); ESIMS m/z: 585 (M+H)$^+$.

2-{4-(4-fluoro-2-methylphenylamino)-5-[4-(4-fluorophenyl)piperidine-1-carbonyl]pyridine-2-sulfonamide}-3-hydroxypropionic acid (compound 133); ESIMS m/z: 575 (M+H)$^+$ Example 146

The following compound was synthesized based on Example 13.

N-{4-(4-fluoro-2-methylphenylamino)-5-[4-(4-fluorophenyl)piperidine-1-carbonyl]pyridin-2-ylsulfonyl}cyclopropanecarboxamide (compound 160); ESIMS m/z: 555 (M+H)$^+$

Example 147

The following compounds were synthesized based on Example 16.

4-(2-chloro-5-methylphenylamino)-N-(ethylcarbamoyl)-5-[4-(4-fluorophenyl)piperidine-1-carbonyl]pyridine-2-sulfonamide (compound 161); ESIMS m/z: 574 (M+H)$^+$ 4-(2-chloro-5-methylphenylamino)-5-[4-(4-fluorophenyl)piperidine-1-carbonyl]-N-(propylcarbamoyl)pyridine-2-sulfonamide (compound 162); ESIMS m/z: 588 (M+H)$^+$ 4-(benzylamino)-N-(ethylcarbamoyl)-5-[4-(4-fluorophenyl)piperidine-1-carbonyl]pyridine-2-sulfonamide (compound 163); ESIMS m/z: 540 (M+H)$^+$ 4-(2,4-dichloro-5-methylphenylamino)-N-(ethylcarbamoyl)-5-[4-(4-fluorophenyl)piperidine-1-carbonyl]pyridine-2-sulfonamide (compound 164); ESIMS m/z: 608 (M+H)$^+$ 4-(2,4-dichloro-5-methylphenylamino)-5-[4-(4-fluorophenyl)piperidine-1-carbonyl]-N-(propylcarbamoyl)pyridine-2-sulfonamide (compound 165); ESIMS m/z: 622 (M+H)$^+$ 4-(4-chloro-2,5-dimethylphenylamino)-N-(ethylcarbamoyl)-5-[4-(4-fluorophenyl)piperidine-1-carbonyl]pyridine-2-sulfonamide (compound 166); ESIMS m/z: 588 (M+H)$^+$ 4-(4-chloro-2,5-dimethylphenylamino)-5-[4-(4-fluorophenyl)piperidine-1-carbonyl]-N-(propylcarbamoyl)pyridine-2-sulfonamide (compound 167); ESIMS m/z: 602 (M+H)$^+$ 4-(4-fluoro-2-methylphenylamino)-5-[4-(4-fluorophenyl)piperidine-1-carbonyl]-N-(propylcarbamoyl)pyridine-2-sulfonamide (compound 168); ESIMS m/z: 572 (M+H)$^+$ 4-(4-chloro-2-methylphenylamino)-N-(ethylcarbamoyl)-5-[4-(4-fluorophenyl)piperidine-1-carbonyl]pyridine-2-sulfonamide (compound 169); ESIMS m/z: 574 (M+H)$^+$ 4-(4-chloro-2-methylphenylamino)-5-[4-(4-fluorophenyl)piperidine-1-carbonyl]-N-(propylcarbamoyl)pyridine-2-sulfonamide (compound 170); ESIMS m/z: 588 (M+H)$^+$ 4-(4-fluoro-2-methylphenylamino)-5-[4-(4-fluorophenyl)piperidine-1-carbonyl]-N-(isopropylcarbamoyl)pyridine-2-sulfonamide (compound 171); ESIMS m/z: 572 (M+H)$^+$ N-(cyclopropylcarbamoyl)-4-(4-fluoro-2-methylphenylamino)-5-[4-(4-fluorophenyl)piperidine-1-carbonyl]pyridine-2-sulfonamide (compound 172); ESIMS m/z: 570 (M+H)$^+$ N-(ethylcarbamoyl)-5-[4-(4-fluorophenyl)piperidine-1-carbonyl]-3-methyl-4-(o-tolylamino)pyridine-2-sulfonamide (compound 226); ESIMS m/z: 554 (M+H)$^+$

Example 148

The following compounds were synthesized based on Example 19.

ethyl 4-(4-chloro-2-methylphenylamino)-5-[4-(4-fluorophenyl)piperidine-1-carbonyl]pyridin-2-ylsulfonylcarbamate (compound 173); ESIMS m/z: 575 (M+H)$^+$ ethyl 4-(4-fluoro-2-methylphenylamino)-5-[4-(4-fluorophenyl)piperidine-1-carbonyl]pyridin-2-ylsulfonylcarbamate (compound 174); ESIMS m/z: 559 (M+H)$^+$ isopropyl 4-(4-fluoro-2-methylphenylamino)-5-[4-(4-fluorophenyl)piperidine-1-carbonyl]pyridin-2-ylsulfonylcarbamate (compound 175); ESIMS m/z: 573 (M+H)$^+$

Example 149

The following compounds were synthesized based on Example 25.

3-chloro-5-[4-(4-fluorophenyl)piperidine-1-carbonyl]-4-(4-methoxy-2-methylphenylamino)pyridine-2-sulfonamide (compound 178); ESIMS m/z: 533 (M+H)$^+$ 3-chloro-4-(2-chloro-4-methoxyphenylamino)-5-[4-(4-fluorophenyl)piperidine-1-carbonyl]pyridine-2-sulfonamide (compound 179); ESIMS m/z: 553 (M+H)$^+$ 3-chloro-4-(3-chloro-2-methylphenylamino)-5-[4-(4-fluorophenyl)piperidine-1-carbonyl]pyridine-2-sulfonamide (compound 180); ESIMS m/z: 537 (M+H)$^+$ 3-chloro-4-(3-chloro-4-methylphenylamino)-5-[4-(4-fluorophenyl)piperidine-1-carbonyl]pyridine-2-sulfonamide (compound 181); ESIMS m/z: 537 (M+H)$^+$ 3-chloro-4-(2,6-difluorophenylamino)-5-[4-(4-fluorophenyl)piperidine-1-carbonyl]pyridine-2-sulfonamide (compound 182); ESIMS m/z: 525 (M+H)$^+$ 3-chloro-4-(cyclopropylamino)-5-[4-(4-fluorophenyl)piperidine-1-carbonyl]pyridine-2-sulfonamide (compound 183); ESIMS m/z: 453 (M+H)$^+$

[6-(4-aminopiperidin-1-ylsulfonyl)-5-chloro-4-(4-fluoro-2-methylphenylamino)pyridin-3-yl][4-(4-fluorophenyl)piperidin-1-yl]methanone (compound 184); ESIMS m/z: 604 (M+H)$^+$ 3-{3-chloro-4-(4-fluoro-2-methylphenylamino)-5-[4-(4-fluorophenyl)piperidine-1-carbonyl]pyridin-2-ylsulfonyl}-4,4-dimethyloxazolidin-2-one (compound 187); ESIMS m/z: 619 (M+H)$^+$ 3-chloro-4-(4-fluoro-2-methylphenylamino)-5-[4-(4-fluorophenyl)piperidine-1-carbonyl]-N-(thiazol-2-yl)pyridine-2-sulfonamide (compound 188); ESIMS m/z: 604 (M+H)$^+$ 3-chloro-N-(3,5-dimethylisoxazol-4-yl)-4-(4-fluoro-2-methylphenylamino)-5-[4-(4-fluorophenyl)piperidine-1-carbonyl]pyridine-2-sulfonamide (compound 189); ESIMS m/z: 616 (M+H)$^+$ 3-chloro-4-(4-fluoro-2-methylphenylamino)-5-[4-(4-fluorophenyl)piperidine-1-carbonyl]-N-(isoxazol-3-yl)pyridine-2-sulfonamide (compound 190); ESIMS m/z: 588 (M+H)$^+$ 3-chloro-4-(4-fluoro-2-methylphenylamino)-5-[4-(4-fluorophenyl)piperidine-1-carbonyl]-N-phenylpyridine-2-sulfonamide (compound 191); ESIMS m/z: 597 (M+H)$^+$

[6-(1H-pyrrolo[3,2-b]pyridin-1-ylsulfonyl)-5-chloro-4-(4-fluoro-2-methylphenylamino)pyridin-3-yl][4-(4-fluorophenyl)piperidin-1-yl]methanone (compound 192); ESIMS m/z: 622 (M+H)$^+$ 3-chloro-4-(4-fluoro-2-methylphenylamino)-5-[4-(4-fluorophenyl)piperidine-1-carbonyl]-N-methoxypyridine-2-sulfonamide (compound 193); ESIMS m/z: 551 (M+H)$^+$ 3-chloro-5-[4-(4-fluorophenyl)piperidine-1-carbonyl]-4-(1-methyl-1H-indazol-5-ylamino)pyridine-2-sulfonamide (compound 242); ESIMS m/z: 543 (M+H)$^+$ 3-chloro-4-(3-chlorophenylamino)-5-[3-(4-fluorophenyl)azetidine-1-carbonyl]pyridine-2-sulfonamide (compound 283); ESIMS m/z: 495 (M+H)$^+$ 5-[3-(4-fluorophenyl)azetidine-1-carbonyl]-3-methyl-4-(0-tolylamino)pyridine-2-sulfonamide (compound 286); ESIMS m/z: 455 (M+H)$^+$

Example 150

The following compounds were synthesized based on Example 35.

2-{3-chloro-4-(4-fluoro-2-methylphenylamino)-5-[4-(4-fluorophenyl)piperidine-1-carbonyl]pyridine-2-sulfonamide}-3-hydroxy-N-methylpropanamide (compound 185); ESIMS m/z: 622 (M+H)$^+$ 2-{3-chloro-4-(4-fluoro-2-methylphenylamino)-5-[4-(4-fluorophenyl)piperidine-1-carbonyl]pyridine-2-sulfonamide}-3-hydroxy-N,N-dimethylpropanamide (compound 186); ESIMS m/z: 636 (M+H)$^+$

Example 151

The following compounds were synthesized based on Example 46.

4-(4-fluoro-2-methylphenylamino)-5-(4-phenylpiperidine-1-carbonyl)pyridine-2-sulfonamide (compound 48); ESIMS m/z: 469 (M+H)+

4-(4-chloro-2-methylphenylamino)-5-(4-phenylpiperidine-1-carbonyl)pyridine-2-sulfonamide (compound 49); ESIMS m/z: 485 (M+H)+

3-chloro-4-(2,4-dimethylpyrimidin-5-ylamino)-5-[4-(4-fluorophenyl)piperidine-1-carbonyl]pyridine-2-sulfonamide (compound 219); ESIMS m/z: 519 (M+H)+

Example 152

The following compound was synthesized based on Example 51.

3-chloro-5-[4-(4-fluorophenyl)-3-oxopiperazine-1-carbonyl]-4-(1-phenylcyclopropylamino)pyridine-2-sulfonamide (compound 278); ESIMS m/z: 544 (M+H)+

Example 153

The following compound was synthesized based on Example 56.

[5-chloro-6-(phenylsulfonyl)-4-(o-tolylamino)pyridin-3-yl][4-(4-fluorophenyl)piperidin-1-yl]methanone (compound 205); ESIMS m/z: 564 (M+H)+

Example 154

The following compounds were synthesized based on Example 57.

4-((1R,2S,4S)-7-oxabicyclo[2.2.1]heptan-2-ylamino)-3-chloro-5-[4-(4-fluorophenyl)piperidine-1-carbonyl]pyridine-2-sulfonamide (compound 217); ESIMS m/z: 509 (M+H)+

4-((1R,2S,4S)-bicyclo[2.2.1]heptan-2-ylamino)-3-chloro-5-[4-(4-fluorophenyl)piperidine-1-carbonyl]pyridine-2-sulfonamide (compound 236); ESIMS m/z: 507 (M+H)+

3-chloro-4-(2,3-dihydro-1H-inden-1-ylamino)-5-[4-(4-fluorophenyl)piperidine-1-carbonyl]pyridine-2-sulfonamide (compound 237); ESIMS m/z: 529 (M+H)+

Example 155

The following compounds were synthesized based on Example 60, step 8.

3-chloro-5-[4-(4-fluorophenyl)-4-hydroxypiperidine-1-carbonyl]-4-(m-tolylamino)pyridine-2-sulfonamide (compound 199); ESIMS m/z: 519 (M+H)+ methyl 1-[5-chloro-6-sulfamoyl-4-(m-tolylamino)nicotinoyl]-4-phenylpiperidine-4-carboxylate (compound 201); ESIMS m/z: 543 (M+H)+

3-chloro-5-[4-(4-fluorophenyl)-1,2,3,6-tetrahydropyridine-1-carbonyl]-4-(m-tolylamino)pyridine-2-sulfonamide (compound 202); ESIMS m/z: 501 (M+H)+

1-[5-chloro-6-sulfamoyl-4-(m-tolylamino)nicotinoyl]-4-phenylpiperidine-4-carboxamide (compound 203); ESIMS m/z: 528 (M+H)+

3-chloro-5-[4-(2-chlorophenyl)piperazine-1-carbonyl]-4-(m-tolylamino)pyridine-2-sulfonamide (compound 206); ESIMS m/z: 520 (M+H)+

3-chloro-5-[4-(4-fluorophenyl)-4-methoxypiperidine-1-carbonyl]-4-(m-tolylamino)pyridine-2-sulfonamide (compound 208); ESIMS m/z: 533 (M+H)+

3-chloro-5-[4-(4-fluorophenyl)-3-oxopiperazine-1-carbonyl]-4-(m-tolylamino)pyridine-2-sulfonamide (compound 209); ESIMS m/z: 518 (M+H)+

5-[4-acetyl-4-(4-fluorophenyl)piperidine-1-carbonyl]-3-chloro-4-(m-tolylamino)pyridine-2-sulfonamide (compound 216); ESIMS m/z: 545 (M+H)+

Example 156

The following compounds were synthesized based on Example 78.

3-chloro-5-[4-(4-fluorophenyl)piperidine-1-carbonyl]-4-(2-methyl-2-phenylhydrazinyl)pyridine-2-sulfonamide (compound 282); ESIMS m/z: 518 (M+H)+

3-chloro-4-(2,5-dicyanophenylamino)-5-[4-(4-fluorophenyl)piperidine-1-carbonyl]pyridine-2-sulfonamide (compound 288); ESIMS m/z: 539 (M+H)+

3-chloro-4-(5-chloro-2-cyanophenylamino)-5-[4-(4-fluorophenyl)piperidine-1-carbonyl]pyridine-2-sulfonamide (compound 290); ESIMS m/z: 548 (M+H)+

3-chloro-5-[4-(4-fluorophenyl)piperidine-1-carbonyl]-4-[2-methyl-4-(methylsulfonyl)phenylamino]pyridine-2-sulfonamide (compound 329); ESIMS m/z: 581 (M+H)+

Example 157

The following compounds were synthesized based on Example 83.

4-(benzylamino)-5-[4-(4-fluorophenyl)-4-methoxypiperidine-1-carbonyl]-3-methylpyridine-2-sulfonamide (compound 262); ESIMS m/z: 513 (M+H)+

3-chloro-5-[3-(4-fluorophenyl)azetidine-1-carbonyl]-4-(1-phenylcyclopropylamino)pyridine-2-sulfonamide (compound 330); ESIMS m/z: 501 (M+H)+

INDUSTRIAL APPLICABILITY

The nitrogen-containing heterocyclic compound or the pharmaceutically acceptable salt thereof of the present invention is useful as a prophylactic and/or therapeutic agent for, for example, skin diseases and the like.

According to the present invention, a nitrogen-containing heterocyclic compound or a pharmaceutically acceptable salt thereof and the like, which are useful as a prophylactic and/or therapeutic agent for skin diseases, are provided.

SEQUENCE LISTING FREE TEXT

SEQ ID NO: 1-explanation of artificial sequence: synthetic DNA

SEQ ID NO: 2-explanation of artificial sequence: synthetic DNA

SEQ ID NO: 3-explanation of artificial sequence: synthetic DNA

SEQ ID NO: 4-explanation of artificial sequence: synthetic DNA

The invention claimed is:

1. A compound represented by the formula (I)

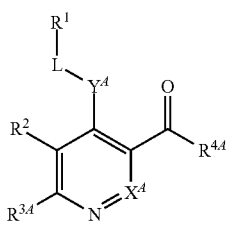

(I)

wherein $X^A$ represents CH or a nitrogen atom, $R^1$ represents cycloalkyl optionally having substituent(s), aryl optionally having substituent(s), an aromatic heterocyclic group optionally having substituent(s), or an aliphatic heterocyclic group optionally having substituent(s), L represents a bond or alkylene, $Y^A$ represents —NH—, —O—, —S—, —NH—NR$^{1a}$— (wherein, R$^{1a}$ represents lower alkyl), or a bond (provided $Y^A$ and L do not represent a bond at the same time), $R^2$ represents a hydrogen atom, cyano, halogen, lower alkyl optionally having substituent(s), or lower alkoxy optionally having substituent(s), $R^{3A}$ represents the following formula ($R^{3A}$-1) or formula ($R^{3A}$-2)

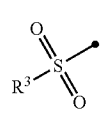

($R^{3A}$-1)

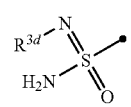

($R^{3A}$-2)

wherein $R^3$ represents hydroxy, lower alkyl optionally having substituent(s), aryl optionally having substituent(s), or —NR$^{3a}$R$^{3b}$ [wherein, R$^{3a}$ and R$^{3b}$ are the same or different and each represents a hydrogen atom, lower alkyl optionally having substituent(s), lower alkoxy optionally having substituent(s), cycloalkyl optionally having substituent(s), aryl optionally having substituent(s), an aromatic heterocyclic group optionally having substituent(s), an aliphatic heterocyclic group optionally having substituent(s) or —C(=O)R$^{3c}$ (wherein, R$^{3'}$ represents lower alkyl optionally having substituent(s), lower alkoxy optionally having substituent(s), lower alkylamino optionally having substituent(s), cycloalkylamino optionally having substituent(s), or cycloalkyl optionally having substituent(s)), or R$^{3a}$ and R$^{3b}$ form, together with the adjacent nitrogen atom, a nitrogen-containing heterocyclic group optionally having substituent(s)], and R$^{3d}$ represents a hydrogen atom, lower alkanoyl, aroyl, or lower alkylcarbamoyl, and R$^{4A}$ represents the following formula (R$^{4A}$-1), formula (R$^{4A}$-2), formula (R$^{4A}$-3), formula (R$^{4A}$-4), formula (R$^{4A}$-5) or formula (R$^{4A}$-6)

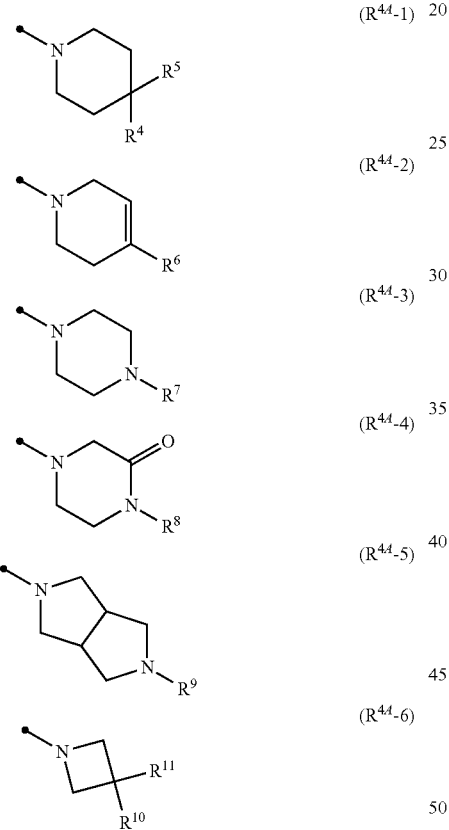

wherein R$^4$ and R$^5$ are the same or different and each represents a hydrogen atom, hydroxy, cyano, lower alkyl optionally having substituent(s), aryl optionally having substituent(s), lower alkoxy optionally having substituent(s), or —C(=O)R$^{4c}$ (wherein, R$^{4c}$ represents amino, alkyl optionally having substituent(s) or lower alkoxy optionally having substituent(s)), or R$^4$ and R$^5$ form, together with the adjacent carbon atom, an aliphatic heterocyclic group optionally having substituent(s), R$^6$, R$^7$, R$^8$ and R$^9$ represents aryl optionally having substituent(s), R$^{10}$ and R$^{11}$ are the same or different and each represents a hydrogen atom, hydroxy, cyano, lower alkyl optionally having substituent(s), aryl optionally having substituent(s), lower alkoxy optionally having substituent(s), or —C(=O)R$^{4c}$ (wherein, R$^{4c}$ represents amino, alkyl optionally having substituent(s) or lower alkoxy optionally having substituent(s)), or R$^{10}$ and R$^{11}$ form, together with the adjacent carbon atom, an aliphatic heterocyclic group optionally having substituent(s), when the lower alkyl, lower alkoxy, or lower alkylamino is substituted, each substituent is the same or different and is selected from the group consisting of halogen, hydroxy, mercapto, nitro, cyano, carboxy, carbamoyl optionally substituted with at least one substituent selected from hydroxy, C$_{1-10}$ alkyl, C$_{1-10}$ alkoxy, and C$_{3-8}$ cycloalkyl, C$_{3-8}$ cycloalkyl, C$_{6-14}$ aryl, an aliphatic heterocyclic group, an aromatic heterocyclic group optionally substituted with at least one C$_{1-10}$ alkyl group, C$_{1-10}$ alkoxy, C$_{3-8}$cycloalkoxy, C$_{6-14}$ aryloxy, C$_{7-16}$ aralkyloxy, C$_{2-11}$ alkanoyloxy, C$_{7-15}$ aroyloxy, C$_{1-10}$ alkylthio, —NR$^X$R$^Y$ (wherein R$^X$ and R$^Y$ are the same or different and each is a hydrogen atom, C$_{1-10}$ alkyl, C$_{3-8}$ cycloalkyl, C$_{6-14}$ aryl, an aromatic heterocyclic group, C$_{7-16}$ aralkyl, C$_{2-11}$ alkanoyl, C$_{7-15}$ aroyl, C$_{1-10}$ alkoxycarbonyl, or C$_{7-16}$ aralkyloxycarbonyl), C$_{2-11}$ alkanoyl, C$_{7-15}$ aroyl, C$_{1-10}$ alkoxycarbonyl, C$_{6-14}$ aryloxycarbonyl, and aliphatic heterocyclic carbonyl, when the aryl or aromatic heterocyclic group is substituted, each substituent is the same or different and is selected from the group consisting of halogen, hydroxy, mercapto, nitro, cyano, carboxy, carbamoyl, C$_{1-10}$ alkyl optionally substituted with at least one substituent selected from halogen, hydroxy, and C$_{1-10}$ alkoxy, C$_{3-8}$ cycloalkyl, C$_{6-14}$ aryl, aliphatic heterocyclic group, aromatic heterocyclic group, C$_{1-10}$ alkoxy optionally substituted with at least one substituent selected from halogen, hydroxy, and C$_{1-10}$ alkoxy, C$_{3-8}$ cycloalkoxy, C$_{6-14}$ aryloxy, C$_{7-16}$ aralkyloxy, C$_{2-11}$ alkanoyloxy, C$_{7-15}$ aroyloxy, C$_{1-10}$ alkylthio, —NR$^{Xa}$R$^{Ya}$ (wherein R$^{Xa}$ and R$^{Ya}$ are the same or different and each is a hydrogen atom, C$_{1-10}$ alkyl, C$_{3-8}$ cycloalkyl, C$_{6-14}$ awl, an aromatic heterocyclic group, C$_{7-16}$ aralkyl, C$_{2-11}$ alkanoyl, C$_{7-15}$ aroyl, C$_{1-10}$ alkoxycarbonyl, or C$_{7-16}$ aralkyloxycarbonyl), C$_{2-11}$ alkanoyl, C$_{7-15}$ aroyl, C$_{1-10}$ alkoxycarbonyl, C$_{6-14}$ aryloxycarbonyl, C$_{1-10}$ alkylcarbamoyl, di-C$_{1-10}$ alkylcarbamoyl, and C$_{1-10}$ alkylsulfonyl, and when the optionally substituted aryl is phenyl fused with optionally substituted cycloalkyl, the substituent further consists of oxo, and when the cycloalkyl, the cycloalkylamino, the aliphatic heterocyclic group, the nitrogen-containing heterocyclic that is formed together with the adjacent nitrogen atom, and the aliphatic heterocyclic group that is formed together with the adjacent nitrogen atom is substituted, each substituent is the same or different and is selected from the group consisting of oxo, halogen, hydroxy, mercapto, nitro, cyano, carboxy, carbamoyl, C$_{1-10}$ alkyl, trifluoromethyl, C$_{3-8}$ cycloalkyl, C$_{6-14}$ aryl, aliphatic heterocyclic group, aromatic heterocyclic group, C$_{1-10}$ alkoxy, C$_{3-8}$ cycloalkoxy, C$_{6-14}$ aryloxy, C$_{7-16}$ aralkyloxy, C$_{2-11}$ alkanoyloxy, C$_{7-15}$ aroyloxy, C$_{1-10}$ alkylthio, —NR$^{Xb}$R$^{Yb}$ (wherein R$^{Xb}$ and R$^{Yb}$ are the same or different and each is a hydrogen atom, C$_{1-10}$ alkyl, C$_{3-8}$ cycloalkyl, C$_{6-14}$ aryl, aromatic heterocyclic group, C$_{7-16}$ aralkyl, C$_{2-11}$ alkanoyl, C$_{7-15}$ aroyl, C$_{1-10}$ alkoxycarbonyl, or C$_{7-16}$ aralkyloxycarbonyl), C$_{2-11}$ alkanoyl, C$_{7-15}$ aroyl, C$_{1-10}$ alkoxycarbonyl, C$_{6-14}$ aryloxycarbonyl, C$_{1-10}$ alkylcarbamoyl, and di-C$_{1-10}$ alkylcarbamoyl, or a pharmaceutically acceptable salt thereof.

2. The compound or the pharmaceutically acceptable salt thereof according to claim 1, wherein L represents a bond.

3. The compound or the pharmaceutically acceptable salt thereof according to claim 1, wherein $R^1$ represents aryl optionally having substituent(s).

4. The compound or the pharmaceutically acceptable salt thereof according to claim 1, wherein $R^2$ represents a hydrogen atom, halogen or lower alkyl optionally having substituent(s).

5. The compound or the pharmaceutically acceptable salt thereof according to claim 1, wherein $R^2$ represents a hydrogen atom.

6. The compound or the pharmaceutically acceptable salt thereof according to claim 1, wherein $R^2$ represents halogen.

7. The compound or the pharmaceutically acceptable salt thereof according to claim 1, wherein $R^2$ represents lower alkyl optionally having substituent(s).

8. The compound or the pharmaceutically acceptable salt thereof according to claim 1, wherein $R^{3A}$ represents the following formula ($R^{3A}$-1)

($R^{3A}$-1)

9. The compound or the pharmaceutically acceptable salt thereof according to claim 8, wherein $R^3$ represents —$NR^{3a}R^{3b}$.

10. The compound or the pharmaceutically acceptable salt thereof according to claim 9, wherein $R^{3a}$ and $R^{3b}$ are the same or different and each represents a hydrogen atom, or an aromatic heterocyclic group optionally having substituent(s).

11. The compound or the pharmaceutically acceptable salt thereof according to claim 9, wherein $R^{3a}$ and $R^{3b}$ each represent a hydrogen atom.

12. The compound or the pharmaceutically acceptable salt thereof according to claim 9, wherein $R^{3a}$ represents a hydrogen atom, and $R^{3b}$ represents an aromatic heterocyclic group optionally having substituent(s).

13. The compound or the pharmaceutically acceptable salt thereof according to claim 1, wherein $R^{4A}$ represents the following formula ($R^{4A}$-1)

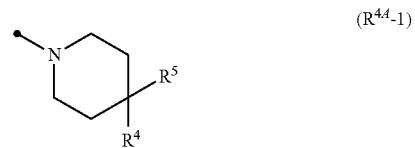

14. The compound or the pharmaceutically acceptable salt thereof according to claim 13, wherein $R^4$ and $R^5$ are the same or different and each represents a hydrogen atom, or aryl optionally having substituent(s).

15. The compound or the pharmaceutically acceptable salt thereof according to claim 1, wherein $X^4$ represents CH.

16. The compound or the pharmaceutically acceptable salt thereof according to claim 1, wherein $Y^A$ represents —NH— or —O—.

17. A medicament comprising, as an active ingredient, the compound or the pharmaceutically acceptable salt thereof according to claim 1.

18. A method of inhibiting C-C chemokine receptor type 10 receptor in a mammal, comprising administering to a mammal in need thereof an effective amount of the compound or the pharmaceutically acceptable salt thereof according to claim 1.

* * * * *

SEQUENCE LISTING

```
<160> NUMBER OF SEQ ID NOS: 4

<210> SEQ ID NO 1
<211> LENGTH: 61
<212> TYPE: DNA
<213> ORGANISM: Artificial Sequence
<220> FEATURE:
<223> OTHER INFORMATION: synthetic DNA

<400> SEQUENCE: 1
cagtcaagct tccaccatgg ggacggaggc cacagagcag gtttcctggg gccatttact c    61

<210> SEQ ID NO 2
<211> LENGTH: 37
<212> TYPE: DNA
<213> ORGANISM: Artificial Sequence
<220> FEATURE:
<223> OTHER INFORMATION: synthetic DNA

<400> SEQUENCE: 2
gttatagcgg ccgcagcctg cccctcctc tagattc                               37

<210> SEQ ID NO 3
<211> LENGTH: 25
<212> TYPE: DNA
<213> ORGANISM: Artificial Sequence
<220> FEATURE:
<223> OTHER INFORMATION: synthetic DNA

<400> SEQUENCE: 3
cggagactct agagggtata taatg                                           25

<210> SEQ ID NO 4
<211> LENGTH: 21
<212> TYPE: DNA
<213> ORGANISM: Artificial Sequence
<220> FEATURE:
<223> OTHER INFORMATION: synthetic DNA

<400> SEQUENCE: 4
ctaatacgac tcactatagg g                                               21
```